US007411058B2

(12) United States Patent
Dowling et al.

(10) Patent No.: US 7,411,058 B2
(45) Date of Patent: Aug. 12, 2008

(54) COLD-ADAPTED EQUINE INFLUENZA VIRUSES

(75) Inventors: Patricia W. Dowling, Pittsburgh, PA (US); Julius S. Youngner, Pittsburgh, PA (US)

(73) Assignee: The University of Pittsburgh - of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 11/438,845

(22) Filed: Jul. 7, 2006

(65) Prior Publication Data

US 2007/0092536 A1 Apr. 26, 2007

Related U.S. Application Data

(60) Division of application No. 10/181,585, filed as application No. PCT/US01/05048 on Feb. 16, 2001, now Pat. No. 7,074,414, which is a continuation-in-part of application No. 09/506,286, filed on Feb. 16, 2000, now Pat. No. 6,482,414.

(51) Int. Cl.

| | |
|---|---|
| ***C07H 21/04*** | (2006.01) |
| ***A61K 39/145*** | (2006.01) |
| ***A61K 39/12*** | (2006.01) |
| ***A01N 63/00*** | (2006.01) |
| ***C12N 7/00*** | (2006.01) |

(52) U.S. Cl. .............. 536/23.72; 424/209.1; 424/204.1; 424/186.1; 424/93.6; 435/235.1

(58) Field of Classification Search ....................... None
See application file for complete search history.

(56) References Cited

U.S. PATENT DOCUMENTS

| | | | | |
|---|---|---|---|---|
| 3,518,347 | A | 6/1970 | Pavilanis et al. | 424/89 |
| 4,631,191 | A | 12/1986 | Dale et al. | 424/88 |
| 4,683,137 | A | 7/1987 | Coggins et al. | 424/89 |
| 4,693,893 | A | 9/1987 | Campbell et al. | 424/89 |
| 4,920,213 | A | 4/1990 | Dale et al. | 536/27 |
| 5,149,531 | A | 9/1992 | Youngner et al. | 424/89 |
| 5,690,937 | A | 11/1997 | Parkin et al. | 424/199.1 |
| 2004/0137015 | A1 | 7/2004 | Dowling et al. | |
| 2007/0092536 | A1 * | 4/2007 | Dowling et al. | 424/209.1 |

FOREIGN PATENT DOCUMENTS

| | | |
|---|---|---|
| WO | WO83/03546 | 10/1983 |
| WO | WO 92/00097 | 1/1992 |
| WO | WO 93/21310 | 10/1993 |
| WO | WO 00/09702 | 2/2000 |

OTHER PUBLICATIONS

GenBank entry for Accession No. M26082, Influenza virus RNA polymerase, Jul. 1989.*
Okazaki, K. et al, "Evolutionary pathways of the PA Genes of Influenza A Viruses", Virology, 1989, vol. 172: pp. 601-608.*
Brundage-Anguish, et al., 1982, *Am J Vet Res*, 43(5), pp. 869-874.
Enami, et al., 1990, *PNAS*, vol. 87, pp. 3802-3805.
Estola, et al., 1976, *Nord Vet med* vol. 28(7-8), pp. 353-356.
Hannant, et al., Feb. 6, 1988, *Vet Rec*, pp. 125-128.
Holmes, et al., 1992, *Equine Infectious Diseases VI: Proceedings of the Sixth International Conference*, Jul. 7-11, 1991, pp. 253-258.
Ilobi, et al., 1998, *Arch Virol*, vol. 143, pp. 891-901.
Kucera, et al., 1977, *Can J Comp Med*, 41(3), pp. 326-331.
Mumford, et al., 1983, *J Hyg* (*Lond*), vol. 90(3), pp. 385-395.
Noble, et al., 1994, *J Gen Virol* vol. 75, pp. 3485-3491.
Reed, et al., 1938, *The American Journal of Hygiene*, vol. 27, pp. 493-497.
Timoney, P.J., 1996, *Comp Immunol Microbiol Infect Dis*, vol. 19(3), pp. 205-211.
USDA, 9 CFR 113.2XX, Oct. 28, 1994, Supplemental Assay Method for Conducting the Hemagglutination Inhibition Assay for Equine Influenza Antibody.
Van Maanen, et al., 1992, *Vet Q*, vol. 14(1), pp. 13-17.
Van Oirschot, et al., 1991, *Zentralbl Veterinarmed [B]*, vol. 38(5), pp. 391-396.
Wood, et al., 1983, *J Hyg* (*Lond*) vol. 90(3), pp. 371-384.
Wilson, et al., 1993, *Vet Clin North Am Equine Practi*, vol. 9(2), pp. 257-282.
Youngner, et al., 1994, *J. of Clinical of Microbiology*, vol. 32(3), pp. 750-754.
Lunn et al., 1999, *Vaccine*, vol. 17, pp. 2245-2258.
Romanova et al., 1997, *Vaccine*, vol. 15, No. 6/7, pp. 653-658.
Talon et al., 2000, *PNAS*, vol. 97, No. 8, pp. 4309-4314.
Daly, et al., 1996, *Journal of General Virology*, vol. 77, pp. 661-671.
Lindstrom, et al., 1998, *Archives of Virology*, vol. 143, No. 8, pp. 1585-1598.

* cited by examiner

*Primary Examiner*—Joseph Woitach
*Assistant Examiner*—Mike Burkhart

(57) ABSTRACT

The present invention provides experimentally-generated cold-adapted equine influenza viruses, and reassortant influenza A viruses comprising at least one genome segment of such an equine influenza virus, wherein the equine influenza virus genome segment confers at least one identifying phenotype of the cold-adapted equine influenza virus, such as cold-adaptation, temperature sensitivity, dominant interference, or attenuation. Such viruses are formulated into therapeutic compositions to protect animals from diseases caused by influenza A viruses, and in particular, to protect horses from disease caused by equine influenza virus. The present invention also includes methods to protect animals from diseases caused by influenza A virus utilizing the claimed therapeutic compositions. Such methods include using a therapeutic composition as a vaccine to generate a protective immune response in an animal prior to exposure to a virulent virus, and using a therapeutic composition as a treatment for an animal that has been recently infected with a virulent virus, or is likely to be subsequently exposed to virulent virus in a few days whereby the therapeutic composition interferes with the growth of the virulent virus, even in the absence of immunity. The present invention also provides methods to produce cold-adapted equine influenza viruses, and reassortant influenza A viruses having at least one genome segment of an equine influenza virus generated by cold-adaptation.

5 Claims, No Drawings

SEQUENCE LISTING

```
<160> NUMBER OF SEQ ID NOS: 130

<210> SEQ ID NO 1
<211> LENGTH: 18
<212> TYPE: DNA
<213> ORGANISM: Artificial
<220> FEATURE:
<223> OTHER INFORMATION: Synthetic Primer
```

-continued

```
<400> SEQUENCE: 1

caggaaacag ctatgacc                                                     18


<210> SEQ ID NO 2
<211> LENGTH: 20
<212> TYPE: DNA
<213> ORGANISM: Artificial
<220> FEATURE:
<223> OTHER INFORMATION: Synthetic Primer

<400> SEQUENCE: 2

taatacgact cactataggg                                                   20


<210> SEQ ID NO 3
<211> LENGTH: 25
<212> TYPE: DNA
<213> ORGANISM: Artificial
<220> FEATURE:
<223> OTHER INFORMATION: Synthetic Primer

<400> SEQUENCE: 3

agcaaaagca ggtcaaatat attca                                             25


<210> SEQ ID NO 4
<211> LENGTH: 26
<212> TYPE: DNA
<213> ORGANISM: Artificial
<220> FEATURE:
<223> OTHER INFORMATION: Synthetic Primer

<400> SEQUENCE: 4

gaaaacacca tggctacaat tattgc                                            26


<210> SEQ ID NO 5
<211> LENGTH: 1241
<212> TYPE: DNA
<213> ORGANISM: Equine influenza virus H3N8
<220> FEATURE:
<221> NAME/KEY: CDS
<222> LOCATION: (28)..(1239)

<400> SEQUENCE: 5

agcaaaagca ggtcaaatat attcaat atg gag aga ata aaa gaa ctg aga gat       54
                              Met Glu Arg Ile Lys Glu Leu Arg Asp
                              1               5

cta atg tca caa tcc cgc acc cgc gag ata cta aca aaa act act gtg        102
Leu Met Ser Gln Ser Arg Thr Arg Glu Ile Leu Thr Lys Thr Thr Val
10                  15                  20                  25

gac cac atg gcc ata atc aag aaa tac aca tca gga aga caa gag aag        150
Asp His Met Ala Ile Ile Lys Lys Tyr Thr Ser Gly Arg Gln Glu Lys
                30                  35                  40

aac ccc gca ctt agg atg aag tgg atg atg gca atg aaa tac cca att        198
Asn Pro Ala Leu Arg Met Lys Trp Met Met Ala Met Lys Tyr Pro Ile
            45                  50                  55

aca gca gat aag agg ata atg gaa atg att cct gag aga aat gaa cag        246
Thr Ala Asp Lys Arg Ile Met Glu Met Ile Pro Glu Arg Asn Glu Gln
        60                  65                  70

ggg caa acc ctt tgg agc aaa acg aac gat gct ggc tca gac cgc gta        294
Gly Gln Thr Leu Trp Ser Lys Thr Asn Asp Ala Gly Ser Asp Arg Val
    75                  80                  85

atg gta tca cct ctg gca gtg aca tgg tgg aat agg aat gga cca aca        342
Met Val Ser Pro Leu Ala Val Thr Trp Trp Asn Arg Asn Gly Pro Thr
90                  95                  100                 105
```

-continued

```
acg agc aca att cat tat cca aaa gtc tac aaa act tat ttt gaa aaa      390
Thr Ser Thr Ile His Tyr Pro Lys Val Tyr Lys Thr Tyr Phe Glu Lys
                110                 115                 120

gtt gaa aga tta aaa cac gga acc ttt ggc ccc gtt cat ttt agg aat      438
Val Glu Arg Leu Lys His Gly Thr Phe Gly Pro Val His Phe Arg Asn
            125                 130                 135

caa gtc aag ata aga cgg aga gtt gat gta aac cct ggt cac gcg gac      486
Gln Val Lys Ile Arg Arg Arg Val Asp Val Asn Pro Gly His Ala Asp
        140                 145                 150

ctc agt gcc aaa gaa gca caa gat gtg atc atg gaa gtt gtt ttc cca      534
Leu Ser Ala Lys Glu Ala Gln Asp Val Ile Met Glu Val Val Phe Pro
    155                 160                 165

aat gaa gtg gga gcc aga att cta aca tcg gaa tca caa cta aca ata      582
Asn Glu Val Gly Ala Arg Ile Leu Thr Ser Glu Ser Gln Leu Thr Ile
170                 175                 180                 185

acc aaa gag aaa aaa gaa gaa ctt cag gac tgc aaa att gcc ccc ttg      630
Thr Lys Glu Lys Lys Glu Glu Leu Gln Asp Cys Lys Ile Ala Pro Leu
                190                 195                 200

atg gta gca tac atg cta gaa aga gag ttg gtc cga aaa aca aga ttc      678
Met Val Ala Tyr Met Leu Glu Arg Glu Leu Val Arg Lys Thr Arg Phe
            205                 210                 215

ctc cca gtg gct ggc gga aca agc agt gta tac att gaa gtg ttg cat      726
Leu Pro Val Ala Gly Gly Thr Ser Ser Val Tyr Ile Glu Val Leu His
        220                 225                 230

ctg act cag gga aca tgc tgg gaa caa atg tac acc cca gga gga gaa      774
Leu Thr Gln Gly Thr Cys Trp Glu Gln Met Tyr Thr Pro Gly Gly Glu
    235                 240                 245

gtt aga aac gat gac att gat caa agt tta att att gct gcc cgg aac      822
Val Arg Asn Asp Asp Ile Asp Gln Ser Leu Ile Ile Ala Ala Arg Asn
250                 255                 260                 265

ata gtg aga aga gcg aca gta tca gca gat cca cta gca tcc ctg ctg      870
Ile Val Arg Arg Ala Thr Val Ser Ala Asp Pro Leu Ala Ser Leu Leu
                270                 275                 280

gaa atg tgc cac agt aca cag att ggt gga ata agg atg gta gac atc      918
Glu Met Cys His Ser Thr Gln Ile Gly Gly Ile Arg Met Val Asp Ile
            285                 290                 295

ctt aag cag aat cca aca gag gaa caa gct gtg gat ata tgc aaa gca      966
Leu Lys Gln Asn Pro Thr Glu Glu Gln Ala Val Asp Ile Cys Lys Ala
        300                 305                 310

gca atg ggg tta aga att agc tca tca ttc agc ttt ggt gga ttc acc     1014
Ala Met Gly Leu Arg Ile Ser Ser Ser Phe Ser Phe Gly Gly Phe Thr
    315                 320                 325

ttt aag aga aca agt gga tca tca gtc aag aga gaa gaa gaa atg ctt     1062
Phe Lys Arg Thr Ser Gly Ser Ser Val Lys Arg Glu Glu Glu Met Leu
330                 335                 340                 345

acg ggc aac ctt caa aca ttg aaa ata aga gtg cat gaa ggc tat gaa     1110
Thr Gly Asn Leu Gln Thr Leu Lys Ile Arg Val His Glu Gly Tyr Glu
                350                 355                 360

gaa ttc aca atg gtc gga aga aga gca aca gcc att ctc aga aag gca     1158
Glu Phe Thr Met Val Gly Arg Arg Ala Thr Ala Ile Leu Arg Lys Ala
            365                 370                 375

acc aga aga ttg att caa ttg ata gta agt ggg aga gat gaa caa tca     1206
Thr Arg Arg Leu Ile Gln Leu Ile Val Ser Gly Arg Asp Glu Gln Ser
        380                 385                 390

att gct gaa gca ata att gta gcc atg gtg ttt tc                      1241
Ile Ala Glu Ala Ile Ile Val Ala Met Val Phe
    395                 400

<210> SEQ ID NO 6
<211> LENGTH: 404
```

-continued

```
<212> TYPE: PRT
<213> ORGANISM: Equine influenza virus H3N8

<400> SEQUENCE: 6

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400
```

-continued

Ala Met Val Phe

<210> SEQ ID NO 7
<211> LENGTH: 1214
<212> TYPE: DNA
<213> ORGANISM: Equine influenza virus H3N8

<400> SEQUENCE: 7
atggagagaa taaaagaact gagagatcta atgtcacaat cccgcacccg cgagatacta 60
acaaaaacta ctgtggacca catggccata atcaagaaat acacatcagg aagacaagag 120
aagaaccccg cacttaggat gaagtggatg atggcaatga aatacccaat tacagcagat 180
aagaggataa tggaaatgat tcctgagaga aatgaacagg ggcaaaccct ttggagcaaa 240
acgaacgatg ctggctcaga ccgcgtaatg gtatcacctc tggcagtgac atggtggaat 300
aggaatggac caacaacgag cacaattcat tatccaaaag tctacaaaac ttattttgaa 360
aaagttgaaa gattaaaaca cggaaccttt ggccccgttc attttaggaa tcaagtcaag 420
ataagacgga gagttgatgt aaaccctggt cacgcggacc tcagtgccaa agaagcacaa 480
gatgtgatca tggaagttgt tttcccaaat gaagtgggag ccagaattct aacatcggaa 540
tcacaactaa caataaccaa agagaaaaaa gaagaacttc aggactgcaa aattgccccc 600
ttgatggtag catacatgct agaaagagag ttggtccgaa aaacaagatt cctcccagtg 660
gctggcggaa caagcagtgt atacattgaa gtgttgcatc tgactcaggg aacatgctgg 720
gaacaaatgt acaccccagg aggagaagtt agaaacgatg acattgatca aagtttaatt 780
attgctgccc ggaacatagt gagaagagcg acagtatcag cagatccact agcatccctg 840
ctggaaatgt gccacagtac acagattggt ggaataagga tggtagacat ccttaagcag 900
aatccaacag aggaacaagc tgtggatata tgcaaagcag caatggggtt aagaattagc 960
tcatcattca gctttggtgg attcaccttt aagagaacaa gtggatcatc agtcaagaga 1020
gaagaagaaa tgcttacggg caaccttcaa acattgaaaa taagagtgca tgaaggctat 1080
gaagaattca caatggtcgg aagaagagca acagccattc tcagaaaggc aaccagaaga 1140
ttgattcaat tgatagtaag tgggagagat gaacaatcaa ttgctgaagc aataattgta 1200
gccatggtgt tttc 1214

<210> SEQ ID NO 8
<211> LENGTH: 1241
<212> TYPE: DNA
<213> ORGANISM: Equine influenza virus H3N8
<220> FEATURE:
<221> NAME/KEY: CDS
<222> LOCATION: (28)..(1239)

<400> SEQUENCE: 8

```
agcaaaagca ggtcaaatat attcaat atg gag aga ata aaa gaa ctg aga gat      54
                              Met Glu Arg Ile Lys Glu Leu Arg Asp
                              1               5

cta atg tca caa tcc cgc acc cgc gag ata cta aca aaa act act gtg      102
Leu Met Ser Gln Ser Arg Thr Arg Glu Ile Leu Thr Lys Thr Thr Val
10                  15                  20                  25

gac cac atg gcc ata atc aag aaa tac aca tca gga aga caa gag aag      150
Asp His Met Ala Ile Ile Lys Lys Tyr Thr Ser Gly Arg Gln Glu Lys
                30                  35                  40

aac ccc gca ctt agg atg aag tgg atg atg gca atg aaa tac cca att      198
Asn Pro Ala Leu Arg Met Lys Trp Met Met Ala Met Lys Tyr Pro Ile
            45                  50                  55
```

-continued

```
aca gca gat aag agg ata atg gaa atg att cct gag aga aat gaa cag      246
Thr Ala Asp Lys Arg Ile Met Glu Met Ile Pro Glu Arg Asn Glu Gln
        60                  65                  70

ggg caa acc ctt tgg agc aaa acg aac gat gct ggc tca gac cgc gta      294
Gly Gln Thr Leu Trp Ser Lys Thr Asn Asp Ala Gly Ser Asp Arg Val
    75                  80                  85

atg gta tca cct ctg gca gtg aca tgg tgg aat agg aat gga cca aca      342
Met Val Ser Pro Leu Ala Val Thr Trp Trp Asn Arg Asn Gly Pro Thr
90                  95                  100                 105

acg agc aca att cat tat cca aaa gtc cac aaa act tat ttt gaa aaa      390
Thr Ser Thr Ile His Tyr Pro Lys Val His Lys Thr Tyr Phe Glu Lys
                110                 115                 120

gtt gaa aga tta aaa cac gga acc ttt ggc ccc gtt cat ttt agg aat      438
Val Glu Arg Leu Lys His Gly Thr Phe Gly Pro Val His Phe Arg Asn
            125                 130                 135

caa gtc aag ata aga cgg aga gtt gat gta aac cct ggt cac gcg gac      486
Gln Val Lys Ile Arg Arg Arg Val Asp Val Asn Pro Gly His Ala Asp
        140                 145                 150

ctc agt gcc aaa gaa gca caa gat gtg atc atg gaa gtt gtt ttc cca      534
Leu Ser Ala Lys Glu Ala Gln Asp Val Ile Met Glu Val Val Phe Pro
    155                 160                 165

aat gaa gtg gga gcc aga att cta aca tcg gaa tca caa cta aca ata      582
Asn Glu Val Gly Ala Arg Ile Leu Thr Ser Glu Ser Gln Leu Thr Ile
170                 175                 180                 185

acc aaa gag aaa aaa gaa gaa ctt cag gac tgc aaa att gcc ccc ttg      630
Thr Lys Glu Lys Lys Glu Glu Leu Gln Asp Cys Lys Ile Ala Pro Leu
                190                 195                 200

atg gta gca tac atg cta gaa aga gag ttg gtc cga aaa aca aga ttc      678
Met Val Ala Tyr Met Leu Glu Arg Glu Leu Val Arg Lys Thr Arg Phe
            205                 210                 215

ctc cca gtg gct ggc gga aca agc agt gta tac att gaa gtg ttg cat      726
Leu Pro Val Ala Gly Gly Thr Ser Ser Val Tyr Ile Glu Val Leu His
        220                 225                 230

ctg act cag gga aca tgc tgg gaa caa atg tac acc cca gga gga gaa      774
Leu Thr Gln Gly Thr Cys Trp Glu Gln Met Tyr Thr Pro Gly Gly Glu
    235                 240                 245

gtt aga aac gat gac att gat caa agt tta att att gct gcc cgg aac      822
Val Arg Asn Asp Asp Ile Asp Gln Ser Leu Ile Ile Ala Ala Arg Asn
250                 255                 260                 265

ata gtg aga aga gcg aca gta tca gca gat cca cta gca tcc ctg ctg      870
Ile Val Arg Arg Ala Thr Val Ser Ala Asp Pro Leu Ala Ser Leu Leu
                270                 275                 280

gaa atg tgc cac agt aca cag att ggt gga ata agg atg gta gac atc      918
Glu Met Cys His Ser Thr Gln Ile Gly Gly Ile Arg Met Val Asp Ile
            285                 290                 295

ctt aag cag aat cca aca gag gaa caa gct gtg gat ata tgc aaa gca      966
Leu Lys Gln Asn Pro Thr Glu Glu Gln Ala Val Asp Ile Cys Lys Ala
        300                 305                 310

gca atg ggg tta aga att agc tca tca ttc agc ttt ggt gga ttc acc     1014
Ala Met Gly Leu Arg Ile Ser Ser Ser Phe Ser Phe Gly Gly Phe Thr
    315                 320                 325

ttt aag aga aca agt gga tca tca gtc aag aga gaa gaa gaa atg ctt     1062
Phe Lys Arg Thr Ser Gly Ser Ser Val Lys Arg Glu Glu Glu Met Leu
330                 335                 340                 345

acg ggc aac ctt caa aca ttg aaa ata aga gtg cat gaa ggc tat gaa     1110
Thr Gly Asn Leu Gln Thr Leu Lys Ile Arg Val His Glu Gly Tyr Glu
                350                 355                 360

gaa ttc aca atg gtc gga aga aga gca aca gcc att ctc aga aag gca     1158
Glu Phe Thr Met Val Gly Arg Arg Ala Thr Ala Ile Leu Arg Lys Ala
```

-continued

```
            365                 370                 375

acc aga aga ttg att caa ttg ata gta agt ggg aga gat gaa caa tca      1206
Thr Arg Arg Leu Ile Gln Leu Ile Val Ser Gly Arg Asp Glu Gln Ser
        380                 385                 390

att gct gaa gca ata att gta gcc atg gtg ttt tc                       1241
Ile Ala Glu Ala Ile Ile Val Ala Met Val Phe
    395                 400


<210> SEQ ID NO 9
<211> LENGTH: 404
<212> TYPE: PRT
<213> ORGANISM: Equine influenza virus H3N8

<400> SEQUENCE: 9

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val His Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
```

-continued

```
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe


<210> SEQ ID NO 10
<211> LENGTH: 1214
<212> TYPE: DNA
<213> ORGANISM: Equine influenza virus H3N8

<400> SEQUENCE: 10

atggagagaa taaaagaact gagagatcta atgtcacaat cccgcacccg cgagatacta     60

acaaaaacta ctgtggacca catggccata atcaagaaat acacatcagg aagacaagag    120

aagaaccccg cacttaggat gaagtggatg atggcaatga aatacccaat tacagcagat    180

aagaggataa tggaaatgat tcctgagaga aatgaacagg ggcaaaccct ttggagcaaa    240

acgaacgatg ctggctcaga ccgcgtaatg gtatcacctc tggcagtgac atggtggaat    300

aggaatggac caacaacgag cacaattcat tatccaaaag tccacaaaac ttattttgaa    360

aaagttgaaa gattaaaaca cggaaccttt ggccccgttc attttaggaa tcaagtcaag    420

ataagacgga gagttgatgt aaaccctggt cacgcggacc tcagtgccaa agaagcacaa    480

gatgtgatca tggaagttgt tttcccaaat gaagtgggag ccagaattct aacatcggaa    540

tcacaactaa caataaccaa agagaaaaaa gaagaacttc aggactgcaa aattgccccc    600

ttgatggtag catacatgct agaaagagag ttggtccgaa aaacaagatt cctcccagtg    660

gctggcggaa caagcagtgt atacattgaa gtgttgcatc tgactcaggg aacatgctgg    720

gaacaaatgt acaccccagg aggagaagtt agaaacgatg acattgatca aagtttaatt    780

attgctgccc ggaacatagt gagaagagcg acagtatcag cagatccact agcatccctg    840

ctggaaatgt gccacagtac acagattggt ggaataagga tggtagacat ccttaagcag    900

aatccaacag aggaacaagc tgtggatata tgcaaagcag caatggggtt aagaattagc    960

tcatcattca gctttggtgg attcaccttt aagagaacaa gtggatcatc agtcaagaga   1020

gaagaagaaa tgcttacggg caaccttcaa acattgaaaa taagagtgca tgaaggctat   1080

gaagaattca caatggtcgg aagaagagca acagccattc tcagaaaggc aaccagaaga   1140

ttgattcaat tgatagtaag tgggagagat gaacaatcaa ttgctgaagc aataattgta   1200

gccatggtgt tttc                                                      1214


<210> SEQ ID NO 11
<211> LENGTH: 27
<212> TYPE: DNA
<213> ORGANISM: Artificial
<220> FEATURE:
<223> OTHER INFORMATION: Synthetic Primer

<400> SEQUENCE: 11

agaattcaca atggtcggaa gaagagc                                         27
```

-continued

```
<210> SEQ ID NO 12
<211> LENGTH: 27
<212> TYPE: DNA
<213> ORGANISM: Artificial
<220> FEATURE:
<223> OTHER INFORMATION: Synthetic Primer

<400> SEQUENCE: 12

agtagaaaca aggtcgtttt taaacaa                                          27


<210> SEQ ID NO 13
<211> LENGTH: 1233
<212> TYPE: DNA
<213> ORGANISM: Equine influenza virus H3N8
<220> FEATURE:
<221> NAME/KEY: CDS
<222> LOCATION: (3)..(1196)

<400> SEQUENCE: 13

ta gaa ttc aca atg gtc gga aga aga gca aca gcc att ctc aga aag         47
   Glu Phe Thr Met Val Gly Arg Arg Ala Thr Ala Ile Leu Arg Lys
   1               5                   10                  15

gca acc aga aga ttg att caa ttg ata gta agt ggg aga gat gaa caa        95
Ala Thr Arg Arg Leu Ile Gln Leu Ile Val Ser Gly Arg Asp Glu Gln
                20                  25                  30

tca att gct gaa gca ata att gta gcc atg gtg ttt tcg caa gaa gat       143
Ser Ile Ala Glu Ala Ile Ile Val Ala Met Val Phe Ser Gln Glu Asp
            35                  40                  45

tgc atg ata aaa gca gtt cga ggc gat ttg aac ttc gtt aat aga gca       191
Cys Met Ile Lys Ala Val Arg Gly Asp Leu Asn Phe Val Asn Arg Ala
        50                  55                  60

aat cag cgc ttg aac ccc atg cat caa ctc ttg agg cat ttc caa aaa       239
Asn Gln Arg Leu Asn Pro Met His Gln Leu Leu Arg His Phe Gln Lys
    65                  70                  75

gat gca aaa gtg ctt ttc cag aat tgg ggg att gaa ccc atc gac aat       287
Asp Ala Lys Val Leu Phe Gln Asn Trp Gly Ile Glu Pro Ile Asp Asn
80                  85                  90                  95

gtg atg gga atg att gga ata ttg cct gac atg acc cca agc acc gag       335
Val Met Gly Met Ile Gly Ile Leu Pro Asp Met Thr Pro Ser Thr Glu
                100                 105                 110

atg tca ttg aga gga gtg aga gtc agc aaa atg gga gtg gat gag tac       383
Met Ser Leu Arg Gly Val Arg Val Ser Lys Met Gly Val Asp Glu Tyr
            115                 120                 125

tcc agc act gag aga gtg gtg gtg agc att gac cgt ttt tta aga gtt       431
Ser Ser Thr Glu Arg Val Val Val Ser Ile Asp Arg Phe Leu Arg Val
        130                 135                 140

cgg gat caa agg gga aac ata cta ctg tcc cct gaa gag gtc agt gaa       479
Arg Asp Gln Arg Gly Asn Ile Leu Leu Ser Pro Glu Glu Val Ser Glu
    145                 150                 155

aca caa gga acg gaa aag ctg aca ata att tat tca tca tca atg atg       527
Thr Gln Gly Thr Glu Lys Leu Thr Ile Ile Tyr Ser Ser Ser Met Met
160                 165                 170                 175

tgg gag att aat ggt ccc gaa tca gtg ttg gtc aat act tat caa tgg       575
Trp Glu Ile Asn Gly Pro Glu Ser Val Leu Val Asn Thr Tyr Gln Trp
                180                 185                 190

atc atc agg aac tgg gaa att gtg aaa att caa tgg tca cag gat ccc       623
Ile Ile Arg Asn Trp Glu Ile Val Lys Ile Gln Trp Ser Gln Asp Pro
            195                 200                 205

aca atg tta tac aat aag ata gaa ttt gag cca ttc cag tcc ctg gtc       671
Thr Met Leu Tyr Asn Lys Ile Glu Phe Glu Pro Phe Gln Ser Leu Val
        210                 215                 220

cct agg gcc acc aga agc caa tac agc ggt ttc gta aga acc ctg ttt       719
```

-continued

```
Pro Arg Ala Thr Arg Ser Gln Tyr Ser Gly Phe Val Arg Thr Leu Phe
    225                 230                 235

cag caa atg cga gat gta ctt gga aca ttt gat act gct caa ata ata      767
Gln Gln Met Arg Asp Val Leu Gly Thr Phe Asp Thr Ala Gln Ile Ile
240                 245                 250                 255

aaa ctc ctc cct ttt gcc gct gct cct ccg gaa cag agt agg atg cag      815
Lys Leu Leu Pro Phe Ala Ala Ala Pro Pro Glu Gln Ser Arg Met Gln
                260                 265                 270

ttc tct tct ttg act gtt aat gta aga gga tcg gga atg agg ata ctt      863
Phe Ser Ser Leu Thr Val Asn Val Arg Gly Ser Gly Met Arg Ile Leu
            275                 280                 285

gta aga ggc aat tcc cca gtg ttc aac tac aat aaa gcc act aag agg      911
Val Arg Gly Asn Ser Pro Val Phe Asn Tyr Asn Lys Ala Thr Lys Arg
        290                 295                 300

ctc aca gtc ctc gga aag gat gca ggt gcg ctt act gaa gac cca gat      959
Leu Thr Val Leu Gly Lys Asp Ala Gly Ala Leu Thr Glu Asp Pro Asp
    305                 310                 315

gaa ggt acg gct gga gta gaa tct gct gtt cta aga ggg ttt ctc att     1007
Glu Gly Thr Ala Gly Val Glu Ser Ala Val Leu Arg Gly Phe Leu Ile
320                 325                 330                 335

tta ggt aaa gaa aac aag aga tat ggc cca gca cta agc atc aat gaa     1055
Leu Gly Lys Glu Asn Lys Arg Tyr Gly Pro Ala Leu Ser Ile Asn Glu
                340                 345                 350

ctg agc aaa ctt gca aaa ggg gag aaa gct aat gtg cta att ggg caa     1103
Leu Ser Lys Leu Ala Lys Gly Glu Lys Ala Asn Val Leu Ile Gly Gln
            355                 360                 365

ggg gac gtg gtg ttg gta atg aaa cgg aaa cgt gac tct agc ata ctt     1151
Gly Asp Val Val Leu Val Met Lys Arg Lys Arg Asp Ser Ser Ile Leu
        370                 375                 380

act gac agc cag aca gcg acc aaa agg att cgg atg gcc atc aat         1196
Thr Asp Ser Gln Thr Ala Thr Lys Arg Ile Arg Met Ala Ile Asn
    385                 390                 395

tagtgttgaa ttgtttaaaa acgaccttgt ttctact                            1233


<210> SEQ ID NO 14
<211> LENGTH: 398
<212> TYPE: PRT
<213> ORGANISM: Equine influenza virus H3N8

<400> SEQUENCE: 14

Glu Phe Thr Met Val Gly Arg Arg Ala Thr Ala Ile Leu Arg Lys Ala
1               5                   10                  15

Thr Arg Arg Leu Ile Gln Leu Ile Val Ser Gly Arg Asp Glu Gln Ser
            20                  25                  30

Ile Ala Glu Ala Ile Ile Val Ala Met Val Phe Ser Gln Glu Asp Cys
        35                  40                  45

Met Ile Lys Ala Val Arg Gly Asp Leu Asn Phe Val Asn Arg Ala Asn
    50                  55                  60

Gln Arg Leu Asn Pro Met His Gln Leu Leu Arg His Phe Gln Lys Asp
65                  70                  75                  80

Ala Lys Val Leu Phe Gln Asn Trp Gly Ile Glu Pro Ile Asp Asn Val
                85                  90                  95

Met Gly Met Ile Gly Ile Leu Pro Asp Met Thr Pro Ser Thr Glu Met
            100                 105                 110

Ser Leu Arg Gly Val Arg Val Ser Lys Met Gly Val Asp Glu Tyr Ser
        115                 120                 125

Ser Thr Glu Arg Val Val Val Ser Ile Asp Arg Phe Leu Arg Val Arg
    130                 135                 140
```

-continued

```
Asp Gln Arg Gly Asn Ile Leu Leu Ser Pro Glu Glu Val Ser Glu Thr
145                 150                 155                 160

Gln Gly Thr Glu Lys Leu Thr Ile Ile Tyr Ser Ser Ser Met Met Trp
                165                 170                 175

Glu Ile Asn Gly Pro Glu Ser Val Leu Val Asn Thr Tyr Gln Trp Ile
            180                 185                 190

Ile Arg Asn Trp Glu Ile Val Lys Ile Gln Trp Ser Gln Asp Pro Thr
        195                 200                 205

Met Leu Tyr Asn Lys Ile Glu Phe Glu Pro Phe Gln Ser Leu Val Pro
    210                 215                 220

Arg Ala Thr Arg Ser Gln Tyr Ser Gly Phe Val Arg Thr Leu Phe Gln
225                 230                 235                 240

Gln Met Arg Asp Val Leu Gly Thr Phe Asp Thr Ala Gln Ile Ile Lys
                245                 250                 255

Leu Leu Pro Phe Ala Ala Ala Pro Pro Glu Gln Ser Arg Met Gln Phe
            260                 265                 270

Ser Ser Leu Thr Val Asn Val Arg Gly Ser Gly Met Arg Ile Leu Val
        275                 280                 285

Arg Gly Asn Ser Pro Val Phe Asn Tyr Asn Lys Ala Thr Lys Arg Leu
    290                 295                 300

Thr Val Leu Gly Lys Asp Ala Gly Ala Leu Thr Glu Asp Pro Asp Glu
305                 310                 315                 320

Gly Thr Ala Gly Val Glu Ser Ala Val Leu Arg Gly Phe Leu Ile Leu
                325                 330                 335

Gly Lys Glu Asn Lys Arg Tyr Gly Pro Ala Leu Ser Ile Asn Glu Leu
            340                 345                 350

Ser Lys Leu Ala Lys Gly Glu Lys Ala Asn Val Leu Ile Gly Gln Gly
        355                 360                 365

Asp Val Val Leu Val Met Lys Arg Lys Arg Asp Ser Ser Ile Leu Thr
    370                 375                 380

Asp Ser Gln Thr Ala Thr Lys Arg Ile Arg Met Ala Ile Asn
385                 390                 395
```

<210> SEQ ID NO 15
<211> LENGTH: 19
<212> TYPE: DNA
<213> ORGANISM: Artificial
<220> FEATURE:
<223> OTHER INFORMATION: Synthetic Primer

<400> SEQUENCE: 15
agccgtacct tcatctggg 19

<210> SEQ ID NO 16
<211> LENGTH: 19
<212> TYPE: DNA
<213> ORGANISM: Artificial
<220> FEATURE:
<223> OTHER INFORMATION: Synthetic Primer

<400> SEQUENCE: 16
agcactgaga gagtggtgg 19

<210> SEQ ID NO 17
<211> LENGTH: 19
<212> TYPE: DNA
<213> ORGANISM: Artificial
<220> FEATURE:

-continued

<223> OTHER INFORMATION: Synthetic Primer

<400> SEQUENCE: 17
gtaagaggca attccccag 19

<210> SEQ ID NO 18
<211> LENGTH: 18
<212> TYPE: DNA
<213> ORGANISM: Artificial
<220> FEATURE:
<223> OTHER INFORMATION: Synthetic Primer

<400> SEQUENCE: 18
cagcttttcc gttccttg 18

<210> SEQ ID NO 19
<211> LENGTH: 1194
<212> TYPE: DNA
<213> ORGANISM: Equine influenza virus H3N8

<400> SEQUENCE: 19
gaattcacaa tggtcggaag aagagcaaca gccattctca gaaaggcaac cagaagattg 60
attcaattga tagtaagtgg gagagatgaa caatcaattg ctgaagcaat aattgtagcc 120
atggtgtttt cgcaagaaga ttgcatgata aaagcagttc gaggcgattt gaacttcgtt 180
aatagagcaa atcagcgctt gaaccccatg catcaactct tgaggcattt ccaaaaagat 240
gcaaaagtgc ttttccagaa ttgggggatt gaacccatcg acaatgtgat gggaatgatt 300
ggaatattgc ctgacatgac cccaagcacc gagatgtcat tgagaggagt gagagtcagc 360
aaaatgggag tggatgagta ctccagcact gagagagtgg tggtgagcat tgaccgtttt 420
ttaagagttc gggatcaaag gggaaacata ctactgtccc ctgaagaggt cagtgaaaca 480
caaggaacgg aaaagctgac aataatttat tcatcatcaa tgatgtggga gattaatggt 540
cccgaatcag tgttggtcaa tacttatcaa tggatcatca ggaactggga aattgtgaaa 600
attcaatggt cacaggatcc cacaatgtta tacaataaga tagaatttga gccattccag 660
tccctggtcc ctagggccac cagaagccaa tacagcggtt tcgtaagaac cctgtttcag 720
caaatgcgag atgtacttgg aacatttgat actgctcaaa taataaaact cctccctttt 780
gccgctgctc ctccggaaca gagtaggatg cagttctctt ctttgactgt taatgtaaga 840
ggatcgggaa tgaggatact tgtaagaggc aattccccag tgttcaacta caataaagcc 900
actaagaggc tcacagtcct cggaaaggat gcaggtgcgc ttactgaaga cccagatgaa 960
ggtacggctg gagtagaatc tgctgttcta agagggtttc tcattttagg taaagaaaac 1020
aagagatatg gcccagcact aagcatcaat gaactgagca aacttgcaaa aggggagaaa 1080
gctaatgtgc taattgggca aggggacgtg gtgttggtaa tgaaacggaa acgtgactct 1140
agcatactta ctgacagcca gacagcgacc aaaaggattc ggatggccat caat 1194

<210> SEQ ID NO 20
<211> LENGTH: 1232
<212> TYPE: DNA
<213> ORGANISM: Equine influenza virus H3N8

<400> SEQUENCE: 20
agaattcaca atggtcggaa gaagagcaac agccattctc agaaaggcaa ccagaagatt 60
gattcaattg atagtaagtg ggagagatga acaatcaatt gctgaagcaa taattgtagc 120
catggtgttt tcgcaagaag attgcatgat aaaagcagtt cgaggcgatt tgaacttcgt 180

-continued

```
taatagagca aatcagcgct tgaaccccat gcatcaactc ttgaggcatt tccaaaaaga    240

tgcaaaagtg cttttccaga attgggggat tgaacccatc gacaatgtga tgggaatgat    300

tggaatattg cctgacatga ccccaagcac cgagatgtca ttgagaggag tgagagtcag    360

caaaatggga gtggatgagt actccagcac tgagagagtg gtggtgagca ttgaccgttt    420

tttaagagtt cgggatcaaa ggggaaacat actactgtcc cctgaagagg tcagtgaaac    480

acaaggaacg gaaaagctga caataattta ttcatcatca atgatgtggg agattaatgg    540

tcccgaatca gtgttggtca atacttatca atggatcatc aggaactggg aaattgtgaa    600

aattcaatgg tcacaggatc ccacaatgtt atacaataag atagaatttg agccattcca    660

gtccctggtc cctagggcca ccagaagcca atacagcggt ttcgtaagaa ccctgtttca    720

gcaaatgcga gatgtacttg gaacatttga tactgctcaa ataataaaac tcctcccttt    780

tgccgctgct cctccggaac agagtaggat gcagttctct tctttgactg ttaatgtaag    840

aggatcggga atgaggatac ttgtaagagg caattcccca gtgttcaact acaataaagc    900

cactaagagg ctcacagtcc tcggaaagga tgcaggtgcg cttactgaag acccagatga    960

aggtacggct ggagtagaat ctgctgttct aagagggttt ctcattttag gtaaagaaaa   1020

caagagatat ggcccagcac taagcatcaa tgaactgagc aaacttgcaa aaggggagaa   1080

agctaatgtg ctaattgggc aaggggacgt ggtgttggta atgaaacgga aacgtgactc   1140

tagcatactt actgacagcc agacagcgac caaaaggatt cggatggcca tcaattagtg   1200

ttgaattgtt taaaaacgac cttgtttcta ct                                 1232


<210> SEQ ID NO 21
<211> LENGTH: 1232
<212> TYPE: DNA
<213> ORGANISM: Equine influenza virus H3N8
<220> FEATURE:
<221> NAME/KEY: CDS
<222> LOCATION: (2)..(1195)

<400> SEQUENCE: 21

a gaa ttc aca atg gtc gga aga aga gca aca gcc att ctc aga aag gca      49
  Glu Phe Thr Met Val Gly Arg Arg Ala Thr Ala Ile Leu Arg Lys Ala
  1               5                   10                  15

acc aga aga ttg att caa ttg ata gta agt ggg aga gat gaa caa tca       97
Thr Arg Arg Leu Ile Gln Leu Ile Val Ser Gly Arg Asp Glu Gln Ser
            20                  25                  30

att gct gaa gca ata att gta gcc atg gtg ttt tcg caa gaa gat tgc      145
Ile Ala Glu Ala Ile Ile Val Ala Met Val Phe Ser Gln Glu Asp Cys
        35                  40                  45

atg ata caa gca gtt cga ggc gat ttg aac ttc gtt aat aga gca aat      193
Met Ile Gln Ala Val Arg Gly Asp Leu Asn Phe Val Asn Arg Ala Asn
    50                  55                  60

cag cgc ttg aac ccc atg cat caa ctc ttg agg cat ttc caa aaa gat      241
Gln Arg Leu Asn Pro Met His Gln Leu Leu Arg His Phe Gln Lys Asp
65                  70                  75                  80

gca aaa gtg ctt ttc cag aat tgg ggg att gaa ccc atc gac aat gtg      289
Ala Lys Val Leu Phe Gln Asn Trp Gly Ile Glu Pro Ile Asp Asn Val
                85                  90                  95

atg gga atg att gga ata ttg cct gac atg acc cca agc acc gag atg      337
Met Gly Met Ile Gly Ile Leu Pro Asp Met Thr Pro Ser Thr Glu Met
            100                 105                 110

tca ttg aga gga gtg aga gtc agc aaa atg gga gtg gat gag tac tcc      385
Ser Leu Arg Gly Val Arg Val Ser Lys Met Gly Val Asp Glu Tyr Ser
        115                 120                 125
```

-continued

```
agc act gag aga gtg gtg gtg agc att gac cgt ttt tta aga gtt cgg      433
Ser Thr Glu Arg Val Val Val Ser Ile Asp Arg Phe Leu Arg Val Arg
    130                 135                 140

gat caa agg gga aac ata cta ctg tcc cct gaa gag gtc agt gaa aca      481
Asp Gln Arg Gly Asn Ile Leu Leu Ser Pro Glu Glu Val Ser Glu Thr
145                 150                 155                 160

caa gga acg gaa aag ctg aca ata att tat tca tca tca atg atg tgg      529
Gln Gly Thr Glu Lys Leu Thr Ile Ile Tyr Ser Ser Ser Met Met Trp
                165                 170                 175

gag att aat ggt ccc gaa tca gtg ttg gtc aat act tat caa tgg atc      577
Glu Ile Asn Gly Pro Glu Ser Val Leu Val Asn Thr Tyr Gln Trp Ile
            180                 185                 190

atc agg aac tgg gaa att gtg aaa att caa tgg tca cag gat ccc aca      625
Ile Arg Asn Trp Glu Ile Val Lys Ile Gln Trp Ser Gln Asp Pro Thr
        195                 200                 205

atg tta tac aat aag ata gaa ttt gag cca ttc cag tcc ctg gtc cct      673
Met Leu Tyr Asn Lys Ile Glu Phe Glu Pro Phe Gln Ser Leu Val Pro
    210                 215                 220

agg gcc acc aga agc caa tac agc ggt ttc gta aga acc ctg ttt cag      721
Arg Ala Thr Arg Ser Gln Tyr Ser Gly Phe Val Arg Thr Leu Phe Gln
225                 230                 235                 240

caa atg cga gat gta ctt gga aca ttt gat act gct caa ata ata aaa      769
Gln Met Arg Asp Val Leu Gly Thr Phe Asp Thr Ala Gln Ile Ile Lys
                245                 250                 255

ctc ctc cct ttt gcc gct gct cct ccg gaa cag agt agg atg cag ttc      817
Leu Leu Pro Phe Ala Ala Ala Pro Pro Glu Gln Ser Arg Met Gln Phe
            260                 265                 270

tct tct ttg act gtt aat gta aga gga tcg gga atg agg ata ctt gta      865
Ser Ser Leu Thr Val Asn Val Arg Gly Ser Gly Met Arg Ile Leu Val
        275                 280                 285

aga ggc aat tcc cca gtg ttc aac tac aat aaa gcc act aag agg ctc      913
Arg Gly Asn Ser Pro Val Phe Asn Tyr Asn Lys Ala Thr Lys Arg Leu
    290                 295                 300

aca gtc ctc gga aaa gat gca ggt gcg ctt act gaa gac cca gat gaa      961
Thr Val Leu Gly Lys Asp Ala Gly Ala Leu Thr Glu Asp Pro Asp Glu
305                 310                 315                 320

ggt acg gct gga gta gaa tct gct gtt cta aga ggg ttt ctc att tta     1009
Gly Thr Ala Gly Val Glu Ser Ala Val Leu Arg Gly Phe Leu Ile Leu
                325                 330                 335

ggt aaa gaa aac aag aga tat ggc cca gca cta agc atc aat gaa ctg     1057
Gly Lys Glu Asn Lys Arg Tyr Gly Pro Ala Leu Ser Ile Asn Glu Leu
            340                 345                 350

agc aaa ctt gca aaa ggg gag aaa gct aat gtg cta att ggg caa ggg     1105
Ser Lys Leu Ala Lys Gly Glu Lys Ala Asn Val Leu Ile Gly Gln Gly
        355                 360                 365

gac gtg gtg ttg gta atg aaa cgg aaa cgt gac tct agc ata ctt act     1153
Asp Val Val Leu Val Met Lys Arg Lys Arg Asp Ser Ser Ile Leu Thr
    370                 375                 380

gac agc cag aca gcg acc aaa agg att cgg atg gcc atc aat             1195
Asp Ser Gln Thr Ala Thr Lys Arg Ile Arg Met Ala Ile Asn
385                 390                 395

tagtgttgaa ttgtttaaaa acgaccttgt ttctact                            1232


<210> SEQ ID NO 22
<211> LENGTH: 398
<212> TYPE: PRT
<213> ORGANISM: Equine influenza virus H3N8

<400> SEQUENCE: 22
```

-continued

```
Glu Phe Thr Met Val Gly Arg Arg Ala Thr Ala Ile Leu Arg Lys Ala
1               5                   10                  15

Thr Arg Arg Leu Ile Gln Leu Ile Val Ser Gly Arg Asp Glu Gln Ser
            20                  25                  30

Ile Ala Glu Ala Ile Ile Val Ala Met Val Phe Ser Gln Glu Asp Cys
        35                  40                  45

Met Ile Gln Ala Val Arg Gly Asp Leu Asn Phe Val Asn Arg Ala Asn
    50                  55                  60

Gln Arg Leu Asn Pro Met His Gln Leu Leu Arg His Phe Gln Lys Asp
65                  70                  75                  80

Ala Lys Val Leu Phe Gln Asn Trp Gly Ile Glu Pro Ile Asp Asn Val
                85                  90                  95

Met Gly Met Ile Gly Ile Leu Pro Asp Met Thr Pro Ser Thr Glu Met
            100                 105                 110

Ser Leu Arg Gly Val Arg Val Ser Lys Met Gly Val Asp Glu Tyr Ser
        115                 120                 125

Ser Thr Glu Arg Val Val Val Ser Ile Asp Arg Phe Leu Arg Val Arg
    130                 135                 140

Asp Gln Arg Gly Asn Ile Leu Leu Ser Pro Glu Glu Val Ser Glu Thr
145                 150                 155                 160

Gln Gly Thr Glu Lys Leu Thr Ile Ile Tyr Ser Ser Ser Met Met Trp
                165                 170                 175

Glu Ile Asn Gly Pro Glu Ser Val Leu Val Asn Thr Tyr Gln Trp Ile
            180                 185                 190

Ile Arg Asn Trp Glu Ile Val Lys Ile Gln Trp Ser Gln Asp Pro Thr
        195                 200                 205

Met Leu Tyr Asn Lys Ile Glu Phe Glu Pro Phe Gln Ser Leu Val Pro
    210                 215                 220

Arg Ala Thr Arg Ser Gln Tyr Ser Gly Phe Val Arg Thr Leu Phe Gln
225                 230                 235                 240

Gln Met Arg Asp Val Leu Gly Thr Phe Asp Thr Ala Gln Ile Ile Lys
                245                 250                 255

Leu Leu Pro Phe Ala Ala Ala Pro Pro Glu Gln Ser Arg Met Gln Phe
            260                 265                 270

Ser Ser Leu Thr Val Asn Val Arg Gly Ser Gly Met Arg Ile Leu Val
        275                 280                 285

Arg Gly Asn Ser Pro Val Phe Asn Tyr Asn Lys Ala Thr Lys Arg Leu
    290                 295                 300

Thr Val Leu Gly Lys Asp Ala Gly Ala Leu Thr Glu Asp Pro Asp Glu
305                 310                 315                 320

Gly Thr Ala Gly Val Glu Ser Ala Val Leu Arg Gly Phe Leu Ile Leu
                325                 330                 335

Gly Lys Glu Asn Lys Arg Tyr Gly Pro Ala Leu Ser Ile Asn Glu Leu
            340                 345                 350

Ser Lys Leu Ala Lys Gly Glu Lys Ala Asn Val Leu Ile Gly Gln Gly
        355                 360                 365

Asp Val Val Leu Val Met Lys Arg Lys Arg Asp Ser Ser Ile Leu Thr
    370                 375                 380

Asp Ser Gln Thr Ala Thr Lys Arg Ile Arg Met Ala Ile Asn
385                 390                 395
```

<210> SEQ ID NO 23
<211> LENGTH: 1194
<212> TYPE: DNA

-continued

<213> ORGANISM: Equine influenza virus H3N8

<400> SEQUENCE: 23

```
gaattcacaa tggtcggaag aagagcaaca gccattctca gaaaggcaac cagaagattg     60

attcaattga tagtaagtgg gagagatgaa caatcaattg ctgaagcaat aattgtagcc    120

atggtgtttt cgcaagaaga ttgcatgata caagcagttc gaggcgattt gaacttcgtt    180

aatagagcaa atcagcgctt gaaccccatg catcaactct tgaggcattt ccaaaaagat    240

gcaaaagtgc ttttccagaa ttgggggatt gaacccatcg acaatgtgat gggaatgatt    300

ggaatattgc ctgacatgac cccaagcacc gagatgtcat tgagaggagt gagagtcagc    360

aaaatgggag tggatgagta ctccagcact gagagagtgg tggtgagcat tgaccgtttt    420

ttaagagttc gggatcaaag gggaaacata ctactgtccc ctgaagaggt cagtgaaaca    480

caaggaacgg aaaagctgac aataatttat tcatcatcaa tgatgtggga gattaatggt    540

cccgaatcag tgttggtcaa tacttatcaa tggatcatca ggaactggga aattgtgaaa    600

attcaatggt cacaggatcc cacaatgtta tacaataaga tagaatttga gccattccag    660

tccctggtcc ctagggccac cagaagccaa tacagcggtt tcgtaagaac cctgtttcag    720

caaatgcgag atgtacttgg aacatttgat actgctcaaa taataaaact cctccctttt    780

gccgctgctc ctccggaaca gagtaggatg cagttctctt ctttgactgt taatgtaaga    840

ggatcgggaa tgaggatact tgtaagaggc aattccccag tgttcaacta caataaagcc    900

actaagaggc tcacagtcct cggaaaagat gcaggtgcgc ttactgaaga cccagatgaa    960

ggtacggctg gagtagaatc tgctgttcta agagggtttc tcattttagg taaagaaaac   1020

aagagatatg gcccagcact aagcatcaat gaactgagca aacttgcaaa aggggagaaa   1080

gctaatgtgc taattgggca aggggacgtg gtgttggtaa tgaaacggaa acgtgactct   1140

agcatactta ctgacagcca gacagcgacc aaaaggattc ggatggccat caat         1194
```

<210> SEQ ID NO 24
<211> LENGTH: 2341
<212> TYPE: DNA
<213> ORGANISM: Equine influenza virus H3N8
<220> FEATURE:
<221> NAME/KEY: CDS
<222> LOCATION: (28)..(2304)

<400> SEQUENCE: 24

```
agcaaaagca ggtcaaatat attcaat atg gag aga ata aaa gaa ctg aga gat      54
                              Met Glu Arg Ile Lys Glu Leu Arg Asp
                              1               5

cta atg tca caa tcc cgc acc cgc gag ata cta aca aaa act act gtg      102
Leu Met Ser Gln Ser Arg Thr Arg Glu Ile Leu Thr Lys Thr Thr Val
10                  15                  20                  25

gac cac atg gcc ata atc aag aaa tac aca tca gga aga caa gag aag      150
Asp His Met Ala Ile Ile Lys Lys Tyr Thr Ser Gly Arg Gln Glu Lys
                30                  35                  40

aac ccc gca ctt agg atg aag tgg atg atg gca atg aaa tac cca att      198
Asn Pro Ala Leu Arg Met Lys Trp Met Met Ala Met Lys Tyr Pro Ile
            45                  50                  55

aca gca gat aag agg ata atg gaa atg att cct gag aga aat gaa cag      246
Thr Ala Asp Lys Arg Ile Met Glu Met Ile Pro Glu Arg Asn Glu Gln
        60                  65                  70

ggg caa acc ctt tgg agc aaa acg aac gat gct ggc tca gac cgc gta      294
Gly Gln Thr Leu Trp Ser Lys Thr Asn Asp Ala Gly Ser Asp Arg Val
    75                  80                  85
```

-continued

```
atg gta tca cct ctg gca gtg aca tgg tgg aat agg aat gga cca aca      342
Met Val Ser Pro Leu Ala Val Thr Trp Trp Asn Arg Asn Gly Pro Thr
90                  95                  100                 105

acg agc aca att cat tat cca aaa gtc tac aaa act tat ttt gaa aaa      390
Thr Ser Thr Ile His Tyr Pro Lys Val Tyr Lys Thr Tyr Phe Glu Lys
                110                 115                 120

gtt gaa aga tta aaa cac gga acc ttt ggc ccc gtt cat ttt agg aat      438
Val Glu Arg Leu Lys His Gly Thr Phe Gly Pro Val His Phe Arg Asn
            125                 130                 135

caa gtc aag ata aga cgg aga gtt gat gta aac cct ggt cac gcg gac      486
Gln Val Lys Ile Arg Arg Arg Val Asp Val Asn Pro Gly His Ala Asp
        140                 145                 150

ctc agt gcc aaa gaa gca caa gat gtg atc atg gaa gtt gtt ttc cca      534
Leu Ser Ala Lys Glu Ala Gln Asp Val Ile Met Glu Val Val Phe Pro
    155                 160                 165

aat gaa gtg gga gcc aga att cta aca tcg gaa tca caa cta aca ata      582
Asn Glu Val Gly Ala Arg Ile Leu Thr Ser Glu Ser Gln Leu Thr Ile
170                 175                 180                 185

acc aaa gag aaa aaa gaa gaa ctt cag gac tgc aaa att gcc ccc ttg      630
Thr Lys Glu Lys Lys Glu Glu Leu Gln Asp Cys Lys Ile Ala Pro Leu
                190                 195                 200

atg gta gca tac atg cta gaa aga gag ttg gtc cga aaa aca aga ttc      678
Met Val Ala Tyr Met Leu Glu Arg Glu Leu Val Arg Lys Thr Arg Phe
            205                 210                 215

ctc cca gtg gct ggc gga aca agc agt gta tac att gaa gtg ttg cat      726
Leu Pro Val Ala Gly Gly Thr Ser Ser Val Tyr Ile Glu Val Leu His
        220                 225                 230

ctg act cag gga aca tgc tgg gaa caa atg tac acc cca gga gga gaa      774
Leu Thr Gln Gly Thr Cys Trp Glu Gln Met Tyr Thr Pro Gly Gly Glu
    235                 240                 245

gtt aga aac gat gac att gat caa agt tta att att gct gcc cgg aac      822
Val Arg Asn Asp Asp Ile Asp Gln Ser Leu Ile Ile Ala Ala Arg Asn
250                 255                 260                 265

ata gtg aga aga gcg aca gta tca gca gat cca cta gca tcc ctg ctg      870
Ile Val Arg Arg Ala Thr Val Ser Ala Asp Pro Leu Ala Ser Leu Leu
                270                 275                 280

gaa atg tgc cac agt aca cag att ggt gga ata agg atg gta gac atc      918
Glu Met Cys His Ser Thr Gln Ile Gly Gly Ile Arg Met Val Asp Ile
            285                 290                 295

ctt aag cag aat cca aca gag gaa caa gct gtg gat ata tgc aaa gca      966
Leu Lys Gln Asn Pro Thr Glu Glu Gln Ala Val Asp Ile Cys Lys Ala
        300                 305                 310

gca atg ggg tta aga att agc tca tca ttc agc ttt ggt gga ttc acc     1014
Ala Met Gly Leu Arg Ile Ser Ser Ser Phe Ser Phe Gly Gly Phe Thr
    315                 320                 325

ttt aag aga aca agt gga tca tca gtc aag aga gaa gaa gaa atg ctt     1062
Phe Lys Arg Thr Ser Gly Ser Ser Val Lys Arg Glu Glu Glu Met Leu
330                 335                 340                 345

acg ggc aac ctt caa aca ttg aaa ata aga gtg cat gaa ggc tat gaa     1110
Thr Gly Asn Leu Gln Thr Leu Lys Ile Arg Val His Glu Gly Tyr Glu
                350                 355                 360

gaa ttc aca atg gtc gga aga aga gca aca gcc att ctc aga aag gca     1158
Glu Phe Thr Met Val Gly Arg Arg Ala Thr Ala Ile Leu Arg Lys Ala
            365                 370                 375

acc aga aga ttg att caa ttg ata gta agt ggg aga gat gaa caa tca     1206
Thr Arg Arg Leu Ile Gln Leu Ile Val Ser Gly Arg Asp Glu Gln Ser
        380                 385                 390

att gct gaa gca ata att gta gcc atg gtg ttt tcg caa gaa gat tgc     1254
Ile Ala Glu Ala Ile Ile Val Ala Met Val Phe Ser Gln Glu Asp Cys
    395                 400                 405
```

-continued

```
atg ata aaa gca gtt cga ggc gat ttg aac ttc gtt aat aga gca aat      1302
Met Ile Lys Ala Val Arg Gly Asp Leu Asn Phe Val Asn Arg Ala Asn
410                 415                 420                 425

cag cgc ttg aac ccc atg cat caa ctc ttg agg cat ttc caa aaa gat      1350
Gln Arg Leu Asn Pro Met His Gln Leu Leu Arg His Phe Gln Lys Asp
                430                 435                 440

gca aaa gtg ctt ttc cag aat tgg ggg att gaa ccc atc gac aat gtg      1398
Ala Lys Val Leu Phe Gln Asn Trp Gly Ile Glu Pro Ile Asp Asn Val
            445                 450                 455

atg gga atg att gga ata ttg cct gac atg acc cca agc acc gag atg      1446
Met Gly Met Ile Gly Ile Leu Pro Asp Met Thr Pro Ser Thr Glu Met
        460                 465                 470

tca ttg aga gga gtg aga gtc agc aaa atg gga gtg gat gag tac tcc      1494
Ser Leu Arg Gly Val Arg Val Ser Lys Met Gly Val Asp Glu Tyr Ser
    475                 480                 485

agc act gag aga gtg gtg gtg agc att gac cgt ttt tta aga gtt cgg      1542
Ser Thr Glu Arg Val Val Val Ser Ile Asp Arg Phe Leu Arg Val Arg
490                 495                 500                 505

gat caa agg gga aac ata cta ctg tcc cct gaa gag gtc agt gaa aca      1590
Asp Gln Arg Gly Asn Ile Leu Leu Ser Pro Glu Glu Val Ser Glu Thr
                510                 515                 520

caa gga acg gaa aag ctg aca ata att tat tca tca tca atg atg tgg      1638
Gln Gly Thr Glu Lys Leu Thr Ile Ile Tyr Ser Ser Ser Met Met Trp
            525                 530                 535

gag att aat ggt ccc gaa tca gtg ttg gtc aat act tat caa tgg atc      1686
Glu Ile Asn Gly Pro Glu Ser Val Leu Val Asn Thr Tyr Gln Trp Ile
        540                 545                 550

atc agg aac tgg gaa att gtg aaa att caa tgg tca cag gat ccc aca      1734
Ile Arg Asn Trp Glu Ile Val Lys Ile Gln Trp Ser Gln Asp Pro Thr
    555                 560                 565

atg tta tac aat aag ata gaa ttt gag cca ttc cag tcc ctg gtc cct      1782
Met Leu Tyr Asn Lys Ile Glu Phe Glu Pro Phe Gln Ser Leu Val Pro
570                 575                 580                 585

agg gcc acc aga agc caa tac agc ggt ttc gta aga acc ctg ttt cag      1830
Arg Ala Thr Arg Ser Gln Tyr Ser Gly Phe Val Arg Thr Leu Phe Gln
                590                 595                 600

caa atg cga gat gta ctt gga aca ttt gat act gct caa ata ata aaa      1878
Gln Met Arg Asp Val Leu Gly Thr Phe Asp Thr Ala Gln Ile Ile Lys
            605                 610                 615

ctc ctc cct ttt gcc gct gct cct ccg gaa cag agt agg atg cag ttc      1926
Leu Leu Pro Phe Ala Ala Ala Pro Pro Glu Gln Ser Arg Met Gln Phe
        620                 625                 630

tct tct ttg act gtt aat gta aga gga tcg gga atg agg ata ctt gta      1974
Ser Ser Leu Thr Val Asn Val Arg Gly Ser Gly Met Arg Ile Leu Val
    635                 640                 645

aga ggc aat tcc cca gtg ttc aac tac aat aaa gcc act aag agg ctc      2022
Arg Gly Asn Ser Pro Val Phe Asn Tyr Asn Lys Ala Thr Lys Arg Leu
650                 655                 660                 665

aca gtc ctc gga aag gat gca ggt gcg ctt act gaa gac cca gat gaa      2070
Thr Val Leu Gly Lys Asp Ala Gly Ala Leu Thr Glu Asp Pro Asp Glu
                670                 675                 680

ggt acg gct gga gta gaa tct gct gtt cta aga ggg ttt ctc att tta      2118
Gly Thr Ala Gly Val Glu Ser Ala Val Leu Arg Gly Phe Leu Ile Leu
            685                 690                 695

ggt aaa gaa aac aag aga tat ggc cca gca cta agc atc aat gaa ctg      2166
Gly Lys Glu Asn Lys Arg Tyr Gly Pro Ala Leu Ser Ile Asn Glu Leu
        700                 705                 710

agc aaa ctt gca aaa ggg gag aaa gct aat gtg cta att ggg caa ggg      2214
Ser Lys Leu Ala Lys Gly Glu Lys Ala Asn Val Leu Ile Gly Gln Gly
```

-continued

```
    715                 720                 725

gac gtg gtg ttg gta atg aaa cgg aaa cgt gac tct agc ata ctt act     2262
Asp Val Val Leu Val Met Lys Arg Lys Arg Asp Ser Ser Ile Leu Thr
730                 735                 740                 745

gac agc cag aca gcg acc aaa agg att cgg atg gcc atc aat             2304
Asp Ser Gln Thr Ala Thr Lys Arg Ile Arg Met Ala Ile Asn
                750                 755

tagtgttgaa ttgtttaaaa acgaccttgt ttctact                            2341


<210> SEQ ID NO 25
<211> LENGTH: 759
<212> TYPE: PRT
<213> ORGANISM: Equine influenza virus H3N8

<400> SEQUENCE: 25

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320
```

-continued

```
Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Leu Arg Gly Val Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Ile Leu
            500                 505                 510

Leu Ser Pro Glu Glu Val Ser Glu Thr Gln Gly Thr Glu Lys Leu Thr
        515                 520                 525

Ile Ile Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Ile Val
545                 550                 555                 560

Lys Ile Gln Trp Ser Gln Asp Pro Thr Met Leu Tyr Asn Lys Ile Glu
                565                 570                 575

Phe Glu Pro Phe Gln Ser Leu Val Pro Arg Ala Thr Arg Ser Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asn Lys Arg Tyr
    690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Val Val Leu Val Met Lys
                725                 730                 735
```

-continued

```
Arg Lys Arg Asp Ser Ser Ile Leu Thr Asp Ser Gln Thr Ala Thr Lys
            740                 745                 750

Arg Ile Arg Met Ala Ile Asn
        755


<210> SEQ ID NO 26
<211> LENGTH: 2277
<212> TYPE: DNA
<213> ORGANISM: Equine influenza virus H3N8

<400> SEQUENCE: 26

atggagagaa taaaagaact gagagatcta atgtcacaat cccgcacccg cgagatacta     60

acaaaaacta ctgtggacca catggccata atcaagaaat acacatcagg aagacaagag    120

aagaaccccg cacttaggat gaagtggatg atggcaatga aatacccaat tacagcagat    180

aagaggataa tggaaatgat tcctgagaga aatgaacagg ggcaaaccct ttggagcaaa    240

acgaacgatg ctggctcaga ccgcgtaatg gtatcacctc tggcagtgac atggtggaat    300

aggaatggac caacaacgag cacaattcat tatccaaaag tctacaaaac ttattttgaa    360

aaagttgaaa gattaaaaca cggaaccttt ggccccgttc attttaggaa tcaagtcaag    420

ataagacgga gagttgatgt aaaccctggt cacgcggacc tcagtgccaa agaagcacaa    480

gatgtgatca tggaagttgt tttcccaaat gaagtgggag ccagaattct aacatcggaa    540

tcacaactaa caataaccaa agagaaaaaa gaagaacttc aggactgcaa aattgccccc    600

ttgatggtag catacatgct agaaagagag ttggtccgaa aaacaagatt cctcccagtg    660

gctggcggaa caagcagtgt atacattgaa gtgttgcatc tgactcaggg aacatgctgg    720

gaacaaatgt acaccccagg aggagaagtt agaaacgatg acattgatca aagtttaatt    780

attgctgccc ggaacatagt gagaagagcg acagtatcag cagatccact agcatccctg    840

ctggaaatgt gccacagtac acagattggt ggaataagga tggtagacat ccttaagcag    900

aatccaacag aggaacaagc tgtggatata tgcaaagcag caatggggtt aagaattagc    960

tcatcattca gctttggtgg attcaccttt aagagaacaa gtggatcatc agtcaagaga   1020

gaagaagaaa tgcttacggg caaccttcaa acattgaaaa taagagtgca tgaaggctat   1080

gaagaattca caatggtcgg aagaagagca acagccattc tcagaaaggc aaccagaaga   1140

ttgattcaat tgatagtaag tgggagagat gaacaatcaa ttgctgaagc aataattgta   1200

gccatggtgt tttcgcaaga agattgcatg ataaaagcag ttcgaggcga tttgaacttc   1260

gttaatagag caaatcagcg cttgaacccc atgcatcaac tcttgaggca tttccaaaaa   1320

gatgcaaaag tgcttttcca gaattggggg attgaaccca tcgacaatgt gatgggaatg   1380

attggaatat tgcctgacat gaccccaagc accgagatgt cattgagagg agtgagagtc   1440

agcaaaatgg gagtggatga gtactccagc actgagagag tggtggtgag cattgaccgt   1500

tttttaagag ttcgggatca aaggggaaac atactactgt cccctgaaga ggtcagtgaa   1560

acacaaggaa cggaaaagct gacaataatt tattcatcat caatgatgtg ggagattaat   1620

ggtcccgaat cagtgttggt caatacttat caatggatca tcaggaactg ggaaattgtg   1680

aaaattcaat ggtcacagga tcccacaatg ttatacaata agatagaatt tgagccattc   1740

cagtccctgg tccctagggc caccagaagc caatacagcg gtttcgtaag aaccctgttt   1800

cagcaaatgc gagatgtact tggaacattt gatactgctc aaataataaa actcctccct   1860

tttgccgctg ctcctccgga acagagtagg atgcagttct cttctttgac tgttaatgta   1920

agaggatcgg gaatgaggat acttgtaaga ggcaattccc cagtgttcaa ctacaataaa   1980
```

-continued

```
gccactaaga ggctcacagt cctcggaaag gatgcaggtg cgcttactga agacccagat   2040

gaaggtacgg ctggagtaga atctgctgtt ctaagagggt ttctcatttt aggtaaagaa   2100

aacaagagat atggcccagc actaagcatc aatgaactga gcaaacttgc aaaaggggag   2160

aaagctaatg tgctaattgg gcaaggggac gtggtgttgg taatgaaacg gaaacgtgac   2220

tctagcatac ttactgacag ccagacagcg accaaaagga ttcggatggc catcaat      2277


<210> SEQ ID NO 27
<211> LENGTH: 2341
<212> TYPE: DNA
<213> ORGANISM: Equine influenza virus H3N8
<220> FEATURE:
<221> NAME/KEY: CDS
<222> LOCATION: (28)..(2304)

<400> SEQUENCE: 27

agcaaaagca ggtcaaatat attcaat atg gag aga ata aaa gaa ctg aga gat      54
                              Met Glu Arg Ile Lys Glu Leu Arg Asp
                              1               5

cta atg tca caa tcc cgc acc cgc gag ata cta aca aaa act act gtg       102
Leu Met Ser Gln Ser Arg Thr Arg Glu Ile Leu Thr Lys Thr Thr Val
10                  15                  20                  25

gac cac atg gcc ata atc aag aaa tac aca tca gga aga caa gag aag       150
Asp His Met Ala Ile Ile Lys Lys Tyr Thr Ser Gly Arg Gln Glu Lys
                30                  35                  40

aac ccc gca ctt agg atg aag tgg atg atg gca atg aaa tac cca att       198
Asn Pro Ala Leu Arg Met Lys Trp Met Met Ala Met Lys Tyr Pro Ile
            45                  50                  55

aca gca gat aag agg ata atg gaa atg att cct gag aga aat gaa cag       246
Thr Ala Asp Lys Arg Ile Met Glu Met Ile Pro Glu Arg Asn Glu Gln
        60                  65                  70

ggg caa acc ctt tgg agc aaa acg aac gat gct ggc tca gac cgc gta       294
Gly Gln Thr Leu Trp Ser Lys Thr Asn Asp Ala Gly Ser Asp Arg Val
    75                  80                  85

atg gta tca cct ctg gca gtg aca tgg tgg aat agg aat gga cca aca       342
Met Val Ser Pro Leu Ala Val Thr Trp Trp Asn Arg Asn Gly Pro Thr
90                  95                  100                 105

acg agc aca att cat tat cca aaa gtc cac aaa act tat ttt gaa aaa       390
Thr Ser Thr Ile His Tyr Pro Lys Val His Lys Thr Tyr Phe Glu Lys
                110                 115                 120

gtt gaa aga tta aaa cac gga acc ttt ggc ccc gtt cat ttt agg aat       438
Val Glu Arg Leu Lys His Gly Thr Phe Gly Pro Val His Phe Arg Asn
            125                 130                 135

caa gtc aag ata aga cgg aga gtt gat gta aac cct ggt cac gcg gac       486
Gln Val Lys Ile Arg Arg Arg Val Asp Val Asn Pro Gly His Ala Asp
        140                 145                 150

ctc agt gcc aaa gaa gca caa gat gtg atc atg gaa gtt gtt ttc cca       534
Leu Ser Ala Lys Glu Ala Gln Asp Val Ile Met Glu Val Val Phe Pro
    155                 160                 165

aat gaa gtg gga gcc aga att cta aca tcg gaa tca caa cta aca ata       582
Asn Glu Val Gly Ala Arg Ile Leu Thr Ser Glu Ser Gln Leu Thr Ile
170                 175                 180                 185

acc aaa gag aaa aaa gaa gaa ctt cag gac tgc aaa att gcc ccc ttg       630
Thr Lys Glu Lys Lys Glu Glu Leu Gln Asp Cys Lys Ile Ala Pro Leu
                190                 195                 200

atg gta gca tac atg cta gaa aga gag ttg gtc cga aaa aca aga ttc       678
Met Val Ala Tyr Met Leu Glu Arg Glu Leu Val Arg Lys Thr Arg Phe
            205                 210                 215

ctc cca gtg gct ggc gga aca agc agt gta tac att gaa gtg ttg cat       726
```

-continued

```
Leu Pro Val Ala Gly Gly Thr Ser Ser Val Tyr Ile Glu Val Leu His
        220                 225                 230

ctg act cag gga aca tgc tgg gaa caa atg tac acc cca gga gga gaa      774
Leu Thr Gln Gly Thr Cys Trp Glu Gln Met Tyr Thr Pro Gly Gly Glu
    235                 240                 245

gtt aga aac gat gac att gat caa agt tta att att gct gcc cgg aac      822
Val Arg Asn Asp Asp Ile Asp Gln Ser Leu Ile Ile Ala Ala Arg Asn
250                 255                 260                 265

ata gtg aga aga gcg aca gta tca gca gat cca cta gca tcc ctg ctg      870
Ile Val Arg Arg Ala Thr Val Ser Ala Asp Pro Leu Ala Ser Leu Leu
                270                 275                 280

gaa atg tgc cac agt aca cag att ggt gga ata agg atg gta gac atc      918
Glu Met Cys His Ser Thr Gln Ile Gly Gly Ile Arg Met Val Asp Ile
            285                 290                 295

ctt aag cag aat cca aca gag gaa caa gct gtg gat ata tgc aaa gca      966
Leu Lys Gln Asn Pro Thr Glu Glu Gln Ala Val Asp Ile Cys Lys Ala
        300                 305                 310

gca atg ggg tta aga att agc tca tca ttc agc ttt ggt gga ttc acc     1014
Ala Met Gly Leu Arg Ile Ser Ser Ser Phe Ser Phe Gly Gly Phe Thr
    315                 320                 325

ttt aag aga aca agt gga tca tca gtc aag aga gaa gaa gaa atg ctt     1062
Phe Lys Arg Thr Ser Gly Ser Ser Val Lys Arg Glu Glu Glu Met Leu
330                 335                 340                 345

acg ggc aac ctt caa aca ttg aaa ata aga gtg cat gaa ggc tat gaa     1110
Thr Gly Asn Leu Gln Thr Leu Lys Ile Arg Val His Glu Gly Tyr Glu
                350                 355                 360

gaa ttc aca atg gtc gga aga aga gca aca gcc att ctc aga aag gca     1158
Glu Phe Thr Met Val Gly Arg Arg Ala Thr Ala Ile Leu Arg Lys Ala
            365                 370                 375

acc aga aga ttg att caa ttg ata gta agt ggg aga gat gaa caa tca     1206
Thr Arg Arg Leu Ile Gln Leu Ile Val Ser Gly Arg Asp Glu Gln Ser
        380                 385                 390

att gct gaa gca ata att gta gcc atg gtg ttt tcg caa gaa gat tgc     1254
Ile Ala Glu Ala Ile Ile Val Ala Met Val Phe Ser Gln Glu Asp Cys
    395                 400                 405

atg ata caa gca gtt cga ggc gat ttg aac ttc gtt aat aga gca aat     1302
Met Ile Gln Ala Val Arg Gly Asp Leu Asn Phe Val Asn Arg Ala Asn
410                 415                 420                 425

cag cgc ttg aac ccc atg cat caa ctc ttg agg cat ttc caa aaa gat     1350
Gln Arg Leu Asn Pro Met His Gln Leu Leu Arg His Phe Gln Lys Asp
                430                 435                 440

gca aaa gtg ctt ttc cag aat tgg ggg att gaa ccc atc gac aat gtg     1398
Ala Lys Val Leu Phe Gln Asn Trp Gly Ile Glu Pro Ile Asp Asn Val
            445                 450                 455

atg gga atg att gga ata ttg cct gac atg acc cca agc acc gag atg     1446
Met Gly Met Ile Gly Ile Leu Pro Asp Met Thr Pro Ser Thr Glu Met
        460                 465                 470

tca ttg aga gga gtg aga gtc agc aaa atg gga gtg gat gag tac tcc     1494
Ser Leu Arg Gly Val Arg Val Ser Lys Met Gly Val Asp Glu Tyr Ser
    475                 480                 485

agc act gag aga gtg gtg gtg agc att gac cgt ttt tta aga gtt cgg     1542
Ser Thr Glu Arg Val Val Val Ser Ile Asp Arg Phe Leu Arg Val Arg
490                 495                 500                 505

gat caa agg gga aac ata cta ctg tcc cct gaa gag gtc agt gaa aca     1590
Asp Gln Arg Gly Asn Ile Leu Leu Ser Pro Glu Glu Val Ser Glu Thr
                510                 515                 520

caa gga acg gaa aag ctg aca ata att tat tca tca tca atg atg tgg     1638
Gln Gly Thr Glu Lys Leu Thr Ile Ile Tyr Ser Ser Ser Met Met Trp
            525                 530                 535
```

-continued

```
gag att aat ggt ccc gaa tca gtg ttg gtc aat act tat caa tgg atc      1686
Glu Ile Asn Gly Pro Glu Ser Val Leu Val Asn Thr Tyr Gln Trp Ile
        540                 545                 550

atc agg aac tgg gaa att gtg aaa att caa tgg tca cag gat ccc aca      1734
Ile Arg Asn Trp Glu Ile Val Lys Ile Gln Trp Ser Gln Asp Pro Thr
    555                 560                 565

atg tta tac aat aag ata gaa ttt gag cca ttc cag tcc ctg gtc cct      1782
Met Leu Tyr Asn Lys Ile Glu Phe Glu Pro Phe Gln Ser Leu Val Pro
570                 575                 580                 585

agg gcc acc aga agc caa tac agc ggt ttc gta aga acc ctg ttt cag      1830
Arg Ala Thr Arg Ser Gln Tyr Ser Gly Phe Val Arg Thr Leu Phe Gln
                590                 595                 600

caa atg cga gat gta ctt gga aca ttt gat act gct caa ata ata aaa      1878
Gln Met Arg Asp Val Leu Gly Thr Phe Asp Thr Ala Gln Ile Ile Lys
            605                 610                 615

ctc ctc cct ttt gcc gct gct cct ccg gaa cag agt agg atg cag ttc      1926
Leu Leu Pro Phe Ala Ala Ala Pro Pro Glu Gln Ser Arg Met Gln Phe
        620                 625                 630

tct tct ttg act gtt aat gta aga gga tcg gga atg agg ata ctt gta      1974
Ser Ser Leu Thr Val Asn Val Arg Gly Ser Gly Met Arg Ile Leu Val
    635                 640                 645

aga ggc aat tcc cca gtg ttc aac tac aat aaa gcc act aag agg ctc      2022
Arg Gly Asn Ser Pro Val Phe Asn Tyr Asn Lys Ala Thr Lys Arg Leu
650                 655                 660                 665

aca gtc ctc gga aaa gat gca ggt gcg ctt act gaa gac cca gat gaa      2070
Thr Val Leu Gly Lys Asp Ala Gly Ala Leu Thr Glu Asp Pro Asp Glu
                670                 675                 680

ggt acg gct gga gta gaa tct gct gtt cta aga ggg ttt ctc att tta      2118
Gly Thr Ala Gly Val Glu Ser Ala Val Leu Arg Gly Phe Leu Ile Leu
            685                 690                 695

ggt aaa gaa aac aag aga tat ggc cca gca cta agc atc aat gaa ctg      2166
Gly Lys Glu Asn Lys Arg Tyr Gly Pro Ala Leu Ser Ile Asn Glu Leu
        700                 705                 710

agc aaa ctt gca aaa ggg gag aaa gct aat gtg cta att ggg caa ggg      2214
Ser Lys Leu Ala Lys Gly Glu Lys Ala Asn Val Leu Ile Gly Gln Gly
    715                 720                 725

gac gtg gtg ttg gta atg aaa cgg aaa cgt gac tct agc ata ctt act      2262
Asp Val Val Leu Val Met Lys Arg Lys Arg Asp Ser Ser Ile Leu Thr
730                 735                 740                 745

gac agc cag aca gcg acc aaa agg att cgg atg gcc atc aat              2304
Asp Ser Gln Thr Ala Thr Lys Arg Ile Arg Met Ala Ile Asn
                750                 755

tagtgttgaa ttgtttaaaa acgaccttgt ttctact                             2341


<210> SEQ ID NO 28
<211> LENGTH: 759
<212> TYPE: PRT
<213> ORGANISM: Equine influenza virus H3N8

<400> SEQUENCE: 28

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
```

-continued

```
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Ile His Tyr Pro
            100                 105                 110

Lys Val His Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Gln Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Leu Arg Gly Val Arg Val
465                 470                 475                 480

Ser Lys Met Gly Val Asp Glu Tyr Ser Ser Thr Glu Arg Val Val Val
                485                 490                 495
```

-continued

```
Ser Ile Asp Arg Phe Leu Arg Val Arg Asp Gln Arg Gly Asn Ile Leu
            500                 505                 510

Leu Ser Pro Glu Glu Val Ser Glu Thr Gln Gly Thr Glu Lys Leu Thr
        515                 520                 525

Ile Ile Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Ile Val
545                 550                 555                 560

Lys Ile Gln Trp Ser Gln Asp Pro Thr Met Leu Tyr Asn Lys Ile Glu
                565                 570                 575

Phe Glu Pro Phe Gln Ser Leu Val Pro Arg Ala Thr Arg Ser Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asn Lys Arg Tyr
    690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755
```

<210> SEQ ID NO 29
<211> LENGTH: 2277
<212> TYPE: DNA
<213> ORGANISM: Equine influenza virus H3N8

<400> SEQUENCE: 29

```
atggagagaa taaaagaact gagagatcta atgtcacaat cccgcacccg cgagatacta     60

acaaaaacta ctgtggacca catggccata atcaagaaat acacatcagg aagacaagag    120

aagaaccccg cacttaggat gaagtggatg atggcaatga aatacccaat tacagcagat    180

aagaggataa tggaaatgat tcctgagaga aatgaacagg ggcaaaccct ttggagcaaa    240

acgaacgatg ctggctcaga ccgcgtaatg gtatcacctc tggcagtgac atggtggaat    300

aggaatggac caacaacgag cacaattcat tatccaaaag tccacaaaac ttattttgaa    360

aaagttgaaa gattaaaaca cggaaccttt ggccccgttc attttaggaa tcaagtcaag    420

ataagacgga gagttgatgt aaaccctggt cacgcggacc tcagtgccaa agaagcacaa    480

gatgtgatca tggaagttgt tttcccaaat gaagtgggag ccagaattct aacatcggaa    540

tcacaactaa caataaccaa agagaaaaaa gaagaacttc aggactgcaa aattgccccc    600
```

-continued

```
ttgatggtag catacatgct agaaagagag ttggtccgaa aaacaagatt cctcccagtg    660

gctggcggaa caagcagtgt atacattgaa gtgttgcatc tgactcaggg aacatgctgg    720

gaacaaatgt acaccccagg aggagaagtt agaaacgatg acattgatca aagtttaatt    780

attgctgccc ggaacatagt gagaagagcg acagtatcag cagatccact agcatccctg    840

ctggaaatgt gccacagtac acagattggt ggaataagga tggtagacat ccttaagcag    900

aatccaacag aggaacaagc tgtggatata tgcaaagcag caatggggtt aagaattagc    960

tcatcattca gctttggtgg attcaccttt aagagaacaa gtggatcatc agtcaagaga   1020

gaagaagaaa tgcttacggg caaccttcaa acattgaaaa taagagtgca tgaaggctat   1080

gaagaattca caatggtcgg aagaagagca acagccattc tcagaaaggc aaccagaaga   1140

ttgattcaat tgatagtaag tgggagagat gaacaatcaa ttgctgaagc aataattgta   1200

gccatggtgt tttcgcaaga agattgcatg atacaagcag ttcgaggcga tttgaacttc   1260

gttaatagag caaatcagcg cttgaacccc atgcatcaac tcttgaggca tttccaaaaa   1320

gatgcaaaag tgcttttcca gaattggggg attgaaccca tcgacaatgt gatgggaatg   1380

attggaatat tgcctgacat gaccccaagc accgagatgt cattgagagg agtgagagtc   1440

agcaaaatgg gagtggatga gtactccagc actgagagag tggtggtgag cattgaccgt   1500

tttttaagag ttcgggatca aaggggaaac atactactgt cccctgaaga ggtcagtgaa   1560

acacaaggaa cggaaaagct gacaataatt tattcatcat caatgatgtg ggagattaat   1620

ggtcccgaat cagtgttggt caatacttat caatggatca tcaggaactg ggaaattgtg   1680

aaaattcaat ggtcacagga tcccacaatg ttatacaata agatagaatt tgagccattc   1740

cagtccctgg tccctagggc caccagaagc caatacagcg gtttcgtaag aaccctgttt   1800

cagcaaatgc gagatgtact tggaacattt gatactgctc aaataataaa actcctccct   1860

tttgccgctg ctcctccgga acagagtagg atgcagttct cttctttgac tgttaatgta   1920

agaggatcgg gaatgaggat acttgtaaga ggcaattccc cagtgttcaa ctacaataaa   1980

gccactaaga ggctcacagt cctcggaaaa gatgcaggtg cgcttactga agacccagat   2040

gaaggtacgg ctggagtaga atctgctgtt ctaagagggt ttctcatttt aggtaaagaa   2100

aacaagagat atggcccagc actaagcatc aatgaactga gcaaacttgc aaaaggggag   2160

aaagctaatg tgctaattgg gcaaggggac gtggtgttgg taatgaaacg gaaacgtgac   2220

tctagcatac ttactgacag ccagacagcg accaaaagga ttcggatggc catcaat      2277
```

<210> SEQ ID NO 30
<211> LENGTH: 21
<212> TYPE: DNA
<213> ORGANISM: Artificial
<220> FEATURE:
<223> OTHER INFORMATION: Synthetic Primer

<400> SEQUENCE: 30

```
agcaaagcag gtgacaaaaa c                                                21
```

<210> SEQ ID NO 31
<211> LENGTH: 19
<212> TYPE: DNA
<213> ORGANISM: Artificial
<220> FEATURE:
<223> OTHER INFORMATION: Synthetic Primer

<400> SEQUENCE: 31

-continued

```
agtagaaaca agggtgttt                                                19


<210> SEQ ID NO 32
<211> LENGTH: 891
<212> TYPE: DNA
<213> ORGANISM: Equine influenza virus H3N8
<220> FEATURE:
<221> NAME/KEY: CDS
<222> LOCATION: (27)..(716)

<400> SEQUENCE: 32

agcaaaagca gggtgacaaa aacata atg gat tcc aac act gtg tca agc ttt      53
                             Met Asp Ser Asn Thr Val Ser Ser Phe
                             1               5

cag gta gac tgt ttt ctt tgg cat gtc cgc aaa cga ttt gca gac caa      101
Gln Val Asp Cys Phe Leu Trp His Val Arg Lys Arg Phe Ala Asp Gln
10                  15                  20                  25

gaa ctg ggt gat gcc cca ttc ctt gac cgg ctt cgc cga gac cag aag      149
Glu Leu Gly Asp Ala Pro Phe Leu Asp Arg Leu Arg Arg Asp Gln Lys
                30                  35                  40

tcc cta aaa gga aga ggt agc act ctt ggt ctg gac atc gaa aca gcc      197
Ser Leu Lys Gly Arg Gly Ser Thr Leu Gly Leu Asp Ile Glu Thr Ala
            45                  50                  55

act cgt gca gga aag cag ata gtg gag cag att ctg gaa gag gaa tca      245
Thr Arg Ala Gly Lys Gln Ile Val Glu Gln Ile Leu Glu Glu Glu Ser
        60                  65                  70

gat gag gca ctt aaa atg acc att gcc tct gtt cct gct tca cgc tac      293
Asp Glu Ala Leu Lys Met Thr Ile Ala Ser Val Pro Ala Ser Arg Tyr
    75                  80                  85

tta act gac atg act ctt gat gag atg tca aga gac tgg ttc atg ctc      341
Leu Thr Asp Met Thr Leu Asp Glu Met Ser Arg Asp Trp Phe Met Leu
90                  95                  100                 105

atg ccc aag cag aaa gta aca ggc tcc cta tgt ata aga atg gac cag      389
Met Pro Lys Gln Lys Val Thr Gly Ser Leu Cys Ile Arg Met Asp Gln
                110                 115                 120

gca atc atg gat aag aac atc ata ctt aaa gca aac ttt agt gtg att      437
Ala Ile Met Asp Lys Asn Ile Ile Leu Lys Ala Asn Phe Ser Val Ile
            125                 130                 135

ttc gaa agg ctg gag aca cta ata cta ctt aga gcc ttc acc gaa gaa      485
Phe Glu Arg Leu Glu Thr Leu Ile Leu Leu Arg Ala Phe Thr Glu Glu
        140                 145                 150

gga gca gtc gtt ggc gaa att tca cca ttg cct tct ctt cca gga cat      533
Gly Ala Val Val Gly Glu Ile Ser Pro Leu Pro Ser Leu Pro Gly His
    155                 160                 165

act aat gag gat gtc aaa aat gca att ggg gtc ctc atc gga gga ctt      581
Thr Asn Glu Asp Val Lys Asn Ala Ile Gly Val Leu Ile Gly Gly Leu
170                 175                 180                 185

aaa tgg aat gat aat acg gtt aga atc tct gaa act cta cag aga ttc      629
Lys Trp Asn Asp Asn Thr Val Arg Ile Ser Glu Thr Leu Gln Arg Phe
                190                 195                 200

gct tgg aga agc agt cat gag aat ggg aga cct tca ttc cct cca aag      677
Ala Trp Arg Ser Ser His Glu Asn Gly Arg Pro Ser Phe Pro Pro Lys
            205                 210                 215

cag aaa cga aaa atg gag aga aca att gag cca gaa gtt tgaagaaata       726
Gln Lys Arg Lys Met Glu Arg Thr Ile Glu Pro Glu Val
        220                 225                 230

agatggttga ttgaagaagt gcgacataga ttgaaaaata cagaaaatag ttttgaacaa    786

ataacattta tgcaagcctt acaactattg cttgaagtag gacaagagat aagaactttc    846

tcgtttcagc ttatttaatg ataaaaaaca cccttgtttc tacta                    891
```

-continued

<210> SEQ ID NO 33
<211> LENGTH: 230
<212> TYPE: PRT
<213> ORGANISM: Equine influenza virus H3N8

<400> SEQUENCE: 33

```
Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Lys Gly Arg Gly Ser
        35                  40                  45

Thr Leu Gly Leu Asp Ile Glu Thr Ala Thr Arg Ala Gly Lys Gln Ile
    50                  55                  60

Val Glu Gln Ile Leu Glu Glu Glu Ser Asp Glu Ala Leu Lys Met Thr
65                  70                  75                  80

Ile Ala Ser Val Pro Ala Ser Arg Tyr Leu Thr Asp Met Thr Leu Asp
                85                  90                  95

Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys Asn Ile
        115                 120                 125

Ile Leu Lys Ala Asn Phe Ser Val Ile Phe Glu Arg Leu Glu Thr Leu
    130                 135                 140

Ile Leu Leu Arg Ala Phe Thr Glu Glu Gly Ala Val Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Lys Trp Asn Asp Asn Thr Val
            180                 185                 190

Arg Ile Ser Glu Thr Leu Gln Arg Phe Ala Trp Arg Ser Ser His Glu
        195                 200                 205

Asn Gly Arg Pro Ser Phe Pro Pro Lys Gln Lys Arg Lys Met Glu Arg
    210                 215                 220

Thr Ile Glu Pro Glu Val
225                 230
```

<210> SEQ ID NO 34
<211> LENGTH: 690
<212> TYPE: DNA
<213> ORGANISM: Equine influenza virus H3N8

<400> SEQUENCE: 34

```
atggattcca acactgtgtc aagctttcag gtagactgtt ttctttggca tgtccgcaaa      60

cgatttgcag accaagaact gggtgatgcc ccattccttg accggcttcg ccgagaccag     120

aagtccctaa aaggaagagg tagcactctt ggtctggaca tcgaaacagc cactcgtgca     180

ggaaagcaga tagtggagca gattctggaa gaggaatcag atgaggcact taaaatgacc     240

attgcctctg ttcctgcttc acgctactta actgacatga ctcttgatga gatgtcaaga     300

gactggttca tgctcatgcc caagcagaaa gtaacaggct ccctatgtat aagaatggac     360

caggcaatca tggataagaa catcatactt aaagcaaact ttagtgtgat tttcgaaagg     420

ctggagacac taatactact tagagccttc accgaagaag gagcagtcgt tggcgaaatt     480

tcaccattgc cttctcttcc aggacatact aatgaggatg tcaaaaatgc aattggggtc     540
```

-continued

```
ctcatcggag gacttaaatg gaatgataat acggttagaa tctctgaaac tctacagaga    600

ttcgcttgga gaagcagtca tgagaatggg agaccttcat tccctccaaa gcagaaacga    660

aaaatggaga gaacaattga gccagaagtt                                     690


<210> SEQ ID NO 35
<211> LENGTH: 888
<212> TYPE: DNA
<213> ORGANISM: Equine influenza virus H3N8

<400> SEQUENCE: 35

caaaagcagg gtgacaaaaa catgatggat tccaacactg tgtcaagctt tcaggtagac     60

tgttttcttt ggcatgtccg caaacgattt gcagaccaag aactgggtga tgccccattc    120

cttgaccggc ttcgccgaga ccagaagtcc ctaaaaggaa gaggtagcac tcttggtctg    180

gacatcgaaa cagccactcg tgcaggaaag cagatagtgg agcagattct ggaagaggaa    240

tcagatgagg cacttaaaat gaccattgcc tctgttcctg cttcacgcta cttaactgac    300

atgactcttg atgagatgtc aagagactgg ttcatgctca tgcccaagca gaaagtaaca    360

ggctccctat gtataagaat ggaccaggca atcatggata agaacatcat acttaaagca    420

aactttagtg tgattttcga aaggctggag acactaatac tacttagagc cttcaccgaa    480

gaaggagcag tcgttggcga aatttcacca ttgccttctc ttccaggaca tactaatgag    540

gatgtcaaaa atgcaattgg ggtcctcatc ggaggactta aatggaatga taatacggtt    600

agaatctctg aaactctaca gagattcgct tggagaagca gtcatgagaa tgggagacct    660

tcattccctc caaagcagaa acgaaaaatg gagagaacaa ttgagccaga agtttgaaga    720

aataagatgg ttgattgaag aagtgcgaca tagattgaaa aatacagaaa atagttttga    780

acaaataaca tttatgcaag ccttacaact attgcttgaa gtagaacaag agataagaac    840

tttctcgttt cagcttattt aatgataaaa aacacccttg tttctact                 888


<210> SEQ ID NO 36
<211> LENGTH: 468
<212> TYPE: DNA
<213> ORGANISM: Equine influenza virus H3N8
<220> FEATURE:
<221> NAME/KEY: CDS
<222> LOCATION: (3)..(293)

<400> SEQUENCE: 36

ac ttt agt gtg att ttc gaa agg ctg gag aca cta ata cta ctt aga        47
   Phe Ser Val Ile Phe Glu Arg Leu Glu Thr Leu Ile Leu Leu Arg
   1               5                   10                  15

gcc ttc acc gaa gaa gga gca gtc gtt ggc gaa att tca cca ttg cct       95
Ala Phe Thr Glu Glu Gly Ala Val Val Gly Glu Ile Ser Pro Leu Pro
                20                  25                  30

tct ctt cca gga cat act aat gag gat gtc aaa aat gca att ggg gtc      143
Ser Leu Pro Gly His Thr Asn Glu Asp Val Lys Asn Ala Ile Gly Val
            35                  40                  45

ctc atc gga gga ctt aaa tgg aat gat aat acg gtt aga atc tct gaa      191
Leu Ile Gly Gly Leu Lys Trp Asn Asp Asn Thr Val Arg Ile Ser Glu
        50                  55                  60

act cta cag aga ttc gct cgg aga agc agt cat gag aat ggg aga cct      239
Thr Leu Gln Arg Phe Ala Arg Arg Ser Ser His Glu Asn Gly Arg Pro
    65                  70                  75

tca ttc cct cca aag cag aaa cga aaa atg gag aga aca att gag cca      287
Ser Phe Pro Pro Lys Gln Lys Arg Lys Met Glu Arg Thr Ile Glu Pro
80                  85                  90                  95
```

-continued

```
gaa gtt tgaagaaata agatggttga ttgaagaagt gcgacataga ttgaaaaata       343
Glu Val

cagaaaatag ttttgaacaa ataacattta tgcaagcctt acaactattg cttgaagtag    403

aacaagagat aagaactttc tcgtttcagc ttatttaatg ataaaaaaca cccttgtttc    463

tacta                                                                468


<210> SEQ ID NO 37
<211> LENGTH: 97
<212> TYPE: PRT
<213> ORGANISM: Equine influenza virus H3N8

<400> SEQUENCE: 37

Phe Ser Val Ile Phe Glu Arg Leu Glu Thr Leu Ile Leu Leu Arg Ala
1               5                   10                  15

Phe Thr Glu Glu Gly Ala Val Val Gly Glu Ile Ser Pro Leu Pro Ser
            20                  25                  30

Leu Pro Gly His Thr Asn Glu Asp Val Lys Asn Ala Ile Gly Val Leu
        35                  40                  45

Ile Gly Gly Leu Lys Trp Asn Asp Asn Thr Val Arg Ile Ser Glu Thr
    50                  55                  60

Leu Gln Arg Phe Ala Arg Arg Ser Ser His Glu Asn Gly Arg Pro Ser
65                  70                  75                  80

Phe Pro Pro Lys Gln Lys Arg Lys Met Glu Arg Thr Ile Glu Pro Glu
                85                  90                  95

Val


<210> SEQ ID NO 38
<211> LENGTH: 293
<212> TYPE: DNA
<213> ORGANISM: Equine influenza virus H3N8

<400> SEQUENCE: 38

actttagtgt gattttcgaa aggctggaga cactaatact acttagagcc ttcaccgaag     60

aaggagcagt cgttggcgaa atttcaccat tgccttctct tccaggacat actaatgagg    120

atgtcaaaaa tgcaattggg gtcctcatcg gaggacttaa atggaatgat aatacggtta    180

gaatctctga aactctacag agattcgctc ggagaagcag tcatgagaat gggagacctt    240

cattccctcc aaagcagaaa cgaaaaatgg agagaacaat tgagccagaa gtt           293


<210> SEQ ID NO 39
<211> LENGTH: 888
<212> TYPE: DNA
<213> ORGANISM: Equine influenza virus H3N8
<220> FEATURE:
<221> NAME/KEY: CDS
<222> LOCATION: (27)..(716)

<400> SEQUENCE: 39

agcaaaagca gggtgacaaa aacata atg gat tcc aac act gtg tca agc ttt      53
                             Met Asp Ser Asn Thr Val Ser Ser Phe
                             1               5

cag gta gac tgt ttt ctt tgg cat gtc cgc aaa cga ttt gca gac caa      101
Gln Val Asp Cys Phe Leu Trp His Val Arg Lys Arg Phe Ala Asp Gln
10                  15                  20                  25

gaa ctg ggt gat gcc cca ttc ctt gac cgg ctt cgc cga gac cag aag      149
Glu Leu Gly Asp Ala Pro Phe Leu Asp Arg Leu Arg Arg Asp Gln Lys
                30                  35                  40

tcc cta aaa gga aga ggt agc act ctt ggt ctg gac atc gaa aca gcc      197
```

-continued

```
Ser Leu Lys Gly Arg Gly Ser Thr Leu Gly Leu Asp Ile Glu Thr Ala
            45                  50                  55

act cgt gca gga aag cag ata gtg gag cag att ctg gaa gag gaa tca      245
Thr Arg Ala Gly Lys Gln Ile Val Glu Gln Ile Leu Glu Glu Glu Ser
        60                  65                  70

gat gag gca ctt aaa atg acc att gcc tct gtt cct gct tca cgc tac      293
Asp Glu Ala Leu Lys Met Thr Ile Ala Ser Val Pro Ala Ser Arg Tyr
    75                  80                  85

tta act gac atg act ctt gat gag atg tca aga gac tgg ttc atg ctc      341
Leu Thr Asp Met Thr Leu Asp Glu Met Ser Arg Asp Trp Phe Met Leu
90                  95                  100                 105

atg ccc aag cag aaa gta aca ggc tcc cta tgt ata aga atg gac cag      389
Met Pro Lys Gln Lys Val Thr Gly Ser Leu Cys Ile Arg Met Asp Gln
                110                 115                 120

gca atc atg gat aag aac atc ata ctt aaa gca aac ttt agt gtg att      437
Ala Ile Met Asp Lys Asn Ile Ile Leu Lys Ala Asn Phe Ser Val Ile
            125                 130                 135

ttc gaa agg ctg gag aca cta ata cta ctt aga gcc ttc acc gaa gaa      485
Phe Glu Arg Leu Glu Thr Leu Ile Leu Leu Arg Ala Phe Thr Glu Glu
        140                 145                 150

gga gca gtc gtt ggc gaa att tca cca ttg cct tct ctt cca gga cat      533
Gly Ala Val Val Gly Glu Ile Ser Pro Leu Pro Ser Leu Pro Gly His
    155                 160                 165

act aat gag gat gtc aaa aat gca att ggg gtc ctc atc gga gga ctt      581
Thr Asn Glu Asp Val Lys Asn Ala Ile Gly Val Leu Ile Gly Gly Leu
170                 175                 180                 185

aaa tgg aat gat aat acg gtt aga atc tct gaa act cta cag aga ttc      629
Lys Trp Asn Asp Asn Thr Val Arg Ile Ser Glu Thr Leu Gln Arg Phe
                190                 195                 200

gct tgg aga agc agt cat gag aat ggg aga cct tca ttc cct cca aag      677
Ala Trp Arg Ser Ser His Glu Asn Gly Arg Pro Ser Phe Pro Pro Lys
            205                 210                 215

cag aaa cga aaa atg gag aga aca att gag cca gaa gtt tgaagaaata       726
Gln Lys Arg Lys Met Glu Arg Thr Ile Glu Pro Glu Val
        220                 225                 230

agatggttga ttgaagaagt gcgacataga ttgaaaaata cagaaaatag ttttgaacaa    786

ataacattta tgcaagcctt acaactattg cttgaagtag aacaagagat aagaactttc    846

tcgtttcagc ttatttaatg ataaaaaaca cccttgtttc ta                       888


<210> SEQ ID NO 40
<211> LENGTH: 230
<212> TYPE: PRT
<213> ORGANISM: Equine influenza virus H3N8

<400> SEQUENCE: 40

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Lys Gly Arg Gly Ser
        35                  40                  45

Thr Leu Gly Leu Asp Ile Glu Thr Ala Thr Arg Ala Gly Lys Gln Ile
    50                  55                  60

Val Glu Gln Ile Leu Glu Glu Glu Ser Asp Glu Ala Leu Lys Met Thr
65                  70                  75                  80

Ile Ala Ser Val Pro Ala Ser Arg Tyr Leu Thr Asp Met Thr Leu Asp
                85                  90                  95
```

-continued

```
Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys Asn Ile
        115                 120                 125

Ile Leu Lys Ala Asn Phe Ser Val Ile Phe Glu Arg Leu Glu Thr Leu
    130                 135                 140

Ile Leu Leu Arg Ala Phe Thr Glu Glu Gly Ala Val Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Lys Trp Asn Asp Asn Thr Val
            180                 185                 190

Arg Ile Ser Glu Thr Leu Gln Arg Phe Ala Trp Arg Ser Ser His Glu
        195                 200                 205

Asn Gly Arg Pro Ser Phe Pro Pro Lys Gln Lys Arg Lys Met Glu Arg
    210                 215                 220

Thr Ile Glu Pro Glu Val
225                 230


<210> SEQ ID NO 41
<211> LENGTH: 690
<212> TYPE: DNA
<213> ORGANISM: Equine influenza virus H3N8

<400> SEQUENCE: 41

atggattcca acactgtgtc aagctttcag gtagactgtt ttctttggca tgtccgcaaa      60

cgatttgcag accaagaact gggtgatgcc ccattccttg accggcttcg ccgagaccag     120

aagtccctaa aaggaagagg tagcactctt ggtctggaca tcgaaacagc cactcgtgca     180

ggaaagcaga tagtggagca gattctggaa gaggaatcag atgaggcact taaaatgacc     240

attgcctctg ttcctgcttc acgctactta actgacatga ctcttgatga gatgtcaaga     300

gactggttca tgctcatgcc caagcagaaa gtaacaggct ccctatgtat aagaatggac     360

caggcaatca tggataagaa catcatactt aaagcaaact ttagtgtgat tttcgaaagg     420

ctggagacac taatactact tagagccttc accgaagaag gagcagtcgt tggcgaaatt     480

tcaccattgc cttctcttcc aggacatact aatgaggatg tcaaaaatgc aattggggtc     540

ctcatcggag gacttaaatg gaatgataat acggttagaa tctctgaaac tctacagaga     600

ttcgcttgga gaagcagtca tgagaatggg agaccttcat tccctccaaa gcagaaacga     660

aaaatggaga gaacaattga gccagaagtt                                     690


<210> SEQ ID NO 42
<211> LENGTH: 1229
<212> TYPE: DNA
<213> ORGANISM: Equine influenza virus H3N8
<220> FEATURE:
<221> NAME/KEY: CDS
<222> LOCATION: (36)..(1229)

<400> SEQUENCE: 42

gaattcggct tagcaaaagc aggcaaacta tttga atg gat gtc aat ccg act        53
                                       Met Asp Val Asn Pro Thr
                                       1               5

cta ctc ttc tta aag gtg cca gcg caa aat gct ata agc aca aca ttc      101
Leu Leu Phe Leu Lys Val Pro Ala Gln Asn Ala Ile Ser Thr Thr Phe
            10                  15                  20

cct tat act gga gat cct ccc tac agt cat gga aca ggg aca gga tac      149
```

-continued

```
Pro Tyr Thr Gly Asp Pro Pro Tyr Ser His Gly Thr Gly Thr Gly Tyr
        25                  30                  35

acc atg gat act gtc aac aga aca cat caa tac tca gaa aag ggg aaa      197
Thr Met Asp Thr Val Asn Arg Thr His Gln Tyr Ser Glu Lys Gly Lys
    40                  45                  50

tgg aca aca aac act gag att gga gca cca caa ctt aat cca atc gat      245
Trp Thr Thr Asn Thr Glu Ile Gly Ala Pro Gln Leu Asn Pro Ile Asp
55                  60                  65                  70

gga ccg ctt cct gaa gac aat gaa cca agt ggg tac gcc caa aca gat      293
Gly Pro Leu Pro Glu Asp Asn Glu Pro Ser Gly Tyr Ala Gln Thr Asp
                75                  80                  85

tgt gta ttg gaa gca atg gct ttc ctt gaa gaa tcc cat ccc gga atc      341
Cys Val Leu Glu Ala Met Ala Phe Leu Glu Glu Ser His Pro Gly Ile
            90                  95                  100

ttt gaa aat tcg tgt ctt gaa aca atg gag gtg gtt cag cag aca aga      389
Phe Glu Asn Ser Cys Leu Glu Thr Met Glu Val Val Gln Gln Thr Arg
        105                 110                 115

gtg gac aaa cta aca caa ggc cga caa act tac gat tgg acc ttg aat      437
Val Asp Lys Leu Thr Gln Gly Arg Gln Thr Tyr Asp Trp Thr Leu Asn
    120                 125                 130

agg aat caa cct gcc gca aca gca ctt gct aat aca att gaa gtg ttc      485
Arg Asn Gln Pro Ala Ala Thr Ala Leu Ala Asn Thr Ile Glu Val Phe
135                 140                 145                 150

aga tca aat gat ctg act tcc agt gag tca ggg aga tta atg gac ttc      533
Arg Ser Asn Asp Leu Thr Ser Ser Glu Ser Gly Arg Leu Met Asp Phe
                155                 160                 165

ctc aaa gat gtc atg gag tcc atg aac aag gaa gaa atg gaa ata aca      581
Leu Lys Asp Val Met Glu Ser Met Asn Lys Glu Glu Met Glu Ile Thr
            170                 175                 180

aca cac ttc caa cgg aag aga aga gta aga gac aac atg aca aag aga      629
Thr His Phe Gln Arg Lys Arg Arg Val Arg Asp Asn Met Thr Lys Arg
        185                 190                 195

atg gtg aca cag aga acc ata ggg aag aaa aaa caa cga tta aac aga      677
Met Val Thr Gln Arg Thr Ile Gly Lys Lys Lys Gln Arg Leu Asn Arg
    200                 205                 210

aag agc tat ctg atc agg gca tta acc tta aac aca atg acc aag gac      725
Lys Ser Tyr Leu Ile Arg Ala Leu Thr Leu Asn Thr Met Thr Lys Asp
215                 220                 225                 230

gct gag aga ggg aaa ttg aaa cga cga gca att gca acc cca gga atg      773
Ala Glu Arg Gly Lys Leu Lys Arg Arg Ala Ile Ala Thr Pro Gly Met
                235                 240                 245

cag ata aga ggg ttt gta tat ttt gtt gaa aca tta gcc cga aga ata      821
Gln Ile Arg Gly Phe Val Tyr Phe Val Glu Thr Leu Ala Arg Arg Ile
            250                 255                 260

tgt gaa aag ctt gaa caa tca gga ttg cca gtt ggc ggt aat gag aaa      869
Cys Glu Lys Leu Glu Gln Ser Gly Leu Pro Val Gly Gly Asn Glu Lys
        265                 270                 275

aag gcc aaa ctg gct aat gtc gtc aga aaa atg atg act aat tcc caa      917
Lys Ala Lys Leu Ala Asn Val Val Arg Lys Met Met Thr Asn Ser Gln
    280                 285                 290

gac act gaa ctc tcc ttc acc atc act ggg gac aat acc aaa tgg aat      965
Asp Thr Glu Leu Ser Phe Thr Ile Thr Gly Asp Asn Thr Lys Trp Asn
295                 300                 305                 310

gaa aat cag aac cca cgc atg ttc ctg gca atg atc aca tac ata act     1013
Glu Asn Gln Asn Pro Arg Met Phe Leu Ala Met Ile Thr Tyr Ile Thr
                315                 320                 325

aga aac cag cca gaa tgg ttc aga aat gtt cta agc att gca ccg att     1061
Arg Asn Gln Pro Glu Trp Phe Arg Asn Val Leu Ser Ile Ala Pro Ile
            330                 335                 340
```

-continued

```
atg ttc tca aat aaa atg gca aga ctg ggg aaa gga tat atg ttt gaa      1109
Met Phe Ser Asn Lys Met Ala Arg Leu Gly Lys Gly Tyr Met Phe Glu
        345                 350                 355

agc aaa agt atg aaa ttg aga act caa ata cca gca gaa atg ctc gca      1157
Ser Lys Ser Met Lys Leu Arg Thr Gln Ile Pro Ala Glu Met Leu Ala
    360                 365                 370

agc att gat ctg aaa tat ttc aat gat tca aca aaa aag aaa att gag      1205
Ser Ile Asp Leu Lys Tyr Phe Asn Asp Ser Thr Lys Lys Lys Ile Glu
375                 380                 385                 390

aag ata cga cca caa gcc gaa ttc                                      1229
Lys Ile Arg Pro Gln Ala Glu Phe
                395


<210> SEQ ID NO 43
<211> LENGTH: 398
<212> TYPE: PRT
<213> ORGANISM: Equine influenza virus H3N8

<400> SEQUENCE: 43

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Asp Leu Thr Ser Ser Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
```

-continued

```
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Gln Ala Glu Phe
385                 390                 395


<210> SEQ ID NO 44
<211> LENGTH: 1194
<212> TYPE: DNA
<213> ORGANISM: Equine influenza virus H3N8

<400> SEQUENCE: 44

atggatgtca atccgactct actcttctta aaggtgccag cgcaaaatgc tataagcaca      60

acattccctt atactggaga tcctccctac agtcatggaa cagggacagg atacaccatg     120

gatactgtca acagaacaca tcaatactca gaaaagggga aatggacaac aaacactgag     180

attggagcac cacaacttaa tccaatcgat ggaccgcttc ctgaagacaa tgaaccaagt     240

gggtacgccc aaacagattg tgtattggaa gcaatggctt tccttgaaga atcccatccc     300

ggaatctttg aaaattcgtg tcttgaaaca atggaggtgg ttcagcagac aagagtggac     360

aaactaacac aaggccgaca aacttacgat tggaccttga ataggaatca acctgccgca     420

acagcacttg ctaatacaat tgaagtgttc agatcaaatg atctgacttc cagtgagtca     480

gggagattaa tggacttcct caaagatgtc atggagtcca tgaacaagga agaaatggaa     540

ataacaacac acttccaacg gaagagaaga gtaagagaca acatgacaaa gagaatggtg     600

acacagagaa ccatagggaa gaaaaaacaa cgattaaaca gaaagagcta tctgatcagg     660

gcattaacct taaacacaat gaccaaggac gctgagagag ggaaattgaa acgacgagca     720

attgcaaccc caggaatgca gataagaggg tttgtatatt ttgttgaaac attagcccga     780

agaatatgtg aaaagcttga acaatcagga ttgccagttg gcggtaatga gaaaaaggcc     840

aaactggcta atgtcgtcag aaaaatgatg actaattccc aagacactga actctccttc     900

accatcactg gggacaatac caaatggaat gaaaatcaga acccacgcat gttcctggca     960

atgatcacat acataactag aaaccagcca gaatggttca gaaatgttct aagcattgca    1020

ccgattatgt tctcaaataa aatggcaaga ctggggaaag gatatatgtt tgaaagcaaa    1080

agtatgaaat tgagaactca aataccagca gaaatgctcg caagcattga tctgaaatat    1140

ttcaatgatt caacaaaaaa gaaaattgag aagatacgac cacaagccga attc          1194


<210> SEQ ID NO 45
<211> LENGTH: 673
<212> TYPE: DNA
<213> ORGANISM: Equine influenza virus H3N8
<220> FEATURE:
<221> NAME/KEY: CDS
<222> LOCATION: (36)..(671)

<400> SEQUENCE: 45
```

-continued

```
gaattcggct tagcaaaagc aggcaaacta tttga atg gat gtc aat ccg act        53
                                       Met Asp Val Asn Pro Thr
                                       1               5

cta ctc ttc tta aag gtg cca gcg caa aat gct ata agc aca aca ttc      101
Leu Leu Phe Leu Lys Val Pro Ala Gln Asn Ala Ile Ser Thr Thr Phe
            10                  15                  20

cct tat act gga gat cct ccc tac agt cat gga aca ggg aca gga tac      149
Pro Tyr Thr Gly Asp Pro Pro Tyr Ser His Gly Thr Gly Thr Gly Tyr
        25                  30                  35

acc atg gat act gtc aac aga aca cat caa tac tca gaa aag ggg aaa      197
Thr Met Asp Thr Val Asn Arg Thr His Gln Tyr Ser Glu Lys Gly Lys
    40                  45                  50

tgg aca aca aac act gag att gga gca cca caa ctt aat cca atc gat      245
Trp Thr Thr Asn Thr Glu Ile Gly Ala Pro Gln Leu Asn Pro Ile Asp
55                  60                  65                  70

gga ccg ctt cct gaa gac aat gaa cca agt ggg tac gcc caa aca gat      293
Gly Pro Leu Pro Glu Asp Asn Glu Pro Ser Gly Tyr Ala Gln Thr Asp
                75                  80                  85

tgt gta ttg gaa gca atg gct ttc ctt gaa gaa tcc cat ccc gga atc      341
Cys Val Leu Glu Ala Met Ala Phe Leu Glu Glu Ser His Pro Gly Ile
            90                  95                  100

ttt gaa aat tcg tgt ctt gaa aca atg gag gtg gtt cag cag aca aga      389
Phe Glu Asn Ser Cys Leu Glu Thr Met Glu Val Val Gln Gln Thr Arg
        105                 110                 115

gtg gac aaa cta aca caa ggc cga caa act tac gat tgg acc ttg aat      437
Val Asp Lys Leu Thr Gln Gly Arg Gln Thr Tyr Asp Trp Thr Leu Asn
    120                 125                 130

agg aat caa cct gcc gca aca gca ctt gct aat aca att gaa gtg ttc      485
Arg Asn Gln Pro Ala Ala Thr Ala Leu Ala Asn Thr Ile Glu Val Phe
135                 140                 145                 150

aga tca aat gat ctg act tcc agt gag tca ggg aga tta atg gac ttc      533
Arg Ser Asn Asp Leu Thr Ser Ser Glu Ser Gly Arg Leu Met Asp Phe
                155                 160                 165

ctc aaa gat gtc atg gag tcc atg aac aag gaa gaa atg gaa ata aca      581
Leu Lys Asp Val Met Glu Ser Met Asn Lys Glu Glu Met Glu Ile Thr
            170                 175                 180

aca cac ttc caa cgg aag aga aga gta aga gac aac atg aca aag aga      629
Thr His Phe Gln Arg Lys Arg Arg Val Arg Asp Asn Met Thr Lys Arg
        185                 190                 195

atg gtg aca cag aga acc ata ggg aag aaa aaa caa cga tta aa           673
Met Val Thr Gln Arg Thr Ile Gly Lys Lys Lys Gln Arg Leu
    200                 205                 210


<210> SEQ ID NO 46
<211> LENGTH: 212
<212> TYPE: PRT
<213> ORGANISM: Equine influenza virus H3N8

<400> SEQUENCE: 46

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80
```

-continued

```
Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Asp Leu Thr Ser Ser Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu
    210


<210> SEQ ID NO 47
<211> LENGTH: 636
<212> TYPE: DNA
<213> ORGANISM: Equine influenza virus H3N8

<400> SEQUENCE: 47

atggatgtca atccgactct actcttctta aaggtgccag cgcaaaatgc tataagcaca      60

acattccctt atactggaga tcctccctac agtcatggaa cagggacagg atacaccatg     120

gatactgtca acagaacaca tcaatactca gaaaagggga aatggacaac aaacactgag     180

attggagcac cacaacttaa tccaatcgat ggaccgcttc ctgaagacaa tgaaccaagt     240

gggtacgccc aaacagattg tgtattggaa gcaatggctt tccttgaaga atcccatccc     300

ggaatctttg aaaattcgtg tcttgaaaca atggaggtgg ttcagcagac aagagtggac     360

aaactaacac aaggccgaca aacttacgat tggaccttga ataggaatca acctgccgca     420

acagcacttg ctaatacaat tgaagtgttc agatcaaatg atctgacttc cagtgagtca     480

gggagattaa tggacttcct caaagatgtc atggagtcca tgaacaagga agaaatggaa     540

ataacaacac acttccaacg gaagagaaga gtaagagaca acatgacaaa gagaatggtg     600

acacagagaa ccatagggaa gaaaaaacaa cgatta                               636


<210> SEQ ID NO 48
<211> LENGTH: 1225
<212> TYPE: DNA
<213> ORGANISM: Equine influenza virus H3N8
<220> FEATURE:
<221> NAME/KEY: CDS
<222> LOCATION: (34)..(1218)

<400> SEQUENCE: 48

gaattcagga gcaaaagcag gcaaactatt tga atg gat gtc aat ccg act cta       54
                                     Met Asp Val Asn Pro Thr Leu
                                     1               5

ctc ttc tta aag gtg cca gcg caa aat gct ata agc aca aca ttc cct       102
Leu Phe Leu Lys Val Pro Ala Gln Asn Ala Ile Ser Thr Thr Phe Pro
        10                  15                  20

tat act gga gat cct ccc tac agt cat gga aca ggg aca gga tac acc       150
Tyr Thr Gly Asp Pro Pro Tyr Ser His Gly Thr Gly Thr Gly Tyr Thr
    25                  30                  35
```

-continued

```
atg gat act gtc aac aga aca cat caa tac tca gaa aag ggg aaa tgg      198
Met Asp Thr Val Asn Arg Thr His Gln Tyr Ser Glu Lys Gly Lys Trp
40                  45                  50                  55

aca aca aac act gag att gga gca cca caa ctt aat cca atc gat gga      246
Thr Thr Asn Thr Glu Ile Gly Ala Pro Gln Leu Asn Pro Ile Asp Gly
                60                  65                  70

ccg ctt cct gaa gac aat gaa cca agt ggg tac gcc caa aca gat tgt      294
Pro Leu Pro Glu Asp Asn Glu Pro Ser Gly Tyr Ala Gln Thr Asp Cys
            75                  80                  85

gta ttg gaa gca atg gct ttc ctt gaa gaa tcc cat ccc gga atc ttt      342
Val Leu Glu Ala Met Ala Phe Leu Glu Glu Ser His Pro Gly Ile Phe
        90                  95                  100

gaa aat tcg tgt ctt gaa aca atg gag gtg gtt cag cag aca aga gtg      390
Glu Asn Ser Cys Leu Glu Thr Met Glu Val Val Gln Gln Thr Arg Val
    105                 110                 115

gac aaa cta aca caa ggc cga caa act tac gat tgg acc ttg aat agg      438
Asp Lys Leu Thr Gln Gly Arg Gln Thr Tyr Asp Trp Thr Leu Asn Arg
120                 125                 130                 135

aat caa cct gcc gca aca gca ctt gct aat aca att gaa gtg ttc aga      486
Asn Gln Pro Ala Ala Thr Ala Leu Ala Asn Thr Ile Glu Val Phe Arg
                140                 145                 150

tca aat gat ctg act tcc agt gag tca ggg aga tta atg gac ttc ctc      534
Ser Asn Asp Leu Thr Ser Ser Glu Ser Gly Arg Leu Met Asp Phe Leu
            155                 160                 165

aaa gat gtc atg gag tcc atg aac aag gaa gaa atg gaa ata aca aca      582
Lys Asp Val Met Glu Ser Met Asn Lys Glu Glu Met Glu Ile Thr Thr
        170                 175                 180

cac ttc caa cgg aag aga aga gta aga gac aac atg aca aag aga atg      630
His Phe Gln Arg Lys Arg Arg Val Arg Asp Asn Met Thr Lys Arg Met
    185                 190                 195

gtg aca cag aga acc ata ggg aag aaa aaa caa cga tta aac aga aag      678
Val Thr Gln Arg Thr Ile Gly Lys Lys Lys Gln Arg Leu Asn Arg Lys
200                 205                 210                 215

agc tat ctg atc agg gca tta acc tta aac aca atg acc aag gac gct      726
Ser Tyr Leu Ile Arg Ala Leu Thr Leu Asn Thr Met Thr Lys Asp Ala
                220                 225                 230

gag aga ggg aaa ttg aaa cga cga gca att gca acc cca gga atg cag      774
Glu Arg Gly Lys Leu Lys Arg Arg Ala Ile Ala Thr Pro Gly Met Gln
            235                 240                 245

ata aga ggg ttt gta tat ttt gtt gaa aca tta gcc cga aga ata tgt      822
Ile Arg Gly Phe Val Tyr Phe Val Glu Thr Leu Ala Arg Arg Ile Cys
        250                 255                 260

gaa aag ctt gaa caa tca gga ttg cca gtt ggc ggt aat gag aaa aag      870
Glu Lys Leu Glu Gln Ser Gly Leu Pro Val Gly Gly Asn Glu Lys Lys
    265                 270                 275

gcc aaa ctg gct aat gtc gtc aga aaa atg atg act aat tcc caa gac      918
Ala Lys Leu Ala Asn Val Val Arg Lys Met Met Thr Asn Ser Gln Asp
280                 285                 290                 295

act gaa ctc tcc ttc acc atc act ggg gac aat acc aaa tgg aat gaa      966
Thr Glu Leu Ser Phe Thr Ile Thr Gly Asp Asn Thr Lys Trp Asn Glu
                300                 305                 310

aat cag aac cca cgc atg ttc ctg gca atg atc aca tac ata act aga     1014
Asn Gln Asn Pro Arg Met Phe Leu Ala Met Ile Thr Tyr Ile Thr Arg
            315                 320                 325

aac cag cca gaa tgg ttc aga aat gtt cta agc att gca ccg att atg     1062
Asn Gln Pro Glu Trp Phe Arg Asn Val Leu Ser Ile Ala Pro Ile Met
        330                 335                 340

ttc tca aat aaa atg gca aga ctg ggg aaa gga tat atg ttt gaa agc     1110
Phe Ser Asn Lys Met Ala Arg Leu Gly Lys Gly Tyr Met Phe Glu Ser
```

-continued

```
    345                 350                 355

aaa agt atg aaa ttg aga act caa ata cca gca gaa atg ctc gca agc      1158
Lys Ser Met Lys Leu Arg Thr Gln Ile Pro Ala Glu Met Leu Ala Ser
360                 365                 370                 375

att gat ctg aaa tat ttc aat gat tca aca aaa aag aaa att gag aag      1206
Ile Asp Leu Lys Tyr Phe Asn Asp Ser Thr Lys Lys Lys Ile Glu Lys
            380                 385                 390

ata cga cca ccc tgaattc                                              1225
Ile Arg Pro Pro
            395


<210> SEQ ID NO 49
<211> LENGTH: 395
<212> TYPE: PRT
<213> ORGANISM: Equine influenza virus H3N8

<400> SEQUENCE: 49

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Asp Leu Thr Ser Ser Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300
```

-continued

```
Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Pro
385                 390                 395


<210> SEQ ID NO 50
<211> LENGTH: 1185
<212> TYPE: DNA
<213> ORGANISM: Equine influenza virus H3N8

<400> SEQUENCE: 50

atggatgtca atccgactct actcttctta aaggtgccag cgcaaaatgc tataagcaca      60

acattccctt atactggaga tcctccctac agtcatggaa cagggacagg atacaccatg     120

gatactgtca acagaacaca tcaatactca gaaaagggga aatggacaac aaacactgag     180

attggagcac cacaacttaa tccaatcgat ggaccgcttc ctgaagacaa tgaaccaagt     240

gggtacgccc aaacagattg tgtattggaa gcaatggctt tccttgaaga atcccatccc     300

ggaatctttg aaaattcgtg tcttgaaaca atggaggtgg ttcagcagac aagagtggac     360

aaactaacac aaggccgaca aacttacgat tggaccttga ataggaatca acctgccgca     420

acagcacttg ctaatacaat tgaagtgttc agatcaaatg atctgacttc cagtgagtca     480

gggagattaa tggacttcct caaagatgtc atggagtcca tgaacaagga agaaatggaa     540

ataacaacac acttccaacg gaagagaaga gtaagagaca acatgacaaa gagaatggtg     600

acacagagaa ccatagggaa gaaaaaacaa cgattaaaca gaaagagcta tctgatcagg     660

gcattaacct taaacacaat gaccaaggac gctgagagag ggaaattgaa acgacgagca     720

attgcaaccc caggaatgca gataagaggg tttgtatatt ttgttgaaac attagcccga     780

agaatatgtg aaaagcttga acaatcagga ttgccagttg gcggtaatga gaaaaaggcc     840

aaactggcta atgtcgtcag aaaaatgatg actaattccc aagacactga actctccttc     900

accatcactg gggacaatac caaatggaat gaaaatcaga acccacgcat gttcctggca     960

atgatcacat acataactag aaaccagcca gaatggttca gaaatgttct aagcattgca    1020

ccgattatgt tctcaaataa aatggcaaga ctggggaaag gatatatgtt tgaaagcaaa    1080

agtatgaaat tgagaactca aataccagca gaaatgctcg caagcattga tctgaaatat    1140

ttcaatgatt caacaaaaaa gaaaattgag aagatacgac caccc                    1185


<210> SEQ ID NO 51
<211> LENGTH: 1221
<212> TYPE: DNA
<213> ORGANISM: Equine influenza virus H3N8

<400> SEQUENCE: 51

gaattcagga aagcaggcaa actatttgaa tggatgtcaa tccgactcta ctcttcttaa      60

aggtgccagc gcaaaatgct ataagcacaa cattccctta tactggagat cctccctaca     120

gtcatggaac agggacagga tacaccatgg atactgtcaa cagaacacat caatactcag     180
```

-continued

```
aaaaggggaa atggacaaca aacactgaga ttggagcacc acaacttaat ccaatcgatg    240

gaccgcttcc tgaagacaat gaaccaagtg ggtacgccca aacagattgt gtattggaag    300

caatggcttt ccttgaagaa tcccatcccg gaatctttga aaattcgtgt cttgaaacaa    360

tggaggtggt tcagcagaca agagtggaca aactaacaca aggccgacaa acttacgatt    420

ggaccttgaa taggaatcaa cctgccgcaa cagcacttgc taatacaatt gaagtgttca    480

gatcaaatga tctgacttcc agtgagtcag ggagattaat ggacttcctc aaagatgtca    540

tggagtccat gaacaaggaa gaaatggaaa taacaacaca cttccaacgg aagagaagag    600

taagagacaa catgacaaag agaatggtga cacagagaac catagggaag aaaaaacaac    660

gattaaacag aaagagctat ctgatcaggg cattaacctt aaacacaatg accaaggacg    720

ctgagagagg gaaattgaaa cgacgagcaa ttgcaacccc aggaatgcag ataagagggt    780

ttgtatattt tgttgaaaca ttagcccgaa gaatatgtga aaagcttgaa caatcaggat    840

tgccagttgg cggtaatgag aaaaaggcca aactggctaa tgtcgtcaga aaaatgatga    900

ctaattccca agacactgaa ctctccttca ccatcactgg ggacaatacc aaatggaatg    960

aaaatcagaa cccacgcatg ttcctggcaa tgatcacata cataactaga aaccagccag   1020

aatggttcag aaatgttcta agcattgcac cgattatgtt ctcaaataaa atggcaagac   1080

tggggaaagg atatatgttt gaaagcaaaa gtatgaaatt gagaactcaa ataccagcag   1140

aaatgctcgc aagcattgat ctgaaatatt tcaatgattc aacaaaaaag aaaattgaga   1200

agatacgacc accctgaatt c                                              1221


<210> SEQ ID NO 52
<211> LENGTH: 20
<212> TYPE: DNA
<213> ORGANISM: Artificial
<220> FEATURE:
<223> OTHER INFORMATION: Synthetic Primer

<400> SEQUENCE: 52

aaaacaagga tttttcacg                                                  20


<210> SEQ ID NO 53
<211> LENGTH: 1234
<212> TYPE: DNA
<213> ORGANISM: Equine influenza virus H3N8
<220> FEATURE:
<221> NAME/KEY: CDS
<222> LOCATION: (1)..(1188)

<400> SEQUENCE: 53

atg aaa ttg aga act caa ata cca gca gaa atg ctc gca agc att gat       48
Met Lys Leu Arg Thr Gln Ile Pro Ala Glu Met Leu Ala Ser Ile Asp
1               5                   10                  15

ctg aaa tat ttc aat gat tca aca aaa aag aaa att gag aag ata cga       96
Leu Lys Tyr Phe Asn Asp Ser Thr Lys Lys Lys Ile Glu Lys Ile Arg
            20                  25                  30

cca ctt ctg gtc gat ggg act gct tca ctg agt cct ggc atg atg atg      144
Pro Leu Leu Val Asp Gly Thr Ala Ser Leu Ser Pro Gly Met Met Met
        35                  40                  45

gga atg ttc aac atg ttg agc act gta cta ggt gta tcc ata tta aac      192
Gly Met Phe Asn Met Leu Ser Thr Val Leu Gly Val Ser Ile Leu Asn
    50                  55                  60

ctg ggc cag agg aaa tac aca aag acc aca tac tgg tgg gat ggt ctg      240
Leu Gly Gln Arg Lys Tyr Thr Lys Thr Thr Tyr Trp Trp Asp Gly Leu
65                  70                  75                  80
```

-continued

```
caa tca tcc gat gat ttt gct ttg ata gtg aat gcg cct aat cat gaa      288
Gln Ser Ser Asp Asp Phe Ala Leu Ile Val Asn Ala Pro Asn His Glu
                85                  90                  95

gga ata cag gct gga gta gac aga ttc tat aga act tgc aaa ctg gtc      336
Gly Ile Gln Ala Gly Val Asp Arg Phe Tyr Arg Thr Cys Lys Leu Val
            100                 105                 110

ggg atc aac atg agc aaa aag aag tcc tac ata aat aga acc ggc aca      384
Gly Ile Asn Met Ser Lys Lys Lys Ser Tyr Ile Asn Arg Thr Gly Thr
        115                 120                 125

ttc gaa ttc aca agc ttt ttc tac cgg tat ggt ttt gtc gcc aat ttc      432
Phe Glu Phe Thr Ser Phe Phe Tyr Arg Tyr Gly Phe Val Ala Asn Phe
    130                 135                 140

agc atg gag cta ccc agt ttt ggg gtt tcc ggg ata aat gaa tct gca      480
Ser Met Glu Leu Pro Ser Phe Gly Val Ser Gly Ile Asn Glu Ser Ala
145                 150                 155                 160

gac atg agc att gga atg aca gtt atc aaa aac aac atg ata aat aat      528
Asp Met Ser Ile Gly Met Thr Val Ile Lys Asn Asn Met Ile Asn Asn
                165                 170                 175

gat ctc ggt ccc gcc acg gca caa atg gca ctc caa ctc ttc att aag      576
Asp Leu Gly Pro Ala Thr Ala Gln Met Ala Leu Gln Leu Phe Ile Lys
            180                 185                 190

gat tat cgg tac aca tac cgg tgc cat aga ggc gat acc cag ata caa      624
Asp Tyr Arg Tyr Thr Tyr Arg Cys His Arg Gly Asp Thr Gln Ile Gln
        195                 200                 205

acc aga aga tcc ttt gag ttg aag aaa ctg tgg gaa cag act cga tca      672
Thr Arg Arg Ser Phe Glu Leu Lys Lys Leu Trp Glu Gln Thr Arg Ser
    210                 215                 220

aag act ggt cta ctg gta tca gat ggg ggt cca aac cta tac aac atc      720
Lys Thr Gly Leu Leu Val Ser Asp Gly Gly Pro Asn Leu Tyr Asn Ile
225                 230                 235                 240

aga aac cta cac atc ccg gaa gtc tgt ttg aaa tgg gag ctg atg gat      768
Arg Asn Leu His Ile Pro Glu Val Cys Leu Lys Trp Glu Leu Met Asp
                245                 250                 255

gaa gat tat aaa ggg agg cta tgt aat cca ttg aat cct ttc gtt agc      816
Glu Asp Tyr Lys Gly Arg Leu Cys Asn Pro Leu Asn Pro Phe Val Ser
            260                 265                 270

cac aaa gaa att gaa tca gtg aac agt gca gta gta atg cct gcg cat      864
His Lys Glu Ile Glu Ser Val Asn Ser Ala Val Val Met Pro Ala His
        275                 280                 285

ggc cct gcc aaa agc atg gag tat gat gct gtt gca aca aca cac tct      912
Gly Pro Ala Lys Ser Met Glu Tyr Asp Ala Val Ala Thr Thr His Ser
    290                 295                 300

tgg atc ccc aag agg aac cgg tcc ata ttg aac aca agt caa agg gga      960
Trp Ile Pro Lys Arg Asn Arg Ser Ile Leu Asn Thr Ser Gln Arg Gly
305                 310                 315                 320

ata ctc gaa gat gag cag atg tat cag aaa tgc tgc aac ctg ttt gaa     1008
Ile Leu Glu Asp Glu Gln Met Tyr Gln Lys Cys Cys Asn Leu Phe Glu
                325                 330                 335

aaa ttc ttc ccc agc agc tca tac aga aga cca gtc gga att tct agt     1056
Lys Phe Phe Pro Ser Ser Ser Tyr Arg Arg Pro Val Gly Ile Ser Ser
            340                 345                 350

atg gtt gag gcc atg gtg tcc agg gcc cgc att gat gca cga att gac     1104
Met Val Glu Ala Met Val Ser Arg Ala Arg Ile Asp Ala Arg Ile Asp
        355                 360                 365

ttc gaa tct gga cgg ata aag aag gat gag ttc gct gag atc atg aag     1152
Phe Glu Ser Gly Arg Ile Lys Lys Asp Glu Phe Ala Glu Ile Met Lys
    370                 375                 380

atc tgt tcc acc att gaa gag ctc aga cgg caa aaa tagtgaattt          1198
Ile Cys Ser Thr Ile Glu Glu Leu Arg Arg Gln Lys
```

-continued 385 390 395 agcttgatct tcgtgaaaaa atgccttgtt tctact 1234

<210> SEQ ID NO 54
<211> LENGTH: 396
<212> TYPE: PRT
<213> ORGANISM: Equine influenza virus H3N8

<400> SEQUENCE: 54

Met Lys Leu Arg Thr Gln Ile Pro Ala Glu Met Leu Ala Ser Ile Asp
1 5 10 15

Leu Lys Tyr Phe Asn Asp Ser Thr Lys Lys Lys Ile Glu Lys Ile Arg
20 25 30

Pro Leu Leu Val Asp Gly Thr Ala Ser Leu Ser Pro Gly Met Met Met
35 40 45

Gly Met Phe Asn Met Leu Ser Thr Val Leu Gly Val Ser Ile Leu Asn
50 55 60

Leu Gly Gln Arg Lys Tyr Thr Lys Thr Thr Tyr Trp Trp Asp Gly Leu
65 70 75 80

Gln Ser Ser Asp Asp Phe Ala Leu Ile Val Asn Ala Pro Asn His Glu
85 90 95

Gly Ile Gln Ala Gly Val Asp Arg Phe Tyr Arg Thr Cys Lys Leu Val
100 105 110

Gly Ile Asn Met Ser Lys Lys Lys Ser Tyr Ile Asn Arg Thr Gly Thr
115 120 125

Phe Glu Phe Thr Ser Phe Phe Tyr Arg Tyr Gly Phe Val Ala Asn Phe
130 135 140

Ser Met Glu Leu Pro Ser Phe Gly Val Ser Gly Ile Asn Glu Ser Ala
145 150 155 160

Asp Met Ser Ile Gly Met Thr Val Ile Lys Asn Asn Met Ile Asn Asn
165 170 175

Asp Leu Gly Pro Ala Thr Ala Gln Met Ala Leu Gln Leu Phe Ile Lys
180 185 190

Asp Tyr Arg Tyr Thr Tyr Arg Cys His Arg Gly Asp Thr Gln Ile Gln
195 200 205

Thr Arg Arg Ser Phe Glu Leu Lys Lys Leu Trp Glu Gln Thr Arg Ser
210 215 220

Lys Thr Gly Leu Leu Val Ser Asp Gly Gly Pro Asn Leu Tyr Asn Ile
225 230 235 240

Arg Asn Leu His Ile Pro Glu Val Cys Leu Lys Trp Glu Leu Met Asp
245 250 255

Glu Asp Tyr Lys Gly Arg Leu Cys Asn Pro Leu Asn Pro Phe Val Ser
260 265 270

His Lys Glu Ile Glu Ser Val Asn Ser Ala Val Val Met Pro Ala His
275 280 285

Gly Pro Ala Lys Ser Met Glu Tyr Asp Ala Val Ala Thr Thr His Ser
290 295 300

Trp Ile Pro Lys Arg Asn Arg Ser Ile Leu Asn Thr Ser Gln Arg Gly
305 310 315 320

Ile Leu Glu Asp Glu Gln Met Tyr Gln Lys Cys Cys Asn Leu Phe Glu
325 330 335

Lys Phe Phe Pro Ser Ser Ser Tyr Arg Arg Pro Val Gly Ile Ser Ser
340 345 350

Met Val Glu Ala Met Val Ser Arg Ala Arg Ile Asp Ala Arg Ile Asp

-continued

```
        355                 360                 365

Phe Glu Ser Gly Arg Ile Lys Lys Asp Glu Phe Ala Glu Ile Met Lys
    370                 375                 380

Ile Cys Ser Thr Ile Glu Glu Leu Arg Arg Gln Lys
385                 390                 395


<210> SEQ ID NO 55
<211> LENGTH: 20
<212> TYPE: DNA
<213> ORGANISM: Artificial
<220> FEATURE:
<223> OTHER INFORMATION: Synthetic Primer

<400> SEQUENCE: 55

taaatagaac cggcacattc                                                  20


<210> SEQ ID NO 56
<211> LENGTH: 17
<212> TYPE: DNA
<213> ORGANISM: Artificial
<220> FEATURE:
<223> OTHER INFORMATION: Synthetic Primer

<400> SEQUENCE: 56

caaagaaatt gaatcag                                                     17


<210> SEQ ID NO 57
<211> LENGTH: 18
<212> TYPE: DNA
<213> ORGANISM: Artificial
<220> FEATURE:
<223> OTHER INFORMATION: Synthetic Primer

<400> SEQUENCE: 57

caagcattac tactgcac                                                    18


<210> SEQ ID NO 58
<211> LENGTH: 19
<212> TYPE: DNA
<213> ORGANISM: Artificial
<220> FEATURE:
<223> OTHER INFORMATION: Synthetic Primer

<400> SEQUENCE: 58

agtctgttcc cacagtttc                                                   19


<210> SEQ ID NO 59
<211> LENGTH: 20
<212> TYPE: DNA
<213> ORGANISM: Artificial
<220> FEATURE:
<223> OTHER INFORMATION: Synthetic Primer

<400> SEQUENCE: 59

gaattcgaat gtgccggttc                                                  20


<210> SEQ ID NO 60
<211> LENGTH: 1188
<212> TYPE: DNA
<213> ORGANISM: Equine influenza virus H3N8

<400> SEQUENCE: 60

atgaaattga gaactcaaat accagcagaa atgctcgcaa gcattgatct gaaatatttc      60

aatgattcaa caaaaaagaa aattgagaag atacgaccac ttctggtcga tgggactgct     120
```

-continued tcactgagtc ctggcatgat gatgggaatg ttcaacatgt tgagcactgt actaggtgta 180
tccatattaa acctgggcca gaggaaatac acaaagacca catactggtg ggatggtctg 240
caatcatccg atgattttgc tttgatagtg aatgcgccta atcatgaagg aatacaggct 300
ggagtagaca gattctatag aacttgcaaa ctggtcggga tcaacatgag caaaaagaag 360
tcctacataa atagaaccgg cacattcgaa ttcacaagct tttctaccg gtatggtttt 420 gtcgccaatt tcagcatgga gctacccagt tttggggttt ccgggataaa tgaatctgca 480
gacatgagca ttggaatgac agttatcaaa aacaacatga taaataatga tctcggtccc 540
gccacggcac aaatggcact ccaactcttc attaaggatt atcggtacac ataccggtgc 600
catagaggcg atacccagat acaaaccaga agatcctttg agttgaagaa actgtgggaa 660
cagactcgat caaagactgg tctactggta tcagatgggg gtccaaacct atacaacatc 720
agaaacctac acatcccgga agtctgtttg aaatgggagc tgatggatga agattataaa 780
gggaggctat gtaatccatt gaatcctttc gttagccaca aagaaattga atcagtgaac 840
agtgcagtag taatgcctgc gcatggccct gccaaaagca tggagtatga tgctgttgca 900
acaacacact cttggatccc caagaggaac cggtccatat tgaacacaag tcaaagggga 960
atactcgaag atgagcagat gtatcagaaa tgctgcaacc tgtttgaaaa attcttcccc 1020
agcagctcat acagaagacc agtcggaatt tctagtatgg ttgaggccat ggtgtccagg 1080
gcccgcattg atgcacgaat tgacttcgaa tctggacgga taaagaagga tgagttcgct 1140
gagatcatga agatctgttc caccattgaa gagctcagac ggcaaaaa 1188

<210> SEQ ID NO 61
<211> LENGTH: 1240
<212> TYPE: DNA
<213> ORGANISM: Equine influenza virus H3N8
<220> FEATURE:
<221> NAME/KEY: CDS
<222> LOCATION: (8)..(1195)

<400> SEQUENCE: 61 caaaagt atg aaa ttg aga act caa ata cca gca gaa atg ctc gca agc 49
Met Lys Leu Arg Thr Gln Ile Pro Ala Glu Met Leu Ala Ser
1 5 10 att gat ctg aaa tat ttc aat gat tca aca aaa aag aaa att gag aag 97
Ile Asp Leu Lys Tyr Phe Asn Asp Ser Thr Lys Lys Lys Ile Glu Lys
15 20 25 30 ata cga cca ctt ctg gtc gat ggg act gct tca ctg agt cct ggc atg 145
Ile Arg Pro Leu Leu Val Asp Gly Thr Ala Ser Leu Ser Pro Gly Met
35 40 45 atg atg gga atg ttc aac atg ttg agc act gta cta ggt gta tcc ata 193
Met Met Gly Met Phe Asn Met Leu Ser Thr Val Leu Gly Val Ser Ile
50 55 60 tta aac ctg ggc cag agg aaa tac aca aag acc aca tac tgg tgg gat 241
Leu Asn Leu Gly Gln Arg Lys Tyr Thr Lys Thr Thr Tyr Trp Trp Asp
65 70 75 ggt ctg caa tca tcc gat gat ttt gct ttg ata gtg aat gcg cct aat 289
Gly Leu Gln Ser Ser Asp Asp Phe Ala Leu Ile Val Asn Ala Pro Asn
80 85 90 cat gaa gga ata cag gct gga gta gac aga ttc tat aga act tgc aaa 337
His Glu Gly Ile Gln Ala Gly Val Asp Arg Phe Tyr Arg Thr Cys Lys
95 100 105 110 ctg gtc ggg atc aac atg agc aaa aag aag tcc tac ata aat aga acc 385
Leu Val Gly Ile Asn Met Ser Lys Lys Lys Ser Tyr Ile Asn Arg Thr
115 120 125

-continued

```
ggc tca ttc gaa ttc aca agc ttt ttc tac cgg tat ggt ttt gtc gcc      433
Gly Ser Phe Glu Phe Thr Ser Phe Phe Tyr Arg Tyr Gly Phe Val Ala
            130                 135                 140

aat ttc agc atg gag cta ccc agt ttt ggg gtt tcc ggg ata aat gaa      481
Asn Phe Ser Met Glu Leu Pro Ser Phe Gly Val Ser Gly Ile Asn Glu
        145                 150                 155

tct gca gac atg agc att gga atg aca gtt atc aaa aac aac atg ata      529
Ser Ala Asp Met Ser Ile Gly Met Thr Val Ile Lys Asn Asn Met Ile
    160                 165                 170

aat aat gat ctc ggt ccc gcc acg gca caa atg gca ctc caa ctc ttc      577
Asn Asn Asp Leu Gly Pro Ala Thr Ala Gln Met Ala Leu Gln Leu Phe
175                 180                 185                 190

att aag gat tat cgg tac aca tac cgg tgc cat aga ggc gat acc cag      625
Ile Lys Asp Tyr Arg Tyr Thr Tyr Arg Cys His Arg Gly Asp Thr Gln
                195                 200                 205

ata caa acc aga aga tcc ttt gag ttg aag aaa ctg tgg gaa cag act      673
Ile Gln Thr Arg Arg Ser Phe Glu Leu Lys Lys Leu Trp Glu Gln Thr
            210                 215                 220

cga tca aag act ggt cta ctg gta tca gat ggg ggt cca aac cta tac      721
Arg Ser Lys Thr Gly Leu Leu Val Ser Asp Gly Gly Pro Asn Leu Tyr
        225                 230                 235

aac atc aga aac cta cac atc ccg gaa gtc tgt ttg aaa tgg gag ctg      769
Asn Ile Arg Asn Leu His Ile Pro Glu Val Cys Leu Lys Trp Glu Leu
    240                 245                 250

atg gat gaa gat tat aaa ggg agg cta tgt aat cca ttg aat cct ttc      817
Met Asp Glu Asp Tyr Lys Gly Arg Leu Cys Asn Pro Leu Asn Pro Phe
255                 260                 265                 270

gtt agc cac aaa gaa att gaa tca gtg aac agt gca gta gta atg cct      865
Val Ser His Lys Glu Ile Glu Ser Val Asn Ser Ala Val Val Met Pro
                275                 280                 285

gcg cat ggc cct gcc aaa agc atg gag tat gat gct gtt gca aca aca      913
Ala His Gly Pro Ala Lys Ser Met Glu Tyr Asp Ala Val Ala Thr Thr
            290                 295                 300

cac tct tgg atc ccc aag agg aac cgg tcc ata ttg aac aca agt caa      961
His Ser Trp Ile Pro Lys Arg Asn Arg Ser Ile Leu Asn Thr Ser Gln
        305                 310                 315

agg gga ata ctc gaa gat gag cag atg tat cag aaa tgc tgc aac ctg     1009
Arg Gly Ile Leu Glu Asp Glu Gln Met Tyr Gln Lys Cys Cys Asn Leu
    320                 325                 330

ttt gaa aaa ttc ttc ccc agc agc tca tac aga aga cca gtc gga att     1057
Phe Glu Lys Phe Phe Pro Ser Ser Ser Tyr Arg Arg Pro Val Gly Ile
335                 340                 345                 350

tct agt atg gtt gag gcc atg gtg tcc agg gcc cgc att gat gca cga     1105
Ser Ser Met Val Glu Ala Met Val Ser Arg Ala Arg Ile Asp Ala Arg
                355                 360                 365

att gac ttc gaa tct gga cgg ata aag aag gat gag ttc gct gag atc     1153
Ile Asp Phe Glu Ser Gly Arg Ile Lys Lys Asp Glu Phe Ala Glu Ile
            370                 375                 380

atg aag atc tgt tcc acc att gaa gag ctc aga cgg caa aaa             1195
Met Lys Ile Cys Ser Thr Ile Glu Glu Leu Arg Arg Gln Lys
        385                 390                 395

tagtgaattt agcttgatct tcgtgaaaaa atgccttgtt ctact                   1240
```

<210> SEQ ID NO 62
<211> LENGTH: 396
<212> TYPE: PRT
<213> ORGANISM: Equine influenza virus H3N8

<400> SEQUENCE: 62

-continued

```
Met Lys Leu Arg Thr Gln Ile Pro Ala Glu Met Leu Ala Ser Ile Asp
1               5                   10                  15

Leu Lys Tyr Phe Asn Asp Ser Thr Lys Lys Lys Ile Glu Lys Ile Arg
            20                  25                  30

Pro Leu Leu Val Asp Gly Thr Ala Ser Leu Ser Pro Gly Met Met Met
        35                  40                  45

Gly Met Phe Asn Met Leu Ser Thr Val Leu Gly Val Ser Ile Leu Asn
    50                  55                  60

Leu Gly Gln Arg Lys Tyr Thr Lys Thr Thr Tyr Trp Trp Asp Gly Leu
65                  70                  75                  80

Gln Ser Ser Asp Asp Phe Ala Leu Ile Val Asn Ala Pro Asn His Glu
                85                  90                  95

Gly Ile Gln Ala Gly Val Asp Arg Phe Tyr Arg Thr Cys Lys Leu Val
            100                 105                 110

Gly Ile Asn Met Ser Lys Lys Lys Ser Tyr Ile Asn Arg Thr Gly Ser
        115                 120                 125

Phe Glu Phe Thr Ser Phe Phe Tyr Arg Tyr Gly Phe Val Ala Asn Phe
    130                 135                 140

Ser Met Glu Leu Pro Ser Phe Gly Val Ser Gly Ile Asn Glu Ser Ala
145                 150                 155                 160

Asp Met Ser Ile Gly Met Thr Val Ile Lys Asn Asn Met Ile Asn Asn
                165                 170                 175

Asp Leu Gly Pro Ala Thr Ala Gln Met Ala Leu Gln Leu Phe Ile Lys
            180                 185                 190

Asp Tyr Arg Tyr Thr Tyr Arg Cys His Arg Gly Asp Thr Gln Ile Gln
        195                 200                 205

Thr Arg Arg Ser Phe Glu Leu Lys Lys Leu Trp Glu Gln Thr Arg Ser
    210                 215                 220

Lys Thr Gly Leu Leu Val Ser Asp Gly Gly Pro Asn Leu Tyr Asn Ile
225                 230                 235                 240

Arg Asn Leu His Ile Pro Glu Val Cys Leu Lys Trp Glu Leu Met Asp
                245                 250                 255

Glu Asp Tyr Lys Gly Arg Leu Cys Asn Pro Leu Asn Pro Phe Val Ser
            260                 265                 270

His Lys Glu Ile Glu Ser Val Asn Ser Ala Val Val Met Pro Ala His
        275                 280                 285

Gly Pro Ala Lys Ser Met Glu Tyr Asp Ala Val Ala Thr Thr His Ser
    290                 295                 300

Trp Ile Pro Lys Arg Asn Arg Ser Ile Leu Asn Thr Ser Gln Arg Gly
305                 310                 315                 320

Ile Leu Glu Asp Glu Gln Met Tyr Gln Lys Cys Cys Asn Leu Phe Glu
                325                 330                 335

Lys Phe Phe Pro Ser Ser Ser Tyr Arg Arg Pro Val Gly Ile Ser Ser
            340                 345                 350

Met Val Glu Ala Met Val Ser Arg Ala Arg Ile Asp Ala Arg Ile Asp
        355                 360                 365

Phe Glu Ser Gly Arg Ile Lys Lys Asp Glu Phe Ala Glu Ile Met Lys
    370                 375                 380

Ile Cys Ser Thr Ile Glu Glu Leu Arg Arg Gln Lys
385                 390                 395
```

<210> SEQ ID NO 63
<211> LENGTH: 1241
<212> TYPE: DNA

-continued

```
<213> ORGANISM: Equine influenza virus H3N8
<220> FEATURE:
<221> NAME/KEY: CDS
<222> LOCATION: (8)..(1195)

<400> SEQUENCE: 63

caaaagt atg aaa ttg aga act caa ata cca gca gaa atg ctc gca agc       49
        Met Lys Leu Arg Thr Gln Ile Pro Ala Glu Met Leu Ala Ser
        1               5                   10

att gat ctg aaa tat ttc aat gat tca aca aaa aag aaa att gag aag       97
Ile Asp Leu Lys Tyr Phe Asn Asp Ser Thr Lys Lys Lys Ile Glu Lys
15                  20                  25                  30

ata cga cca ctt ctg gtc gat ggg act gct tca ctg agt cct ggc atg      145
Ile Arg Pro Leu Leu Val Asp Gly Thr Ala Ser Leu Ser Pro Gly Met
                35                  40                  45

atg atg gga atg ttc aac atg ttg agc act gta cta ggt gta tcc ata      193
Met Met Gly Met Phe Asn Met Leu Ser Thr Val Leu Gly Val Ser Ile
            50                  55                  60

tta aac ctg ggc cag agg aaa tac aca aag acc aca tac tgg tgg gat      241
Leu Asn Leu Gly Gln Arg Lys Tyr Thr Lys Thr Thr Tyr Trp Trp Asp
        65                  70                  75

ggt ctg caa tca tcc gat gat ttt gct ttg ata gtg aat gcg cct aat      289
Gly Leu Gln Ser Ser Asp Asp Phe Ala Leu Ile Val Asn Ala Pro Asn
    80                  85                  90

cat gaa gga ata cag gct gga gta gac aga ttc tat aga act tgc aaa      337
His Glu Gly Ile Gln Ala Gly Val Asp Arg Phe Tyr Arg Thr Cys Lys
95                  100                 105                 110

ctg gtc ggg atc aac atg agc aaa aag aag tcc tac ata aat aga acc      385
Leu Val Gly Ile Asn Met Ser Lys Lys Lys Ser Tyr Ile Asn Arg Thr
                115                 120                 125

ggc aca ttc gaa ttc aca agc ttt ttc tac cgg tat ggt ttt gtc gcc      433
Gly Thr Phe Glu Phe Thr Ser Phe Phe Tyr Arg Tyr Gly Phe Val Ala
            130                 135                 140

aat ttc agc atg gag cta ccc agt ttt ggg gtt tcc ggg ata aat gaa      481
Asn Phe Ser Met Glu Leu Pro Ser Phe Gly Val Ser Gly Ile Asn Glu
        145                 150                 155

tct gca gac atg agc att gga atg aca gtt atc aaa aac aac atg ata      529
Ser Ala Asp Met Ser Ile Gly Met Thr Val Ile Lys Asn Asn Met Ile
    160                 165                 170

aat aat gat ctc ggt ccc gcc acg gca caa atg gca ctc caa ctc ttc      577
Asn Asn Asp Leu Gly Pro Ala Thr Ala Gln Met Ala Leu Gln Leu Phe
175                 180                 185                 190

att aag gat tat cgg tac aca tac cgg tgt caa aga ggc gat acc cag      625
Ile Lys Asp Tyr Arg Tyr Thr Tyr Arg Cys Gln Arg Gly Asp Thr Gln
                195                 200                 205

ata caa acc aga aga tcc ttt gag ttg aag aaa ctg tgg gaa cag act      673
Ile Gln Thr Arg Arg Ser Phe Glu Leu Lys Lys Leu Trp Glu Gln Thr
            210                 215                 220

cga tca aag act ggt cta ctg gta tca gat ggg ggt cca aac cta tac      721
Arg Ser Lys Thr Gly Leu Leu Val Ser Asp Gly Gly Pro Asn Leu Tyr
        225                 230                 235

aac atc aga aac cta cac atc ccg gaa gtc tgt ttg aaa tgg gag ctg      769
Asn Ile Arg Asn Leu His Ile Pro Glu Val Cys Leu Lys Trp Glu Leu
    240                 245                 250

atg gat gaa gat tat aaa ggg agg cta tgt aat cca ttg aat cct ttc      817
Met Asp Glu Asp Tyr Lys Gly Arg Leu Cys Asn Pro Leu Asn Pro Phe
255                 260                 265                 270

gtt agc cac aaa gaa att gaa tca gtg aac agt gca gta gta atg cct      865
Val Ser His Lys Glu Ile Glu Ser Val Asn Ser Ala Val Val Met Pro
                275                 280                 285
```

-continued

```
gcg cat ggc cct gcc aaa agc atg gag tat gat gct gtt gca aca aca      913
Ala His Gly Pro Ala Lys Ser Met Glu Tyr Asp Ala Val Ala Thr Thr
            290                 295                 300

cac tct tgg atc ccc aag agg aac cgg tcc ata ttg aac aca agt caa      961
His Ser Trp Ile Pro Lys Arg Asn Arg Ser Ile Leu Asn Thr Ser Gln
        305                 310                 315

agg gga ata ctc gaa gat gag cag atg tat cag aaa tgc tgc aac ctg     1009
Arg Gly Ile Leu Glu Asp Glu Gln Met Tyr Gln Lys Cys Cys Asn Leu
    320                 325                 330

ttt gaa aaa ttc ttc ccc agc agc tca tac aga aaa cca gtc gga att     1057
Phe Glu Lys Phe Phe Pro Ser Ser Ser Tyr Arg Lys Pro Val Gly Ile
335                 340                 345                 350

tct agt atg gtt gag gcc atg gtg tcc agg gcc cgc att gat gca cga     1105
Ser Ser Met Val Glu Ala Met Val Ser Arg Ala Arg Ile Asp Ala Arg
                355                 360                 365

att gac ttc gaa tct gga cgg ata aag aag gat gag ttc gct gag atc     1153
Ile Asp Phe Glu Ser Gly Arg Ile Lys Lys Asp Glu Phe Ala Glu Ile
            370                 375                 380

atg aag atc tgt tcc acc att gaa gag ctc aga cgg caa aaa             1195
Met Lys Ile Cys Ser Thr Ile Glu Glu Leu Arg Arg Gln Lys
        385                 390                 395

tagtgaattt agcttgatct tcgtgaaaaa atgccttgtt tctact                  1241


<210> SEQ ID NO 64
<211> LENGTH: 396
<212> TYPE: PRT
<213> ORGANISM: Equine influenza virus H3N8

<400> SEQUENCE: 64

Met Lys Leu Arg Thr Gln Ile Pro Ala Glu Met Leu Ala Ser Ile Asp
1               5                   10                  15

Leu Lys Tyr Phe Asn Asp Ser Thr Lys Lys Lys Ile Glu Lys Ile Arg
            20                  25                  30

Pro Leu Leu Val Asp Gly Thr Ala Ser Leu Ser Pro Gly Met Met Met
        35                  40                  45

Gly Met Phe Asn Met Leu Ser Thr Val Leu Gly Val Ser Ile Leu Asn
    50                  55                  60

Leu Gly Gln Arg Lys Tyr Thr Lys Thr Thr Tyr Trp Trp Asp Gly Leu
65                  70                  75                  80

Gln Ser Ser Asp Asp Phe Ala Leu Ile Val Asn Ala Pro Asn His Glu
                85                  90                  95

Gly Ile Gln Ala Gly Val Asp Arg Phe Tyr Arg Thr Cys Lys Leu Val
            100                 105                 110

Gly Ile Asn Met Ser Lys Lys Lys Ser Tyr Ile Asn Arg Thr Gly Thr
        115                 120                 125

Phe Glu Phe Thr Ser Phe Phe Tyr Arg Tyr Gly Phe Val Ala Asn Phe
    130                 135                 140

Ser Met Glu Leu Pro Ser Phe Gly Val Ser Gly Ile Asn Glu Ser Ala
145                 150                 155                 160

Asp Met Ser Ile Gly Met Thr Val Ile Lys Asn Asn Met Ile Asn Asn
                165                 170                 175

Asp Leu Gly Pro Ala Thr Ala Gln Met Ala Leu Gln Leu Phe Ile Lys
            180                 185                 190

Asp Tyr Arg Tyr Thr Tyr Arg Cys Gln Arg Gly Asp Thr Gln Ile Gln
        195                 200                 205

Thr Arg Arg Ser Phe Glu Leu Lys Lys Leu Trp Glu Gln Thr Arg Ser
    210                 215                 220
```

-continued

```
Lys Thr Gly Leu Leu Val Ser Asp Gly Gly Pro Asn Leu Tyr Asn Ile
225                 230                 235                 240

Arg Asn Leu His Ile Pro Glu Val Cys Leu Lys Trp Glu Leu Met Asp
                245                 250                 255

Glu Asp Tyr Lys Gly Arg Leu Cys Asn Pro Leu Asn Pro Phe Val Ser
            260                 265                 270

His Lys Glu Ile Glu Ser Val Asn Ser Ala Val Val Met Pro Ala His
        275                 280                 285

Gly Pro Ala Lys Ser Met Glu Tyr Asp Ala Val Ala Thr Thr His Ser
    290                 295                 300

Trp Ile Pro Lys Arg Asn Arg Ser Ile Leu Asn Thr Ser Gln Arg Gly
305                 310                 315                 320

Ile Leu Glu Asp Glu Gln Met Tyr Gln Lys Cys Cys Asn Leu Phe Glu
                325                 330                 335

Lys Phe Phe Pro Ser Ser Ser Tyr Arg Lys Pro Val Gly Ile Ser Ser
            340                 345                 350

Met Val Glu Ala Met Val Ser Arg Ala Arg Ile Asp Ala Arg Ile Asp
        355                 360                 365

Phe Glu Ser Gly Arg Ile Lys Lys Asp Glu Phe Ala Glu Ile Met Lys
    370                 375                 380

Ile Cys Ser Thr Ile Glu Glu Leu Arg Arg Gln Lys
385                 390                 395


<210> SEQ ID NO 65
<211> LENGTH: 1188
<212> TYPE: DNA
<213> ORGANISM: Equine influenza virus H3N8

<400> SEQUENCE: 65

atgaaattga gaactcaaat accagcagaa atgctcgcaa gcattgatct gaaatatttc      60

aatgattcaa caaaaaagaa aattgagaag atacgaccac ttctggtcga tgggactgct     120

tcactgagtc ctggcatgat gatgggaatg ttcaacatgt tgagcactgt actaggtgta     180

tccatattaa acctgggcca gaggaaatac acaaagacca catactggtg ggatggtctg     240

caatcatccg atgattttgc tttgatagtg aatgcgccta atcatgaagg aatacaggct     300

ggagtagaca gattctatag aacttgcaaa ctggtcggga tcaacatgag caaaaagaag     360

tcctacataa atagaaccgg cacattcgaa ttcacaagct ttttctaccg gtatggtttt     420

gtcgccaatt tcagcatgga gctacccagt tttggggttt ccgggataaa tgaatctgca     480

gacatgagca ttggaatgac agttatcaaa aacaacatga taaataatga tctcggtccc     540

gccacggcac aaatggcact ccaactcttc attaaggatt atcggtacac ataccggtgt     600

caaagaggcg atacccagat acaaaccaga agatcctttg agttgaagaa actgtgggaa     660

cagactcgat caaagactgg tctactggta tcagatgggg gtccaaacct atacaacatc     720

agaaacctac acatcccgga agtctgtttg aaatgggagc tgatggatga agattataaa     780

gggaggctat gtaatccatt gaatcctttc gttagccaca aagaaattga atcagtgaac     840

agtgcagtag taatgcctgc gcatggccct gccaaaagca tggagtatga tgctgttgca     900

acaacacact cttggatccc caagaggaac cggtccatat tgaacacaag tcaaagggga     960

atactcgaag atgagcagat gtatcagaaa tgctgcaacc tgtttgaaaa attcttcccc    1020

agcagctcat acagaaaacc agtcggaatt tctagtatgg ttgaggccat ggtgtccagg    1080

gcccgcattg atgcacgaat tgacttcgaa tctggacgga taaagaagga tgagttcgct    1140
```

-continued

```
gagatcatga agatctgttc caccattgaa gagctcagac ggcaaaaa              1188


<210> SEQ ID NO 66
<211> LENGTH: 1241
<212> TYPE: DNA
<213> ORGANISM: Equine influenza virus H3N8
<220> FEATURE:
<221> NAME/KEY: CDS
<222> LOCATION: (8)..(1195)

<400> SEQUENCE: 66

caaaagt atg aaa ttg aga act caa ata cca gca gaa atg ctc gca agc       49
        Met Lys Leu Arg Thr Gln Ile Pro Ala Glu Met Leu Ala Ser
        1               5                   10

att gat ctg aaa tat ttc aat gat tca aca aaa aag aaa att gag aag       97
Ile Asp Leu Lys Tyr Phe Asn Asp Ser Thr Lys Lys Lys Ile Glu Lys
15                  20                  25                  30

ata cga cca ctt ctg gtc gat ggg act gct tca ctg agt cct ggc atg      145
Ile Arg Pro Leu Leu Val Asp Gly Thr Ala Ser Leu Ser Pro Gly Met
                35                  40                  45

atg atg gga atg ttc aac atg ttg agc act gta cta ggt gta tcc ata      193
Met Met Gly Met Phe Asn Met Leu Ser Thr Val Leu Gly Val Ser Ile
            50                  55                  60

tta aac ctg ggc cag agg aaa tac aca aag acc aca tac tgg tgg gat      241
Leu Asn Leu Gly Gln Arg Lys Tyr Thr Lys Thr Thr Tyr Trp Trp Asp
        65                  70                  75

ggt ctg caa tca tcc gat gat ttt gct ttg ata gtg aat gcg cct aat      289
Gly Leu Gln Ser Ser Asp Asp Phe Ala Leu Ile Val Asn Ala Pro Asn
    80                  85                  90

cat gaa gga ata cag gct gga gta gac aga ttc tat aga act tgc aaa      337
His Glu Gly Ile Gln Ala Gly Val Asp Arg Phe Tyr Arg Thr Cys Lys
95                  100                 105                 110

ctg gtc ggg atc aac atg agc aaa aag aag tcc tac ata aat aga acc      385
Leu Val Gly Ile Asn Met Ser Lys Lys Lys Ser Tyr Ile Asn Arg Thr
                115                 120                 125

ggc aca ttc gaa ttc aca agc ttt ttc tac cgg tat ggt ttt gtc gcc      433
Gly Thr Phe Glu Phe Thr Ser Phe Phe Tyr Arg Tyr Gly Phe Val Ala
            130                 135                 140

aat ttc agc atg gag cta ccc agt ttt ggg gtt tcc ggg ata aat gaa      481
Asn Phe Ser Met Glu Leu Pro Ser Phe Gly Val Ser Gly Ile Asn Glu
        145                 150                 155

tct gca gac atg agc att gga atg aca gtt atc aaa aac aac atg ata      529
Ser Ala Asp Met Ser Ile Gly Met Thr Val Ile Lys Asn Asn Met Ile
    160                 165                 170

aat aat gat ctc ggt ccc gcc acg gca caa atg gca ctc caa ctc ttc      577
Asn Asn Asp Leu Gly Pro Ala Thr Ala Gln Met Ala Leu Gln Leu Phe
175                 180                 185                 190

att aag gat tat cgg tac aca tac cgg tgt caa aga ggc gat acc cag      625
Ile Lys Asp Tyr Arg Tyr Thr Tyr Arg Cys Gln Arg Gly Asp Thr Gln
                195                 200                 205

ata caa acc aga aga tcc ttt gag ttg aag aaa ctg tgg gaa cag act      673
Ile Gln Thr Arg Arg Ser Phe Glu Leu Lys Lys Leu Trp Glu Gln Thr
            210                 215                 220

cga tca aag act ggt cta ctg gta tca gat ggg ggt cca aac cta tac      721
Arg Ser Lys Thr Gly Leu Leu Val Ser Asp Gly Gly Pro Asn Leu Tyr
        225                 230                 235

aac atc aga aac cta cac atc ccg gaa gtc tgt ttg aaa tgg gag ctg      769
Asn Ile Arg Asn Leu His Ile Pro Glu Val Cys Leu Lys Trp Glu Leu
    240                 245                 250

atg gat gaa gat tat aaa ggg agg cta tgt aat cca ttg aat cct ttc      817
```

-continued

```
Met Asp Glu Asp Tyr Lys Gly Arg Leu Cys Asn Pro Leu Asn Pro Phe
255                 260                 265                 270

gtt agc cac aaa gaa att gaa tca gtg aac agt gca gta gta atg cct      865
Val Ser His Lys Glu Ile Glu Ser Val Asn Ser Ala Val Val Met Pro
                275                 280                 285

gcg cat ggc cct gcc aaa agc atg gag tat gat gct gtt gca aca aca      913
Ala His Gly Pro Ala Lys Ser Met Glu Tyr Asp Ala Val Ala Thr Thr
            290                 295                 300

cac tct tgg atc ccc aag agg aac cgg tcc ata ttg aac aca agt caa      961
His Ser Trp Ile Pro Lys Arg Asn Arg Ser Ile Leu Asn Thr Ser Gln
        305                 310                 315

agg gga ata ctc gaa gat gag cag atg tat cag aaa tgc tgc aac ctg     1009
Arg Gly Ile Leu Glu Asp Glu Gln Met Tyr Gln Lys Cys Cys Asn Leu
    320                 325                 330

ttt gaa aaa ttc ttc ccc agc agc tca tac aga aga cca gtc gga att     1057
Phe Glu Lys Phe Phe Pro Ser Ser Ser Tyr Arg Arg Pro Val Gly Ile
335                 340                 345                 350

tct agt atg gtt gag gcc atg gtg tcc agg gcc cgc att gat gca cga     1105
Ser Ser Met Val Glu Ala Met Val Ser Arg Ala Arg Ile Asp Ala Arg
                355                 360                 365

att gac ttc gaa tct gga cgg ata aag aag gat gag ttc gct gag atc     1153
Ile Asp Phe Glu Ser Gly Arg Ile Lys Lys Asp Glu Phe Ala Glu Ile
            370                 375                 380

atg aag atc tgt tcc acc att gaa gag ctc aga cgg caa aaa             1195
Met Lys Ile Cys Ser Thr Ile Glu Glu Leu Arg Arg Gln Lys
        385                 390                 395

tagtgaattt agcttgatct tcgtgaaaaa atgccttgtt tctact                  1241


<210> SEQ ID NO 67
<211> LENGTH: 396
<212> TYPE: PRT
<213> ORGANISM: Equine influenza virus H3N8

<400> SEQUENCE: 67

Met Lys Leu Arg Thr Gln Ile Pro Ala Glu Met Leu Ala Ser Ile Asp
1               5                   10                  15

Leu Lys Tyr Phe Asn Asp Ser Thr Lys Lys Lys Ile Glu Lys Ile Arg
            20                  25                  30

Pro Leu Leu Val Asp Gly Thr Ala Ser Leu Ser Pro Gly Met Met Met
        35                  40                  45

Gly Met Phe Asn Met Leu Ser Thr Val Leu Gly Val Ser Ile Leu Asn
    50                  55                  60

Leu Gly Gln Arg Lys Tyr Thr Lys Thr Thr Tyr Trp Trp Asp Gly Leu
65                  70                  75                  80

Gln Ser Ser Asp Asp Phe Ala Leu Ile Val Asn Ala Pro Asn His Glu
                85                  90                  95

Gly Ile Gln Ala Gly Val Asp Arg Phe Tyr Arg Thr Cys Lys Leu Val
            100                 105                 110

Gly Ile Asn Met Ser Lys Lys Lys Ser Tyr Ile Asn Arg Thr Gly Thr
        115                 120                 125

Phe Glu Phe Thr Ser Phe Phe Tyr Arg Tyr Gly Phe Val Ala Asn Phe
    130                 135                 140

Ser Met Glu Leu Pro Ser Phe Gly Val Ser Gly Ile Asn Glu Ser Ala
145                 150                 155                 160

Asp Met Ser Ile Gly Met Thr Val Ile Lys Asn Asn Met Ile Asn Asn
                165                 170                 175

Asp Leu Gly Pro Ala Thr Ala Gln Met Ala Leu Gln Leu Phe Ile Lys
```

-continued

```
            180                 185                 190

Asp Tyr Arg Tyr Thr Tyr Arg Cys Gln Arg Gly Asp Thr Gln Ile Gln
        195                 200                 205

Thr Arg Arg Ser Phe Glu Leu Lys Lys Leu Trp Glu Gln Thr Arg Ser
    210                 215                 220

Lys Thr Gly Leu Leu Val Ser Asp Gly Gly Pro Asn Leu Tyr Asn Ile
225                 230                 235                 240

Arg Asn Leu His Ile Pro Glu Val Cys Leu Lys Trp Glu Leu Met Asp
                245                 250                 255

Glu Asp Tyr Lys Gly Arg Leu Cys Asn Pro Leu Asn Pro Phe Val Ser
            260                 265                 270

His Lys Glu Ile Glu Ser Val Asn Ser Ala Val Val Met Pro Ala His
        275                 280                 285

Gly Pro Ala Lys Ser Met Glu Tyr Asp Ala Val Ala Thr Thr His Ser
    290                 295                 300

Trp Ile Pro Lys Arg Asn Arg Ser Ile Leu Asn Thr Ser Gln Arg Gly
305                 310                 315                 320

Ile Leu Glu Asp Glu Gln Met Tyr Gln Lys Cys Cys Asn Leu Phe Glu
                325                 330                 335

Lys Phe Phe Pro Ser Ser Ser Tyr Arg Arg Pro Val Gly Ile Ser Ser
            340                 345                 350

Met Val Glu Ala Met Val Ser Arg Ala Arg Ile Asp Ala Arg Ile Asp
        355                 360                 365

Phe Glu Ser Gly Arg Ile Lys Lys Asp Glu Phe Ala Glu Ile Met Lys
    370                 375                 380

Ile Cys Ser Thr Ile Glu Glu Leu Arg Arg Gln Lys
385                 390                 395


<210> SEQ ID NO 68
<211> LENGTH: 2341
<212> TYPE: DNA
<213> ORGANISM: Equine influenza virus H3N8
<220> FEATURE:
<221> NAME/KEY: misc_feature
<222> LOCATION: (489)..(489)
<223> OTHER INFORMATION: The 'Xaa' at amino acid location 489 stands
      for Thr, or Ser.
<220> FEATURE:
<221> NAME/KEY: CDS
<222> LOCATION: (25)..(2295)

<400> SEQUENCE: 68

agcaaaagca ggcaaactat ttga atg gat gtc aat ccg act cta ctc ttc        51
                           Met Asp Val Asn Pro Thr Leu Leu Phe
                           1               5

tta aag gtg cca gcg caa aat gct ata agc aca aca ttc cct tat act       99
Leu Lys Val Pro Ala Gln Asn Ala Ile Ser Thr Thr Phe Pro Tyr Thr
10                  15                  20                  25

gga gat cct ccc tac agt cat gga aca ggg aca gga tac acc atg gat      147
Gly Asp Pro Pro Tyr Ser His Gly Thr Gly Thr Gly Tyr Thr Met Asp
                30                  35                  40

act gtc aac aga aca cat caa tac tca gaa aag ggg aaa tgg aca aca      195
Thr Val Asn Arg Thr His Gln Tyr Ser Glu Lys Gly Lys Trp Thr Thr
            45                  50                  55

aac act gag att gga gca cca caa ctt aat cca atc gat gga ccg ctt      243
Asn Thr Glu Ile Gly Ala Pro Gln Leu Asn Pro Ile Asp Gly Pro Leu
        60                  65                  70

cct gaa gac aat gaa cca agt ggg tac gcc caa aca gat tgt gta ttg      291
Pro Glu Asp Asn Glu Pro Ser Gly Tyr Ala Gln Thr Asp Cys Val Leu
```

-continued

```
    75                  80                  85

gaa gca atg gct ttc ctt gaa gaa tcc cat ccc gga atc ttt gaa aat      339
Glu Ala Met Ala Phe Leu Glu Glu Ser His Pro Gly Ile Phe Glu Asn
90                  95                  100                 105

tcg tgt ctt gaa aca atg gag gtg gtt cag cag aca aga gtg gac aaa      387
Ser Cys Leu Glu Thr Met Glu Val Val Gln Gln Thr Arg Val Asp Lys
                110                 115                 120

cta aca caa ggc cga caa act tac gat tgg acc ttg aat agg aat caa      435
Leu Thr Gln Gly Arg Gln Thr Tyr Asp Trp Thr Leu Asn Arg Asn Gln
            125                 130                 135

cct gcc gca aca gca ctt gct aat aca att gaa gtg ttc aga tca aat      483
Pro Ala Ala Thr Ala Leu Ala Asn Thr Ile Glu Val Phe Arg Ser Asn
        140                 145                 150

gat ctg act tcc agt gag tca ggg aga tta atg gac ttc ctc aaa gat      531
Asp Leu Thr Ser Ser Glu Ser Gly Arg Leu Met Asp Phe Leu Lys Asp
    155                 160                 165

gtc atg gag tcc atg aac aag gaa gaa atg gaa ata aca aca cac ttc      579
Val Met Glu Ser Met Asn Lys Glu Glu Met Glu Ile Thr Thr His Phe
170                 175                 180                 185

caa cgg aag aga aga gta aga gac aac atg aca aag aga atg gtg aca      627
Gln Arg Lys Arg Arg Val Arg Asp Asn Met Thr Lys Arg Met Val Thr
                190                 195                 200

cag aga acc ata ggg aag aaa aaa caa cga tta aac aga aag agc tat      675
Gln Arg Thr Ile Gly Lys Lys Lys Gln Arg Leu Asn Arg Lys Ser Tyr
            205                 210                 215

ctg atc agg gca tta acc tta aac aca atg acc aag gac gct gag aga      723
Leu Ile Arg Ala Leu Thr Leu Asn Thr Met Thr Lys Asp Ala Glu Arg
        220                 225                 230

ggg aaa ttg aaa cga cga gca att gca acc cca gga atg cag ata aga      771
Gly Lys Leu Lys Arg Arg Ala Ile Ala Thr Pro Gly Met Gln Ile Arg
    235                 240                 245

ggg ttt gta tat ttt gtt gaa aca tta gcc cga aga ata tgt gaa aag      819
Gly Phe Val Tyr Phe Val Glu Thr Leu Ala Arg Arg Ile Cys Glu Lys
250                 255                 260                 265

ctt gaa caa tca gga ttg cca gtt ggc ggt aat gag aaa aag gcc aaa      867
Leu Glu Gln Ser Gly Leu Pro Val Gly Gly Asn Glu Lys Lys Ala Lys
                270                 275                 280

ctg gct aat gtc gtc aga aaa atg atg act aat tcc caa gac act gaa      915
Leu Ala Asn Val Val Arg Lys Met Met Thr Asn Ser Gln Asp Thr Glu
            285                 290                 295

ctc tcc ttc acc atc act ggg gac aat acc aaa tgg aat gaa aat cag      963
Leu Ser Phe Thr Ile Thr Gly Asp Asn Thr Lys Trp Asn Glu Asn Gln
        300                 305                 310

aac cca cgc atg ttc ctg gca atg atc aca tac ata act aga aac cag     1011
Asn Pro Arg Met Phe Leu Ala Met Ile Thr Tyr Ile Thr Arg Asn Gln
    315                 320                 325

cca gaa tgg ttc aga aat gtt cta agc att gca ccg att atg ttc tca     1059
Pro Glu Trp Phe Arg Asn Val Leu Ser Ile Ala Pro Ile Met Phe Ser
330                 335                 340                 345

aat aaa atg gca aga ctg ggg aaa gga tat atg ttt gaa agc aaa agt     1107
Asn Lys Met Ala Arg Leu Gly Lys Gly Tyr Met Phe Glu Ser Lys Ser
                350                 355                 360

atg aaa ttg aga act caa ata cca gca gaa atg ctc gca agc att gat     1155
Met Lys Leu Arg Thr Gln Ile Pro Ala Glu Met Leu Ala Ser Ile Asp
            365                 370                 375

ctg aaa tat ttc aat gat tca aca aaa aag aaa att gag aag ata cga     1203
Leu Lys Tyr Phe Asn Asp Ser Thr Lys Lys Lys Ile Glu Lys Ile Arg
        380                 385                 390

cca ctt ctg gtc gat ggg act gct tca ctg agt cct ggc atg atg atg     1251
```

-continued

```
Pro Leu Leu Val Asp Gly Thr Ala Ser Leu Ser Pro Gly Met Met Met
    395                 400                 405

gga atg ttc aac atg ttg agc act gta cta ggt gta tcc ata tta aac     1299
Gly Met Phe Asn Met Leu Ser Thr Val Leu Gly Val Ser Ile Leu Asn
410                 415                 420                 425

ctg ggc cag agg aaa tac aca aag acc aca tac tgg tgg gat ggt ctg     1347
Leu Gly Gln Arg Lys Tyr Thr Lys Thr Thr Tyr Trp Trp Asp Gly Leu
                430                 435                 440

caa tca tcc gat gat ttt gct ttg ata gtg aat gcg cct aat cat gaa     1395
Gln Ser Ser Asp Asp Phe Ala Leu Ile Val Asn Ala Pro Asn His Glu
            445                 450                 455

gga ata cag gct gga gta gac aga ttc tat aga act tgc aaa ctg gtc     1443
Gly Ile Gln Ala Gly Val Asp Arg Phe Tyr Arg Thr Cys Lys Leu Val
        460                 465                 470

ggg atc aac atg agc aaa aag aag tcc tac ata aat aga acc ggc wca     1491
Gly Ile Asn Met Ser Lys Lys Lys Ser Tyr Ile Asn Arg Thr Gly Xaa
    475                 480                 485

ttc gaa ttc aca agc ttt ttc tac cgg tat ggt ttt gtc gcc aat ttc     1539
Phe Glu Phe Thr Ser Phe Phe Tyr Arg Tyr Gly Phe Val Ala Asn Phe
490                 495                 500                 505

agc atg gag cta ccc agt ttt ggg gtt tcc ggg ata aat gaa tct gca     1587
Ser Met Glu Leu Pro Ser Phe Gly Val Ser Gly Ile Asn Glu Ser Ala
                510                 515                 520

gac atg agc att gga atg aca gtt atc aaa aac aac atg ata aat aat     1635
Asp Met Ser Ile Gly Met Thr Val Ile Lys Asn Asn Met Ile Asn Asn
            525                 530                 535

gat ctc ggt ccc gcc acg gca caa atg gca ctc caa ctc ttc att aag     1683
Asp Leu Gly Pro Ala Thr Ala Gln Met Ala Leu Gln Leu Phe Ile Lys
        540                 545                 550

gat tat cgg tac aca tac cgg tgc cat aga ggc gat acc cag ata caa     1731
Asp Tyr Arg Tyr Thr Tyr Arg Cys His Arg Gly Asp Thr Gln Ile Gln
    555                 560                 565

acc aga aga tcc ttt gag ttg aag aaa ctg tgg gaa cag act cga tca     1779
Thr Arg Arg Ser Phe Glu Leu Lys Lys Leu Trp Glu Gln Thr Arg Ser
570                 575                 580                 585

aag act ggt cta ctg gta tca gat ggg ggt cca aac cta tac aac atc     1827
Lys Thr Gly Leu Leu Val Ser Asp Gly Gly Pro Asn Leu Tyr Asn Ile
                590                 595                 600

aga aac cta cac atc ccg gaa gtc tgt ttg aaa tgg gag ctg atg gat     1875
Arg Asn Leu His Ile Pro Glu Val Cys Leu Lys Trp Glu Leu Met Asp
            605                 610                 615

gaa gat tat aaa ggg agg cta tgt aat cca ttg aat cct ttc gtt agc     1923
Glu Asp Tyr Lys Gly Arg Leu Cys Asn Pro Leu Asn Pro Phe Val Ser
        620                 625                 630

cac aaa gaa att gaa tca gtg aac agt gca gta gta atg cct gcg cat     1971
His Lys Glu Ile Glu Ser Val Asn Ser Ala Val Val Met Pro Ala His
    635                 640                 645

ggc cct gcc aaa agc atg gag tat gat gct gtt gca aca aca cac tct     2019
Gly Pro Ala Lys Ser Met Glu Tyr Asp Ala Val Ala Thr Thr His Ser
650                 655                 660                 665

tgg atc ccc aag agg aac cgg tcc ata ttg aac aca agt caa agg gga     2067
Trp Ile Pro Lys Arg Asn Arg Ser Ile Leu Asn Thr Ser Gln Arg Gly
                670                 675                 680

ata ctc gaa gat gag cag atg tat cag aaa tgc tgc aac ctg ttt gaa     2115
Ile Leu Glu Asp Glu Gln Met Tyr Gln Lys Cys Cys Asn Leu Phe Glu
            685                 690                 695

aaa ttc ttc ccc agc agc tca tac aga aga cca gtc gga att tct agt     2163
Lys Phe Phe Pro Ser Ser Ser Tyr Arg Arg Pro Val Gly Ile Ser Ser
        700                 705                 710
```

-continued

```
atg gtt gag gcc atg gtg tcc agg gcc cgc att gat gca cga att gac     2211
Met Val Glu Ala Met Val Ser Arg Ala Arg Ile Asp Ala Arg Ile Asp
    715                 720                 725

ttc gaa tct gga cgg ata aag aag gat gag ttc gct gag atc atg aag     2259
Phe Glu Ser Gly Arg Ile Lys Lys Asp Glu Phe Ala Glu Ile Met Lys
730                 735                 740                 745

atc tgt tcc acc att gaa gag ctc aga cgg caa aaa tagtgaattt          2305
Ile Cys Ser Thr Ile Glu Glu Leu Arg Arg Gln Lys
                750                 755

agcttgatct tcgtgaaaaa atgccttgtt tctact                             2341


<210> SEQ ID NO 69
<211> LENGTH: 757
<212> TYPE: PRT
<213> ORGANISM: Equine influenza virus H3N8
<220> FEATURE:
<221> NAME/KEY: misc_feature
<222> LOCATION: (489)..(489)
<223> OTHER INFORMATION: The 'Xaa' at location 489 stands for Thr, or
      Ser.

<400> SEQUENCE: 69

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Asp Leu Thr Ser Ser Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
```

-continued

```
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Leu Leu Val Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Arg Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Xaa Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Met Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Thr Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Lys Gly Arg Leu
    610                 615                 620

Cys Asn Pro Leu Asn Pro Phe Val Ser His Lys Glu Ile Glu Ser Val
625                 630                 635                 640

Asn Ser Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700
```

-continued

```
Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Asp Glu Phe Ala Glu Ile Met Lys Ile Cys Ser Thr Ile Glu Glu
            740                 745                 750

Leu Arg Arg Gln Lys
        755
```

<210> SEQ ID NO 70
<211> LENGTH: 2271
<212> TYPE: DNA
<213> ORGANISM: Equine influenza virus H3N8

<400> SEQUENCE: 70

```
atggatgtca atccgactct actcttctta aaggtgccag cgcaaaatgc tataagcaca     60

acattccctt atactggaga tcctccctac agtcatggaa cagggacagg atacaccatg    120

gatactgtca acagaacaca tcaatactca gaaaagggga aatggacaac aaacactgag    180

attggagcac cacaacttaa tccaatcgat ggaccgcttc ctgaagacaa tgaaccaagt    240

gggtacgccc aaacagattg tgtattggaa gcaatggctt tccttgaaga atcccatccc    300

ggaatctttg aaaattcgtg tcttgaaaca atggaggtgg ttcagcagac aagagtggac    360

aaactaacac aaggccgaca aacttacgat tggaccttga ataggaatca acctgccgca    420

acagcacttg ctaatacaat tgaagtgttc agatcaaatg atctgacttc cagtgagtca    480

gggagattaa tggacttcct caaagatgtc atggagtcca tgaacaagga agaaatggaa    540

ataacaacac acttccaacg gaagagaaga gtaagagaca acatgacaaa gagaatggtg    600

acacagagaa ccatagggaa gaaaaaacaa cgattaaaca gaaagagcta tctgatcagg    660

gcattaacct taaacacaat gaccaaggac gctgagagag ggaaattgaa acgacgagca    720

attgcaaccc caggaatgca gataagaggg tttgtatatt ttgttgaaac attagcccga    780

agaatatgtg aaaagcttga acaatcagga ttgccagttg gcggtaatga gaaaaaggcc    840

aaactggcta atgtcgtcag aaaaatgatg actaattccc aagacactga actctccttc    900

accatcactg gggacaatac caaatggaat gaaaatcaga acccacgcat gttcctggca    960

atgatcacat acataactag aaaccagcca gaatggttca gaaatgttct aagcattgca   1020

ccgattatgt tctcaaataa aatggcaaga ctggggaaag gatatatgtt tgaaagcaaa   1080

agtatgaaat tgagaactca aataccagca gaaatgctcg caagcattga tctgaaatat   1140

ttcaatgatt caacaaaaaa gaaaattgag aagatacgac cacttctggt cgatgggact   1200

gcttcactga gtcctggcat gatgatggga atgttcaaca tgttgagcac tgtactaggt   1260

gtatccatat taaacctggg ccagaggaaa tacacaaaga ccacatactg gtgggatggt   1320

ctgcaatcat ccgatgattt tgctttgata gtgaatgcgc ctaatcatga aggaatacag   1380

gctggagtag acagattcta tagaacttgc aaactggtcg ggatcaacat gagcaaaaag   1440

aagtcctaca taaatagaac cggcwcattc gaattcacaa gctttttcta ccggtatggt   1500

tttgtcgcca atttcagcat ggagctaccc agttttgggg tttccgggat aaatgaatct   1560

gcagacatga gcattggaat gacagttatc aaaaacaaca tgataaataa tgatctcggt   1620

cccgccacgg cacaaatggc actccaactc ttcattaagg attatcggta cacataccgg   1680

tgccatagag gcgataccca gatacaaacc agaagatcct ttgagttgaa gaaactgtgg   1740
```

-continued

```
gaacagactc gatcaaagac tggtctactg gtatcagatg ggggtccaaa cctatacaac   1800

atcagaaacc tacacatccc ggaagtctgt ttgaaatggg agctgatgga tgaagattat   1860

aaagggaggc tatgtaatcc attgaatcct ttcgttagcc acaaagaaat tgaatcagtg   1920

aacagtgcag tagtaatgcc tgcgcatggc cctgccaaaa gcatggagta tgatgctgtt   1980

gcaacaacac actcttggat ccccaagagg aaccggtcca tattgaacac aagtcaaagg   2040

ggaatactcg aagatgagca gatgtatcag aaatgctgca acctgtttga aaaattcttc   2100

cccagcagct catacagaag accagtcgga atttctagta tggttgaggc catggtgtcc   2160

agggcccgca ttgatgcacg aattgacttc gaatctggac ggataaagaa ggatgagttc   2220

gctgagatca tgaagatctg ttccaccatt gaagagctca gacggcaaaa a            2271


<210> SEQ ID NO 71
<211> LENGTH: 2341
<212> TYPE: DNA
<213> ORGANISM: Equine influenza virus H3N8
<220> FEATURE:
<221> NAME/KEY: misc_feature
<222> LOCATION: (707)..(707)
<223> OTHER INFORMATION: The 'Xaa' at amino acid location 707 stands
      for Arg, or Lys.
<220> FEATURE:
<221> NAME/KEY: CDS
<222> LOCATION: (25)..(2295)

<400> SEQUENCE: 71

agcaaaagca ggcaaactat ttga atg gat gtc aat ccg act cta ctc ttc        51
                           Met Asp Val Asn Pro Thr Leu Leu Phe
                           1               5

tta aag gtg cca gcg caa aat gct ata agc aca aca ttc cct tat act       99
Leu Lys Val Pro Ala Gln Asn Ala Ile Ser Thr Thr Phe Pro Tyr Thr
10                  15                  20                  25

gga gat cct ccc tac agt cat gga aca ggg aca gga tac acc atg gat      147
Gly Asp Pro Pro Tyr Ser His Gly Thr Gly Thr Gly Tyr Thr Met Asp
                30                  35                  40

act gtc aac aga aca cat caa tac tca gaa aag ggg aaa tgg aca aca      195
Thr Val Asn Arg Thr His Gln Tyr Ser Glu Lys Gly Lys Trp Thr Thr
            45                  50                  55

aac act gag att gga gca cca caa ctt aat cca atc gat gga ccg ctt      243
Asn Thr Glu Ile Gly Ala Pro Gln Leu Asn Pro Ile Asp Gly Pro Leu
        60                  65                  70

cct gaa gac aat gaa cca agt ggg tac gcc caa aca gat tgt gta ttg      291
Pro Glu Asp Asn Glu Pro Ser Gly Tyr Ala Gln Thr Asp Cys Val Leu
    75                  80                  85

gaa gca atg gct ttc ctt gaa gaa tcc cat ccc gga atc ttt gaa aat      339
Glu Ala Met Ala Phe Leu Glu Glu Ser His Pro Gly Ile Phe Glu Asn
90                  95                  100                 105

tcg tgt ctt gaa aca atg gag gtg gtt cag cag aca aga gtg gac aaa      387
Ser Cys Leu Glu Thr Met Glu Val Val Gln Gln Thr Arg Val Asp Lys
                110                 115                 120

cta aca caa ggc cga caa act tac gat tgg acc ttg aat agg aat caa      435
Leu Thr Gln Gly Arg Gln Thr Tyr Asp Trp Thr Leu Asn Arg Asn Gln
            125                 130                 135

cct gcc gca aca gca ctt gct aat aca att gaa gtg ttc aga tca aat      483
Pro Ala Ala Thr Ala Leu Ala Asn Thr Ile Glu Val Phe Arg Ser Asn
        140                 145                 150

gat ctg act tcc agt gag tca ggg aga tta atg gac ttc ctc aaa gat      531
Asp Leu Thr Ser Ser Glu Ser Gly Arg Leu Met Asp Phe Leu Lys Asp
    155                 160                 165

gtc atg gag tcc atg aac aag gaa gaa atg gaa ata aca aca cac ttc      579
```

-continued

```
Val Met Glu Ser Met Asn Lys Glu Glu Met Glu Ile Thr Thr His Phe
170                 175                 180                 185

caa cgg aag aga aga gta aga gac aac atg aca aag aga atg gtg aca      627
Gln Arg Lys Arg Arg Val Arg Asp Asn Met Thr Lys Arg Met Val Thr
                190                 195                 200

cag aga acc ata ggg aag aaa aaa caa cga tta aac aga aag agc tat      675
Gln Arg Thr Ile Gly Lys Lys Lys Gln Arg Leu Asn Arg Lys Ser Tyr
            205                 210                 215

ctg atc agg gca tta acc tta aac aca atg acc aag gac gct gag aga      723
Leu Ile Arg Ala Leu Thr Leu Asn Thr Met Thr Lys Asp Ala Glu Arg
        220                 225                 230

ggg aaa ttg aaa cga cga gca att gca acc cca gga atg cag ata aga      771
Gly Lys Leu Lys Arg Arg Ala Ile Ala Thr Pro Gly Met Gln Ile Arg
    235                 240                 245

ggg ttt gta tat ttt gtt gaa aca tta gcc cga aga ata tgt gaa aag      819
Gly Phe Val Tyr Phe Val Glu Thr Leu Ala Arg Arg Ile Cys Glu Lys
250                 255                 260                 265

ctt gaa caa tca gga ttg cca gtt ggc ggt aat gag aaa aag gcc aaa      867
Leu Glu Gln Ser Gly Leu Pro Val Gly Gly Asn Glu Lys Lys Ala Lys
                270                 275                 280

ctg gct aat gtc gtc aga aaa atg atg act aat tcc caa gac act gaa      915
Leu Ala Asn Val Val Arg Lys Met Met Thr Asn Ser Gln Asp Thr Glu
            285                 290                 295

ctc tcc ttc acc atc act ggg gac aat acc aaa tgg aat gaa aat cag      963
Leu Ser Phe Thr Ile Thr Gly Asp Asn Thr Lys Trp Asn Glu Asn Gln
        300                 305                 310
aac cca cgc atg ttc ctg gca atg atc aca tac ata act aga aac cag     1011
Asn Pro Arg Met Phe Leu Ala Met Ile Thr Tyr Ile Thr Arg Asn Gln
    315                 320                 325

cca gaa tgg ttc aga aat gtt cta agc att gca ccg att atg ttc tca     1059
Pro Glu Trp Phe Arg Asn Val Leu Ser Ile Ala Pro Ile Met Phe Ser
330                 335                 340                 345

aat aaa atg gca aga ctg ggg aaa gga tat atg ttt gaa agc aaa agt     1107
Asn Lys Met Ala Arg Leu Gly Lys Gly Tyr Met Phe Glu Ser Lys Ser
                350                 355                 360

atg aaa ttg aga act caa ata cca gca gaa atg ctc gca agc att gat     1155
Met Lys Leu Arg Thr Gln Ile Pro Ala Glu Met Leu Ala Ser Ile Asp
            365                 370                 375

ctg aaa tat ttc aat gat tca aca aaa aag aaa att gag aag ata cga     1203
Leu Lys Tyr Phe Asn Asp Ser Thr Lys Lys Lys Ile Glu Lys Ile Arg
        380                 385                 390

cca ctt ctg gtc gat ggg act gct tca ctg agt cct ggc atg atg atg     1251
Pro Leu Leu Val Asp Gly Thr Ala Ser Leu Ser Pro Gly Met Met Met
    395                 400                 405

gga atg ttc aac atg ttg agc act gta cta ggt gta tcc ata tta aac     1299
Gly Met Phe Asn Met Leu Ser Thr Val Leu Gly Val Ser Ile Leu Asn
410                 415                 420                 425

ctg ggc cag agg aaa tac aca aag acc aca tac tgg tgg gat ggt ctg     1347
Leu Gly Gln Arg Lys Tyr Thr Lys Thr Thr Tyr Trp Trp Asp Gly Leu
                430                 435                 440

caa tca tcc gat gat ttt gct ttg ata gtg aat gcg cct aat cat gaa     1395
Gln Ser Ser Asp Asp Phe Ala Leu Ile Val Asn Ala Pro Asn His Glu
            445                 450                 455

gga ata cag gct gga gta gac aga ttc tat aga act tgc aaa ctg gtc     1443
Gly Ile Gln Ala Gly Val Asp Arg Phe Tyr Arg Thr Cys Lys Leu Val
        460                 465                 470

ggg atc aac atg agc aaa aag aag tcc tac ata aat aga acc ggc aca     1491
Gly Ile Asn Met Ser Lys Lys Lys Ser Tyr Ile Asn Arg Thr Gly Thr
    475                 480                 485

ttc gaa ttc aca agc ttt ttc tac cgg tat ggt ttt gtc gcc aat ttc     1539
```

-continued

```
Phe Glu Phe Thr Ser Phe Phe Tyr Arg Tyr Gly Phe Val Ala Asn Phe
490                 495                 500                 505

agc atg gag cta ccc agt ttt ggg gtt tcc ggg ata aat gaa tct gca      1587
Ser Met Glu Leu Pro Ser Phe Gly Val Ser Gly Ile Asn Glu Ser Ala
                510                 515                 520

gac atg agc att gga atg aca gtt atc aaa aac aac atg ata aat aat      1635
Asp Met Ser Ile Gly Met Thr Val Ile Lys Asn Asn Met Ile Asn Asn
            525                 530                 535

gat ctc ggt ccc gcc acg gca caa atg gca ctc caa ctc ttc att aag      1683
Asp Leu Gly Pro Ala Thr Ala Gln Met Ala Leu Gln Leu Phe Ile Lys
        540                 545                 550

gat tat cgg tac aca tac cgg tgt caa aga ggc gat acc cag ata caa      1731
Asp Tyr Arg Tyr Thr Tyr Arg Cys Gln Arg Gly Asp Thr Gln Ile Gln
    555                 560                 565

acc aga aga tcc ttt gag ttg aag aaa ctg tgg gaa cag act cga tca      1779
Thr Arg Arg Ser Phe Glu Leu Lys Lys Leu Trp Glu Gln Thr Arg Ser
570                 575                 580                 585

aag act ggt cta ctg gta tca gat ggg ggt cca aac cta tac aac atc      1827
Lys Thr Gly Leu Leu Val Ser Asp Gly Gly Pro Asn Leu Tyr Asn Ile
                590                 595                 600

aga aac cta cac atc ccg gaa gtc tgt ttg aaa tgg gag ctg atg gat      1875
Arg Asn Leu His Ile Pro Glu Val Cys Leu Lys Trp Glu Leu Met Asp
            605                 610                 615

gaa gat tat aaa ggg agg cta tgt aat cca ttg aat cct ttc gtt agc      1923
Glu Asp Tyr Lys Gly Arg Leu Cys Asn Pro Leu Asn Pro Phe Val Ser
        620                 625                 630

cac aaa gaa att gaa tca gtg aac agt gca gta gta atg cct gcg cat      1971
His Lys Glu Ile Glu Ser Val Asn Ser Ala Val Val Met Pro Ala His
    635                 640                 645

ggc cct gcc aaa agc atg gag tat gat gct gtt gca aca aca cac tct      2019
Gly Pro Ala Lys Ser Met Glu Tyr Asp Ala Val Ala Thr Thr His Ser
650                 655                 660                 665

tgg atc ccc aag agg aac cgg tcc ata ttg aac aca agt caa agg gga      2067
Trp Ile Pro Lys Arg Asn Arg Ser Ile Leu Asn Thr Ser Gln Arg Gly
                670                 675                 680

ata ctc gaa gat gag cag atg tat cag aaa tgc tgc aac ctg ttt gaa      2115
Ile Leu Glu Asp Glu Gln Met Tyr Gln Lys Cys Cys Asn Leu Phe Glu
            685                 690                 695

aaa ttc ttc ccc agc agc tca tac aga ara cca gtc gga att tct agt      2163
Lys Phe Phe Pro Ser Ser Ser Tyr Arg Xaa Pro Val Gly Ile Ser Ser
        700                 705                 710

atg gtt gag gcc atg gtg tcc agg gcc cgc att gat gca cga att gac      2211
Met Val Glu Ala Met Val Ser Arg Ala Arg Ile Asp Ala Arg Ile Asp
    715                 720                 725

ttc gaa tct gga cgg ata aag aag gat gag ttc gct gag atc atg aag      2259
Phe Glu Ser Gly Arg Ile Lys Lys Asp Glu Phe Ala Glu Ile Met Lys
730                 735                 740                 745

atc tgt tcc acc att gaa gag ctc aga cgg caa aaa tagtgaattt           2305
Ile Cys Ser Thr Ile Glu Glu Leu Arg Arg Gln Lys
                750                 755

agcttgatct tcgtgaaaaa atgccttgtt tctact                              2341
```

```
<210> SEQ ID NO 72
<211> LENGTH: 757
<212> TYPE: PRT
<213> ORGANISM: Equine influenza virus H3N8
<220> FEATURE:
<221> NAME/KEY: misc_feature
<222> LOCATION: (707)..(707)
<223> OTHER INFORMATION: The 'Xaa' at location 707 stands for
      Arg, or Lys.
```

-continued

<400> SEQUENCE: 72

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Ile Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Asp Leu Thr Ser Ser Glu Ser
145                 150                 155                 160

Gly Arg Leu Met Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Val Thr Gln Arg Thr Ile Gly Lys Lys
        195                 200                 205

Lys Gln Arg Leu Asn Arg Lys Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Leu Leu Val Asp Gly Thr
385                 390                 395                 400

Ala Ser Leu Ser Pro Gly Met Met Met Gly Met Phe Asn Met Leu Ser
```

-continued

```
                405                 410                 415
Thr Val Leu Gly Val Ser Ile Leu Asn Leu Gly Gln Arg Lys Tyr Thr
            420                 425                 430
Lys Thr Thr Tyr Trp Trp Asp Gly Leu Gln Ser Ser Asp Asp Phe Ala
        435                 440                 445
Leu Ile Val Asn Ala Pro Asn His Glu Gly Ile Gln Ala Gly Val Asp
    450                 455                 460
Arg Phe Tyr Arg Thr Cys Lys Leu Val Gly Ile Asn Met Ser Lys Lys
465                 470                 475                 480
Lys Ser Tyr Ile Asn Arg Thr Gly Thr Phe Glu Phe Thr Ser Phe Phe
                485                 490                 495
Tyr Arg Tyr Gly Phe Val Ala Asn Phe Ser Met Glu Leu Pro Ser Phe
            500                 505                 510
Gly Val Ser Gly Ile Asn Glu Ser Ala Asp Met Ser Ile Gly Met Thr
        515                 520                 525
Val Ile Lys Asn Asn Met Ile Asn Asn Asp Leu Gly Pro Ala Thr Ala
    530                 535                 540
Gln Met Ala Leu Gln Leu Phe Ile Lys Asp Tyr Arg Tyr Thr Tyr Arg
545                 550                 555                 560
Cys Gln Arg Gly Asp Thr Gln Ile Gln Thr Arg Arg Ser Phe Glu Leu
                565                 570                 575
Lys Lys Leu Trp Glu Gln Thr Arg Ser Lys Thr Gly Leu Leu Val Ser
            580                 585                 590
Asp Gly Gly Pro Asn Leu Tyr Asn Ile Arg Asn Leu His Ile Pro Glu
        595                 600                 605
Val Cys Leu Lys Trp Glu Leu Met Asp Glu Asp Tyr Lys Gly Arg Leu
    610                 615                 620
Cys Asn Pro Leu Asn Pro Phe Val Ser His Lys Glu Ile Glu Ser Val
625                 630                 635                 640
Asn Ser Ala Val Val Met Pro Ala His Gly Pro Ala Lys Ser Met Glu
                645                 650                 655
Tyr Asp Ala Val Ala Thr Thr His Ser Trp Ile Pro Lys Arg Asn Arg
            660                 665                 670
Ser Ile Leu Asn Thr Ser Gln Arg Gly Ile Leu Glu Asp Glu Gln Met
        675                 680                 685
Tyr Gln Lys Cys Cys Asn Leu Phe Glu Lys Phe Phe Pro Ser Ser Ser
    690                 695                 700
Tyr Arg Xaa Pro Val Gly Ile Ser Ser Met Val Glu Ala Met Val Ser
705                 710                 715                 720
Arg Ala Arg Ile Asp Ala Arg Ile Asp Phe Glu Ser Gly Arg Ile Lys
                725                 730                 735
Lys Asp Glu Phe Ala Glu Ile Met Lys Ile Cys Ser Thr Ile Glu Glu
            740                 745                 750
Leu Arg Arg Gln Lys
        755
```

<210> SEQ ID NO 73
<211> LENGTH: 2271
<212> TYPE: DNA
<213> ORGANISM: Equine influenza virus H3N8

<400> SEQUENCE: 73

```
atggatgtca atccgactct actcttctta aaggtgccag cgcaaaatgc tataagcaca      60
acattccctt atactggaga tcctccctac agtcatggaa cagggacagg atacaccatg     120
```

-continued

```
gatactgtca acagaacaca tcaatactca gaaaagggga aatggacaac aaacactgag    180
attggagcac cacaacttaa tccaatcgat ggaccgcttc ctgaagacaa tgaaccaagt    240
gggtacgccc aaacagattg tgtattggaa gcaatggctt tccttgaaga atcccatccc    300
ggaatctttg aaaattcgtg tcttgaaaca atggaggtgg ttcagcagac aagagtggac    360
aaactaacac aaggccgaca aacttacgat tggaccttga ataggaatca acctgccgca    420
acagcacttg ctaatacaat tgaagtgttc agatcaaatg atctgacttc cagtgagtca    480
gggagattaa tggacttcct caaagatgtc atggagtcca tgaacaagga agaaatggaa    540
ataacaacac acttccaacg gaagagaaga gtaagagaca acatgacaaa gagaatggtg    600
acacagagaa ccatagggaa gaaaaaacaa cgattaaaca gaaagagcta tctgatcagg    660
gcattaacct taaacacaat gaccaaggac gctgagagag ggaaattgaa acgacgagca    720
attgcaaccc caggaatgca gataagaggg tttgtatatt ttgttgaaac attagcccga    780
agaatatgtg aaaagcttga acaatcagga ttgccagttg gcggtaatga gaaaaaggcc    840
aaactggcta atgtcgtcag aaaaatgatg actaattccc aagacactga actctccttc    900
accatcactg gggacaatac caaatggaat gaaaatcaga acccacgcat gttcctggca    960
atgatcacat acataactag aaaccagcca gaatggttca gaaatgttct aagcattgca   1020
ccgattatgt tctcaaataa aatggcaaga ctggggaaag gatatatgtt tgaaagcaaa   1080
agtatgaaat tgagaactca aataccagca gaaatgctcg caagcattga tctgaaatat   1140
ttcaatgatt caacaaaaaa gaaaattgag aagatacgac cacttctggt cgatgggact   1200
gcttcactga gtcctggcat gatgatggga atgttcaaca tgttgagcac tgtactaggt   1260
gtatccatat taaacctggg ccagaggaaa tacacaaaga ccacatactg gtgggatggt   1320
ctgcaatcat ccgatgattt tgctttgata gtgaatgcgc ctaatcatga aggaatacag   1380
gctggagtag acagattcta tagaacttgc aaactggtcg ggatcaacat gagcaaaaag   1440
aagtcctaca taaatagaac cggcacattc gaattcacaa gctttttcta ccggtatggt   1500
tttgtcgcca atttcagcat ggagctaccc agttttgggg tttccgggat aaatgaatct   1560
gcagacatga gcattggaat gacagttatc aaaaacaaca tgataaataa tgatctcggt   1620
cccgccacgg cacaaatggc actccaactc ttcattaagg attatcggta cacataccgg   1680
tgtcaaagag gcgataccca gatacaaacc agaagatcct ttgagttgaa gaaactgtgg   1740
gaacagactc gatcaaagac tggtctactg gtatcagatg gggtccaaa cctatacaac   1800
atcagaaacc tacacatccc ggaagtctgt ttgaaatggg agctgatgga tgaagattat   1860
aaagggaggc tatgtaatcc attgaatcct ttcgttagcc acaaagaaat tgaatcagtg   1920
aacagtgcag tagtaatgcc tgcgcatggc cctgccaaaa gcatggagta tgatgctgtt   1980
gcaacaacac actcttggat ccccaagagg aaccggtcca tattgaacac aagtcaaagg   2040
ggaatactcg aagatgagca gatgtatcag aaatgctgca acctgtttga aaaattcttc   2100
cccagcagct catacagaar accagtcgga atttctagta tggttgaggc catggtgtcc   2160
agggcccgca ttgatgcacg aattgacttc gaatctggac ggataaagaa ggatgagttc   2220
gctgagatca tgaagatctg ttccaccatt gaagagctca gacggcaaaa a            2271
```

<210> SEQ ID NO 74
<211> LENGTH: 25
<212> TYPE: DNA
<213> ORGANISM: Artificial
<220> FEATURE:

-continued

<223> OTHER INFORMATION: Synthetic Primer

<400> SEQUENCE: 74
ggggcgggta cccaaactat ctcca                                    25

<210> SEQ ID NO 75
<211> LENGTH: 27
<212> TYPE: DNA
<213> ORGANISM: Artificial
<220> FEATURE:
<223> OTHER INFORMATION: Synthetic Primer

<400> SEQUENCE: 75
gggggctcga gtactttttt ggacagt                                  27

<210> SEQ ID NO 76
<211> LENGTH: 1228
<212> TYPE: DNA
<213> ORGANISM: Equine influenza virus H3N8
<220> FEATURE:
<221> NAME/KEY: CDS
<222> LOCATION: (3)..(1166)

<400> SEQUENCE: 76

```
gg ggc ggg tac cca aac tat ctc caa gct tgg aag caa gta tta gca      47
   Gly Gly Tyr Pro Asn Tyr Leu Gln Ala Trp Lys Gln Val Leu Ala
   1               5                   10                  15

gaa cta caa gac ctt gag aac gaa gaa aag acc cct aag acc aag aat     95
Glu Leu Gln Asp Leu Glu Asn Glu Glu Lys Thr Pro Lys Thr Lys Asn
                20                  25                  30

atg aaa aaa aca agc caa ttg aaa tgg gca ctc ggt gaa aat atg gca   143
Met Lys Lys Thr Ser Gln Leu Lys Trp Ala Leu Gly Glu Asn Met Ala
            35                  40                  45

cca gag aaa gtg gat ttt gag gat tgt aaa gac atc aat gat ttg aaa   191
Pro Glu Lys Val Asp Phe Glu Asp Cys Lys Asp Ile Asn Asp Leu Lys
        50                  55                  60

cag tat gac agt gat gag cca gaa aca agg tct ctt gca agt tgg att   239
Gln Tyr Asp Ser Asp Glu Pro Glu Thr Arg Ser Leu Ala Ser Trp Ile
    65                  70                  75

caa agt gag ttc aac aaa gct tgt gag ctg aca gat tca agc tgg ata   287
Gln Ser Glu Phe Asn Lys Ala Cys Glu Leu Thr Asp Ser Ser Trp Ile
80                  85                  90                  95

gag ctc gat gaa att ggg gag gat att gcc cca ata gaa tac att gcg   335
Glu Leu Asp Glu Ile Gly Glu Asp Ile Ala Pro Ile Glu Tyr Ile Ala
                100                 105                 110

agc atg agg aga aat tat ttt act gct gag gtt tcc cat tgt aga gca   383
Ser Met Arg Arg Asn Tyr Phe Thr Ala Glu Val Ser His Cys Arg Ala
            115                 120                 125

aca gaa tat ata atg aag gga gtg tac atc aac act gct cta ctc aat   431
Thr Glu Tyr Ile Met Lys Gly Val Tyr Ile Asn Thr Ala Leu Leu Asn
        130                 135                 140

gca tcc tgt gct gcg atg gat gaa ttc caa tta att ccg atg ata agc   479
Ala Ser Cys Ala Ala Met Asp Glu Phe Gln Leu Ile Pro Met Ile Ser
    145                 150                 155

aaa tgc agg acc aaa gaa ggg aga agg aag aca aat tta tat gga ttc   527
Lys Cys Arg Thr Lys Glu Gly Arg Arg Lys Thr Asn Leu Tyr Gly Phe
160                 165                 170                 175

ata ata aag gga agg tcc cat tta agg aat gat acc gac gtg gta aac   575
Ile Ile Lys Gly Arg Ser His Leu Arg Asn Asp Thr Asp Val Val Asn
                180                 185                 190

ttt gta agt atg gaa ttt tct ctc act gat cca aga ttt gag cca cat   623
Phe Val Ser Met Glu Phe Ser Leu Thr Asp Pro Arg Phe Glu Pro His
```

-continued

```
            195                 200                 205

aaa tgg gaa aaa tac tgc gtt cta gaa att gga gac atg ctc cta agg      671
Lys Trp Glu Lys Tyr Cys Val Leu Glu Ile Gly Asp Met Leu Leu Arg
        210                 215                 220

act gct gta ggt caa gtg tca aga ccc atg ttt ttg tat gta agg aca      719
Thr Ala Val Gly Gln Val Ser Arg Pro Met Phe Leu Tyr Val Arg Thr
    225                 230                 235

aat gga acc tct aaa att aaa atg aaa cgg gga atg gaa atg aga cgc      767
Asn Gly Thr Ser Lys Ile Lys Met Lys Arg Gly Met Glu Met Arg Arg
240                 245                 250                 255

tgc ctc ctt cag tct ctg caa cag att gaa agc atg atc gaa gct gag      815
Cys Leu Leu Gln Ser Leu Gln Gln Ile Glu Ser Met Ile Glu Ala Glu
                260                 265                 270

tcc tca gtc aaa gaa aag gac atg acc aaa gaa ttc ttt gag aac aaa      863
Ser Ser Val Lys Glu Lys Asp Met Thr Lys Glu Phe Phe Glu Asn Lys
            275                 280                 285

tca gag aca tgg cct ata gga gag tcc ccc aaa gga gtg gaa gag ggc      911
Ser Glu Thr Trp Pro Ile Gly Glu Ser Pro Lys Gly Val Glu Glu Gly
        290                 295                 300

tca atc ggg aag gtt tgc agg acc tta tta gca aaa tct gtg ttt aac      959
Ser Ile Gly Lys Val Cys Arg Thr Leu Leu Ala Lys Ser Val Phe Asn
    305                 310                 315

agt ttg tat gca tct cca caa ctg gaa ggg ttt tca gct gaa tct agg     1007
Ser Leu Tyr Ala Ser Pro Gln Leu Glu Gly Phe Ser Ala Glu Ser Arg
320                 325                 330                 335

aaa tta ctt ctc att gtt cag gcc ctt agg gat aac ctg gaa cct gga     1055
Lys Leu Leu Leu Ile Val Gln Ala Leu Arg Asp Asn Leu Glu Pro Gly
                340                 345                 350

acc ttt gat att ggg ggg tta tat gaa tca att gag gag tgc ctg att     1103
Thr Phe Asp Ile Gly Gly Leu Tyr Glu Ser Ile Glu Glu Cys Leu Ile
            355                 360                 365

aat gat ccc tgg gtt ttg ctc aat gca tct tgg ttc aac tcc ttc ctt     1151
Asn Asp Pro Trp Val Leu Leu Asn Ala Ser Trp Phe Asn Ser Phe Leu
        370                 375                 380

aca cat gca ctg aag tagttgtagc aatgctacta tttgctatcc atactgtcca     1206
Thr His Ala Leu Lys
    385

aaaaagtact cgagccccca ag                                            1228


<210> SEQ ID NO 77
<211> LENGTH: 388
<212> TYPE: PRT
<213> ORGANISM: Equine influenza virus H3N8

<400> SEQUENCE: 77

Gly Gly Tyr Pro Asn Tyr Leu Gln Ala Trp Lys Gln Val Leu Ala Glu
1               5                   10                  15

Leu Gln Asp Leu Glu Asn Glu Glu Lys Thr Pro Lys Thr Lys Asn Met
            20                  25                  30

Lys Lys Thr Ser Gln Leu Lys Trp Ala Leu Gly Glu Asn Met Ala Pro
        35                  40                  45

Glu Lys Val Asp Phe Glu Asp Cys Lys Asp Ile Asn Asp Leu Lys Gln
    50                  55                  60

Tyr Asp Ser Asp Glu Pro Glu Thr Arg Ser Leu Ala Ser Trp Ile Gln
65                  70                  75                  80

Ser Glu Phe Asn Lys Ala Cys Glu Leu Thr Asp Ser Ser Trp Ile Glu
                85                  90                  95

Leu Asp Glu Ile Gly Glu Asp Ile Ala Pro Ile Glu Tyr Ile Ala Ser
```

-continued

```
            100                 105                 110

Met Arg Arg Asn Tyr Phe Thr Ala Glu Val Ser His Cys Arg Ala Thr
        115                 120                 125

Glu Tyr Ile Met Lys Gly Val Tyr Ile Asn Thr Ala Leu Leu Asn Ala
    130                 135                 140

Ser Cys Ala Ala Met Asp Glu Phe Gln Leu Ile Pro Met Ile Ser Lys
145                 150                 155                 160

Cys Arg Thr Lys Glu Gly Arg Arg Lys Thr Asn Leu Tyr Gly Phe Ile
                165                 170                 175

Ile Lys Gly Arg Ser His Leu Arg Asn Asp Thr Asp Val Val Asn Phe
            180                 185                 190

Val Ser Met Glu Phe Ser Leu Thr Asp Pro Arg Phe Glu Pro His Lys
        195                 200                 205

Trp Glu Lys Tyr Cys Val Leu Glu Ile Gly Asp Met Leu Leu Arg Thr
    210                 215                 220

Ala Val Gly Gln Val Ser Arg Pro Met Phe Leu Tyr Val Arg Thr Asn
225                 230                 235                 240

Gly Thr Ser Lys Ile Lys Met Lys Arg Gly Met Glu Met Arg Arg Cys
                245                 250                 255

Leu Leu Gln Ser Leu Gln Gln Ile Glu Ser Met Ile Glu Ala Glu Ser
            260                 265                 270

Ser Val Lys Glu Lys Asp Met Thr Lys Glu Phe Phe Glu Asn Lys Ser
        275                 280                 285

Glu Thr Trp Pro Ile Gly Glu Ser Pro Lys Gly Val Glu Glu Gly Ser
    290                 295                 300

Ile Gly Lys Val Cys Arg Thr Leu Leu Ala Lys Ser Val Phe Asn Ser
305                 310                 315                 320

Leu Tyr Ala Ser Pro Gln Leu Glu Gly Phe Ser Ala Glu Ser Arg Lys
                325                 330                 335

Leu Leu Leu Ile Val Gln Ala Leu Arg Asp Asn Leu Glu Pro Gly Thr
            340                 345                 350

Phe Asp Ile Gly Gly Leu Tyr Glu Ser Ile Glu Glu Cys Leu Ile Asn
        355                 360                 365

Asp Pro Trp Val Leu Leu Asn Ala Ser Trp Phe Asn Ser Phe Leu Thr
    370                 375                 380

His Ala Leu Lys
385


<210> SEQ ID NO 78
<211> LENGTH: 18
<212> TYPE: DNA
<213> ORGANISM: Artificial
<220> FEATURE:
<223> OTHER INFORMATION: Synthetic Primer

<400> SEQUENCE: 78

gcaaatgcag gaccaaag                                                18


<210> SEQ ID NO 79
<211> LENGTH: 18
<212> TYPE: DNA
<213> ORGANISM: Artificial
<220> FEATURE:
<223> OTHER INFORMATION: Synthetic Primer

<400> SEQUENCE: 79

gactgaggac tcagcttc                                                18
```

-continued

<210> SEQ ID NO 80
<211> LENGTH: 19
<212> TYPE: DNA
<213> ORGANISM: Artificial
<220> FEATURE:
<223> OTHER INFORMATION: Synthetic Primer

<400> SEQUENCE: 80
caatatcctc cccaatttc 19

<210> SEQ ID NO 81
<211> LENGTH: 19
<212> TYPE: DNA
<213> ORGANISM: Artificial
<220> FEATURE:
<223> OTHER INFORMATION: Synthetic Primer

<400> SEQUENCE: 81
ggaaggtttg caggacctt 19

<210> SEQ ID NO 82
<211> LENGTH: 1164
<212> TYPE: DNA
<213> ORGANISM: Equine influenza virus H3N8

<400> SEQUENCE: 82
ggcgggtacc caaactatct ccaagcttgg aagcaagtat tagcagaact acaagacctt 60
gagaacgaag aaaagacccc taagaccaag aatatgaaaa aaacaagcca attgaaatgg 120
gcactcggtg aaaatatggc accagagaaa gtggattttg aggattgtaa agacatcaat 180
gatttgaaac agtatgacag tgatgagcca gaaacaaggt ctcttgcaag ttggattcaa 240
agtgagttca acaaagcttg tgagctgaca gattcaagct ggatagagct cgatgaaatt 300
ggggaggata ttgccccaat agaatacatt gcgagcatga ggagaaatta ttttactgct 360
gaggtttccc attgtagagc aacagaatat ataatgaagg gagtgtacat caacactgct 420
ctactcaatg catcctgtgc tgcgatggat gaattccaat taattccgat gataagcaaa 480
tgcaggacca aagaagggag aaggaagaca aatttatatg gattcataat aaagggaagg 540
tcccatttaa ggaatgatac cgacgtggta aactttgtaa gtatggaatt ttctctcact 600
gatccaagat ttgagccaca taaatgggaa aaatactgcg ttctagaaat tggagacatg 660
ctcctaagga ctgctgtagg tcaagtgtca agacccatgt ttttgtatgt aaggacaaat 720
ggaacctcta aaattaaaat gaaacgggga atggaaatga gacgctgcct ccttcagtct 780
ctgcaacaga ttgaaagcat gatcgaagct gagtcctcag tcaaagaaaa ggacatgacc 840
aaagaattct ttgagaacaa atcagagaca tggcctatag gagagtcccc caaaggagtg 900
gaagagggct caatcgggaa ggtttgcagg accttattag caaaatctgt gtttaacagt 960
ttgtatgcat ctccacaact ggaagggttt tcagctgaat ctaggaaatt acttctcatt 1020
gttcaggccc ttagggataa cctggaacct ggaacctttg atattggggg gttatatgaa 1080
tcaattgagg agtgcctgat taatgatccc tgggttttgc tcaatgcatc ttggttcaac 1140
tccttcctta cacatgcact gaag 1164

<210> SEQ ID NO 83
<211> LENGTH: 1223
<212> TYPE: DNA
<213> ORGANISM: Equine influenza virus H3N8

<400> SEQUENCE: 83

```
ggggcgggta cccaaactat ctccaagctt ggaagcaagt attagcagaa ctacaagacc      60
ttgagaacga agaaaagacc cctaagacca agaatatgaa aaaaacaagc caattgaaat     120
gggcactcgg tgaaaatatg gcaccagaga aagtggattt tgaggattgt aaagacatca     180
atgatttgaa acagtatgac agtgatgagc cagaaacaag gtctcttgca agttggattc     240
aaagtgagtt caacaaagct tgtgagctga cagattcaag ctggatagag ctcgatgaaa     300
ttggggagga tattgcccca atagaataca ttgcgagcat gaggagaaat tattttactg     360
ctgaggtttc ccattgtaga gcaacagaat atataatgaa gggagtgtac atcaacactg     420
ctctactcaa tgcatcctgt gctgcgatgg atgaattcca attaattccg atgataagca     480
aatgcaggac caaagaaggg agaaggaaga caaatttata tggattcata ataaagggaa     540
ggtcccattt aaggaatgat accgacgtgg taaactttgt aagtatggaa ttttctctca     600
ctgatccaag atttgagcca cataaatggg aaaaatactg cgttctagaa attggagaca     660
tgctcctaag gactgctgta ggtcaagtgt caagacccat gtttttgtat gtaaggacaa     720
atggaacctc taaaattaaa atgaaatggg gaatggaaat gagacgctgc ctccttcagt     780
ctctgcaaca gattgaaagc atgatcgaag ctgagtcctc agtcaaagaa aaggacatga     840
ccaaagaatt ctttgagaac aaatcagaga catggcctat aggagagtcc cccaaaggag     900
tggaagaggg ctcaatcggg aaggtttgca ggaccttatt agcaaaatct gtgtttaaca     960
gtttgtatgc atctccacaa ctggaagggt tttcagctga atctaggaaa ttacttctca    1020
ttgttcaggc ccttagggat aacctggaac ctggaacctt tgatattggg gggttatatg    1080
aatcaattga ggagtgcctg attaatgatc cctgggtttt gctcaatgca tcttggttca    1140
actccttcct tacacatgca ctgaagtagt tgtagcaatg ctactatttg ctatccatac    1200
tgtccaaaaa agtactcgag ccc                                            1223
```

<210> SEQ ID NO 84
<211> LENGTH: 1233
<212> TYPE: DNA
<213> ORGANISM: Equine influenza virus H3N8
<220> FEATURE:
<221> NAME/KEY: CDS
<222> LOCATION: (3)..(1172)

<400> SEQUENCE: 84

```
at gaa aag ggt ata aac cca aac tat ctc caa gct tgg aag caa gta        47
   Glu Lys Gly Ile Asn Pro Asn Tyr Leu Gln Ala Trp Lys Gln Val
   1               5                   10                  15

tta gca gaa cta caa gac ctt gag aac gaa gaa aag acc cct aag acc       95
Leu Ala Glu Leu Gln Asp Leu Glu Asn Glu Glu Lys Thr Pro Lys Thr
                20                  25                  30

aag aat atg aaa aaa aca agc caa ttg aaa tgg gca ctc ggt gaa aat      143
Lys Asn Met Lys Lys Thr Ser Gln Leu Lys Trp Ala Leu Gly Glu Asn
            35                  40                  45

atg gca cca gag aaa gtg gat ttt gag gat tgt aaa gac atc aat gat      191
Met Ala Pro Glu Lys Val Asp Phe Glu Asp Cys Lys Asp Ile Asn Asp
        50                  55                  60

ttg aaa cag tat gac agt gat gag cca gaa aca agg tct ctt gca agt      239
Leu Lys Gln Tyr Asp Ser Asp Glu Pro Glu Thr Arg Ser Leu Ala Ser
    65                  70                  75

tgg att caa agt gag ttc aac aaa gct tgt gag ctg aca gat tca agc      287
Trp Ile Gln Ser Glu Phe Asn Lys Ala Cys Glu Leu Thr Asp Ser Ser
80                  85                  90                  95
```

-continued

```
tgg ata gag ctc gat gaa att ggg gag gat att gcc cca ata gaa tac      335
Trp Ile Glu Leu Asp Glu Ile Gly Glu Asp Ile Ala Pro Ile Glu Tyr
                100                 105                 110

att gcg agc atg agg aga aat tat ttt act gct gag gtt tcc cat tgt      383
Ile Ala Ser Met Arg Arg Asn Tyr Phe Thr Ala Glu Val Ser His Cys
            115                 120                 125

aga gca aca gaa tat ata atg aag gga gtg tac atc aac act gct cta      431
Arg Ala Thr Glu Tyr Ile Met Lys Gly Val Tyr Ile Asn Thr Ala Leu
        130                 135                 140

ctc aat gca tcc tgt gct gcg atg gat gaa ttc caa tta att ccg atg      479
Leu Asn Ala Ser Cys Ala Ala Met Asp Glu Phe Gln Leu Ile Pro Met
    145                 150                 155

ata agc aaa tgc agg acc aaa gaa ggg aga agg aag aca aat tta tat      527
Ile Ser Lys Cys Arg Thr Lys Glu Gly Arg Arg Lys Thr Asn Leu Tyr
160                 165                 170                 175

gga ttc ata ata aag gga agg tcc cat tta agg aat gat acc gac gtg      575
Gly Phe Ile Ile Lys Gly Arg Ser His Leu Arg Asn Asp Thr Asp Val
                180                 185                 190

gta aac ttt gta agt atg gaa ttt tct ctc act gat cca aga ttt gag      623
Val Asn Phe Val Ser Met Glu Phe Ser Leu Thr Asp Pro Arg Phe Glu
            195                 200                 205

cca cat aaa tgg gaa aaa tac tgc gtt cta gaa att gga gac atg ctc      671
Pro His Lys Trp Glu Lys Tyr Cys Val Leu Glu Ile Gly Asp Met Leu
        210                 215                 220

cta agg act gct gta ggt caa gtg tca aga ccc atg ttt ttg tat gta      719
Leu Arg Thr Ala Val Gly Gln Val Ser Arg Pro Met Phe Leu Tyr Val
    225                 230                 235

agg aca aat gga acc tct aaa att aaa atg aaa tgg gga atg gaa atg      767
Arg Thr Asn Gly Thr Ser Lys Ile Lys Met Lys Trp Gly Met Glu Met
240                 245                 250                 255

aga cgc tgc ctc ctt cag tct ctg caa cag att gaa agc atg atc gaa      815
Arg Arg Cys Leu Leu Gln Ser Leu Gln Gln Ile Glu Ser Met Ile Glu
                260                 265                 270

gct gag tcc tca gtc aaa gaa aag gac atg acc aaa gaa ttc ttt gag      863
Ala Glu Ser Ser Val Lys Glu Lys Asp Met Thr Lys Glu Phe Phe Glu
            275                 280                 285

aac aaa tca gag aca tgg cct ata gga gag tcc ccc aaa gga gtg gaa      911
Asn Lys Ser Glu Thr Trp Pro Ile Gly Glu Ser Pro Lys Gly Val Glu
        290                 295                 300

gag ggc tca atc ggg aag gtt tgc agg acc tta tta gca aaa tct gtg      959
Glu Gly Ser Ile Gly Lys Val Cys Arg Thr Leu Leu Ala Lys Ser Val
    305                 310                 315

ttt aac agt ttg tat gca tct cca caa ctg gaa ggg ttt tca gct gaa     1007
Phe Asn Ser Leu Tyr Ala Ser Pro Gln Leu Glu Gly Phe Ser Ala Glu
320                 325                 330                 335

tct agg aaa tta ctt ctc att gtt cag gcc ctt agg gat aac ctg gaa     1055
Ser Arg Lys Leu Leu Leu Ile Val Gln Ala Leu Arg Asp Asn Leu Glu
                340                 345                 350

cct gga acc ttt gat att ggg ggg tta tat gaa tca att gag gag tgc     1103
Pro Gly Thr Phe Asp Ile Gly Gly Leu Tyr Glu Ser Ile Glu Glu Cys
            355                 360                 365

ctg att aat gat ccc tgg gtt ttg ctc aat gca tct tgg ttc aac tcc     1151
Leu Ile Asn Asp Pro Trp Val Leu Leu Asn Ala Ser Trp Phe Asn Ser
        370                 375                 380

ttc ctt aca cat gca ctg aag tagttgtagc aatgctacta tttgctatcc        1202
Phe Leu Thr His Ala Leu Lys
    385                 390

atactgtcca aaaaagtacc ttgtttctac t                                  1233
```

-continued

<210> SEQ ID NO 85
<211> LENGTH: 390
<212> TYPE: PRT
<213> ORGANISM: Equine influenza virus H3N8

<400> SEQUENCE: 85

```
Glu Lys Gly Ile Asn Pro Asn Tyr Leu Gln Ala Trp Lys Gln Val Leu
1               5                   10                  15

Ala Glu Leu Gln Asp Leu Glu Asn Glu Glu Lys Thr Pro Lys Thr Lys
            20                  25                  30

Asn Met Lys Lys Thr Ser Gln Leu Lys Trp Ala Leu Gly Glu Asn Met
        35                  40                  45

Ala Pro Glu Lys Val Asp Phe Glu Asp Cys Lys Asp Ile Asn Asp Leu
    50                  55                  60

Lys Gln Tyr Asp Ser Asp Glu Pro Glu Thr Arg Ser Leu Ala Ser Trp
65                  70                  75                  80

Ile Gln Ser Glu Phe Asn Lys Ala Cys Glu Leu Thr Asp Ser Ser Trp
                85                  90                  95

Ile Glu Leu Asp Glu Ile Gly Glu Asp Ile Ala Pro Ile Glu Tyr Ile
            100                 105                 110

Ala Ser Met Arg Arg Asn Tyr Phe Thr Ala Glu Val Ser His Cys Arg
        115                 120                 125

Ala Thr Glu Tyr Ile Met Lys Gly Val Tyr Ile Asn Thr Ala Leu Leu
    130                 135                 140

Asn Ala Ser Cys Ala Ala Met Asp Glu Phe Gln Leu Ile Pro Met Ile
145                 150                 155                 160

Ser Lys Cys Arg Thr Lys Glu Gly Arg Arg Lys Thr Asn Leu Tyr Gly
                165                 170                 175

Phe Ile Ile Lys Gly Arg Ser His Leu Arg Asn Asp Thr Asp Val Val
            180                 185                 190

Asn Phe Val Ser Met Glu Phe Ser Leu Thr Asp Pro Arg Phe Glu Pro
        195                 200                 205

His Lys Trp Glu Lys Tyr Cys Val Leu Glu Ile Gly Asp Met Leu Leu
    210                 215                 220

Arg Thr Ala Val Gly Gln Val Ser Arg Pro Met Phe Leu Tyr Val Arg
225                 230                 235                 240

Thr Asn Gly Thr Ser Lys Ile Lys Met Lys Trp Gly Met Glu Met Arg
                245                 250                 255

Arg Cys Leu Leu Gln Ser Leu Gln Gln Ile Glu Ser Met Ile Glu Ala
            260                 265                 270

Glu Ser Ser Val Lys Glu Lys Asp Met Thr Lys Glu Phe Phe Glu Asn
        275                 280                 285

Lys Ser Glu Thr Trp Pro Ile Gly Glu Ser Pro Lys Gly Val Glu Glu
    290                 295                 300

Gly Ser Ile Gly Lys Val Cys Arg Thr Leu Leu Ala Lys Ser Val Phe
305                 310                 315                 320

Asn Ser Leu Tyr Ala Ser Pro Gln Leu Glu Gly Phe Ser Ala Glu Ser
                325                 330                 335

Arg Lys Leu Leu Leu Ile Val Gln Ala Leu Arg Asp Asn Leu Glu Pro
            340                 345                 350

Gly Thr Phe Asp Ile Gly Gly Leu Tyr Glu Ser Ile Glu Glu Cys Leu
        355                 360                 365

Ile Asn Asp Pro Trp Val Leu Leu Asn Ala Ser Trp Phe Asn Ser Phe
    370                 375                 380
```

-continued

```
Leu Thr His Ala Leu Lys
385                 390


<210> SEQ ID NO 86
<211> LENGTH: 1170
<212> TYPE: DNA
<213> ORGANISM: Equine influenza virus H3N8

<400> SEQUENCE: 86

gaaaagggta taaacccaaa ctatctccaa gcttggaagc aagtattagc agaactacaa      60

gaccttgaga acgaagaaaa gacccctaag accaagaata tgaaaaaaac aagccaattg     120

aaatgggcac tcggtgaaaa tatggcacca gagaaagtgg attttgagga ttgtaaagac     180

atcaatgatt tgaaacagta tgacagtgat gagccagaaa caaggtctct tgcaagttgg     240

attcaaagtg agttcaacaa agcttgtgag ctgacagatt caagctggat agagctcgat     300

gaaattgggg aggatattgc ccaatagaa tacattgcga gcatgaggag aaattatttt     360

actgctgagg tttcccattg tagagcaaca gaatatataa tgaagggagt gtacatcaac     420

actgctctac tcaatgcatc ctgtgctgcg atggatgaat tccaattaat tccgatgata     480

agcaaatgca ggaccaaaga agggagaagg aagacaaatt tatatggatt cataataaag     540

ggaaggtccc atttaaggaa tgataccgac gtggtaaact ttgtaagtat ggaattttct     600

ctcactgatc caagatttga gccacataaa tgggaaaaat actgcgttct agaaattgga     660

gacatgctcc taaggactgc tgtaggtcaa gtgtcaagac ccatgttttt gtatgtaagg     720

acaaatggaa cctctaaaat taaaatgaaa tggggaatgg aaatgagacg ctgcctcctt     780

cagtctctgc aacagattga aagcatgatc gaagctgagt cctcagtcaa agaaaaggac     840

atgaccaaag aattctttga gaacaaatca gagacatggc ctataggaga gtcccccaaa     900

ggagtggaag agggctcaat cggaaaggtt tgcaggacct tattagcaaa atctgtgttt     960

aacagtttgt atgcatctcc acaactggaa gggttttcag ctgaatctag gaaattactt    1020

ctcattgttc aggcccttag ggataacctg gaacctggaa cctttgatat tggggggtta    1080

tatgaatcaa ttgaggagtg cctgattaat gatccctggg ttttgctcaa tgcatcttgg    1140

ttcaactcct tccttacaca tgcactgaag                                     1170


<210> SEQ ID NO 87
<211> LENGTH: 1478
<212> TYPE: DNA
<213> ORGANISM: Equine influenza virus H3N8
<220> FEATURE:
<221> NAME/KEY: CDS
<222> LOCATION: (29)..(1438)

<400> SEQUENCE: 87

gaattcagga gcaaagcagg agtttaaa atg aat cca aat caa aag ata ata        52
                                Met Asn Pro Asn Gln Lys Ile Ile
                                1               5

gca att gga tct gca tca ttg gga ata cta atc ctc aac gtc acc ctc       100
Ala Ile Gly Ser Ala Ser Leu Gly Ile Leu Ile Leu Asn Val Thr Leu
    10                  15                  20

cat gca gtc agc att ata gta aca gta ctg gtc ctc aat aac aat gga       148
His Ala Val Ser Ile Ile Val Thr Val Leu Val Leu Asn Asn Asn Gly
25                  30                  35                  40

aca ggt ctg aac tgc aac ggg acg atc ata aga gag tac aat gaa aca       196
Thr Gly Leu Asn Cys Asn Gly Thr Ile Ile Arg Glu Tyr Asn Glu Thr
                45                  50                  55

gta aga gta gaa aga att act caa tgg tat aat act agt aca att gag       244
```

-continued

```
Val Arg Val Glu Arg Ile Thr Gln Trp Tyr Asn Thr Ser Thr Ile Glu
            60                  65                  70

tac ata gag aga cct tca aat gaa tac tac atg aac aac acc gaa cca      292
Tyr Ile Glu Arg Pro Ser Asn Glu Tyr Tyr Met Asn Asn Thr Glu Pro
        75                  80                  85

ctt tgt gag gcc cag ggc ttt gca cca ttt tcc aaa gat aat gga ata      340
Leu Cys Glu Ala Gln Gly Phe Ala Pro Phe Ser Lys Asp Asn Gly Ile
    90                  95                  100

cga att ggg tcg aga ggc cat gtt ttt gta ata aga gaa cct ttt gtc      388
Arg Ile Gly Ser Arg Gly His Val Phe Val Ile Arg Glu Pro Phe Val
105                 110                 115                 120

tca tgt tcg ccc tca gaa tgt aga acc ttt ttc ctc aca cag ggc tca      436
Ser Cys Ser Pro Ser Glu Cys Arg Thr Phe Phe Leu Thr Gln Gly Ser
                125                 130                 135

tta ctc aat gac aaa cat tct aac ggc aca gtg aag gac cga agt cca      484
Leu Leu Asn Asp Lys His Ser Asn Gly Thr Val Lys Asp Arg Ser Pro
            140                 145                 150

tat agg act ttg atg agt gtc aaa ata ggg caa tca cct aat gtg tat      532
Tyr Arg Thr Leu Met Ser Val Lys Ile Gly Gln Ser Pro Asn Val Tyr
        155                 160                 165

caa gct agg ttt gaa tcg gtg gca tgg tca gca aca gca tgc cat gat      580
Gln Ala Arg Phe Glu Ser Val Ala Trp Ser Ala Thr Ala Cys His Asp
    170                 175                 180

gga aaa aaa tgg atg aca gtt gga gtc aca ggg ccc gat aat caa gca      628
Gly Lys Lys Trp Met Thr Val Gly Val Thr Gly Pro Asp Asn Gln Ala
185                 190                 195                 200

gtt gca gta gtg aac tat gga ggt gtt ccg gtt gat att att aat tca      676
Val Ala Val Val Asn Tyr Gly Gly Val Pro Val Asp Ile Ile Asn Ser
                205                 210                 215

tgg gca ggg gat atc tta aga acc caa gaa tcg tca tgc acc tgc att      724
Trp Ala Gly Asp Ile Leu Arg Thr Gln Glu Ser Ser Cys Thr Cys Ile
            220                 225                 230

aaa gga gac tgt tat tgg gtg atg act gat gga ccg gca aac aga caa      772
Lys Gly Asp Cys Tyr Trp Val Met Thr Asp Gly Pro Ala Asn Arg Gln
        235                 240                 245

gct aaa tat agg ata ttc aaa gca aaa gat gga aga ata att ggg cag      820
Ala Lys Tyr Arg Ile Phe Lys Ala Lys Asp Gly Arg Ile Ile Gly Gln
    250                 255                 260

act gat ata agt ttc aat ggg gga cac ata gag gag tgt tct tgt tac      868
Thr Asp Ile Ser Phe Asn Gly Gly His Ile Glu Glu Cys Ser Cys Tyr
265                 270                 275                 280

ccc aat gaa ggg aag gta gaa tgc ata tgc agg gac aac tgg act gga      916
Pro Asn Glu Gly Lys Val Glu Cys Ile Cys Arg Asp Asn Trp Thr Gly
                285                 290                 295

aca aat aga cca att ctg gta ata tct tct gat cta tcg tac aca gtc      964
Thr Asn Arg Pro Ile Leu Val Ile Ser Ser Asp Leu Ser Tyr Thr Val
            300                 305                 310

gga tat ttg tgt gct ggc att ccc act gac act cct agg gga gag gat     1012
Gly Tyr Leu Cys Ala Gly Ile Pro Thr Asp Thr Pro Arg Gly Glu Asp
        315                 320                 325

agt caa ttc aca ggc tca tgt aca agc cct ttg gga aat aaa gga tac     1060
Ser Gln Phe Thr Gly Ser Cys Thr Ser Pro Leu Gly Asn Lys Gly Tyr
    330                 335                 340

ggt gta aaa ggt ttc ggg ttt cga caa gga aat gac gta tgg gcc gga     1108
Gly Val Lys Gly Phe Gly Phe Arg Gln Gly Asn Asp Val Trp Ala Gly
345                 350                 355                 360

agg aca att agt agg act tca aga tca gga ttc gaa ata ata aaa atc     1156
Arg Thr Ile Ser Arg Thr Ser Arg Ser Gly Phe Glu Ile Ile Lys Ile
                365                 370                 375
```

-continued

```
agg aat ggt tgg aca cag aac agt aaa gac caa atc aga agg caa gtg      1204
Arg Asn Gly Trp Thr Gln Asn Ser Lys Asp Gln Ile Arg Arg Gln Val
            380                 385                 390

att att gat aac cca aat tgg tca gga tat agc ggt tct ttc aca ttg      1252
Ile Ile Asp Asn Pro Asn Trp Ser Gly Tyr Ser Gly Ser Phe Thr Leu
        395                 400                 405

ccg gtt gaa cta aca aaa aag gga tgt tta gtc ccc tgt ttc tgg gtt      1300
Pro Val Glu Leu Thr Lys Lys Gly Cys Leu Val Pro Cys Phe Trp Val
    410                 415                 420

gaa atg att aga ggt aaa cct gaa gaa aca aca ata tgg acc tct agc      1348
Glu Met Ile Arg Gly Lys Pro Glu Glu Thr Thr Ile Trp Thr Ser Ser
425                 430                 435                 440

agc tcc att gtg atg tgt gga gta gat cat aaa att gcc agt tgg tca      1396
Ser Ser Ile Val Met Cys Gly Val Asp His Lys Ile Ala Ser Trp Ser
                445                 450                 455

tgg cac gat gga gct att ctt ccc ttt gac atc gat aag atg              1438
Trp His Asp Gly Ala Ile Leu Pro Phe Asp Ile Asp Lys Met
            460                 465                 470

taatttacga aaaaaactcc ttgtttctac tcctgaattc                          1478


<210> SEQ ID NO 88
<211> LENGTH: 470
<212> TYPE: PRT
<213> ORGANISM: Equine influenza virus H3N8

<400> SEQUENCE: 88

Met Asn Pro Asn Gln Lys Ile Ile Ala Ile Gly Ser Ala Ser Leu Gly
1               5                   10                  15

Ile Leu Ile Leu Asn Val Thr Leu His Ala Val Ser Ile Ile Val Thr
            20                  25                  30

Val Leu Val Leu Asn Asn Asn Gly Thr Gly Leu Asn Cys Asn Gly Thr
        35                  40                  45

Ile Ile Arg Glu Tyr Asn Glu Thr Val Arg Val Glu Arg Ile Thr Gln
    50                  55                  60

Trp Tyr Asn Thr Ser Thr Ile Glu Tyr Ile Glu Arg Pro Ser Asn Glu
65                  70                  75                  80

Tyr Tyr Met Asn Asn Thr Glu Pro Leu Cys Glu Ala Gln Gly Phe Ala
                85                  90                  95

Pro Phe Ser Lys Asp Asn Gly Ile Arg Ile Gly Ser Arg Gly His Val
            100                 105                 110

Phe Val Ile Arg Glu Pro Phe Val Ser Cys Ser Pro Ser Glu Cys Arg
        115                 120                 125

Thr Phe Phe Leu Thr Gln Gly Ser Leu Leu Asn Asp Lys His Ser Asn
    130                 135                 140

Gly Thr Val Lys Asp Arg Ser Pro Tyr Arg Thr Leu Met Ser Val Lys
145                 150                 155                 160

Ile Gly Gln Ser Pro Asn Val Tyr Gln Ala Arg Phe Glu Ser Val Ala
                165                 170                 175

Trp Ser Ala Thr Ala Cys His Asp Gly Lys Lys Trp Met Thr Val Gly
            180                 185                 190

Val Thr Gly Pro Asp Asn Gln Ala Val Ala Val Val Asn Tyr Gly Gly
        195                 200                 205

Val Pro Val Asp Ile Ile Asn Ser Trp Ala Gly Asp Ile Leu Arg Thr
    210                 215                 220

Gln Glu Ser Ser Cys Thr Cys Ile Lys Gly Asp Cys Tyr Trp Val Met
225                 230                 235                 240
```

-continued

```
Thr Asp Gly Pro Ala Asn Arg Gln Ala Lys Tyr Arg Ile Phe Lys Ala
                245                 250                 255

Lys Asp Gly Arg Ile Ile Gly Gln Thr Asp Ile Ser Phe Asn Gly Gly
            260                 265                 270

His Ile Glu Glu Cys Ser Cys Tyr Pro Asn Glu Gly Lys Val Glu Cys
        275                 280                 285

Ile Cys Arg Asp Asn Trp Thr Gly Thr Asn Arg Pro Ile Leu Val Ile
    290                 295                 300

Ser Ser Asp Leu Ser Tyr Thr Val Gly Tyr Leu Cys Ala Gly Ile Pro
305                 310                 315                 320

Thr Asp Thr Pro Arg Gly Glu Asp Ser Gln Phe Thr Gly Ser Cys Thr
                325                 330                 335

Ser Pro Leu Gly Asn Lys Gly Tyr Gly Val Lys Gly Phe Gly Phe Arg
            340                 345                 350

Gln Gly Asn Asp Val Trp Ala Gly Arg Thr Ile Ser Arg Thr Ser Arg
        355                 360                 365

Ser Gly Phe Glu Ile Ile Lys Ile Arg Asn Gly Trp Thr Gln Asn Ser
    370                 375                 380

Lys Asp Gln Ile Arg Arg Gln Val Ile Ile Asp Asn Pro Asn Trp Ser
385                 390                 395                 400

Gly Tyr Ser Gly Ser Phe Thr Leu Pro Val Glu Leu Thr Lys Lys Gly
                405                 410                 415

Cys Leu Val Pro Cys Phe Trp Val Glu Met Ile Arg Gly Lys Pro Glu
            420                 425                 430

Glu Thr Thr Ile Trp Thr Ser Ser Ser Ser Ile Val Met Cys Gly Val
        435                 440                 445

Asp His Lys Ile Ala Ser Trp Ser Trp His Asp Gly Ala Ile Leu Pro
    450                 455                 460

Phe Asp Ile Asp Lys Met
465                 470
```

<210> SEQ ID NO 89
<211> LENGTH: 1410
<212> TYPE: DNA
<213> ORGANISM: Equine influenza virus H3N8

<400> SEQUENCE: 89

```
atgaatccaa atcaaaagat aatagcaatt ggatctgcat cattgggaat actaatcctc      60

aacgtcaccc tccatgcagt cagcattata gtaacagtac tggtcctcaa taacaatgga     120

acaggtctga actgcaacgg gacgatcata agagagtaca atgaaacagt aagagtagaa     180

agaattactc aatggtataa tactagtaca attgagtaca tagagagacc ttcaaatgaa     240

tactacatga acaacaccga accactttgt gaggcccagg gctttgcacc attttccaaa     300

gataatggaa tacgaattgg gtcgagaggc catgtttttg taataagaga accttttgtc     360

tcatgttcgc cctcagaatg tagaaccttt ttcctcacac agggctcatt actcaatgac     420

aaacattcta acggcacagt gaaggaccga agtccatata ggactttgat gagtgtcaaa     480

atagggcaat cacctaatgt gtatcaagct aggtttgaat cggtggcatg gtcagcaaca     540

gcatgccatg atggaaaaaa atggatgaca gttggagtca cagggcccga taatcaagca     600

gttgcagtag tgaactatgg aggtgttccg gttgatatta ttaattcatg ggcaggggat     660

atcttaagaa cccaagaatc gtcatgcacc tgcattaaag gagactgtta ttgggtgatg     720

actgatggac cggcaaacag acaagctaaa tataggatat tcaaagcaaa agatggaaga     780
```

-continued

```
ataattgggc agactgatat aagtttcaat gggggacaca tagaggagtg ttcttgttac    840

cccaatgaag ggaaggtaga atgcatatgc agggacaact ggactggaac aaatagacca    900

attctggtaa tatcttctga tctatcgtac acagtcggat atttgtgtgc tggcattccc    960

actgacactc ctaggggaga ggatagtcaa ttcacaggct catgtacaag ccctttggga   1020

aataaaggat acggtgtaaa aggtttcggg tttcgacaag gaaatgacgt atgggccgga   1080

aggacaatta gtaggacttc aagatcagga ttcgaaataa taaaaatcag gaatggttgg   1140

acacagaaca gtaaagacca aatcagaagg caagtgatta ttgataaccc aaattggtca   1200

ggatatagcg gttctttcac attgccggtt gaactaacaa aaaagggatg tttagtcccc   1260

tgtttctggg ttgaaatgat tagaggtaaa cctgaagaaa caacaatatg gacctctagc   1320

agctccattg tgatgtgtgg agtagatcat aaaattgcca gttggtcatg gcacgatgga   1380

gctattcttc cctttgacat cgataagatg                                     1410


<210> SEQ ID NO 90
<211> LENGTH: 17
<212> TYPE: DNA
<213> ORGANISM: Artificial
<220> FEATURE:
<223> OTHER INFORMATION: Synthetic Primer

<400> SEQUENCE: 90

gtgacttggg tcctcaa                                                     17


<210> SEQ ID NO 91
<211> LENGTH: 19
<212> TYPE: DNA
<213> ORGANISM: Artificial
<220> FEATURE:
<223> OTHER INFORMATION: Synthetic Primer

<400> SEQUENCE: 91

accccgacca ctcaagatg                                                   19


<210> SEQ ID NO 92
<211> LENGTH: 20
<212> TYPE: DNA
<213> ORGANISM: Artificial
<220> FEATURE:
<223> OTHER INFORMATION: Synthetic Primer

<400> SEQUENCE: 92

catatactac ctggagaagg                                                  20


<210> SEQ ID NO 93
<211> LENGTH: 19
<212> TYPE: DNA
<213> ORGANISM: Artificial
<220> FEATURE:
<223> OTHER INFORMATION: Synthetic Primer

<400> SEQUENCE: 93

atagtccgct tttgtagcc                                                   19


<210> SEQ ID NO 94
<211> LENGTH: 1216
<212> TYPE: DNA
<213> ORGANISM: Equine influenza virus H3N8

<400> SEQUENCE: 94

agcaaaagca ggtatgatcc aaaatggaag actttgtgcg acagtgcttc aatccaatga     60
```

-continued

```
tcgtcgagct tgcggaaaag gcaatgaaag aatatggaga ggacccgaaa attgaaacaa    120

acaaatttgc agcaatatgc actcacttgg aagtctgctt catgtactcg gatttccact    180

ttattaatga actgggtgag tcagtgatca tagagtctgg tgatccaaat gctcttttga    240

aacacagatt tgaaatcatt gaagggagag atcgaacaat ggcatggaca gtagtaaaca    300

gcatctgcaa caccacaaga gctgaaaaac ccaagtttct cccagattta tacgactata    360

aggagaacag atttgttgaa attggtgtga caaggagaga agttcacata tactacctgg    420

agaaggccaa caaaataaag tctgagaaaa cacatatcca cattttctca tttacaggag    480

aggaaatggc tacaaaagcg gactatactc ttgatgaaga gagtagagcc aggatcaaga    540

ccagactatt caccataaga caagaaatgg ccagtagagg cctctgggat tcctttcgtc    600

agtccgagag aggcgaagag acaattgaag aaagatttga aatcacaggg acgatgcgca    660

ggcttgccaa ttacagtctc ccaccgaact tctccagcct tgaaaatttt agagtctatg    720

tggatggatt cgaaccgaac ggctgcattg agagtaagct ttctcaaatg tccaaagaag    780

taaatgccag aatcgagcca ttttcaaaga caacaccccg accactcaag atgccaggtg    840

gtccaccctg ccatcagcga tctaaattct tgctaatgga tgctctgaaa ttgagtattg    900

aggacccaag tcacgaggga gagggaatac cactatatga tgctatcaaa tgcatgaaaa    960

ctttctttgg atggaaagag cccagtgttg ttaaaccaca tgaaaagggt ataaacccaa   1020

actatctcca agcttggaag caagtattag cagaactaca agaccttgag aacgaagaaa   1080

agacccctaa gaccaagaat atgaaaaaaa caagccaatt gaaatgggca ctcggtgaaa   1140

atatggcacc agagaaagtg gattttgagg attgtaaaga catcaatgat ttgaaacagt   1200

atgacagtga tgagcc                                                   1216


<210> SEQ ID NO 95
<211> LENGTH: 1193
<212> TYPE: DNA
<213> ORGANISM: Equine influenza virus H3N8
<220> FEATURE:
<221> NAME/KEY: CDS
<222> LOCATION: (1)..(1191)

<400> SEQUENCE: 95

atg gaa gac ttt gtg cga cag tgc ttc aat cca atg atc gtc gag ctt       48
Met Glu Asp Phe Val Arg Gln Cys Phe Asn Pro Met Ile Val Glu Leu
1               5                   10                  15

gcg gaa aag gca atg aaa gaa tat gga gag gac ccg aaa att gaa aca       96
Ala Glu Lys Ala Met Lys Glu Tyr Gly Glu Asp Pro Lys Ile Glu Thr
            20                  25                  30

aac aaa ttt gca gca ata tgc act cac ttg gaa gtc tgc ttc atg tac      144
Asn Lys Phe Ala Ala Ile Cys Thr His Leu Glu Val Cys Phe Met Tyr
        35                  40                  45

tcg gat ttc cac ttt att aat gaa ctg ggt gag tca gtg atc ata gag      192
Ser Asp Phe His Phe Ile Asn Glu Leu Gly Glu Ser Val Ile Ile Glu
    50                  55                  60

tct ggt gat cca aat gct ctt ttg aaa cac aga ttt gaa atc att gaa      240
Ser Gly Asp Pro Asn Ala Leu Leu Lys His Arg Phe Glu Ile Ile Glu
65                  70                  75                  80

ggg aga gat cga aca atg gca tgg aca gta gta aac agc atc tgc aac      288
Gly Arg Asp Arg Thr Met Ala Trp Thr Val Val Asn Ser Ile Cys Asn
                85                  90                  95

acc aca aga gct gaa aaa ccc aag ttt ctc cca gat tta tac gac tat      336
Thr Thr Arg Ala Glu Lys Pro Lys Phe Leu Pro Asp Leu Tyr Asp Tyr
            100                 105                 110
```

-continued

```
aag gag aac aga ttt gtt gaa att ggt gtg aca agg aga gaa gtt cac      384
Lys Glu Asn Arg Phe Val Glu Ile Gly Val Thr Arg Arg Glu Val His
        115                 120                 125

ata tac tac ctg gag aag gcc aac aaa ata aag tct gag aaa aca cat      432
Ile Tyr Tyr Leu Glu Lys Ala Asn Lys Ile Lys Ser Glu Lys Thr His
    130                 135                 140

atc cac att ttc tca ttt aca gga gag gaa atg gct aca aaa gcg gac      480
Ile His Ile Phe Ser Phe Thr Gly Glu Glu Met Ala Thr Lys Ala Asp
145                 150                 155                 160

tat act ctt gat gaa gag agt aga gcc agg atc aag acc aga cta ttc      528
Tyr Thr Leu Asp Glu Glu Ser Arg Ala Arg Ile Lys Thr Arg Leu Phe
                165                 170                 175

acc ata aga caa gaa atg gcc agt aga ggc ctc tgg gat tcc ttt cgt      576
Thr Ile Arg Gln Glu Met Ala Ser Arg Gly Leu Trp Asp Ser Phe Arg
            180                 185                 190

cag tcc gag aga ggc gaa gag aca att gaa gaa aga ttt gaa atc aca      624
Gln Ser Glu Arg Gly Glu Glu Thr Ile Glu Glu Arg Phe Glu Ile Thr
        195                 200                 205

ggg acg atg cgc agg ctt gcc aat tac agt ctc cca ccg aac ttc tcc      672
Gly Thr Met Arg Arg Leu Ala Asn Tyr Ser Leu Pro Pro Asn Phe Ser
    210                 215                 220

agc ctt gaa aat ttt aga gtc tat gtg gat gga ttc gaa ccg aac ggc      720
Ser Leu Glu Asn Phe Arg Val Tyr Val Asp Gly Phe Glu Pro Asn Gly
225                 230                 235                 240

tgc att gag agt aag ctt tct caa atg tcc aaa gaa gta aat gcc aga      768
Cys Ile Glu Ser Lys Leu Ser Gln Met Ser Lys Glu Val Asn Ala Arg
                245                 250                 255

atc gag cca ttt tca aag aca aca ccc cga cca ctc aag atg cca ggt      816
Ile Glu Pro Phe Ser Lys Thr Thr Pro Arg Pro Leu Lys Met Pro Gly
            260                 265                 270

ggt cca ccc tgc cat cag cga tct aaa ttc ttg cta atg gat gct ctg      864
Gly Pro Pro Cys His Gln Arg Ser Lys Phe Leu Leu Met Asp Ala Leu
        275                 280                 285

aaa ttg agt att gag gac cca agt cac gag gga gag gga ata cca cta      912
Lys Leu Ser Ile Glu Asp Pro Ser His Glu Gly Glu Gly Ile Pro Leu
    290                 295                 300

tat gat gct atc aaa tgc atg aaa act ttc ttt gga tgg aaa gag ccc      960
Tyr Asp Ala Ile Lys Cys Met Lys Thr Phe Phe Gly Trp Lys Glu Pro
305                 310                 315                 320

agt gtt gtt aaa cca cat gaa aag ggt ata aac cca aac tat ctc caa     1008
Ser Val Val Lys Pro His Glu Lys Gly Ile Asn Pro Asn Tyr Leu Gln
                325                 330                 335

gct tgg aag caa gta tta gca gaa cta caa gac ctt gag aac gaa gaa     1056
Ala Trp Lys Gln Val Leu Ala Glu Leu Gln Asp Leu Glu Asn Glu Glu
            340                 345                 350

aag acc cct aag acc aag aat atg aaa aaa aca agc caa ttg aaa tgg     1104
Lys Thr Pro Lys Thr Lys Asn Met Lys Lys Thr Ser Gln Leu Lys Trp
        355                 360                 365

gca ctc ggt gaa aat atg gca cca gag aaa gtg gat ttt gag gat tgt     1152
Ala Leu Gly Glu Asn Met Ala Pro Glu Lys Val Asp Phe Glu Asp Cys
    370                 375                 380

aaa gac atc aat gat ttg aaa cag tat gac agt gat gag cc              1193
Lys Asp Ile Asn Asp Leu Lys Gln Tyr Asp Ser Asp Glu
385                 390                 395
```

<210> SEQ ID NO 96
<211> LENGTH: 397
<212> TYPE: PRT
<213> ORGANISM: Equine influenza virus H3N8

-continued

<400> SEQUENCE: 96

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Leu Gly Glu Ser Val Ile Ile Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Arg Ala Glu Lys Pro Lys Phe Leu Pro Asp Leu Tyr Asp Tyr
            100                 105                 110

Lys Glu Asn Arg Phe Val Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Arg Leu Ala Asn Tyr Ser Leu Pro Pro Asn Phe Ser
    210                 215                 220

Ser Leu Glu Asn Phe Arg Val Tyr Val Asp Gly Phe Glu Pro Asn Gly
225                 230                 235                 240

Cys Ile Glu Ser Lys Leu Ser Gln Met Ser Lys Glu Val Asn Ala Arg
                245                 250                 255

Ile Glu Pro Phe Ser Lys Thr Thr Pro Arg Pro Leu Lys Met Pro Gly
            260                 265                 270

Gly Pro Pro Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Ser Val Val Lys Pro His Glu Lys Gly Ile Asn Pro Asn Tyr Leu Gln
                325                 330                 335

Ala Trp Lys Gln Val Leu Ala Glu Leu Gln Asp Leu Glu Asn Glu Glu
            340                 345                 350

Lys Thr Pro Lys Thr Lys Asn Met Lys Lys Thr Ser Gln Leu Lys Trp
        355                 360                 365

Ala Leu Gly Glu Asn Met Ala Pro Glu Lys Val Asp Phe Glu Asp Cys
    370                 375                 380

Lys Asp Ile Asn Asp Leu Lys Gln Tyr Asp Ser Asp Glu
385                 390                 395

-continued

<210> SEQ ID NO 97
<211> LENGTH: 1217
<212> TYPE: DNA
<213> ORGANISM: Equine influenza virus H3N8

<400> SEQUENCE: 97
agcaaaagca ggtactgatc caaaatggaa gactttgtgc gacagtgctt caatccaatg 60
atcgtcgagc ttgcggaaaa ggcaatgaaa gaatatggag aggacccgaa aattgaaaca 120
aacaaatttg cagcaatatg cactcacttg gaagtctgct tcatgtactc ggatttccac 180
tttattaatg aactgggtaa gtcagtgatc atagagtctg gtgatccaaa tgctcttttg 240
aaacacagat ttgaaatcat tgaagggaga gatcgaacaa tggcatggac agtagtaaac 300
agcatctgca acaccacaag agctgaaaaa cccaagtttc tcccagattt atacgactat 360
aaggagaaca gatttgttga aattggtgtg acaaggagag aagttcacat atactacctg 420
gagaaggcca acaaaataaa gtctgagaaa acacatatcc acatttttctc atttacagga 480 gaggaaatga ctacaaaagc ggactatact cttgatgaag agagtagagc caggatcaag 540
accagactat tcaccataag acaagaaatg gccagtagag gcctctggga ttcctttcgt 600
cagtccgaga gaggcgaaga gacaattgaa gaaagatttg aaatcacagg gacgatgcgc 660
aggcttgcca attacagtct cccaccgaac ttctccagcc ttgaaaattt tagagtctat 720
gtggatggat tcgaaccgaa cggctgcatt gagagtaagc tttctcaaat gtccaaagaa 780
gtaaatgcca gaatcgagcc attttcaaag acaacacccc gaccactcaa gatgccaggt 840
ggtccaccct gccatcagcg atctaaattc ttgctaatgg atgctctgaa attaagtatt 900
gaggacccaa gtcacgaggg agagggaata ccactatatg atgctatcaa atgcatgaaa 960
actttctttg gatggaaaga gcccagtgtt gttaaaccac atgaaaaggg tataaaccca 1020
aactatctcc aagcttggaa gcaagtatta gcagaactac aagaccttga gaacgaagaa 1080
aagaccccta agaccaagaa tatgaaaaaa acaagccaat tgaaatgggc actcggtgaa 1140
aatatggcac cagagaaagt ggattttgag gattgtaaag acatcaatga tttgaaacag 1200
tatgacagtg atgagcc 1217

<210> SEQ ID NO 98
<211> LENGTH: 1193
<212> TYPE: DNA
<213> ORGANISM: Equine influenza virus H3N8
<220> FEATURE:
<221> NAME/KEY: CDS
<222> LOCATION: (1)..(1191)

<400> SEQUENCE: 98

```
atg gaa gac ttt gtg cga cag tgc ttc aat cca atg atc gtc gag ctt       48
Met Glu Asp Phe Val Arg Gln Cys Phe Asn Pro Met Ile Val Glu Leu
1               5                   10                  15

gcg gaa aag gca atg aaa gaa tat gga gag gac ccg aaa att gaa aca       96
Ala Glu Lys Ala Met Lys Glu Tyr Gly Glu Asp Pro Lys Ile Glu Thr
            20                  25                  30

aac aaa ttt gca gca ata tgc act cac ttg gaa gtc tgc ttc atg tac      144
Asn Lys Phe Ala Ala Ile Cys Thr His Leu Glu Val Cys Phe Met Tyr
        35                  40                  45

tcg gat ttc cac ttt att aat gaa ctg ggt aag tca gtg atc ata gag      192
Ser Asp Phe His Phe Ile Asn Glu Leu Gly Lys Ser Val Ile Ile Glu
    50                  55                  60

tct ggt gat cca aat gct ctt ttg aaa cac aga ttt gaa atc att gaa      240
Ser Gly Asp Pro Asn Ala Leu Leu Lys His Arg Phe Glu Ile Ile Glu
65                  70                  75                  80
```

-continued

```
ggg aga gat cga aca atg gca tgg aca gta gta aac agc atc tgc aac      288
Gly Arg Asp Arg Thr Met Ala Trp Thr Val Val Asn Ser Ile Cys Asn
                85                  90                  95

acc aca aga gct gaa aaa ccc aag ttt ctc cca gat tta tac gac tat      336
Thr Thr Arg Ala Glu Lys Pro Lys Phe Leu Pro Asp Leu Tyr Asp Tyr
            100                 105                 110

aag gag aac aga ttt gtt gaa att ggt gtg aca agg aga gaa gtt cac      384
Lys Glu Asn Arg Phe Val Glu Ile Gly Val Thr Arg Arg Glu Val His
        115                 120                 125

ata tac tac ctg gag aag gcc aac aaa ata aag tct gag aaa aca cat      432
Ile Tyr Tyr Leu Glu Lys Ala Asn Lys Ile Lys Ser Glu Lys Thr His
    130                 135                 140

atc cac att ttc tca ttt aca gga gag gaa atg act aca aaa gcg gac      480
Ile His Ile Phe Ser Phe Thr Gly Glu Glu Met Thr Thr Lys Ala Asp
145                 150                 155                 160

tat act ctt gat gaa gag agt aga gcc agg atc aag acc aga cta ttc      528
Tyr Thr Leu Asp Glu Glu Ser Arg Ala Arg Ile Lys Thr Arg Leu Phe
                165                 170                 175

acc ata aga caa gaa atg gcc agt aga ggc ctc tgg gat tcc ttt cgt      576
Thr Ile Arg Gln Glu Met Ala Ser Arg Gly Leu Trp Asp Ser Phe Arg
            180                 185                 190

cag tcc gag aga ggc gaa gag aca att gaa gaa aga ttt gaa atc aca      624
Gln Ser Glu Arg Gly Glu Glu Thr Ile Glu Glu Arg Phe Glu Ile Thr
        195                 200                 205

ggg acg atg cgc agg ctt gcc aat tac agt ctc cca ccg aac ttc tcc      672
Gly Thr Met Arg Arg Leu Ala Asn Tyr Ser Leu Pro Pro Asn Phe Ser
    210                 215                 220

agc ctt gaa aat ttt aga gtc tat gtg gat gga ttc gaa ccg aac ggc      720
Ser Leu Glu Asn Phe Arg Val Tyr Val Asp Gly Phe Glu Pro Asn Gly
225                 230                 235                 240

tgc att gag agt aag ctt tct caa atg tcc aaa gaa gta aat gcc aga      768
Cys Ile Glu Ser Lys Leu Ser Gln Met Ser Lys Glu Val Asn Ala Arg
                245                 250                 255

atc gag cca ttt tca aag aca aca ccc cga cca ctc aag atg cca ggt      816
Ile Glu Pro Phe Ser Lys Thr Thr Pro Arg Pro Leu Lys Met Pro Gly
            260                 265                 270

ggt cca ccc tgc cat cag cga tct aaa ttc ttg cta atg gat gct ctg      864
Gly Pro Pro Cys His Gln Arg Ser Lys Phe Leu Leu Met Asp Ala Leu
        275                 280                 285

aaa tta agt att gag gac cca agt cac gag gga gag gga ata cca cta      912
Lys Leu Ser Ile Glu Asp Pro Ser His Glu Gly Glu Gly Ile Pro Leu
    290                 295                 300

tat gat gct atc aaa tgc atg aaa act ttc ttt gga tgg aaa gag ccc      960
Tyr Asp Ala Ile Lys Cys Met Lys Thr Phe Phe Gly Trp Lys Glu Pro
305                 310                 315                 320

agt gtt gtt aaa cca cat gaa aag ggt ata aac cca aac tat ctc caa     1008
Ser Val Val Lys Pro His Glu Lys Gly Ile Asn Pro Asn Tyr Leu Gln
                325                 330                 335

gct tgg aag caa gta tta gca gaa cta caa gac ctt gag aac gaa gaa     1056
Ala Trp Lys Gln Val Leu Ala Glu Leu Gln Asp Leu Glu Asn Glu Glu
            340                 345                 350

aag acc cct aag acc aag aat atg aaa aaa aca agc caa ttg aaa tgg     1104
Lys Thr Pro Lys Thr Lys Asn Met Lys Lys Thr Ser Gln Leu Lys Trp
        355                 360                 365

gca ctc ggt gaa aat atg gca cca gag aaa gtg gat ttt gag gat tgt     1152
Ala Leu Gly Glu Asn Met Ala Pro Glu Lys Val Asp Phe Glu Asp Cys
    370                 375                 380

aaa gac atc aat gat ttg aaa cag tat gac agt gat gag cc              1193
Lys Asp Ile Asn Asp Leu Lys Gln Tyr Asp Ser Asp Glu
```

-continued 385 390 395

<210> SEQ ID NO 99
<211> LENGTH: 397
<212> TYPE: PRT
<213> ORGANISM: Equine influenza virus H3N8

<400> SEQUENCE: 99

Met Glu Asp Phe Val Arg Gln Cys Phe Asn Pro Met Ile Val Glu Leu
1 5 10 15

Ala Glu Lys Ala Met Lys Glu Tyr Gly Glu Asp Pro Lys Ile Glu Thr
20 25 30

Asn Lys Phe Ala Ala Ile Cys Thr His Leu Glu Val Cys Phe Met Tyr
35 40 45

Ser Asp Phe His Phe Ile Asn Glu Leu Gly Lys Ser Val Ile Ile Glu
50 55 60

Ser Gly Asp Pro Asn Ala Leu Leu Lys His Arg Phe Glu Ile Ile Glu
65 70 75 80

Gly Arg Asp Arg Thr Met Ala Trp Thr Val Val Asn Ser Ile Cys Asn
85 90 95

Thr Thr Arg Ala Glu Lys Pro Lys Phe Leu Pro Asp Leu Tyr Asp Tyr
100 105 110

Lys Glu Asn Arg Phe Val Glu Ile Gly Val Thr Arg Arg Glu Val His
115 120 125

Ile Tyr Tyr Leu Glu Lys Ala Asn Lys Ile Lys Ser Glu Lys Thr His
130 135 140

Ile His Ile Phe Ser Phe Thr Gly Glu Glu Met Thr Thr Lys Ala Asp
145 150 155 160

Tyr Thr Leu Asp Glu Glu Ser Arg Ala Arg Ile Lys Thr Arg Leu Phe
165 170 175

Thr Ile Arg Gln Glu Met Ala Ser Arg Gly Leu Trp Asp Ser Phe Arg
180 185 190

Gln Ser Glu Arg Gly Glu Glu Thr Ile Glu Glu Arg Phe Glu Ile Thr
195 200 205

Gly Thr Met Arg Arg Leu Ala Asn Tyr Ser Leu Pro Pro Asn Phe Ser
210 215 220

Ser Leu Glu Asn Phe Arg Val Tyr Val Asp Gly Phe Glu Pro Asn Gly
225 230 235 240

Cys Ile Glu Ser Lys Leu Ser Gln Met Ser Lys Glu Val Asn Ala Arg
245 250 255

Ile Glu Pro Phe Ser Lys Thr Thr Pro Arg Pro Leu Lys Met Pro Gly
260 265 270

Gly Pro Pro Cys His Gln Arg Ser Lys Phe Leu Leu Met Asp Ala Leu
275 280 285

Lys Leu Ser Ile Glu Asp Pro Ser His Glu Gly Glu Gly Ile Pro Leu
290 295 300

Tyr Asp Ala Ile Lys Cys Met Lys Thr Phe Phe Gly Trp Lys Glu Pro
305 310 315 320

Ser Val Val Lys Pro His Glu Lys Gly Ile Asn Pro Asn Tyr Leu Gln
325 330 335

Ala Trp Lys Gln Val Leu Ala Glu Leu Gln Asp Leu Glu Asn Glu Glu
340 345 350

Lys Thr Pro Lys Thr Lys Asn Met Lys Lys Thr Ser Gln Leu Lys Trp
355 360 365

-continued

```
Ala Leu Gly Glu Asn Met Ala Pro Glu Lys Val Asp Phe Glu Asp Cys
    370                 375                 380

Lys Asp Ile Asn Asp Leu Lys Gln Tyr Asp Ser Asp Glu
385                 390                 395
```

<210> SEQ ID NO 100
<211> LENGTH: 2148
<212> TYPE: DNA
<213> ORGANISM: Equine influenza virus H3N8
<220> FEATURE:
<221> NAME/KEY: misc_feature
<222> LOCATION: (577)..(577)
<223> OTHER INFORMATION: The 'Xaa' at amino acid location 577 stands for Arg, or Trp.
<220> FEATURE:
<221> NAME/KEY: CDS
<222> LOCATION: (1)..(2148)

<400> SEQUENCE: 100

```
atg gaa gac ttt gtg cga cag tgc ttc aat cca atg atc gtc gag ctt       48
Met Glu Asp Phe Val Arg Gln Cys Phe Asn Pro Met Ile Val Glu Leu
1               5                   10                  15

gcg gaa aag gca atg aaa gaa tat gga gag gac ccg aaa att gaa aca       96
Ala Glu Lys Ala Met Lys Glu Tyr Gly Glu Asp Pro Lys Ile Glu Thr
            20                  25                  30

aac aaa ttt gca gca ata tgc act cac ttg gaa gtc tgc ttc atg tac      144
Asn Lys Phe Ala Ala Ile Cys Thr His Leu Glu Val Cys Phe Met Tyr
        35                  40                  45

tcg gat ttc cac ttt att aat gaa ctg ggt gag tca gtg atc ata gag      192
Ser Asp Phe His Phe Ile Asn Glu Leu Gly Glu Ser Val Ile Ile Glu
    50                  55                  60

tct ggt gat cca aat gct ctt ttg aaa cac aga ttt gaa atc att gaa      240
Ser Gly Asp Pro Asn Ala Leu Leu Lys His Arg Phe Glu Ile Ile Glu
65                  70                  75                  80

ggg aga gat cga aca atg gca tgg aca gta gta aac agc atc tgc aac      288
Gly Arg Asp Arg Thr Met Ala Trp Thr Val Val Asn Ser Ile Cys Asn
                85                  90                  95

acc aca aga gct gaa aaa ccc aag ttt ctc cca gat tta tac gac tat      336
Thr Thr Arg Ala Glu Lys Pro Lys Phe Leu Pro Asp Leu Tyr Asp Tyr
            100                 105                 110

aag gag aac aga ttt gtt gaa att ggt gtg aca agg aga gaa gtt cac      384
Lys Glu Asn Arg Phe Val Glu Ile Gly Val Thr Arg Arg Glu Val His
        115                 120                 125

ata tac tac ctg gag aag gcc aac aaa ata aag tct gag aaa aca cat      432
Ile Tyr Tyr Leu Glu Lys Ala Asn Lys Ile Lys Ser Glu Lys Thr His
    130                 135                 140

atc cac att ttc tca ttt aca gga gag gaa atg gct aca aaa gcg gac      480
Ile His Ile Phe Ser Phe Thr Gly Glu Glu Met Ala Thr Lys Ala Asp
145                 150                 155                 160

tat act ctt gat gaa gag agt aga gcc agg atc aag acc aga cta ttc      528
Tyr Thr Leu Asp Glu Glu Ser Arg Ala Arg Ile Lys Thr Arg Leu Phe
                165                 170                 175

acc ata aga caa gaa atg gcc agt aga ggc ctc tgg gat tcc ttt cgt      576
Thr Ile Arg Gln Glu Met Ala Ser Arg Gly Leu Trp Asp Ser Phe Arg
            180                 185                 190

cag tcc gag aga ggc gaa gag aca att gaa gaa aga ttt gaa atc aca      624
Gln Ser Glu Arg Gly Glu Glu Thr Ile Glu Glu Arg Phe Glu Ile Thr
        195                 200                 205

ggg acg atg cgc agg ctt gcc aat tac agt ctc cca ccg aac ttc tcc      672
Gly Thr Met Arg Arg Leu Ala Asn Tyr Ser Leu Pro Pro Asn Phe Ser
    210                 215                 220

agc ctt gaa aat ttt aga gtc tat gtg gat gga ttc gaa ccg aac ggc      720
```

-continued

```
Ser Leu Glu Asn Phe Arg Val Tyr Val Asp Gly Phe Glu Pro Asn Gly
225                 230                 235                 240

tgc att gag agt aag ctt tct caa atg tcc aaa gaa gta aat gcc aga      768
Cys Ile Glu Ser Lys Leu Ser Gln Met Ser Lys Glu Val Asn Ala Arg
                245                 250                 255

atc gag cca ttt tca aag aca aca ccc cga cca ctc aag atg cca ggt      816
Ile Glu Pro Phe Ser Lys Thr Thr Pro Arg Pro Leu Lys Met Pro Gly
            260                 265                 270

ggt cca ccc tgc cat cag cga tct aaa ttc ttg cta atg gat gct ctg      864
Gly Pro Pro Cys His Gln Arg Ser Lys Phe Leu Leu Met Asp Ala Leu
        275                 280                 285

aaa ttg agt att gag gac cca agt cac gag gga gag gga ata cca cta      912
Lys Leu Ser Ile Glu Asp Pro Ser His Glu Gly Glu Gly Ile Pro Leu
    290                 295                 300

tat gat gct atc aaa tgc atg aaa act ttc ttt gga tgg aaa gag ccc      960
Tyr Asp Ala Ile Lys Cys Met Lys Thr Phe Phe Gly Trp Lys Glu Pro
305                 310                 315                 320

agt gtt gtt aaa cca cat gaa aag ggt ata aac cca aac tat ctc caa     1008
Ser Val Val Lys Pro His Glu Lys Gly Ile Asn Pro Asn Tyr Leu Gln
                325                 330                 335

gct tgg aag caa gta tta gca gaa cta caa gac ctt gag aac gaa gaa     1056
Ala Trp Lys Gln Val Leu Ala Glu Leu Gln Asp Leu Glu Asn Glu Glu
            340                 345                 350

aag acc cct aag acc aag aat atg aaa aaa aca agc caa ttg aaa tgg     1104
Lys Thr Pro Lys Thr Lys Asn Met Lys Lys Thr Ser Gln Leu Lys Trp
        355                 360                 365

gca ctc ggt gaa aat atg gca cca gag aaa gtg gat ttt gag gat tgt     1152
Ala Leu Gly Glu Asn Met Ala Pro Glu Lys Val Asp Phe Glu Asp Cys
    370                 375                 380

aaa gac atc aat gat ttg aaa cag tat gac agt gat gag cca gaa aca     1200
Lys Asp Ile Asn Asp Leu Lys Gln Tyr Asp Ser Asp Glu Pro Glu Thr
385                 390                 395                 400

agg tct ctt gca agt tgg att caa agt gag ttc aac aaa gct tgt gag     1248
Arg Ser Leu Ala Ser Trp Ile Gln Ser Glu Phe Asn Lys Ala Cys Glu
                405                 410                 415

ctg aca gat tca agc tgg ata gag ctc gat gaa att ggg gag gat att     1296
Leu Thr Asp Ser Ser Trp Ile Glu Leu Asp Glu Ile Gly Glu Asp Ile
            420                 425                 430

gcc cca ata gaa tac att gcg agc atg agg aga aat tat ttt act gct     1344
Ala Pro Ile Glu Tyr Ile Ala Ser Met Arg Arg Asn Tyr Phe Thr Ala
        435                 440                 445

gag gtt tcc cat tgt aga gca aca gaa tat ata atg aag gga gtg tac     1392
Glu Val Ser His Cys Arg Ala Thr Glu Tyr Ile Met Lys Gly Val Tyr
    450                 455                 460

atc aac act gct cta ctc aat gca tcc tgt gct gcg atg gat gaa ttc     1440
Ile Asn Thr Ala Leu Leu Asn Ala Ser Cys Ala Ala Met Asp Glu Phe
465                 470                 475                 480

caa tta att ccg atg ata agc aaa tgc agg acc aaa gaa ggg aga agg     1488
Gln Leu Ile Pro Met Ile Ser Lys Cys Arg Thr Lys Glu Gly Arg Arg
                485                 490                 495

aag aca aat tta tat gga ttc ata ata aag gga agg tcc cat tta agg     1536
Lys Thr Asn Leu Tyr Gly Phe Ile Ile Lys Gly Arg Ser His Leu Arg
            500                 505                 510

aat gat acc gac gtg gta aac ttt gta agt atg gaa ttt tct ctc act     1584
Asn Asp Thr Asp Val Val Asn Phe Val Ser Met Glu Phe Ser Leu Thr
        515                 520                 525

gat cca aga ttt gag cca cat aaa tgg gaa aaa tac tgc gtt cta gaa     1632
Asp Pro Arg Phe Glu Pro His Lys Trp Glu Lys Tyr Cys Val Leu Glu
    530                 535                 540
```

-continued

```
att gga gac atg ctc cta agg act gct gta ggt caa gtg tca aga ccc     1680
Ile Gly Asp Met Leu Leu Arg Thr Ala Val Gly Gln Val Ser Arg Pro
545                 550                 555                 560

atg ttt ttg tat gta agg aca aat gga acc tct aaa att aaa atg aaa     1728
Met Phe Leu Tyr Val Arg Thr Asn Gly Thr Ser Lys Ile Lys Met Lys
                565                 570                 575

ygg gga atg gaa atg aga cgc tgc ctc ctt cag tct ctg caa cag att     1776
Xaa Gly Met Glu Met Arg Arg Cys Leu Leu Gln Ser Leu Gln Gln Ile
            580                 585                 590

gaa agc atg atc gaa gct gag tcc tca gtc aaa gaa aag gac atg acc     1824
Glu Ser Met Ile Glu Ala Glu Ser Ser Val Lys Glu Lys Asp Met Thr
        595                 600                 605

aaa gaa ttc ttt gag aac aaa tca gag aca tgg cct ata gga gag tcc     1872
Lys Glu Phe Phe Glu Asn Lys Ser Glu Thr Trp Pro Ile Gly Glu Ser
    610                 615                 620

ccc aaa gga gtg gaa gag ggc tca atc ggg aag gtt tgc agg acc tta     1920
Pro Lys Gly Val Glu Glu Gly Ser Ile Gly Lys Val Cys Arg Thr Leu
625                 630                 635                 640

tta gca aaa tct gtg ttt aac agt ttg tat gca tct cca caa ctg gaa     1968
Leu Ala Lys Ser Val Phe Asn Ser Leu Tyr Ala Ser Pro Gln Leu Glu
                645                 650                 655

ggg ttt tca gct gaa tct agg aaa tta ctt ctc att gtt cag gcc ctt     2016
Gly Phe Ser Ala Glu Ser Arg Lys Leu Leu Leu Ile Val Gln Ala Leu
            660                 665                 670

agg gat aac ctg gaa cct gga acc ttt gat att ggg ggg tta tat gaa     2064
Arg Asp Asn Leu Glu Pro Gly Thr Phe Asp Ile Gly Gly Leu Tyr Glu
        675                 680                 685

tca att gag gag tgc ctg att aat gat ccc tgg gtt ttg ctc aat gca     2112
Ser Ile Glu Glu Cys Leu Ile Asn Asp Pro Trp Val Leu Leu Asn Ala
    690                 695                 700

tct tgg ttc aac tcc ttc ctt aca cat gca ctg aag                     2148
Ser Trp Phe Asn Ser Phe Leu Thr His Ala Leu Lys
705                 710                 715


<210> SEQ ID NO 101
<211> LENGTH: 716
<212> TYPE: PRT
<213> ORGANISM: Equine influenza virus H3N8
<220> FEATURE:
<221> NAME/KEY: misc_feature
<222> LOCATION: (577)..(577)
<223> OTHER INFORMATION: The 'Xaa' at location 577 stands for Arg, or
      Trp.

<400> SEQUENCE: 101

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Leu Gly Glu Ser Val Ile Ile Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Arg Ala Glu Lys Pro Lys Phe Leu Pro Asp Leu Tyr Asp Tyr
            100                 105                 110

Lys Glu Asn Arg Phe Val Glu Ile Gly Val Thr Arg Arg Glu Val His
```

-continued

```
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Arg Leu Ala Asn Tyr Ser Leu Pro Pro Asn Phe Ser
    210                 215                 220

Ser Leu Glu Asn Phe Arg Val Tyr Val Asp Gly Phe Glu Pro Asn Gly
225                 230                 235                 240

Cys Ile Glu Ser Lys Leu Ser Gln Met Ser Lys Glu Val Asn Ala Arg
                245                 250                 255

Ile Glu Pro Phe Ser Lys Thr Thr Pro Arg Pro Leu Lys Met Pro Gly
            260                 265                 270

Gly Pro Pro Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Ser Val Val Lys Pro His Glu Lys Gly Ile Asn Pro Asn Tyr Leu Gln
                325                 330                 335

Ala Trp Lys Gln Val Leu Ala Glu Leu Gln Asp Leu Glu Asn Glu Glu
            340                 345                 350

Lys Thr Pro Lys Thr Lys Asn Met Lys Lys Thr Ser Gln Leu Lys Trp
        355                 360                 365

Ala Leu Gly Glu Asn Met Ala Pro Glu Lys Val Asp Phe Glu Asp Cys
    370                 375                 380

Lys Asp Ile Asn Asp Leu Lys Gln Tyr Asp Ser Asp Glu Pro Glu Thr
385                 390                 395                 400

Arg Ser Leu Ala Ser Trp Ile Gln Ser Glu Phe Asn Lys Ala Cys Glu
                405                 410                 415

Leu Thr Asp Ser Ser Trp Ile Glu Leu Asp Glu Ile Gly Glu Asp Ile
            420                 425                 430

Ala Pro Ile Glu Tyr Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Glu Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Phe Glu Pro His Lys Trp Glu Lys Tyr Cys Val Leu Glu
    530                 535                 540
```

-continued

```
Ile Gly Asp Met Leu Leu Arg Thr Ala Val Gly Gln Val Ser Arg Pro
545                 550                 555                 560

Met Phe Leu Tyr Val Arg Thr Asn Gly Thr Ser Lys Ile Lys Met Lys
                565                 570                 575

Xaa Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Ile Gly Gly Leu Tyr Glu
        675                 680                 685

Ser Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715


<210> SEQ ID NO 102
<211> LENGTH: 2148
<212> TYPE: DNA
<213> ORGANISM: Equine influenza virus H3N8
<220> FEATURE:
<221> NAME/KEY: CDS
<222> LOCATION: (1)..(2148)

<400> SEQUENCE: 102

atg gaa gac ttt gtg cga cag tgc ttc aat cca atg atc gtc gag ctt       48
Met Glu Asp Phe Val Arg Gln Cys Phe Asn Pro Met Ile Val Glu Leu
1               5                   10                  15

gcg gaa aag gca atg aaa gaa tat gga gag gac ccg aaa att gaa aca       96
Ala Glu Lys Ala Met Lys Glu Tyr Gly Glu Asp Pro Lys Ile Glu Thr
            20                  25                  30

aac aaa ttt gca gca ata tgc act cac ttg gaa gtc tgc ttc atg tac      144
Asn Lys Phe Ala Ala Ile Cys Thr His Leu Glu Val Cys Phe Met Tyr
        35                  40                  45

tcg gat ttc cac ttt att aat gaa ctg ggt aag tca gtg atc ata gag      192
Ser Asp Phe His Phe Ile Asn Glu Leu Gly Lys Ser Val Ile Ile Glu
    50                  55                  60

tct ggt gat cca aat gct ctt ttg aaa cac aga ttt gaa atc att gaa      240
Ser Gly Asp Pro Asn Ala Leu Leu Lys His Arg Phe Glu Ile Ile Glu
65                  70                  75                  80

ggg aga gat cga aca atg gca tgg aca gta gta aac agc atc tgc aac      288
Gly Arg Asp Arg Thr Met Ala Trp Thr Val Val Asn Ser Ile Cys Asn
                85                  90                  95

acc aca aga gct gaa aaa ccc aag ttt ctc cca gat tta tac gac tat      336
Thr Thr Arg Ala Glu Lys Pro Lys Phe Leu Pro Asp Leu Tyr Asp Tyr
            100                 105                 110

aag gag aac aga ttt gtt gaa att ggt gtg aca agg aga gaa gtt cac      384
Lys Glu Asn Arg Phe Val Glu Ile Gly Val Thr Arg Arg Glu Val His
        115                 120                 125

ata tac tac ctg gag aag gcc aac aaa ata aag tct gag aaa aca cat      432
Ile Tyr Tyr Leu Glu Lys Ala Asn Lys Ile Lys Ser Glu Lys Thr His
```

-continued

```
    130                 135                 140

atc cac att ttc tca ttt aca gga gag gaa atg act aca aaa gcg gac      480
Ile His Ile Phe Ser Phe Thr Gly Glu Glu Met Thr Thr Lys Ala Asp
145                 150                 155                 160

tat act ctt gat gaa gag agt aga gcc agg atc aag acc aga cta ttc      528
Tyr Thr Leu Asp Glu Glu Ser Arg Ala Arg Ile Lys Thr Arg Leu Phe
                165                 170                 175

acc ata aga caa gaa atg gcc agt aga ggc ctc tgg gat tcc ttt cgt      576
Thr Ile Arg Gln Glu Met Ala Ser Arg Gly Leu Trp Asp Ser Phe Arg
            180                 185                 190

cag tcc gag aga ggc gaa gag aca att gaa gaa aga ttt gaa atc aca      624
Gln Ser Glu Arg Gly Glu Glu Thr Ile Glu Glu Arg Phe Glu Ile Thr
        195                 200                 205

ggg acg atg cgc agg ctt gcc aat tac agt ctc cca ccg aac ttc tcc      672
Gly Thr Met Arg Arg Leu Ala Asn Tyr Ser Leu Pro Pro Asn Phe Ser
    210                 215                 220

agc ctt gaa aat ttt aga gtc tat gtg gat gga ttc gaa ccg aac ggc      720
Ser Leu Glu Asn Phe Arg Val Tyr Val Asp Gly Phe Glu Pro Asn Gly
225                 230                 235                 240

tgc att gag agt aag ctt tct caa atg tcc aaa gaa gta aat gcc aga      768
Cys Ile Glu Ser Lys Leu Ser Gln Met Ser Lys Glu Val Asn Ala Arg
                245                 250                 255

atc gag cca ttt tca aag aca aca ccc cga cca ctc aag atg cca ggt      816
Ile Glu Pro Phe Ser Lys Thr Thr Pro Arg Pro Leu Lys Met Pro Gly
            260                 265                 270

ggt cca ccc tgc cat cag cga tct aaa ttc ttg cta atg gat gct ctg      864
Gly Pro Pro Cys His Gln Arg Ser Lys Phe Leu Leu Met Asp Ala Leu
        275                 280                 285

aaa tta agt att gag gac cca agt cac gag gga gag gga ata cca cta      912
Lys Leu Ser Ile Glu Asp Pro Ser His Glu Gly Glu Gly Ile Pro Leu
    290                 295                 300

tat gat gct atc aaa tgc atg aaa act ttc ttt gga tgg aaa gag ccc      960
Tyr Asp Ala Ile Lys Cys Met Lys Thr Phe Phe Gly Trp Lys Glu Pro
305                 310                 315                 320

agt gtt gtt aaa cca cat gaa aag ggt ata aac cca aac tat ctc caa     1008
Ser Val Val Lys Pro His Glu Lys Gly Ile Asn Pro Asn Tyr Leu Gln
                325                 330                 335

gct tgg aag caa gta tta gca gaa cta caa gac ctt gag aac gaa gaa     1056
Ala Trp Lys Gln Val Leu Ala Glu Leu Gln Asp Leu Glu Asn Glu Glu
            340                 345                 350

aag acc cct aag acc aag aat atg aaa aaa aca agc caa ttg aaa tgg     1104
Lys Thr Pro Lys Thr Lys Asn Met Lys Lys Thr Ser Gln Leu Lys Trp
        355                 360                 365

gca ctc ggt gaa aat atg gca cca gag aaa gtg gat ttt gag gat tgt     1152
Ala Leu Gly Glu Asn Met Ala Pro Glu Lys Val Asp Phe Glu Asp Cys
    370                 375                 380

aaa gac atc aat gat ttg aaa cag tat gac agt gat gag cca gaa aca     1200
Lys Asp Ile Asn Asp Leu Lys Gln Tyr Asp Ser Asp Glu Pro Glu Thr
385                 390                 395                 400

agg tct ctt gca agt tgg att caa agt gag ttc aac aaa gct tgt gag     1248
Arg Ser Leu Ala Ser Trp Ile Gln Ser Glu Phe Asn Lys Ala Cys Glu
                405                 410                 415

ctg aca gat tca agc tgg ata gag ctc gat gaa att ggg gag gat att     1296
Leu Thr Asp Ser Ser Trp Ile Glu Leu Asp Glu Ile Gly Glu Asp Ile
            420                 425                 430

gcc cca ata gaa tac att gcg agc atg agg aga aat tat ttt act gct     1344
Ala Pro Ile Glu Tyr Ile Ala Ser Met Arg Arg Asn Tyr Phe Thr Ala
        435                 440                 445

gag gtt tcc cat tgt aga gca aca gaa tat ata atg aag gga gtg tac     1392
```

-continued

```
Glu Val Ser His Cys Arg Ala Thr Glu Tyr Ile Met Lys Gly Val Tyr
    450                 455                 460

atc aac act gct cta ctc aat gca tcc tgt gct gcg atg gat gaa ttc      1440
Ile Asn Thr Ala Leu Leu Asn Ala Ser Cys Ala Ala Met Asp Glu Phe
465                 470                 475                 480

caa tta att ccg atg ata agc aaa tgc agg acc aaa gaa ggg aga agg      1488
Gln Leu Ile Pro Met Ile Ser Lys Cys Arg Thr Lys Glu Gly Arg Arg
                485                 490                 495

aag aca aat tta tat gga ttc ata ata aag gga agg tcc cat tta agg      1536
Lys Thr Asn Leu Tyr Gly Phe Ile Ile Lys Gly Arg Ser His Leu Arg
            500                 505                 510

aat gat acc gac gtg gta aac ttt gta agt atg gaa ttt tct ctc act      1584
Asn Asp Thr Asp Val Val Asn Phe Val Ser Met Glu Phe Ser Leu Thr
        515                 520                 525

gat cca aga ttt gag cca cat aaa tgg gaa aaa tac tgc gtt cta gaa      1632
Asp Pro Arg Phe Glu Pro His Lys Trp Glu Lys Tyr Cys Val Leu Glu
    530                 535                 540

att gga gac atg ctc cta agg act gct gta ggt caa gtg tca aga ccc      1680
Ile Gly Asp Met Leu Leu Arg Thr Ala Val Gly Gln Val Ser Arg Pro
545                 550                 555                 560

atg ttt ttg tat gta agg aca aat gga acc tct aaa att aaa atg aaa      1728
Met Phe Leu Tyr Val Arg Thr Asn Gly Thr Ser Lys Ile Lys Met Lys
                565                 570                 575

tgg gga atg gaa atg aga cgc tgc ctc ctt cag tct ctg caa cag att      1776
Trp Gly Met Glu Met Arg Arg Cys Leu Leu Gln Ser Leu Gln Gln Ile
            580                 585                 590

gaa agc atg atc gaa gct gag tcc tca gtc aaa gaa aag gac atg acc      1824
Glu Ser Met Ile Glu Ala Glu Ser Ser Val Lys Glu Lys Asp Met Thr
        595                 600                 605

aaa gaa ttc ttt gag aac aaa tca gag aca tgg cct ata gga gag tcc      1872
Lys Glu Phe Phe Glu Asn Lys Ser Glu Thr Trp Pro Ile Gly Glu Ser
    610                 615                 620

ccc aaa gga gtg gaa gag ggc tca atc ggg aag gtt tgc agg acc tta      1920
Pro Lys Gly Val Glu Glu Gly Ser Ile Gly Lys Val Cys Arg Thr Leu
625                 630                 635                 640

tta gca aar tct gtg ttt aac agt ttg tat gca tct cca caa ctg gaa      1968
Leu Ala Lys Ser Val Phe Asn Ser Leu Tyr Ala Ser Pro Gln Leu Glu
                645                 650                 655

ggg ttt tca gct gaa tct agg aaa tta ctt ctc att gtt cag gcc ctt      2016
Gly Phe Ser Ala Glu Ser Arg Lys Leu Leu Leu Ile Val Gln Ala Leu
            660                 665                 670

agg gat aac ctg gaa cct gga acc ttt gat att ggg ggg tta tat gaa      2064
Arg Asp Asn Leu Glu Pro Gly Thr Phe Asp Ile Gly Gly Leu Tyr Glu
        675                 680                 685

tca att gag gag tgc ctg att aat gat ccc tgg gtt ttg ctc aat gca      2112
Ser Ile Glu Glu Cys Leu Ile Asn Asp Pro Trp Val Leu Leu Asn Ala
    690                 695                 700

tct tgg ttc aac tcc ttc ctt aca cat gca ctg aag                      2148
Ser Trp Phe Asn Ser Phe Leu Thr His Ala Leu Lys
705                 710                 715


<210> SEQ ID NO 103
<211> LENGTH: 716
<212> TYPE: PRT
<213> ORGANISM: Equine influenza virus H3N8

<400> SEQUENCE: 103

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
```

-continued

```
            20                  25                  30

Asn Lys Phe Ala Ala Ile Cys Thr His Leu Glu Val Cys Phe Met Tyr
        35                  40                  45

Ser Asp Phe His Phe Ile Asn Glu Leu Gly Lys Ser Val Ile Ile Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Arg Ala Glu Lys Pro Lys Phe Leu Pro Asp Leu Tyr Asp Tyr
            100                 105                 110

Lys Glu Asn Arg Phe Val Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Thr Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Arg Leu Ala Asn Tyr Ser Leu Pro Pro Asn Phe Ser
    210                 215                 220

Ser Leu Glu Asn Phe Arg Val Tyr Val Asp Gly Phe Glu Pro Asn Gly
225                 230                 235                 240

Cys Ile Glu Ser Lys Leu Ser Gln Met Ser Lys Glu Val Asn Ala Arg
                245                 250                 255

Ile Glu Pro Phe Ser Lys Thr Thr Pro Arg Pro Leu Lys Met Pro Gly
            260                 265                 270

Gly Pro Pro Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Ser Val Val Lys Pro His Glu Lys Gly Ile Asn Pro Asn Tyr Leu Gln
                325                 330                 335

Ala Trp Lys Gln Val Leu Ala Glu Leu Gln Asp Leu Glu Asn Glu Glu
            340                 345                 350

Lys Thr Pro Lys Thr Lys Asn Met Lys Lys Thr Ser Gln Leu Lys Trp
        355                 360                 365

Ala Leu Gly Glu Asn Met Ala Pro Glu Lys Val Asp Phe Glu Asp Cys
    370                 375                 380

Lys Asp Ile Asn Asp Leu Lys Gln Tyr Asp Ser Asp Glu Pro Glu Thr
385                 390                 395                 400

Arg Ser Leu Ala Ser Trp Ile Gln Ser Glu Phe Asn Lys Ala Cys Glu
                405                 410                 415

Leu Thr Asp Ser Ser Trp Ile Glu Leu Asp Glu Ile Gly Glu Asp Ile
            420                 425                 430

Ala Pro Ile Glu Tyr Ile Ala Ser Met Arg Arg Asn Tyr Phe Thr Ala
        435                 440                 445
```

-continued

```
Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Glu Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Phe Glu Pro His Lys Trp Glu Lys Tyr Cys Val Leu Glu
    530                 535                 540

Ile Gly Asp Met Leu Leu Arg Thr Ala Val Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Ile Gly Gly Leu Tyr Glu
        675                 680                 685

Ser Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715


<210> SEQ ID NO 104
<211> LENGTH: 738
<212> TYPE: DNA
<213> ORGANISM: Equine influenza virus H3N8
<220> FEATURE:
<221> NAME/KEY: CDS
<222> LOCATION: (1)..(738)

<400> SEQUENCE: 104

agc aaa agc agg gta gat aat cac tca ctg agt gac atc aaa atc atg       48
Ser Lys Ser Arg Val Asp Asn His Ser Leu Ser Asp Ile Lys Ile Met
1               5                   10                  15

gcg tct caa ggc acc aaa cga tct tat gag cag atg gaa act gat ggg       96
Ala Ser Gln Gly Thr Lys Arg Ser Tyr Glu Gln Met Glu Thr Asp Gly
            20                  25                  30

gaa cgc caa aat gca act gaa atc aga gca tct gtc gga agg atg gtg      144
Glu Arg Gln Asn Ala Thr Glu Ile Arg Ala Ser Val Gly Arg Met Val
        35                  40                  45

gga gga atc ggt cgg ttt tat gtt cag atg tgt act gag ctt aaa cta      192
Gly Gly Ile Gly Arg Phe Tyr Val Gln Met Cys Thr Glu Leu Lys Leu
    50                  55                  60
```

-continued

```
aac gac cat gaa ggg cgg ctg att cag aac agc ata aca ata gaa agg      240
Asn Asp His Glu Gly Arg Leu Ile Gln Asn Ser Ile Thr Ile Glu Arg
65                  70                  75                  80

atg gta ctt tcg gca ttc gac gaa aga aga aac aag tac ctc gag gag      288
Met Val Leu Ser Ala Phe Asp Glu Arg Arg Asn Lys Tyr Leu Glu Glu
                85                  90                  95

cat ccc agt gct ggg aaa gac cct aag aaa acg gga ggc ccg ata tac      336
His Pro Ser Ala Gly Lys Asp Pro Lys Lys Thr Gly Gly Pro Ile Tyr
            100                 105                 110

aga agg aaa gat ggg aaa tgg atg aga gaa ctc atc ctc cat gat aaa      384
Arg Arg Lys Asp Gly Lys Trp Met Arg Glu Leu Ile Leu His Asp Lys
        115                 120                 125

gaa gaa atc atg agg atc tgg cgt cag gcc aac aat ggt gaa gac gct      432
Glu Glu Ile Met Arg Ile Trp Arg Gln Ala Asn Asn Gly Glu Asp Ala
    130                 135                 140

act gct ggt ctt act cat atg atg atc tgg cac tcc aat ctc aat gac      480
Thr Ala Gly Leu Thr His Met Met Ile Trp His Ser Asn Leu Asn Asp
145                 150                 155                 160

acc aca tac cac aga aca agg gct ctt gtt cgg act ggg atg gat ccc      528
Thr Thr Tyr His Arg Thr Arg Ala Leu Val Arg Thr Gly Met Asp Pro
                165                 170                 175

aga atg tgc tct ctg atg caa gga tca acc ctc cca cgg aga tct gga      576
Arg Met Cys Ser Leu Met Gln Gly Ser Thr Leu Pro Arg Arg Ser Gly
            180                 185                 190

gct gct ggt gct gca gta aaa ggt gtt gga aca atg gta atg gaa ctc      624
Ala Ala Gly Ala Ala Val Lys Gly Val Gly Thr Met Val Met Glu Leu
        195                 200                 205

atc aga atg atc aaa cgc ggg ata aat gat cga aat ttc tgg aga ggt      672
Ile Arg Met Ile Lys Arg Gly Ile Asn Asp Arg Asn Phe Trp Arg Gly
    210                 215                 220

gaa aat ggt cga aga acc aga att gcc tat gaa aga atg tgc aat atc      720
Glu Asn Gly Arg Arg Thr Arg Ile Ala Tyr Glu Arg Met Cys Asn Ile
225                 230                 235                 240

ctc aaa ggg aaa ttt cag                                              738
Leu Lys Gly Lys Phe Gln
                245


<210> SEQ ID NO 105
<211> LENGTH: 246
<212> TYPE: PRT
<213> ORGANISM: Equine influenza virus H3N8

<400> SEQUENCE: 105

Ser Lys Ser Arg Val Asp Asn His Ser Leu Ser Asp Ile Lys Ile Met
1               5                   10                  15

Ala Ser Gln Gly Thr Lys Arg Ser Tyr Glu Gln Met Glu Thr Asp Gly
            20                  25                  30

Glu Arg Gln Asn Ala Thr Glu Ile Arg Ala Ser Val Gly Arg Met Val
        35                  40                  45

Gly Gly Ile Gly Arg Phe Tyr Val Gln Met Cys Thr Glu Leu Lys Leu
    50                  55                  60

Asn Asp His Glu Gly Arg Leu Ile Gln Asn Ser Ile Thr Ile Glu Arg
65                  70                  75                  80

Met Val Leu Ser Ala Phe Asp Glu Arg Arg Asn Lys Tyr Leu Glu Glu
                85                  90                  95

His Pro Ser Ala Gly Lys Asp Pro Lys Lys Thr Gly Gly Pro Ile Tyr
            100                 105                 110

Arg Arg Lys Asp Gly Lys Trp Met Arg Glu Leu Ile Leu His Asp Lys
        115                 120                 125
```

-continued

```
Glu Glu Ile Met Arg Ile Trp Arg Gln Ala Asn Asn Gly Glu Asp Ala
    130                 135                 140

Thr Ala Gly Leu Thr His Met Met Ile Trp His Ser Asn Leu Asn Asp
145                 150                 155                 160

Thr Thr Tyr His Arg Thr Arg Ala Leu Val Arg Thr Gly Met Asp Pro
                165                 170                 175

Arg Met Cys Ser Leu Met Gln Gly Ser Thr Leu Pro Arg Arg Ser Gly
            180                 185                 190

Ala Ala Gly Ala Ala Val Lys Gly Val Gly Thr Met Val Met Glu Leu
        195                 200                 205

Ile Arg Met Ile Lys Arg Gly Ile Asn Asp Arg Asn Phe Trp Arg Gly
    210                 215                 220

Glu Asn Gly Arg Arg Thr Arg Ile Ala Tyr Glu Arg Met Cys Asn Ile
225                 230                 235                 240

Leu Lys Gly Lys Phe Gln
                245


<210> SEQ ID NO 106
<211> LENGTH: 693
<212> TYPE: DNA
<213> ORGANISM: Equine influenza virus H3N8
<220> FEATURE:
<221> NAME/KEY: CDS
<222> LOCATION: (1)..(693)

<400> SEQUENCE: 106

atg gcg tct caa ggc acc aaa cga tct tat gag cag atg gaa act gat       48
Met Ala Ser Gln Gly Thr Lys Arg Ser Tyr Glu Gln Met Glu Thr Asp
1               5                   10                  15

ggg gaa cgc caa aat gca act gaa atc aga gca tct gtc gga agg atg       96
Gly Glu Arg Gln Asn Ala Thr Glu Ile Arg Ala Ser Val Gly Arg Met
            20                  25                  30

gtg gga gga atc ggt cgg ttt tat gtt cag atg tgt act gag ctt aaa      144
Val Gly Gly Ile Gly Arg Phe Tyr Val Gln Met Cys Thr Glu Leu Lys
        35                  40                  45

cta aac gac cat gaa ggg cgg ctg att cag aac agc ata aca ata gaa      192
Leu Asn Asp His Glu Gly Arg Leu Ile Gln Asn Ser Ile Thr Ile Glu
    50                  55                  60

agg atg gta ctt tcg gca ttc gac gaa aga aga aac aag tac ctc gag      240
Arg Met Val Leu Ser Ala Phe Asp Glu Arg Arg Asn Lys Tyr Leu Glu
65                  70                  75                  80

gag cat ccc agt gct ggg aaa gac cct aag aaa acg gga ggc ccg ata      288
Glu His Pro Ser Ala Gly Lys Asp Pro Lys Lys Thr Gly Gly Pro Ile
                85                  90                  95

tac aga agg aaa gat ggg aaa tgg atg aga gaa ctc atc ctc cat gat      336
Tyr Arg Arg Lys Asp Gly Lys Trp Met Arg Glu Leu Ile Leu His Asp
            100                 105                 110

aaa gaa gaa atc atg agg atc tgg cgt cag gcc aac aat ggt gaa gac      384
Lys Glu Glu Ile Met Arg Ile Trp Arg Gln Ala Asn Asn Gly Glu Asp
        115                 120                 125

gct act gct ggt ctt act cat atg atg atc tgg cac tcc aat ctc aat      432
Ala Thr Ala Gly Leu Thr His Met Met Ile Trp His Ser Asn Leu Asn
    130                 135                 140

gac acc aca tac cac aga aca agg gct ctt gtt cgg act ggg atg gat      480
Asp Thr Thr Tyr His Arg Thr Arg Ala Leu Val Arg Thr Gly Met Asp
145                 150                 155                 160

ccc aga atg tgc tct ctg atg caa gga tca acc ctc cca cgg aga tct      528
Pro Arg Met Cys Ser Leu Met Gln Gly Ser Thr Leu Pro Arg Arg Ser
                165                 170                 175
```

-continued

```
gga gct gct ggt gct gca gta aaa ggt gtt gga aca atg gta atg gaa      576
Gly Ala Ala Gly Ala Ala Val Lys Gly Val Gly Thr Met Val Met Glu
            180                 185                 190

ctc atc aga atg atc aaa cgc ggg ata aat gat cga aat ttc tgg aga      624
Leu Ile Arg Met Ile Lys Arg Gly Ile Asn Asp Arg Asn Phe Trp Arg
        195                 200                 205

ggt gaa aat ggt cga aga acc aga att gcc tat gaa aga atg tgc aat      672
Gly Glu Asn Gly Arg Arg Thr Arg Ile Ala Tyr Glu Arg Met Cys Asn
    210                 215                 220

atc ctc aaa ggg aaa ttt cag                                          693
Ile Leu Lys Gly Lys Phe Gln
225                 230


<210> SEQ ID NO 107
<211> LENGTH: 231
<212> TYPE: PRT
<213> ORGANISM: Equine influenza virus H3N8

<400> SEQUENCE: 107

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Val Gln Met Cys Thr Glu Leu Lys
        35                  40                  45

Leu Asn Asp His Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Lys Asp Gly Lys Trp Met Arg Glu Leu Ile Leu His Asp
            100                 105                 110

Lys Glu Glu Ile Met Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Thr Thr Tyr His Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln
225                 230


<210> SEQ ID NO 108
<211> LENGTH: 738
<212> TYPE: DNA
<213> ORGANISM: Equine influenza virus H3N8
<220> FEATURE:
<221> NAME/KEY: CDS
<222> LOCATION: (1)..(738)
```

-continued

<400> SEQUENCE: 108

```
agc aaa agc agg gta gat aat cac tca ctg agt gac atc aaa atc atg       48
Ser Lys Ser Arg Val Asp Asn His Ser Leu Ser Asp Ile Lys Ile Met
1               5                   10                  15

gcg tct caa ggc acc aaa cga tct tat gag cag atg gaa act gat ggg       96
Ala Ser Gln Gly Thr Lys Arg Ser Tyr Glu Gln Met Glu Thr Asp Gly
            20                  25                  30

gaa cgc caa aat gca act gaa atc aga gca tct gtc gga agg atg gtg      144
Glu Arg Gln Asn Ala Thr Glu Ile Arg Ala Ser Val Gly Arg Met Val
        35                  40                  45

gga gga atc ggt cgg ttt tat gtt cag atg tgt act gag ctt aaa cta      192
Gly Gly Ile Gly Arg Phe Tyr Val Gln Met Cys Thr Glu Leu Lys Leu
    50                  55                  60

aac gac cat gaa ggg cgg ctg att cag aac agc ata aca ata gaa agg      240
Asn Asp His Glu Gly Arg Leu Ile Gln Asn Ser Ile Thr Ile Glu Arg
65                  70                  75                  80

atg gta ctt tcg gca ttc gac gaa aga aga aac aag tac ctc gag gag      288
Met Val Leu Ser Ala Phe Asp Glu Arg Arg Asn Lys Tyr Leu Glu Glu
                85                  90                  95

cat ccc agt gct ggg aaa gac cct aag aaa acg gga ggc ccg ata tac      336
His Pro Ser Ala Gly Lys Asp Pro Lys Lys Thr Gly Gly Pro Ile Tyr
            100                 105                 110

aga agg aaa gat ggg aaa tgg atg aga gaa ctc atc ctc cat gat aaa      384
Arg Arg Lys Asp Gly Lys Trp Met Arg Glu Leu Ile Leu His Asp Lys
        115                 120                 125

gaa gaa atc atg agg atc tgg cgt cag gcc aac aat ggt gaa gac gct      432
Glu Glu Ile Met Arg Ile Trp Arg Gln Ala Asn Asn Gly Glu Asp Ala
    130                 135                 140

act gct ggt ctt act cat atg atg atc tgg cac tcc aat ctc aat gac      480
Thr Ala Gly Leu Thr His Met Met Ile Trp His Ser Asn Leu Asn Asp
145                 150                 155                 160

acc aca tac caa aga aca agg gct ctt gtt cgg act ggg atg gat ccc      528
Thr Thr Tyr Gln Arg Thr Arg Ala Leu Val Arg Thr Gly Met Asp Pro
                165                 170                 175

aga atg tgc tct ctg atg caa gga tca acc ctc cca cgg aga tct gga      576
Arg Met Cys Ser Leu Met Gln Gly Ser Thr Leu Pro Arg Arg Ser Gly
            180                 185                 190

gct gct ggt gct gca gta aaa ggt gtt gga aca atg gta atg gaa ctc      624
Ala Ala Gly Ala Ala Val Lys Gly Val Gly Thr Met Val Met Glu Leu
        195                 200                 205

atc aga atg atc aaa cgc ggg ata aat gat cga aat ttc tgg aga ggt      672
Ile Arg Met Ile Lys Arg Gly Ile Asn Asp Arg Asn Phe Trp Arg Gly
    210                 215                 220

gaa aat ggt cga aga acc aga att gcc tat gaa aga atg tgc aat atc      720
Glu Asn Gly Arg Arg Thr Arg Ile Ala Tyr Glu Arg Met Cys Asn Ile
225                 230                 235                 240

ctc aaa ggg aaa ttt cag                                              738
Leu Lys Gly Lys Phe Gln
                245
```

<210> SEQ ID NO 109
<211> LENGTH: 246
<212> TYPE: PRT
<213> ORGANISM: Equine influenza virus H3N8

<400> SEQUENCE: 109

```
Ser Lys Ser Arg Val Asp Asn His Ser Leu Ser Asp Ile Lys Ile Met
1               5                   10                  15

Ala Ser Gln Gly Thr Lys Arg Ser Tyr Glu Gln Met Glu Thr Asp Gly
            20                  25                  30
```

```
Glu Arg Gln Asn Ala Thr Glu Ile Arg Ala Ser Val Gly Arg Met Val
        35                  40                  45

Gly Gly Ile Gly Arg Phe Tyr Val Gln Met Cys Thr Glu Leu Lys Leu
    50                  55                  60

Asn Asp His Glu Gly Arg Leu Ile Gln Asn Ser Ile Thr Ile Glu Arg
65                  70                  75                  80

Met Val Leu Ser Ala Phe Asp Glu Arg Arg Asn Lys Tyr Leu Glu Glu
                85                  90                  95

His Pro Ser Ala Gly Lys Asp Pro Lys Lys Thr Gly Gly Pro Ile Tyr
            100                 105                 110

Arg Arg Lys Asp Gly Lys Trp Met Arg Glu Leu Ile Leu His Asp Lys
        115                 120                 125

Glu Glu Ile Met Arg Ile Trp Arg Gln Ala Asn Asn Gly Glu Asp Ala
    130                 135                 140

Thr Ala Gly Leu Thr His Met Met Ile Trp His Ser Asn Leu Asn Asp
145                 150                 155                 160

Thr Thr Tyr Gln Arg Thr Arg Ala Leu Val Arg Thr Gly Met Asp Pro
                165                 170                 175

Arg Met Cys Ser Leu Met Gln Gly Ser Thr Leu Pro Arg Arg Ser Gly
            180                 185                 190

Ala Ala Gly Ala Ala Val Lys Gly Val Gly Thr Met Val Met Glu Leu
        195                 200                 205

Ile Arg Met Ile Lys Arg Gly Ile Asn Asp Arg Asn Phe Trp Arg Gly
    210                 215                 220

Glu Asn Gly Arg Arg Thr Arg Ile Ala Tyr Glu Arg Met Cys Asn Ile
225                 230                 235                 240

Leu Lys Gly Lys Phe Gln
                245


<210> SEQ ID NO 110
<211> LENGTH: 693
<212> TYPE: DNA
<213> ORGANISM: Equine influenza virus H3N8
<220> FEATURE:
<221> NAME/KEY: CDS
<222> LOCATION: (1)..(693)

<400> SEQUENCE: 110

atg gcg tct caa ggc acc aaa cga tct tat gag cag atg gaa act gat       48
Met Ala Ser Gln Gly Thr Lys Arg Ser Tyr Glu Gln Met Glu Thr Asp
1               5                   10                  15

ggg gaa cgc caa aat gca act gaa atc aga gca tct gtc gga agg atg       96
Gly Glu Arg Gln Asn Ala Thr Glu Ile Arg Ala Ser Val Gly Arg Met
            20                  25                  30

gtg gga gga atc ggt cgg ttt tat gtt cag atg tgt act gag ctt aaa      144
Val Gly Gly Ile Gly Arg Phe Tyr Val Gln Met Cys Thr Glu Leu Lys
        35                  40                  45

cta aac gac cat gaa ggg cgg ctg att cag aac agc ata aca ata gaa      192
Leu Asn Asp His Glu Gly Arg Leu Ile Gln Asn Ser Ile Thr Ile Glu
    50                  55                  60

agg atg gta ctt tcg gca ttc gac gaa aga aga aac aag tac ctc gag      240
Arg Met Val Leu Ser Ala Phe Asp Glu Arg Arg Asn Lys Tyr Leu Glu
65                  70                  75                  80

gag cat ccc agt gct ggg aaa gac cct aag aaa acg gga ggc ccg ata      288
Glu His Pro Ser Ala Gly Lys Asp Pro Lys Lys Thr Gly Gly Pro Ile
                85                  90                  95

tac aga agg aaa gat ggg aaa tgg atg aga gaa ctc atc ctc cat gat      336
```

-continued

```
Tyr Arg Arg Lys Asp Gly Lys Trp Met Arg Glu Leu Ile Leu His Asp
            100                 105                 110

aaa gaa gaa atc atg agg atc tgg cgt cag gcc aac aat ggt gaa gac      384
Lys Glu Glu Ile Met Arg Ile Trp Arg Gln Ala Asn Asn Gly Glu Asp
        115                 120                 125

gct act gct ggt ctt act cat atg atg atc tgg cac tcc aat ctc aat      432
Ala Thr Ala Gly Leu Thr His Met Met Ile Trp His Ser Asn Leu Asn
    130                 135                 140

gac acc aca tac caa aga aca agg gct ctt gtt cgg act ggg atg gat      480
Asp Thr Thr Tyr Gln Arg Thr Arg Ala Leu Val Arg Thr Gly Met Asp
145                 150                 155                 160

ccc aga atg tgc tct ctg atg caa gga tca acc ctc cca cgg aga tct      528
Pro Arg Met Cys Ser Leu Met Gln Gly Ser Thr Leu Pro Arg Arg Ser
                165                 170                 175

gga gct gct ggt gct gca gta aaa ggt gtt gga aca atg gta atg gaa      576
Gly Ala Ala Gly Ala Ala Val Lys Gly Val Gly Thr Met Val Met Glu
            180                 185                 190

ctc atc aga atg atc aaa cgc ggg ata aat gat cga aat ttc tgg aga      624
Leu Ile Arg Met Ile Lys Arg Gly Ile Asn Asp Arg Asn Phe Trp Arg
        195                 200                 205

ggt gaa aat ggt cga aga acc aga att gcc tat gaa aga atg tgc aat      672
Gly Glu Asn Gly Arg Arg Thr Arg Ile Ala Tyr Glu Arg Met Cys Asn
    210                 215                 220

atc ctc aaa ggg aaa ttt cag                                          693
Ile Leu Lys Gly Lys Phe Gln
225                 230


<210> SEQ ID NO 111
<211> LENGTH: 231
<212> TYPE: PRT
<213> ORGANISM: Equine influenza virus H3N8

<400> SEQUENCE: 111

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Val Gln Met Cys Thr Glu Leu Lys
        35                  40                  45

Leu Asn Asp His Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Lys Asp Gly Lys Trp Met Arg Glu Leu Ile Leu His Asp
            100                 105                 110

Lys Glu Glu Ile Met Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190
```

-continued

```
Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln
225                 230


<210> SEQ ID NO 112
<211> LENGTH: 245
<212> TYPE: PRT
<213> ORGANISM: Equine influenza virus H3N8

<400> SEQUENCE: 112

Ser Lys Ser Arg Val Asp Asn His Ser Leu Ser Asp Ile Lys Ile Met
1               5                   10                  15

Ala Ser Gln Gly Thr Lys Arg Ser Tyr Glu Gln Met Glu Thr Asp Gly
            20                  25                  30

Glu Arg Gln Asn Ala Thr Glu Ile Arg Ala Ser Val Gly Arg Met Val
        35                  40                  45

Val Gly Ile Gly Arg Phe Tyr Val Gln Met Cys Thr Glu Leu Lys Leu
    50                  55                  60

Asn Asp His Glu Gly Arg Leu Ile Gln Asn Ser Met Thr Ile Glu Arg
65                  70                  75                  80

Met Val Leu Ser Ala Phe Asp Glu Arg Arg Asn Lys Tyr Leu Glu Glu
                85                  90                  95

His Pro Ser Ala Gly Lys Asp Pro Lys Lys Thr Gly Gly Pro Ile Tyr
            100                 105                 110

Arg Arg Lys Asp Gly Lys Trp Met Arg Glu Leu Ile Leu His Asp Lys
        115                 120                 125

Glu Glu Ile Met Arg Ile Trp Arg Gln Ala Asn Asn Gly Glu Asp Ala
    130                 135                 140

Thr Ala Gly Leu Thr His Met Met Ile Trp His Ser Asn Leu Asn Asp
145                 150                 155                 160

Thr Thr Tyr Gln Arg Thr Arg Ala Leu Val Arg Thr Gly Met Asp Pro
                165                 170                 175

Arg Met Cys Ser Met Met Gln Gly Ser Thr Leu Pro Arg Arg Ser Gly
            180                 185                 190

Ala Ala Gly Ala Ala Val Lys Gly Val Gly Thr Met Val Met Glu Leu
        195                 200                 205

Ile Arg Met Ile Lys Arg Gly Ile Asn Asp Arg Asn Phe Trp Arg Ser
    210                 215                 220

Glu Asn Gly Arg Arg Thr Arg Ile Ala Tyr Glu Arg Met Cys Asn Ile
225                 230                 235                 240

Leu Lys Gly Lys Phe
                245


<210> SEQ ID NO 113
<211> LENGTH: 690
<212> TYPE: DNA
<213> ORGANISM: Equine influenza virus H3N8
<220> FEATURE:
<221> NAME/KEY: CDS
<222> LOCATION: (1)..(690)

<400> SEQUENCE: 113

atg gcg tct caa ggc acc aaa cga tct tat gag cag atg gaa act gat       48
Met Ala Ser Gln Gly Thr Lys Arg Ser Tyr Glu Gln Met Glu Thr Asp
1               5                   10                  15
```

-continued

```
ggg gaa cgc caa aat gca act gaa atc aga gca tct gtc gga agg atg       96
Gly Glu Arg Gln Asn Ala Thr Glu Ile Arg Ala Ser Val Gly Arg Met
            20                  25                  30

gtg gta gga atc ggt cgg ttt tat gtt cag atg tgt act gag ctt aaa      144
Val Val Gly Ile Gly Arg Phe Tyr Val Gln Met Cys Thr Glu Leu Lys
        35                  40                  45

cta aac gac cat gaa ggg cgg ctg att cag aac agc atg aca ata gaa      192
Leu Asn Asp His Glu Gly Arg Leu Ile Gln Asn Ser Met Thr Ile Glu
    50                  55                  60

agg atg gta ctt tcg gca ttc gac gaa aga aga aac aag tac ctc gag      240
Arg Met Val Leu Ser Ala Phe Asp Glu Arg Arg Asn Lys Tyr Leu Glu
65                  70                  75                  80

gag cat ccc agt gct ggg aaa gac cct aag aaa acg gga ggc ccg ata      288
Glu His Pro Ser Ala Gly Lys Asp Pro Lys Lys Thr Gly Gly Pro Ile
                85                  90                  95

tac aga agg aaa gat ggg aaa tgg atg aga gaa ctc atc ctc cat gat      336
Tyr Arg Arg Lys Asp Gly Lys Trp Met Arg Glu Leu Ile Leu His Asp
            100                 105                 110

aaa gaa gaa atc atg agg atc tgg cgt cag gcc aac aat ggt gaa gac      384
Lys Glu Glu Ile Met Arg Ile Trp Arg Gln Ala Asn Asn Gly Glu Asp
        115                 120                 125

gct act gct ggt ctt act cat atg atg atc tgg cac tcc aat ctc aat      432
Ala Thr Ala Gly Leu Thr His Met Met Ile Trp His Ser Asn Leu Asn
    130                 135                 140

gac acc aca tac caa aga aca agg gct ctt gtt cgg act ggg atg gat      480
Asp Thr Thr Tyr Gln Arg Thr Arg Ala Leu Val Arg Thr Gly Met Asp
145                 150                 155                 160

ccc aga atg tgc tct atg atg caa gga tca acc ctc cca cgg aga tct      528
Pro Arg Met Cys Ser Met Met Gln Gly Ser Thr Leu Pro Arg Arg Ser
                165                 170                 175

gga gct gct ggt gct gca gta aaa ggt gtt gga aca atg gta atg gaa      576
Gly Ala Ala Gly Ala Ala Val Lys Gly Val Gly Thr Met Val Met Glu
            180                 185                 190

ctc atc aga atg atc aaa cgc gga ata aat gat cga aat ttc tgg aga      624
Leu Ile Arg Met Ile Lys Arg Gly Ile Asn Asp Arg Asn Phe Trp Arg
        195                 200                 205

agt gaa aat ggt cga aga acc aga att gcc tat gaa aga atg tgc aat      672
Ser Glu Asn Gly Arg Arg Thr Arg Ile Ala Tyr Glu Arg Met Cys Asn
    210                 215                 220

atc ctc aaa ggg aaa ttt                                              690
Ile Leu Lys Gly Lys Phe
225                 230


<210> SEQ ID NO 114
<211> LENGTH: 230
<212> TYPE: PRT
<213> ORGANISM: Equine influenza virus H3N8

<400> SEQUENCE: 114

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Val Val Gly Ile Gly Arg Phe Tyr Val Gln Met Cys Thr Glu Leu Lys
        35                  40                  45

Leu Asn Asp His Glu Gly Arg Leu Ile Gln Asn Ser Met Thr Ile Glu
    50                  55                  60

Arg Met Val Leu Ser Ala Phe Asp Glu Arg Arg Asn Lys Tyr Leu Glu
65                  70                  75                  80
```

-continued

```
Glu His Pro Ser Ala Gly Lys Asp Pro Lys Lys Thr Gly Gly Pro Ile
                85                  90                  95

Tyr Arg Arg Lys Asp Gly Lys Trp Met Arg Glu Leu Ile Leu His Asp
            100                 105                 110

Lys Glu Glu Ile Met Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Met Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Ser Glu Asn Gly Arg Arg Thr Arg Ile Ala Tyr Glu Arg Met Cys Asn
    210                 215                 220

Ile Leu Lys Gly Lys Phe
225                 230


<210> SEQ ID NO 115
<211> LENGTH: 735
<212> TYPE: DNA
<213> ORGANISM: Equine influenza virus H3N8
<220> FEATURE:
<221> NAME/KEY: CDS
<222> LOCATION: (1)..(735)

<400> SEQUENCE: 115

agc aaa agc agg gta gat aat cac tca ctg agt gac atc aaa atc atg       48
Ser Lys Ser Arg Val Asp Asn His Ser Leu Ser Asp Ile Lys Ile Met
1               5                   10                  15

gcg tct caa ggc acc aaa cga tct tat gag cag atg gaa act gat ggg       96
Ala Ser Gln Gly Thr Lys Arg Ser Tyr Glu Gln Met Glu Thr Asp Gly
            20                  25                  30

gaa cgc caa aat gca act gaa atc aga gca tct gtc gga agg atg gtg      144
Glu Arg Gln Asn Ala Thr Glu Ile Arg Ala Ser Val Gly Arg Met Val
        35                  40                  45

gta gga atc ggt cgg ttt tat gtt cag atg tgt act gag ctt aaa cta      192
Val Gly Ile Gly Arg Phe Tyr Val Gln Met Cys Thr Glu Leu Lys Leu
    50                  55                  60

aac gac cat gaa ggg cgg ctg att cag aac agc atg aca ata gaa agg      240
Asn Asp His Glu Gly Arg Leu Ile Gln Asn Ser Met Thr Ile Glu Arg
65                  70                  75                  80

atg gta ctt tcg gca ttc gac gaa aga aga aac aag tac ctc gag gag      288
Met Val Leu Ser Ala Phe Asp Glu Arg Arg Asn Lys Tyr Leu Glu Glu
                85                  90                  95

cat ccc agt gct ggg aaa gac cct aag aaa acg gga ggc ccg ata tac      336
His Pro Ser Ala Gly Lys Asp Pro Lys Lys Thr Gly Gly Pro Ile Tyr
            100                 105                 110

aga agg aaa gat ggg aaa tgg atg aga gaa ctc atc ctc cat gat aaa      384
Arg Arg Lys Asp Gly Lys Trp Met Arg Glu Leu Ile Leu His Asp Lys
        115                 120                 125

gaa gaa atc atg agg atc tgg cgt cag gcc aac aat ggt gaa gac gct      432
Glu Glu Ile Met Arg Ile Trp Arg Gln Ala Asn Asn Gly Glu Asp Ala
    130                 135                 140

act gct ggt ctt act cat atg atg atc tgg cac tcc aat ctc aat gac      480
```

-continued

```
Thr Ala Gly Leu Thr His Met Met Ile Trp His Ser Asn Leu Asn Asp
145                 150                 155                 160

acc aca tac caa aga aca agg gct ctt gtt cgg act ggg atg gat ccc      528
Thr Thr Tyr Gln Arg Thr Arg Ala Leu Val Arg Thr Gly Met Asp Pro
                165                 170                 175

aga atg tgc tct ctg atg caa gga tca acc ctc cca cgg aga tct gga      576
Arg Met Cys Ser Leu Met Gln Gly Ser Thr Leu Pro Arg Arg Ser Gly
            180                 185                 190

gct gct ggt gct gca gta aaa ggt gtt gga aca atg gta atg gaa ctc      624
Ala Ala Gly Ala Ala Val Lys Gly Val Gly Thr Met Val Met Glu Leu
        195                 200                 205

atc aga atg atc aaa cgc gga ata aat gat cga aat ttc tgg aga agt      672
Ile Arg Met Ile Lys Arg Gly Ile Asn Asp Arg Asn Phe Trp Arg Ser
    210                 215                 220

gaa aat ggt cga aga acc aga att gcc tat gaa aga atg tgc aat atc      720
Glu Asn Gly Arg Arg Thr Arg Ile Ala Tyr Glu Arg Met Cys Asn Ile
225                 230                 235                 240

ctc aaa ggg aaa ttt                                                  735
Leu Lys Gly Lys Phe
                245


<210> SEQ ID NO 116
<211> LENGTH: 245
<212> TYPE: PRT
<213> ORGANISM: Equine influenza virus H3N8

<400> SEQUENCE: 116

Ser Lys Ser Arg Val Asp Asn His Ser Leu Ser Asp Ile Lys Ile Met
1               5                   10                  15

Ala Ser Gln Gly Thr Lys Arg Ser Tyr Glu Gln Met Glu Thr Asp Gly
            20                  25                  30

Glu Arg Gln Asn Ala Thr Glu Ile Arg Ala Ser Val Gly Arg Met Val
        35                  40                  45

Val Gly Ile Gly Arg Phe Tyr Val Gln Met Cys Thr Glu Leu Lys Leu
    50                  55                  60

Asn Asp His Glu Gly Arg Leu Ile Gln Asn Ser Met Thr Ile Glu Arg
65                  70                  75                  80

Met Val Leu Ser Ala Phe Asp Glu Arg Arg Asn Lys Tyr Leu Glu Glu
                85                  90                  95

His Pro Ser Ala Gly Lys Asp Pro Lys Lys Thr Gly Gly Pro Ile Tyr
            100                 105                 110

Arg Arg Lys Asp Gly Lys Trp Met Arg Glu Leu Ile Leu His Asp Lys
        115                 120                 125

Glu Glu Ile Met Arg Ile Trp Arg Gln Ala Asn Asn Gly Glu Asp Ala
    130                 135                 140

Thr Ala Gly Leu Thr His Met Met Ile Trp His Ser Asn Leu Asn Asp
145                 150                 155                 160

Thr Thr Tyr Gln Arg Thr Arg Ala Leu Val Arg Thr Gly Met Asp Pro
                165                 170                 175

Arg Met Cys Ser Leu Met Gln Gly Ser Thr Leu Pro Arg Arg Ser Gly
            180                 185                 190

Ala Ala Gly Ala Ala Val Lys Gly Val Gly Thr Met Val Met Glu Leu
        195                 200                 205

Ile Arg Met Ile Lys Arg Gly Ile Asn Asp Arg Asn Phe Trp Arg Ser
    210                 215                 220

Glu Asn Gly Arg Arg Thr Arg Ile Ala Tyr Glu Arg Met Cys Asn Ile
225                 230                 235                 240
```

```
Leu Lys Gly Lys Phe
                245


<210> SEQ ID NO 117
<211> LENGTH: 690
<212> TYPE: DNA
<213> ORGANISM: Equine influenza virus H3N8
<220> FEATURE:
<221> NAME/KEY: CDS
<222> LOCATION: (1)..(690)

<400> SEQUENCE: 117

atg gcg tct caa ggc acc aaa cga tct tat gag cag atg gaa act gat        48
Met Ala Ser Gln Gly Thr Lys Arg Ser Tyr Glu Gln Met Glu Thr Asp
1               5                   10                  15

ggg gaa cgc caa aat gca act gaa atc aga gca tct gtc gga agg atg        96
Gly Glu Arg Gln Asn Ala Thr Glu Ile Arg Ala Ser Val Gly Arg Met
            20                  25                  30

gtg gta gga atc ggt cgg ttt tat gtt cag atg tgt act gag ctt aaa       144
Val Val Gly Ile Gly Arg Phe Tyr Val Gln Met Cys Thr Glu Leu Lys
        35                  40                  45

cta aac gac cat gaa ggg cgg ctg att cag aac agc atg aca ata gaa       192
Leu Asn Asp His Glu Gly Arg Leu Ile Gln Asn Ser Met Thr Ile Glu
    50                  55                  60

agg atg gta ctt tcg gca ttc gac gaa aga aga aac aag tac ctc gag       240
Arg Met Val Leu Ser Ala Phe Asp Glu Arg Arg Asn Lys Tyr Leu Glu
65                  70                  75                  80

gag cat ccc agt gct ggg aaa gac cct aag aaa acg gga ggc ccg ata       288
Glu His Pro Ser Ala Gly Lys Asp Pro Lys Lys Thr Gly Gly Pro Ile
                85                  90                  95

tac aga agg aaa gat ggg aaa tgg atg aga gaa ctc atc ctc cat gat       336
Tyr Arg Arg Lys Asp Gly Lys Trp Met Arg Glu Leu Ile Leu His Asp
            100                 105                 110

aaa gaa gaa atc atg agg atc tgg cgt cag gcc aac aat ggt gaa gac       384
Lys Glu Glu Ile Met Arg Ile Trp Arg Gln Ala Asn Asn Gly Glu Asp
        115                 120                 125

gct act gct ggt ctt act cat atg atg atc tgg cac tcc aat ctc aat       432
Ala Thr Ala Gly Leu Thr His Met Met Ile Trp His Ser Asn Leu Asn
    130                 135                 140

gac acc aca tac caa aga aca agg gct ctt gtt cgg act ggg atg gat       480
Asp Thr Thr Tyr Gln Arg Thr Arg Ala Leu Val Arg Thr Gly Met Asp
145                 150                 155                 160

ccc aga atg tgc tct ctg atg caa gga tca acc ctc cca cgg aga tct       528
Pro Arg Met Cys Ser Leu Met Gln Gly Ser Thr Leu Pro Arg Arg Ser
                165                 170                 175

gga gct gct ggt gct gca gta aaa ggt gtt gga aca atg gta atg gaa       576
Gly Ala Ala Gly Ala Ala Val Lys Gly Val Gly Thr Met Val Met Glu
            180                 185                 190

ctc atc aga atg atc aaa cgc gga ata aat gat cga aat ttc tgg aga       624
Leu Ile Arg Met Ile Lys Arg Gly Ile Asn Asp Arg Asn Phe Trp Arg
        195                 200                 205

agt gaa aat ggt cga aga acc aga att gcc tat gaa aga atg tgc aat       672
Ser Glu Asn Gly Arg Arg Thr Arg Ile Ala Tyr Glu Arg Met Cys Asn
    210                 215                 220

atc ctc aaa ggg aaa ttt                                               690
Ile Leu Lys Gly Lys Phe
225                 230


<210> SEQ ID NO 118
<211> LENGTH: 230
<212> TYPE: PRT
```

-continued

<213> ORGANISM: Equine influenza virus H3N8

<400> SEQUENCE: 118

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Val Val Gly Ile Gly Arg Phe Tyr Val Gln Met Cys Thr Glu Leu Lys
        35                  40                  45

Leu Asn Asp His Glu Gly Arg Leu Ile Gln Asn Ser Met Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Lys Asp Gly Lys Trp Met Arg Glu Leu Ile Leu His Asp
            100                 105                 110

Lys Glu Glu Ile Met Arg Ile Trp Arg Gln Ala Asn Asn Gly Glu Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Ser Glu Asn Gly Arg Arg Thr Arg Ile Ala Tyr Glu Arg Met Cys Asn
    210                 215                 220

Ile Leu Lys Gly Lys Phe
225                 230

<210> SEQ ID NO 119
<211> LENGTH: 679
<212> TYPE: DNA
<213> ORGANISM: Equine influenza virus H3N8

<400> SEQUENCE: 119
atggccttgc agtaaccagt gggtatgact ttgagaagga aggatactct ctggttggaa 60
ttgatccttt caaactactc cagaacagcc aaattttcag tctaatcaga ccgaaagaaa 120
acccagcaca caagagccag ttggtgtgga tggcatgcca ttctgcagca tttgaggacc 180
tgagagtttt gaatttcatt agaggaacca aagtaatccc aagaggacag ttagcaacca 240
gaggagtgca aattgcttca aatgaaaaca tggagacaat agattctagc acactcgaac 300
tgagaagcaa atattgggca ataaggacca gaagtggagg aaacaccagt caacagagag 360
catctgcagg acagataagt gtgcaaccta ctttctcagt gcagagaaat cttccctttg 420
aaagagcaac cattatggct gcattcactg ggaacactga ggggaggact tccgacatga 480
gaacggaaat cataaggatg atggaaaatg ccaaatcaga agatgtgtct ttccaggggc 540
ggggagtctt cgagctctcg gacgaaaagg caacgaaccc gatcgtgcct tcctttgaca 600
tgagcaatga agggtcttat ttcttcggag acaatgctga ggagtttgac agttaaagaa 660

-continued aaataccctt gtttctact 679

<210> SEQ ID NO 120
<211> LENGTH: 225
<212> TYPE: PRT
<213> ORGANISM: Equine influenza virus H3N8
<220> FEATURE:
<221> NAME/KEY: MISC_FEATURE
<222> LOCATION: (225)..(225)
<223> OTHER INFORMATION: Xaa = unknown

<400> SEQUENCE: 120

```
Gly Leu Ala Val Thr Ser Gly Tyr Asp Phe Glu Lys Glu Gly Tyr Ser
1               5                   10                  15

Leu Val Gly Ile Asp Pro Phe Lys Leu Leu Gln Asn Ser Gln Ile Phe
            20                  25                  30

Ser Leu Ile Arg Pro Lys Glu Asn Pro Ala His Lys Ser Gln Leu Val
        35                  40                  45

Trp Met Ala Cys His Ser Ala Ala Phe Glu Asp Leu Arg Val Leu Asn
    50                  55                  60

Phe Ile Arg Gly Thr Lys Val Ile Pro Arg Gly Gln Leu Ala Thr Arg
65                  70                  75                  80

Gly Val Gln Ile Ala Ser Asn Glu Asn Met Glu Thr Ile Asp Ser Ser
                85                  90                  95

Thr Leu Glu Leu Arg Ser Lys Tyr Trp Ala Ile Arg Thr Arg Ser Gly
            100                 105                 110

Gly Asn Thr Ser Gln Gln Arg Ala Ser Ala Gly Gln Ile Ser Val Gln
        115                 120                 125

Pro Thr Phe Ser Val Gln Arg Asn Leu Pro Phe Glu Arg Ala Thr Ile
    130                 135                 140

Met Ala Ala Phe Thr Gly Asn Thr Glu Gly Arg Thr Ser Asp Met Arg
145                 150                 155                 160

Thr Glu Ile Ile Arg Met Met Glu Asn Ala Lys Ser Glu Asp Val Ser
                165                 170                 175

Phe Gln Gly Arg Gly Val Phe Glu Leu Ser Asp Glu Lys Ala Thr Asn
            180                 185                 190

Pro Ile Val Pro Ser Phe Asp Met Ser Asn Glu Gly Ser Tyr Phe Phe
        195                 200                 205

Gly Asp Asn Ala Glu Glu Phe Asp Ser Arg Lys Ile Pro Leu Phe Leu
    210                 215                 220

Xaa
225
```

<210> SEQ ID NO 121
<211> LENGTH: 656
<212> TYPE: DNA
<213> ORGANISM: Equine influenza virus H3N8

<400> SEQUENCE: 121

```
atggccttgc agtaaccagt gggtatgact ttgagaagga aggatactct ctggttggaa     60

ttgatccttt caaactactc cagaacagcc aaattttcag tctaatcaga ccgaaagaaa    120

acccagcaca caagagccag ttggtgtgga tggcatgcca ttctgcagca tttgaggacc    180

tgagagtttt gaatttcatt agaggaacca aagtaatccc aagaggacag ttagcaacca    240

gaggagtgca aattgcttca aatgaaaaca tggagacaat agattctagc acactcgaac    300

tgagaagcaa atattgggca ataaggacca gaagtggagg aaacaccagt caacagagag    360
```

-continued

```
catctgcagg acagataagt gtgcaaccta ctttctcagt gcagagaaat cttccctttg    420

aaagagcaac cattatggct gcattcactg ggaacactga ggggaggact tccgacatga    480

gaacggaaat cataaggatg atggaaaatg ccaaatcaga agatgtgtct ttccaggggc    540

ggggagtctt cgagctctcg gacgaaaagg caacgaaccc gatcgtgcct tcctttgaca    600

tgagcaatga agggtcttat ttcttcggag acaatgctga ggagtttgac agttaa        656


<210> SEQ ID NO 122
<211> LENGTH: 217
<212> TYPE: PRT
<213> ORGANISM: Equine influenza virus H3N8

<400> SEQUENCE: 122

Gly Leu Ala Val Thr Ser Gly Tyr Asp Phe Glu Lys Glu Gly Tyr Ser
1               5                   10                  15

Leu Val Gly Ile Asp Pro Phe Lys Leu Leu Gln Asn Ser Gln Ile Phe
            20                  25                  30

Ser Leu Ile Arg Pro Lys Glu Asn Pro Ala His Lys Ser Gln Leu Val
        35                  40                  45

Trp Met Ala Cys His Ser Ala Ala Phe Glu Asp Leu Arg Val Leu Asn
    50                  55                  60

Phe Ile Arg Gly Thr Lys Val Ile Pro Arg Gly Gln Leu Ala Thr Arg
65                  70                  75                  80

Gly Val Gln Ile Ala Ser Asn Glu Asn Met Glu Thr Ile Asp Ser Ser
                85                  90                  95

Thr Leu Glu Leu Arg Ser Lys Tyr Trp Ala Ile Arg Thr Arg Ser Gly
            100                 105                 110

Gly Asn Thr Ser Gln Gln Arg Ala Ser Ala Gly Gln Ile Ser Val Gln
        115                 120                 125

Pro Thr Phe Ser Val Gln Arg Asn Leu Pro Phe Glu Arg Ala Thr Ile
    130                 135                 140

Met Ala Ala Phe Thr Gly Asn Thr Glu Gly Arg Thr Ser Asp Met Arg
145                 150                 155                 160

Thr Glu Ile Ile Arg Met Met Glu Asn Ala Lys Ser Glu Asp Val Ser
                165                 170                 175

Phe Gln Gly Arg Gly Val Phe Glu Leu Ser Asp Glu Lys Ala Thr Asn
            180                 185                 190

Pro Ile Val Pro Ser Phe Asp Met Ser Asn Glu Gly Ser Tyr Phe Phe
        195                 200                 205

Gly Asp Asn Ala Glu Glu Phe Asp Ser
    210                 215


<210> SEQ ID NO 123
<211> LENGTH: 679
<212> TYPE: DNA
<213> ORGANISM: Equine influenza virus H3N8

<400> SEQUENCE: 123

atggccttgc agtaaccagt gggtatgact ttgagaagga aggatactct ctggttggaa     60

ttgatccttt caaactactc cagaacagcc aaattttcag tctaatcaga ccgaaagaaa    120

acccagcaca caggagccag ttggtgtgga tggcatgcca ttctgcagca tttgaggacc    180

tgagagtttt gaatttcatt agaggaacca aagtaatccc aagaggacag ttagcaacca    240

gaggagtgca aattgcttca aatgaaaaca tggagacaat agattctagc acactcgaac    300

tgagaagcaa atattgggca ataaggacca gaagtggagg aaacaccagt caacagagag    360
```

-continued

```
catctgcagg acagataagt gtgcaaccta ctttctcagt gcagagaaat cttccctttg    420

aaagagcaac cattatggct gcattcactg ggaacactga ggggaggact tccgacatga    480

gaacggaaat cataaggatg atggaaaatg ccaaatcaga agatgtgtct ttccaggggc    540

ggggagtctt cgagctctcg gacgaaaagg caacgaaccc gatcgtgcct tcctttgaca    600

tgagcaatga agggtcttat ttcttcggag acaatgctga ggagtttgac agttaaagaa    660

aaataccctt gtttctact                                                 679
```

<210> SEQ ID NO 124
<211> LENGTH: 225
<212> TYPE: PRT
<213> ORGANISM: Equine influenza virus H3N8
<220> FEATURE:
<221> NAME/KEY: MISC_FEATURE
<222> LOCATION: (225)..(225)
<223> OTHER INFORMATION: Xaa = unknown

<400> SEQUENCE: 124

```
Gly Leu Ala Val Thr Ser Gly Tyr Asp Phe Glu Lys Glu Gly Tyr Ser
1               5                   10                  15

Leu Val Gly Ile Asp Pro Phe Lys Leu Leu Gln Asn Ser Gln Ile Phe
            20                  25                  30

Ser Leu Ile Arg Pro Lys Glu Asn Pro Ala His Arg Ser Gln Leu Val
        35                  40                  45

Trp Met Ala Cys His Ser Ala Ala Phe Glu Asp Leu Arg Val Leu Asn
    50                  55                  60

Phe Ile Arg Gly Thr Lys Val Ile Pro Arg Gly Gln Leu Ala Thr Arg
65                  70                  75                  80

Gly Val Gln Ile Ala Ser Asn Glu Asn Met Glu Thr Ile Asp Ser Ser
                85                  90                  95

Thr Leu Glu Leu Arg Ser Lys Tyr Trp Ala Ile Arg Thr Arg Ser Gly
            100                 105                 110

Gly Asn Thr Ser Gln Gln Arg Ala Ser Ala Gly Gln Ile Ser Val Gln
        115                 120                 125

Pro Thr Phe Ser Val Gln Arg Asn Leu Pro Phe Glu Arg Ala Thr Ile
    130                 135                 140

Met Ala Ala Phe Thr Gly Asn Thr Glu Gly Arg Thr Ser Asp Met Arg
145                 150                 155                 160

Thr Glu Ile Ile Arg Met Met Glu Asn Ala Lys Ser Glu Asp Val Ser
                165                 170                 175

Phe Gln Gly Arg Gly Val Phe Glu Leu Ser Asp Glu Lys Ala Thr Asn
            180                 185                 190

Pro Ile Val Pro Ser Phe Asp Met Ser Asn Glu Gly Ser Tyr Phe Phe
        195                 200                 205

Gly Asp Asn Ala Glu Glu Phe Asp Ser Arg Lys Ile Pro Leu Phe Leu
    210                 215                 220

Xaa
225
```

<210> SEQ ID NO 125
<211> LENGTH: 656
<212> TYPE: DNA
<213> ORGANISM: Equine influenza virus H3N8

<400> SEQUENCE: 125

```
atggccttgc agtaaccagt gggtatgact ttgagaagga aggatactct ctggttggaa     60
```

-continued

```
ttgatccttt caaactactc cagaacagcc aaattttcag tctaatcaga ccgaaagaaa    120

acccagcaca caggagccag ttggtgtgga tggcatgcca ttctgcagca tttgaggacc    180

tgagagtttt gaatttcatt agaggaacca aagtaatccc aagaggacag ttagcaacca    240

gaggagtgca aattgcttca aatgaaaaca tggagacaat agattctagc acactcgaac    300

tgagaagcaa atattgggca ataaggacca gaagtggagg aaacaccagt caacagagag    360

catctgcagg acagataagt gtgcaaccta ctttctcagt gcagagaaat cttccctttg    420

aaagagcaac cattatggct gcattcactg ggaacactga ggggaggact tccgacatga    480

gaacggaaat cataaggatg atggaaaatg ccaaatcaga agatgtgtct ttccaggggc    540

ggggagtctt cgagctctcg gacgaaaagg caacgaaccc gatcgtgcct tcctttgaca    600

tgagcaatga agggtcttat ttcttcggag acaatgctga ggagtttgac agttaa        656
```

<210> SEQ ID NO 126
<211> LENGTH: 217
<212> TYPE: PRT
<213> ORGANISM: Equine influenza virus H3N8

<400> SEQUENCE: 126

```
Gly Leu Ala Val Thr Ser Gly Tyr Asp Phe Glu Lys Glu Gly Tyr Ser
1               5                   10                  15

Leu Val Gly Ile Asp Pro Phe Lys Leu Leu Gln Asn Ser Gln Ile Phe
            20                  25                  30

Ser Leu Ile Arg Pro Lys Glu Asn Pro Ala His Arg Ser Gln Leu Val
        35                  40                  45

Trp Met Ala Cys His Ser Ala Ala Phe Glu Asp Leu Arg Val Leu Asn
    50                  55                  60

Phe Ile Arg Gly Thr Lys Val Ile Pro Arg Gly Gln Leu Ala Thr Arg
65                  70                  75                  80

Gly Val Gln Ile Ala Ser Asn Glu Asn Met Glu Thr Ile Asp Ser Ser
                85                  90                  95

Thr Leu Glu Leu Arg Ser Lys Tyr Trp Ala Ile Arg Thr Arg Ser Gly
            100                 105                 110

Gly Asn Thr Ser Gln Gln Arg Ala Ser Ala Gly Gln Ile Ser Val Gln
        115                 120                 125

Pro Thr Phe Ser Val Gln Arg Asn Leu Pro Phe Glu Arg Ala Thr Ile
    130                 135                 140

Met Ala Ala Phe Thr Gly Asn Thr Glu Gly Arg Thr Ser Asp Met Arg
145                 150                 155                 160

Thr Glu Ile Ile Arg Met Met Glu Asn Ala Lys Ser Glu Asp Val Ser
                165                 170                 175

Phe Gln Gly Arg Gly Val Phe Glu Leu Ser Asp Glu Lys Ala Thr Asn
            180                 185                 190

Pro Ile Val Pro Ser Phe Asp Met Ser Asn Glu Gly Ser Tyr Phe Phe
        195                 200                 205

Gly Asp Asn Ala Glu Glu Phe Asp Ser
    210                 215
```

<210> SEQ ID NO 127
<211> LENGTH: 665
<212> TYPE: DNA
<213> ORGANISM: Equine influenza virus H3N8

<400> SEQUENCE: 127

-continued

```
accagtgggt atgactttga gaaggaagga tactctctgg ttggaattga tcctttcaaa     60

ctactccaga acagccaaat tttcagtcta atcagaccga aagaaaaccc agcacacagg    120

agccagttgg tgtggatggc atgccattct gcagcatttg aggacctgag agttttgaat    180

ttcattagag gaaccaaagt aatcccaaga ggacagttag caaccagagg agtgcaaatt    240

gcttcaaatg aaaacatgga gacaatagat tctagcacac tcgaactgag aagcaaatat    300

tgggcaataa ggaccagaag tggaggaaac accagtcaac agagagcatc tgcaggacag    360

ataagtgtgc aacctacttt ctcagtgcag agaaatcttc cctttgaaag agcaaccatt    420

atggctgcat tcactgggaa cactgagggg aggacttccg acatgagaac ggaaatcata    480

aggatgatgg aaaatgccaa atcagaagat gtgtctttcc aggggcgggg agtcttcgag    540

ctctcggacg aaaaggcaac gaacccgatc gtgccttcct ttgacatgag caatgaaggg    600

tcttatttct tcggagacaa tgctgaggag tttgacagtt aaagaaaaat acccttgttt    660

ctact                                                                665
```

```
<210> SEQ ID NO 128
<211> LENGTH: 221
<212> TYPE: PRT
<213> ORGANISM: Equine influenza virus H3N8
<220> FEATURE:
<221> NAME/KEY: MISC_FEATURE
<222> LOCATION: (221)..(221)
<223> OTHER INFORMATION: Xaa = unknown

<400> SEQUENCE: 128

Thr Ser Gly Tyr Asp Phe Glu Lys Glu Gly Tyr Ser Leu Val Gly Ile
1               5                   10                  15

Asp Pro Phe Lys Leu Leu Gln Asn Ser Gln Ile Phe Ser Leu Ile Arg
            20                  25                  30

Pro Lys Glu Asn Pro Ala His Arg Ser Gln Leu Val Trp Met Ala Cys
        35                  40                  45

His Ser Ala Ala Phe Glu Asp Leu Arg Val Leu Asn Phe Ile Arg Gly
    50                  55                  60

Thr Lys Val Ile Pro Arg Gly Gln Leu Ala Thr Arg Gly Val Gln Ile
65                  70                  75                  80

Ala Ser Asn Glu Asn Met Glu Thr Ile Asp Ser Ser Thr Leu Glu Leu
                85                  90                  95

Arg Ser Lys Tyr Trp Ala Ile Arg Thr Arg Ser Gly Gly Asn Thr Ser
            100                 105                 110

Gln Gln Arg Ala Ser Ala Gly Gln Ile Ser Val Gln Pro Thr Phe Ser
        115                 120                 125

Val Gln Arg Asn Leu Pro Phe Glu Arg Ala Thr Ile Met Ala Ala Phe
    130                 135                 140

Thr Gly Asn Thr Glu Gly Arg Thr Ser Asp Met Arg Thr Glu Ile Ile
145                 150                 155                 160

Arg Met Met Glu Asn Ala Lys Ser Glu Asp Val Ser Phe Gln Gly Arg
                165                 170                 175

Gly Val Phe Glu Leu Ser Asp Glu Lys Ala Thr Asn Pro Ile Val Pro
            180                 185                 190

Ser Phe Asp Met Ser Asn Glu Gly Ser Tyr Phe Phe Gly Asp Asn Ala
        195                 200                 205

Glu Glu Phe Asp Ser Arg Lys Ile Pro Leu Phe Leu Xaa
    210                 215                 220
```

-continued

<210> SEQ ID NO 129
<211> LENGTH: 642
<212> TYPE: DNA
<213> ORGANISM: Equine influenza virus H3N8

<400> SEQUENCE: 129
accagtgggt atgactttga gaaggaagga tactctctgg ttggaattga tcctttcaaa 60
ctactccaga acagccaaat tttcagtcta atcagaccga aagaaaaccc agcacacagg 120
agccagttgg tgtggatggc atgccattct gcagcatttg aggacctgag agttttgaat 180
ttcattagag gaaccaaagt aatcccaaga ggacagttag caaccagagg agtgcaaatt 240
gcttcaaatg aaaacatgga gacaatagat tctagcacac tcgaactgag aagcaaatat 300
tgggcaataa ggaccagaag tggaggaaac accagtcaac agagagcatc tgcaggacag 360
ataagtgtgc aacctacttt ctcagtgcag agaaatcttc cctttgaaag agcaaccatt 420
atggctgcat tcactgggaa cactgagggg aggacttccg acatgagaac ggaaatcata 480
aggatgatgg aaaatgccaa atcagaagat gtgtctttcc aggggcgggg agtcttcgag 540
ctctcggacg aaaaggcaac gaacccgatc gtgccttcct ttgacatgag caatgaaggg 600
tcttatttct tcggagacaa tgctgaggag tttgacagtt aa 642

<210> SEQ ID NO 130
<211> LENGTH: 213
<212> TYPE: PRT
<213> ORGANISM: Equine influenza virus H3N8

<400> SEQUENCE: 130

Thr Ser Gly Tyr Asp Phe Glu Lys Glu Gly Tyr Ser Leu Val Gly Ile
1 5 10 15

Asp Pro Phe Lys Leu Leu Gln Asn Ser Gln Ile Phe Ser Leu Ile Arg
20 25 30

Pro Lys Glu Asn Pro Ala His Arg Ser Gln Leu Val Trp Met Ala Cys
35 40 45

His Ser Ala Ala Phe Glu Asp Leu Arg Val Leu Asn Phe Ile Arg Gly
50 55 60

Thr Lys Val Ile Pro Arg Gly Gln Leu Ala Thr Arg Gly Val Gln Ile
65 70 75 80

Ala Ser Asn Glu Asn Met Glu Thr Ile Asp Ser Ser Thr Leu Glu Leu
85 90 95

Arg Ser Lys Tyr Trp Ala Ile Arg Thr Arg Ser Gly Gly Asn Thr Ser
100 105 110

Gln Gln Arg Ala Ser Ala Gly Gln Ile Ser Val Gln Pro Thr Phe Ser
115 120 125

Val Gln Arg Asn Leu Pro Phe Glu Arg Ala Thr Ile Met Ala Ala Phe
130 135 140

Thr Gly Asn Thr Glu Gly Arg Thr Ser Asp Met Arg Thr Glu Ile Ile
145 150 155 160

Arg Met Met Glu Asn Ala Lys Ser Glu Asp Val Ser Phe Gln Gly Arg
165 170 175

Gly Val Phe Glu Leu Ser Asp Glu Lys Ala Thr Asn Pro Ile Val Pro
180 185 190

Ser Phe Asp Met Ser Asn Glu Gly Ser Tyr Phe Phe Gly Asp Asn Ala
195 200 205

Glu Glu Phe Asp Ser
210

COLD-ADAPTED EQUINE INFLUENZA VIRUSES

CROSS-REFERENCE TO RELATED APPLICATION

This application is a Divisional of U.S. patent application Ser. No. 10/181,585, filed Nov. 25, 2002; now U.S. Pat. No. 7,074,414 which is a 35 U.S.C. § 371 filing of International PCT Application No. PCT/US01/05048, filed Feb. 16, 2001; which is a CIP of U.S. patent application Ser. No. 09/506,286, filed Feb. 16, 2000, now issued as U.S. Pat. No. 6,482,414 B1; all of which are entitled "COLD-ADAPTED EQUINE INFLUENZA VIRUSES" and incorporated herein by reference in its entirety.

FIELD OF THE INVENTION

The present invention relates to nucleic acids and proteins of experimentally-generated cold-adapted equine influenza viruses, and particularly to cold-adapted equine influenza viruses having additional phenotypes, such as attenuation, dominant interference, or temperature sensitivity. The invention also includes reassortant influenza A viruses which contain at least one genome segment from such an equine influenza virus, such that the reassortant virus includes certain phenotypes of the donor equine influenza virus. The invention further includes genetically-engineered equine influenza viruses, produced through reverse genetics, which comprise certain identifying phenotypes of a cold-adapted equine influenza virus of the present invention. The present invention also relates to the use of these viruses in therapeutic compositions to protect animals from diseases caused by influenza viruses.

BACKGROUND OF THE INVENTION

Equine influenza virus has been recognized as a major respiratory pathogen in horses since about 1956. Disease symptoms caused by equine influenza virus can be severe, and are often followed by secondary bacterial infections. Two subtypes of equine influenza virus are recognized, namely subtype-1, the prototype being A/Equine/Prague1/56 (H7N7), and subtype-2, the prototype being A/Equine/Miami/1/63 (H3N8). Presently, the predominant virus subtype is subtype-2, which has further diverged among Eurasian and North American isolates in recent years. The currently licensed vaccine for equine influenza is an inactivated (killed) virus vaccine. This vaccine provides minimal, if any, protection for horses, and can produce undesirable side effects, for example, inflammatory reactions at the site of injection. See, e.g., Mumford, 1987, *Equine Infectious Disease IV*, 207-217, and Mumford, et al., 1993, *Vaccine* 11, 1172-1174. Furthermore, current modalities cannot be used in young foals, because they cannot overcome maternal immunity, and can induce tolerance in a younger animal. Based on the severity of disease, there remains a need for safe, effective therapeutic compositions to protect horses against equine influenza disease.

Production of therapeutic compositions comprising cold-adapted human influenza viruses is described, for example, in Maassab, et al., 1960, *Nature* 7,612-614, and Maassab, et al., 1969, *J. Immunol* 102, 728-732. Furthermore, these researchers noted that cold-adapted human influenza viruses, i.e., viruses that have been adapted to grow at lower than normal temperatures, tend to have a phenotype wherein the virus is temperature sensitive; that is, the virus does not grow well at certain higher, non-permissive temperatures at which the wild-type virus will grow and replicate. Various cold-adapted human influenza A viruses, produced by reassortment with existing cold-adapted human influenza A viruses, have been shown to elicit good immune responses in vaccinated individuals, and certain live attenuated cold-adapted reassortant human influenza A viruses have proven to protect humans against challenge with wild-type virus. See, e.g., Clements, et al., 1986, *J. Clin. Microbiol.* 23, 73-76. In U.S. Pat. No. 5,149,531, by Youngner, et al., issued Sep. 22, 1992, the inventors of the present invention further demonstrated that certain reassortant cold-adapted human influenza A viruses also possess a dominant interference phenotype, i.e., they inhibit the growth of their corresponding parental wild-type strain as well as heterologous influenza A viruses.

U.S. Pat. No. 4,683,137, by Coggins et al., issued Jul. 28, 1987, and U.S. Pat. No. 4,693,893, by Campbell, issued Sep. 15, 1987, disclose attenuated therapeutic compositions produced by reassortment of wild-type equine influenza viruses with attenuated, cold-adapted human influenza A viruses. Although these therapeutic compositions appear to be generally safe and effective in horses, they pose a significant danger of introducing into the environment a virus containing both human and equine influenza genes.

SUMMARY OF THE INVENTION

The present invention provides nucleic acids and proteins of experimentally-generated cold-adapted equine influenza viruses, and reassortant influenza A viruses.

Examples of cold-adapted equine influenza viruses of the present invention include EIV-P821, identified by accession No. ATCC VR-2625; EIV-P824, identified by accession No. ATCC VR-2624; EIV-MSV+5, identified by accession No. ATCC VR-627; and progeny of such viruses. Cold-adapted equine influenza viruses of the invention, and their methods of making, are disclosed in related U.S. Pat. No. 6,177,082, by Dowling et al., issued Jan. 23, 2001; and WO 00/09702, by Dowling et al., published Feb. 24, 2000, both of which are incorporated herein by reference in their entirety.

The present invention also describes nucleic acid molecules encoding wild-type and cold-adapted equine influenza proteins PB2, NS, PB1, PA and NA. One embodiment of the present invention is an isolated equine nucleic acid molecule having a nucleic acid sequence selected from a group consisting of SEQ ID NO:5, SEQ ID NO:7, SEQ ID NO:8, SEQ ID NO:10, SEQ ID NO:13, SEQ ID NO:19, SEQ ID NO:20, SEQ ID NO:21, SEQ ID NO:23, SEQ ID NO:24, SEQ ID NO:26, SEQ ID NO:27, SEQ ID NO:29, SEQ ID NO:32, SEQ ID NO:34, SEQ ID NO:35, SEQ ID NO:36, SEQ ID NO:38, SEQ ID NO:39, SEQ ID NO:41, SEQ ID NO:42, SEQ ID NO:44, SEQ ID NO:45, SEQ ID NO:47, SEQ ID NO:48, SEQ ID NO:50, SEQ ID NO:51, SEQ ID NO:53, SEQ ID NO:60, SEQ ID NO:61, SEQ ID NO:63, SEQ ID NO:65, SEQ ID NO:66, SEQ ID NO:68, SEQ ID NO:70, SEQ ID NO:71, SEQ ID NO:73, SEQ ID NO:76, SEQ ID NO:82, SEQ ID NO:83, SEQ ID NO:84, SEQ ID NO:86, SEQ ID NO:87, SEQ ID NO:89, SEQ ID NO:94, SEQ ID NO:95, SEQ ID NO:97, SEQ ID NO:98, SEQ ID NO:100 and SEQ ID NO:102 and a nucleic acid molecule comprising a nucleic acid sequence which is fully complementary to any of such nucleic acid sequences. Another embodiment of the present invention is an isolated equine nucleic acid molecule that encodes a protein comprising an amino acid sequence selected from the group consisting of SEQ ID NO:6, SEQ ID NO:9, SEQ ID NO:14, SEQ ID NO:22, SEQ ID NO:25, SEQ ID NO:28, SEQ ID NO:33, SEQ ID NO:37, SEQ ID NO:40, SEQ ID NO:43, SEQ ID NO:46, SEQ ID NO:49, SEQ ID NO:54, SEQ ID NO:62, SEQ ID NO:64, SEQ ID NO:67, SEQ ID NO:69, SEQ ID NO:72, SEQ ID NO:77, SEQ ID NO:85, SEQ ID NO:88, SEQ ID NO:96, SEQ ID NO:99, SEQ ID NO:101 and SEQ ID NO:103. Another embodiment is an isolated equine influenza protein that comprises an amino acid sequence selected from a group consisting of SEQ ID NO:6, SEQ ID NO:9, SEQ ID NO:14, SEQ ID NO:22, SEQ ID NO:25, SEQ ID NO:28, SEQ ID NO:33, SEQ ID NO:37, SEQ ID NO:40, SEQ ID NO:43, SEQ ID NO:46, SEQ ID NO:49, SEQ ID NO:54, SEQ ID NO:62, SEQ ID NO:64, SEQ ID NO:67, SEQ ID NO:69, SEQ ID NO:72, SEQ ID NO:77, SEQ ID NO:85, SEQ ID NO:88, SEQ ID NO:96, SEQ ID NO:99, SEQ ID NO:101 and SEQ ID NO:103. Also included in the present invention is a virus that include any of these nucleic acid molecules or proteins. In one embodiment, such a virus is equine influenza virus or a reassortant virus.

DETAILED DESCRIPTION OF THE INVENTION

The present invention provides nucleic acids and proteins of experimentally-generated cold-adapted equine influenza viruses comprising certain defined phenotypes, which are disclosed herein. It is to be noted that the term "a" or "an" entity, refers to one or more of that entity; for example, "a cold-adapted equine influenza virus" can include one or more cold-adapted equine influenza viruses. As such, the terms "a" (or "an"), "one or more," and "at least one" can be used interchangeably herein. It is also to be noted that the terms "comprising," "including," and "having" can be used interchangeably. Furthermore, an item "selected from the group consisting of" refers to one or more of the items in that group, including combinations thereof.

A cold-adapted equine influenza virus of the present invention is a virus that has been generated in the laboratory, and as such, is not a virus as occurs in nature. Since the present invention also includes those viruses having the identifying phenotypes of such a cold-adapted equine influenza virus, an equine influenza virus isolated from a mixture of naturally-occurring viruses, i.e., removed from its natural milieu, but having the claimed phenotypes, is included in the present invention. A cold-adapted equine influenza virus of the present invention does not require any specific level of purity. For example, a cold-adapted equine influenza virus grown in embryonated chicken eggs may be in a mixture with the allantoic fluid (AF), and a cold-adapted equine influenza virus grown in tissue culture cells may be in a mixture with disrupted cells and tissue culture mediua As used herein, an "equine influenza virus" is an influenza virus that infects and grows in equids, e.g., horses or ponies. As used herein, "growth" of a virus denotes the ability of the virus to reproduce or "replicate" itself in a permissive host cell. As such, the terms, "growth of a virus" and "replication of a virus" are used interchangeably herein. Growth or replication of a virus in a particular host cell can be demonstrated and measured by standard methods well-known to those skilled in the art of virology. For example, samples containing infectious virus, e.g., as contained in nasopharyngeal secretions from an infected horse, are tested for their ability to cause cytopathic effect (CPE), e.g., virus plaques, in tissue culture cells. Infectious virus may also be detected by inoculation of a sample into the allantoic cavity of embryonated chicken eggs, and then testing the AF of eggs thus inoculated for its ability to agglutinate red blood cells, i.e., cause hemagglutination, due to the presence of the influenza virus hemagglutinin (HA) protein in the AF.

Cold-adapted equine influenza viruses of the present invention are characterized primarily by one or more of the following identifying phenotypes: cold-adaptation, temperature sensitivity, dominant interference, and/or attenuation. As used herein, the phrase "an equine influenza virus comprises the identifying phenotype(s) of cold-adaptation, temperature sensitivity, dominant interference, and/or attenuation" refers to a virus having such a phenotype(s). Examples of such viruses include, but are not limited to, EIV-P821, identified by accession No. ATCC VR-2625, EIV-P824, identified by accession No. ATCC VR-2624, and EIV-MSV+5, identified by accession No. ATCC VR-2627, as well as EIV-MSV0, EIV, MSV+1, EIV-MSV+2, EIV-MSV+3, and EIV-MSV+4.

Pursuant to 37 CFR § 1.802 (a-c), cold-adapted equine influenza viruses, designated herein as EIV-P821, an EIV-P824 were deposited with the American Type Culture Collection (ATCC, 10801 University Boulevard, Manassas, Va. 20110-2209) under the Budapest Treaty as ATCC Accession Nos. ATCC VR-2625, and ATCC VR-2624, respectively, on Jul. 11, 1998. Cold-adapted equine influenza virus EIV-MSV+5 was deposited with the ATCC as ATCC Accession No. ATCC VR-2627 on Aug. 3, 1998. Pursuant to 37 CFR§ 1.806, the deposits are made for a term of at least thirty (30) years and at least five (5) years after the most recent request for the furnishing of a sample of the deposit was received by the depository. Pursuant to 37 CFR § 1.808 (a)(2), all restrictions imposed by the depositor on the availability to the public will be irrevocably removed upon the granting of the patent.

The present invention includes nucleic acid molecules isolated from equine influenza virus wild type strain A/equine/Kentucky/1/91 (H3N8), and cold-adapted equine influenza virus EIV-P821.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA As such, "isolated" does not reflect the extent to which the nucleic acid molecule has been purified.

The present invention includes nucleic acid molecules encoding wild-type and cold-adapted equine influenza virus proteins. Nucleic acid molecules of the present invention can be prepared by methods known to one skilled in the art. Proteins of the present invention can be prepared by methods known to one skilled in the art, i.e., recombinant DNA technology. Preferred nucleic acid molecules have coding strands comprising nucleic acid sequences SEQ ID NO:5, SEQ ID NO:7, SEQ ID NO:8, SEQ ID NO:10, SEQ ID NO:13, SEQ ID NO:19, SEQ ID NO:20, SEQ ID NO:21, SEQ ID NO:23, SEQ ID NO:24, SEQ ID NO:26, SEQ ID NO:27, SEQ ID NO:29, SEQ ID NO:32, SEQ ID NO:34, SEQ ID NO:35, SEQ ID NO:36, SEQ ID NO:38, SEQ ID NO:39, SEQ ID NO:41, SEQ ID NO:42, SEQ ID NO:44, SEQ ID NO:45, SEQ ID NO:47, SEQ ID NO:48, SEQ ID NO:50, SEQ ID NO:51, SEQ ID NO:53, SEQ ID NO:60, SEQ ID NO:61, SEQ ID NO:63, SEQ ID NO:65, SEQ ID NO:66, SEQ ID NO:68, SEQ ID NO:70, SEQ ID NO:71, SEQ ID NO:73, SEQ ID NO:76, SEQ ID NO:82, SEQ ID NO:83, SEQ ID NO:84, SEQ ID NO:86, SEQ ID NO:87, SEQ ID NO:89, SEQ ID NO:94, SEQ ID NO:95, SEQ ID NO:97, SEQ ID NO:98, SEQ ID NO:100 and SEQ ID NO:102 and/or a complement thereof. Complements are defined as two single strands of nucleic acid in which the nucleotide sequence is such that they will hybridize as a result of base-pairing throughout their full length. Given a nucleotide sequence, one of ordinary skill in the art can deduce the complement.

Preferred nucleic acid molecules encoding equine influenza PB2 proteins are $nei_{wt}PB2_{2341}$, $nei_{wt}PB2_{2277}$, $nei_{ca1}PB2_{2341}$, and/or $nei_{ca1}PB2_{2277}$, the coding strands of which are represented by SEQ ID NO:24, SEQ ID NO:26, SEQ ID NO:27, and/or SEQ ID NO:29.

Preferred nucleic acid molecules encoding equine influenza NS proteins are $nei_{wt1}NS_{891}$, $nei_{wt1}NS_{690}$, $nei_{wt3}NS_{888}$, $nei_{wt4}NS_{468}$, $nei_{wt4}NS_{293}$, $nei_{ca1}NS_{888}$, and/or $nei_{ca1}NS_{690}$, the coding strands of which are represented by SEQ ID NO:32, SEQ ID NO:34, SEQ ID NO:35, SEQ ID NO:36, SEQ ID NO:38, SEQ ID NO:39 and/or SEQ ID NO:41.

Preferred nucleic acid molecules encoding equine influenza PB1-N proteins are $nei_{wt1}PB1\text{-}N_{1229}$, $nei_{wt1}PB1\text{-}N_{1194}$, $nei_{wt2}PB1\text{-}N_{673}$, $nei_{wt2}PB1\text{-}N_{636}$, $nei_{ca1}PB1\text{-}N_{1225}$, $nei_{ca1}PB1\text{-}N_{1185}$, $nei_{ca2}PB1\text{-}N_{1221}$, and/or $nei_{ca2}PB1\text{-}N_{1185}$, the coding strands of which are represented by SEQ ID NO:42, SEQ ID NO:44, SEQ ID NO:45, SEQ ID NO:47, SEQ ID NO:48, SEQ ID NO:50, and/or SEQ ID NO:51.

Preferred nucleic acid molecules encoding equine influenza PB1-C proteins are $nei_{wt1}PB1\text{-}C_{1234}$, $nei_{wt1}PB1\text{-}C_{1188}$, $nei_{wt2}PB1\text{-}C_{1240}$, $nei_{ca1}$PB1-C1241, $nei_{ca1}PB1\text{-}C_{1188}$, and/or $nei_{ca2}PB1\text{-}C_{1241}$, the coding strands of which are represented by SEQ ID NO:53, SEQ ID NO:60, SEQ ID NO:61, SEQ ID NO:63, SEQ ID NO:65, SEQ ID NO:66, and/or SEQ ID NO:94.

Preferred nucleic acid molecules encoding equine influenza PB1 proteins are $nei_{wt}PB1_{2341}$, $nei_{wt}PB1_{2271}$, $nei_{ca1}PB1_{2341}$, $nei_{ca1}PB1_{2271}$, the coding strands of which are represented by SEQ ID NO:68, SEQ ID NO:70, SEQ ID NO:71, and/or SEQ ID NO:73.

Preferred nucleic acid molecules encoding equine influenza PA-C proteins are $nei_{wt1}PA\text{-}N_{1228}$, $nei_{wt1}PA\text{-}C_{1164}$, $nei_{wt2}PA\text{-}C_{1223}$, $nei_{ca1}PA\text{-}C_{1233}$, and $nei_{ca1}PA\text{-}C_{1170}$, the coding strands of which are represented by SEQ ID NO:76, SEQ ID NO:82, SEQ ID NO:83, SEQ ID NO:84, and/or SEQ ID NO:86.

Preferred nucleic acid molecules encoding equine influenza PA-N proteins are $nei_{wt}PA\text{-}N_{1216}$, $nei_{wt}PA\text{-}N_{1193}$, $nei_{ca}PA\text{-}N_{1217}$, and $nei_{ca}PA\text{-}N_{1193}$, the coding strands of which are represented by SEQ ID NO:94, SEQ ID NO:95, SEQ ID NO:97 and SEQ ID NO:98.

Preferred nucleic acid molecules encoding equine influenza PA proteins are $nei_{wt}PA_{2148}$ and $nei_{ca}PA_{2148}$, the coding strands of which are represented by SEQ ID NO:100 and SEQ ID NO:102.

Preferred nucleic acid molecules encoding equine influenza NA proteins are $nei_{ca}NA_{1478}$ and $nei_{ca}NA_{1410}$, the coding strands of which are represented by SEQ ID NO:87 and SEQ ID NO:89.

The present invention includes proteins comprising SEQ ID NO:6, SEQ ID NO:9, SEQ ID NO:14, SEQ ID NO:22, SEQ ID NO:25, SEQ ID NO:28, SEQ ID NO:33, SEQ ID NO:37, SEQ ID NO:40, SEQ ID NO:43, SEQ ID NO:46, SEQ ID NO:49, SEQ ID NO:54, SEQ ID NO:62, SEQ ID NO:64, SEQ ID NO:67, SEQ ID NO:69, SEQ ID NO:72, SEQ ID NO:77, SEQ ID NO:85, SEQ ID NO:88, SEQ ID NO:96, SEQ ID NO:99, SEQ ID NO:101 and SEQ ID NO:103 as well as nucleic acid molecules encoding such proteins.

Preferred equine influenza PB2-N proteins of the present invention include proteins encoded by a nucleic acid molecule comprising $nei_{wt}PB2\text{-}N_{1241}$, $nei_{wt}PB2\text{-}N_{1214}$, $nei_{ca1}PB2\text{-}N_{1241}$, $nei_{ca1}PB2\text{-}N_{1214}$ $nei_{ca2}$, and/or PB2-$N1_{1214}$. Preferred equine influenza PB2-N proteins are $P_{wt}PB2\text{-}N_{404}$, $P_{ca1}PB2\text{-}N_{404}$, and/or $P_{ca2}PB2\text{-}N_{404}$. In one embodiment, a preferred equine influenza PB2-N protein of the present invention is encoded by SEQ ID NO:5, SEQ ID NO:7, SEQ ID NO:8, and/or SEQ ID NO:10, and, as such, has an amino acid sequence that includes SEQ ID NO:6 and/or SEQ ID NO:9.

Preferred equine influenza PB2-C proteins of the present invention include proteins encoded by a nucleic acid molecule comprising $nei_{wt1}PB2\text{-}C_{1233}$, $nei_{wt2}PB2\text{-}C_{1232}$, $nei_{wt}PB2\text{-}C_{1194}$, $nei_{ca1}PB2\text{-}C_{1232}$, and/or $nei_{ca1}PB2\text{-}C_{1194}$. In one embodiment, a preferred equine influenza PB2-C protein of the present invention is encoded by SEQ ID NO:13, SEQ ID NO:20, SEQ ID NO:19, SEQ ID NO:21, and/or SEQ ID NO:23, and, as such, has an amino acid sequence that includes SEQ ID NO:14 and/or SEQ ID NO:22.

Preferred equine influenza PB2 proteins of the present invention include proteins encoded by a nucleic acid molecule comprising $nei_{wt}PB2_{2341}$, $nei_{wt}PB2_{2277}$, $nei_{ca1}PB2_{2341}$, and or $nei_{ca1}PB2_{2277}$. In one embodiment, a preferred equine influenza PB2 protein of the present invention is encoded by SEQ ID NO:24, SEQ ID NO:26, SEQ ID NO:27, and/or SEQ ID NO:29, and, as such, has an amino acid sequence that includes SEQ ID NO:25 and/or SEQ ID NO:28.

Preferred equine influenza NS proteins of the present invention include proteins encoded by a nucleic acid molecule comprising $nei_{wt1}NS_{891}$, $nei_{wt1}NS_{690}$, $nei_{wt3}NS_{888}$, $nei_{wt4}NS_{468}$, $nei_{wt4}NS_{293}$, $nei_{ca1}NS_{888}$, and/or $nei_{ca1}NS_{690}$. Preferred equine influenza NS proteins are $Pei_{wt}NS_{230}$, $Pei_{wt4}NS_{97}$, and/or $Pei_{ca1}NS_{230}$. In one embodiment, a preferred equine influenza NS protein of the present invention is encoded by SEQ ID NO:32, SEQ ID NO:34, SEQ ID NO:35, SEQ ID NO:36, SEQ ID NO:38, SEQ ID NO:39 and/or SEQ ID NO:41, and, as such, has an amino acid sequence that includes SEQ ID NO:33, SEQ ID NO:37 and/or SEQ ID NO:40.

Preferred equine influenza PB1-N proteins of the present invention include $nei_{wt2}PB1\text{-}N_{673}$, $nei_{wt2}$PB1-N636, $nei_{ca1}PB21\text{-}N_{1225}$, $nei_{ca1}PB1\text{-}N_{1185}$, and/or $nei_{ca2}PB1\text{-}N_{1221}$. Preferred equine influenza PB1-N proteins are $Pei_{wt1}PB1\text{-}N_{398}$, $P_{wt2}PB1\text{-}N_{212}$, and/or $P_{ca1}PB11\text{-}N_{395}$. In one embodiment, a preferred equine influenza PB1-N protein of the present invention is encoded by SEQ ID NO:42, SEQ ID NO:44, SEQ ID NO:45, SEQ ID NO:47, SEQ ID NO:48, SEQ ID NO:50, and/or SEQ ID NO:51, and, as such, has an amino acid sequence that includes SEQ ID NO:43, SEQ ID NO:46 and/or SEQ ID NO:49.

Preferred equine influenza PB1-C proteins of the present invention include proteins encoded by a nucleic acid molecule comprising $nei_{wt1}PB1\text{-}C_{1234}$, $nei_{wt1}PB1C_{1188}$, $nei_{wt2}PB1\text{-}C_{1240}$, $nei_{ca1}PB1\text{-}C_{1241}$, $nei_{ca1}PB1\text{-}C_{1188}$, and/or $nei_{ca2}PB1\text{-}C_{1241}$. Preferred equine influenza PB1-C proteins are $Pei_{wt1}PB1\text{-}C_{396}$, $Pei_{wt2}PB1\text{-}C_{396}$ $Pei_{ca1}PB1\text{-}C_{396}$, and/or $Pei_{ca2}PB1\text{-}C_{396}$. In one embodiment, a preferred equine influenza PB1-C protein of the present invention is encoded by SEQ ID NO:53, SEQ ID NO:60, SEQ ID NO:61, SEQ ID NO:63, SEQ ID NO:65, and/or SEQ ID NO:66, and, as such, has an amino acid sequence that includes SEQ ID NO:54, SEQ ID NO:62, SEQ ID NO:64, and/or SEQ ID NO:67.

Preferred equine influenza PB1 proteins of the present invention include proteins encoded by a nucleic acid molecule comprising $nei_{wt}PB1_{2341}$, $nei_{wt}PB1_{2271}$, $nei_{ca1}PB1_{2341}$, $nei_{ca1}PB1_{2271}$. Preferred equine influenza PB1 proteins are $Pei_{wt}PB1_{757}$, and/or $Pei_{ca1}PB1_{757}$. In one embodiment, a preferred equine influenza PB1 protein of the present invention is encoded by SEQ ID NO:68, SEQ ID NO:70, SEQ ID NO:71, and/or SEQ ID NO:73, and, as such, has an amino acid sequence that includes SEQ ID NO:69 and/or SEQ ID NO:72.

Preferred equine influenza PA-C proteins of the present invention include proteins encoded by a nucleic acid molecule comprising $nei_{wt1}PA\text{-}C_{1228}$, $nei_{wt1}PA\text{-}C_{1164}$, $nei_{wt2}PA\text{-}C_{1223}$, $nei_{ca1}PA\text{-}C_{1233}$, and/or $nei_{ca1}PA\text{-}C_{1170}$. Preferred equine influenza PA-C proteins are $Pei_{wt1}PA\text{-}C_{388}$, and/or $Pei_{ca1}PA\text{-}C_{390}$. In one embodiment, a preferred equine influenza PA-C protein of the present invention is encoded by SEQ ID NO:76, SEQ ID NO:82, SEQ ID NO:83, SEQ ID NO:84, and/or SEQ ID NO:86, and, as such, has an amino acid sequence that includes SEQ ID NO:77 and/or SEQ ID NO:85.

Preferred equine influenza PA-N proteins of the present invention include proteins encoded by a nucleic acid molecule comprising $nei_{wt}PA\text{-}N_{1216}$, $nei_{wt}PA\text{-}N_{1193}$, $nei_{ca}PA\text{-}N_{1217}$ and $nei_{ca}PA\text{-}N_{1193}$. Preferred equine influenza PA-N proteins are $Pei_{wt}PA\text{-}N_{397}$ and/or $Pei_{ca}PA\text{-}N_{397}$. In one embodiment, a preferred equine influenza PA-N protein of the present invention is encoded by SEQ ID NO:94, SEQ ID NO:95, SEQ ID NO:97, and/or SEQ ID NO:98, and, as such, has an amino acid sequence that includes SEQ ID NO:96 and/or SEQ ID NO:99.

Preferred equine influenza PA proteins of the present invention include proteins encoded by a nucleic acid molecule comprising $nei_{wt}PA_{2148}$ and $nei_{ca}PA_{2148}$. Preferred equine influenza PA proteins are $Pei_{wt}PA_{716}$ and/or $Pei_{ca}PA_{716}$. In one embodiment, a preferred equine influenza PA protein of the present invention is encoded by SEQ ID NO:100 and/or SEQ ID NO:102, and, as such, has an amino acid sequence that includes SEQ ID NO:101 and/or SEQ ID NO:103.

Preferred equine influenza NA proteins of the present invention include proteins encoded by a nucleic acid molecule comprising $nei_{ca}NA_{1478}$ and $nei_{ca}NA_{1410}$. A preferred equine influenza NA protein is $Pei_{ca}NA_{470}$. In one embodiment, a preferred equine influenza NA protein of the present invention is encoded by SEQ ID NO:87 and/or SEQ ID NO:89, and, as such, has an amino acid sequence that includes SEQ ID NO:88.

The present invention includes a nucleic acid molecule comprising a cold-adapted equine influenza virus encoding a PB2-N protein having an amino acid sequence comprising SEQ ID NO:9. Another embodiment of the present invention includes a nucleic acid molecule comprising a cold-adapted equine influenza virus encoding a PB2-C protein having an amino acid sequence comprising SEQ ID NO:22. Another embodiment of the present invention includes a nucleic acid molecule comprising a cold-adapted equine influenza virus encoding a PB2 protein having an amino acid sequence comprising SEQ ID NO:28. Another embodiment of the present invention includes a nucleic acid molecule comprising a cold-adapted equine influenza virus encoding a NS protein having an amino acid sequence comprising SEQ ID NO:40. Another embodiment of the present invention includes a nucleic acid molecule comprising a cold-adapted equine influenza virus encoding a PB1-N protein having an amino acid sequence comprising SEQ ID NO:49. Another embodiment of the present invention includes a nucleic acid molecule comprising a cold-adapted equine influenza virus encoding a PA-C protein having an amino acid sequence comprising SEQ ID NO:85. Another embodiment of the present invention includes a nucleic acid molecule comprising a cold-adapted equine influenza virus encoding a PB1-C protein having an amino acid sequence comprising SEQ ID NO:64 and/or SEQ ID NO:67. Another embodiment of the present invention includes a nucleic acid molecule comprising a cold-adapted equine influenza virus encoding a PB1 protein having an amino acid sequence comprising SEQ ID NO:72. Another embodiment of the present invention includes a nucleic acid molecule comprising a cold-adapted equine influenza virus encoding a PA-N protein having an amino acid sequence comprising SEQ ID NO:99. Another embodiment of the present invention includes a nucleic acid molecule comprising a cold-adapted equine influenza virus encoding a PA protein having an amino acid sequence comprising SEQ ID NO:103. Another embodiment of the present invention includes a nucleic acid molecule comprising a cold-adapted equine influenza virus encoding a NA protein having an amino acid sequence comprising SEQ ID NO:88. It should be noted that since nucleic acid sequencing technology is not entirely error-free, the nucleic acid sequences and amino acid sequences presented herein represent, respectively, apparent nucleic acid sequences of nucleic acid molecules of the present invention and apparent amino acid sequences of PB2-N, PB2-C, PB2, NS, PB1-N, PB1-C, PB1, PA-C, PA-N, PA, and NA proteins of the present invention.

Another embodiment of the present invention is an antibody that selectively binds to an wild-type virus PB2-N, PB2-C, PB2, NS, PB1-N, PB1-C, PB1, PA-C, PA-N, PA and NA protein of the present invention. Another embodiment of the present invention is an antibody that selectively binds to a cold-adapted virus PB2-N, PB2-C, PB2, NS, PB1-N, PB1-C, PB1, PA-C, PA-N, PA and NA protein of the present invention. Preferred antibodies selectively bind to SEQ ID NO:6, SEQ ID NO:9, SEQ ID NO:14, SEQ ID NO:22, SEQ ID NO:25, SEQ ID NO:28, SEQ ID NO:33, SEQ ID NO:37, SEQ ID NO:40, SEQ ID NO:43, SEQ ID NO:46, SEQ ID NO:49, SEQ ID NO:54, SEQ ID NO:62, SEQ ID NO:64, SEQ ID NO:67, SEQ ID NO:69, SEQ ID NO:72, SEQ ID NO:77, SEQ ID NO:85, SEQ ID NO:88, SEQ ID NO:96, SEQ ID NO:99, SEQ ID NO:101 and SEQ ID NO:103.

The following examples are provided for the purposes of illustration and are not intended to limit the scope of the present invention.

EXAMPLE 1

This example describes the cloning and sequencing of equine influenza PB2 protein (RNA-directed RNA polymerase) nucleic acid molecules corresponding to the N-terminal portion of the protein, for wild type or cold-adapted equine influenza viruses.

A. Nucleic acid molecules encoding wild type or cold-adapted equine influenza virus PB2-N proteins were produced as follows. A PCR product containing a N-terminal portion of the equine PB2 gene was produced by PCR amplification from equine influenza virus DNA, and primers w570 and w571, designated SEQ ID NO:3 and SEQ ID NO:4, respectively. A nucleic acid molecule of 1241 nucleotides encoding a wild type PB2-N protein, denoted $nei_{wt}PB2\text{-}N_{1241}$, with a coding strand having a nucleic acid sequence designated SEQ ID No:5 was produced by further PCR amplification using the above described PCR product as a template and cloned into pCR 2.1 ®TA cloning vector, available from Invitrogen, Carlsbad, Calif., using standard procedures recommended by the manufacturer. The primers used were the T7 primer, designated by SEQ ID NO:2 and the REV primer, designated by SEQ ID NO:1. Plasmid DNA was purified using a mini-prep method available from Qiagen, Valencia, Calif. PCR products were prepared for sequencing using a PRISM™ Dye Terminator Cycle Sequencing Ready Reaction kit, a PRISM™ dRhodamine Terminator Cycle Sequencing Ready Reaction kit, or a PRISM™ BIGDYE™ Terminator Cycle Sequencing Ready Reaction kit, all available from PE Applied Biosystems, Foster City, Calif., following the manufacturer's protocoL Specific PCR conditions used with the kit were a rapid ramp to 95° C., hold for 10 seconds followed by a rapid ramp to 50° C. with a 5 second hold then a rapid ramp to 60° C. with a 4 minute hold, repeating for 25 cycles. T7 and REV primers were used in one reaction. PCR products were purified by ethanol/magnesium chloride precipitation. Automated sequencing of DNA samples was performed using an ABI PRISM™ Model 377 with XL upgrade DNA Sequencer, available from PE Applied Biosystems.

Translation of SEQ ID NO:5 indicates that nucleic acid molecule nei$_{wt}$PB2-N$_{1241}$ encodes a N-terminal portion of influenza PB2 protein of about 404 amino acids, referred to herein as P$_{wt}$PB2-N$_{404}$, having amino acid sequence SEQ ID NO:6, assuming an open reading frame in which the initiation codon spans from nucleotide 28 though nucleotide 30 of SEQ ID NO:5, and the last codon spans from nucleotide 1237 through nucleotide 1239. The region encoding P$_{wt}$PB2-N$_{404}$, designated nei$_{wt}$PB2-N$_{1214}$, and having a coding strand comprising nucleotides 28 to 1239 of SEQ ID NO:5 is represented by SEQ ID NO:7.

B. A nucleic acid molecule of 1239 nucleotides encoding a N-terminal portion of influenza PB2 cold-adapted equine influenza virus PB2-N protein, denoted nei$_{cal}$PB2-N$_{1241}$, with a coding strand having a sequence designated SEQ ID NO:8 was produced, and sequenced as described in part A.

Translation of SEQ ID NO:8 indicates that nucleic acid molecule nei$_{cal}$PB2-N$_{1241}$ encodes a terminal portion of equine influenza PB-2 protein of about 404 amino acids, referred to herein as P$_{cal}$PB2-N404, having amino acid sequence SEQ ID NO:9, assuming an open reading frame in which the initiation codon spans from nucleotide 28 though nucleotide 30 of SEQ ID NO:8 and the last codon spans from nucleotide 1237 though nucleotide 1239. The region encoding P$_{cal}$PB2-N$_{404}$, designated nei$_{cal}$PB2-N$_{1214}$, and having a coding strand comprising nucleotides 28 to 1239 of SEQ ID NO:8, is represented by SEQ ID NO:10.

PCR amplification of a second nucleic acid molecule encoding a cold-adapted equine influenza PB2-N protein in the same manner resulted in molecules nei$_{ca2}$PB2-N$_{1241}$, identical to nei$_{ca1}$PB2-N$_{1241}$, and nei$_{ca2}$PB2-N$_{1214}$, identical to nei$_{ca1}$PB2-N$_{1214}$.

C. Comparison of the nucleic acid sequences of the coding strands of nei$_{wt}$PB2-N$_{1241}$ (SEQ ID NO:5) and nei$_{cal}$PB2-N$_{1241}$ (SEQ ID NO:8) by DNA alignment reveals the following difference: a T to C base shift at base 370. Comparison of the amino acid sequences of proteins P$_{wt}$PB2-N$_{404}$ (SEQ ID NO:6) and P$_{cal}$PB2-N$_{404}$ (SEQ ID NO:9) reveals the following difference: a Y to H shift at amino acid 124 relating to the a T to C shift at base 370 in the DNA sequence.

EXAMPLE 2

This example describes the cloning and sequencing of equine influenza PB2 protein (RNA-directed RNA polymerase) nucleic acid molecules corresponding to the C-terminal portion of the protein, for wild type or cold-adapted equine influenza viruses.

A. Nucleic acid molecules encoding wild type or cold-adapted equine influenza virus PB2-C proteins were produced as follows. A PCR product containing the C-terminal portion of the equine PB2 gene was produced by PCR amplification using from equine influenza virus DNA and primers w572 and w573, designated SEQ ID NO:11 and SEQ ID NO:12, respectively. A nucleic acid molecule of 1233 nucleotides encoding a wild type PB2-C protein, denoted nei$_{wt}$ PB2-C$_{1233}$, with a coding strand having a nucleic acid sequence designated SEQ ID NO:13 was produced by further PCR amplification using the above-described PCR product as a template and cloned as described in Example 1B. Plasmid DNA was purified and sequenced as in Example 1A, except that different primers were used in the sequencing kits. T7 and REV were used in one instance; efPB2-al, designated SEQ ID NO:15 and efPB2-s1, designated SEQ ID NO:16 were used in another instance, and efPB2-a2, designated SEQ ID NO:17 and efPB2-s2, designated SEQ ID NO:18 were used in another instance.

Translation of SEQ ID NO:13 indicates that nucleic acid molecule nei$_{wt}$PB2-C$_{1233}$ encodes a C-terminal portion of influenza PB2 protein of about 398 amino acids, referred to herein as P$_{wt}$PB2-C$_{398}$, having amino acid sequence SEQ ID NO:14, assuming an open reading frame having a first codon spans from nucleotide 3 through nucleotide 5 and a termination codon which spans from nucleotide 1197 through nucleotide 1199 of SEQ ID NO:13. Because SEQ ID NO:13 is only a partial gene sequence, it does not contain an initiation codon. The region encoding P$_{wt}$PB2-C$_{398}$, designated nei$_{wt}$ PB2-C$_{1194}$, and having a coding strand comprising nucleotides 3 to 1196 of SEQ ID NO:-13 is represented by SEQ ID NO:19.

PCR amplification of a second nucleic acid molecule encoding a wild type equine influenza PB2-N protein in the same manner resulted in a nucleic acid molecule of 1232 nucleotides denoted nei$_{wt2}$PB2-C$_{1232}$, with a coding strand with a sequence designated SEQ ID NO:20. nei$_{wt2}$PB2-C$_{1232}$ is identical to nei$_{wt1}$PB2-C$_{1233}$, expect that nei$_{wt2}$PB2-C$_{1232}$ lacks one nucleotide on the 5'-end. Translation of SEQ ID NO:-20 indicates that nucleic acid molecule nei$_{wt2}$PB2-C$_{1232}$ also encodes P$_{wt}$PB2-C398 (SEQ ID NO:14), assuming an open reading frame having a first codon which spans from nucleotide 2 through nucleotide 4 and a termination codon spans from nucleotide 1196 through nucleotide 1198 of SEQ ID NO:20. Because SEQ ID NO:20 is only a partial gene sequence, it does not contain an initiation codon. The nucleic acid molecule having a coding strand comprising nucleotides 2 to 1195 of SEQ ID NO:20, denoted nei$_{wt2}$PB2-C$_{1194}$, is identical to SEQ ID NO:19.

B. A nucleic acid molecule of 1232 nucleotides encoding a C-terminal portion of influenza PB2 cold-adapted equine influenza virus protein, denoted nei$_{cal}$PB2-C$_{1232}$, and having a coding strand having a sequence designated SEQ ID NO:21 was produced as described in part A, except that the pCR®-Blunt cloning vector was used.

Translation of SEQ ID NO:21 indicates that nucleic acid molecule nei$_{cal}$PB2-C$_{1232}$ encodes a C-terminal portion of equine influenza PB-2 protein of about 398 amino acids, referred to herein as P$_{cal}$PB2-C$_{398}$, having amino acid sequence SEQ ID NO:22, assuming an open reading frame having a first codon which spans from nucleotide 2 through nucleotide 4 and a termination codon spans from nucleotide 1196 through nucleotide 1198 of SEQ ID NO:21. Because SEQ ID NO:21 is only a partial gene sequence, it does not contain an initiation codon. The region encoding P$_{cal}$PB2-C$_{398}$, designated nei$_{cal}$PB2-C$_{1194}$, and having a coding strand comprising nucleotides 2 to 1195 of SEQ ID NO:21, is represented by SEQ ID NO:23.

PCR amplification of a second nucleic acid molecule encoding a cold-adapted equine influenza PB2-C protein in the same manner resulted in molecules nei$_{ca2}$PB2-C$_{1231}$, containing one less nucleotide at the 3' end than nei$_{ca1}$PB2-N$_{1241}$, and nei$_{ca2}$PB2-N$_{1214}$, identical to nei$_{ca1}$PB2-N$_{1214}$.

C. Comparison of the nucleic acid sequences of the coding strands of nei$_{wt1}$PB2-C$_{1233}$ (SEQ ID NO:13) and nei$_{cal}$PB2-C$_{1232}$ (SEQ ID NO:21) by DNA alignment reveals the following differences: an A to C base shift at base 153 of SEQ ID NO:13 and a G to A base shift at base 929 of SEQ ID NO:13. Comparison of the amino acid sequences of proteins $P_{wt}$PB2-$C_{398}$(SEQ ID NO:14) and $P_{cal}$PB2-$_{398}$ (SEQ ID NO:22) reveals the following difference: a K to Q shift at amino acid 51 when relating to the an A to C base shift at base 153 in the DNA sequences. There is no amino acid shift resulting from the G to A base shift at base 929.

EXAMPLE 3

This example describes the cloning and sequencing of equine influenza PB2 protein (RNA-directed RNA polymerase) nucleic acid molecules for wild type or cold-adapted equine influenza viruses.

A. Nucleic acid molecules encoding wild type or cold-adapted equine influenza virus PB2 proteins were produced as follows. The wild type or cold-adapted equine influenza genes were cloned in two fragments, the N-terminal portion was produced as in Example 1 and the C-terminal portion of the gene was produced as in Example 2. The DNA sequence for the wild type equine influenza PB2 gene was generated by combining the consensus sequences for the wild type PB2-N protein , denoted $nei_{wt}$PB2-$N_{1241}$ (SEQ ID NO:5) with the gene fragments for the wild type PB2-C protein, denoted $nei_{wt1}$PB2-$C_{1233}$ (SEQ ID NO:13) and $nei_{wt2}$PB2-C $_{1232}$ (SEQ ID NO:-2a20). The result of combining the consensus sequences from the N-terminal and C-terminal portions of the PB2 wild type influenza virus yielded a complete DNA sequence denoted $nei_{wt}PB2_{2341}$ (SEQ ID NO:24). Translation of SEQ ID NO:24 indicates tat the nucleic acid molecule $nei_{wt}PB2_{2341}$ encodes a full length equine influenza PB2 protein of about 759 amino acids referred to herein as $Pei_{wt}$ $PB2_{759}$, having amino acid sequence SEQ ID NO:25 assuming an open reading frame in which the initiation codon spans from nucleotide 28 through nucleotide 30 of SEQ ID NO: 24 and the termination codon spans from nucleotide 2305 through nucleotide 2307 of SEQ ID NO:24. The region encoding $Pei_{wt}PB2_{759}$. designated $nei_{wt}PB2_{2277}$, and having a coding strand comprising nucleotides 28 to 2304 of SEQ ID NO:24, is SEQ ID NO:26.

B. A DNA sequence of 2341 nucleotides encoding a cold-adapted equine influenza virus PB2 , denoted $nei_{cal}PB2_{2341}$, with a sequence denoted SEQ ID NO:27 was produced by combining the sequences for the N-terminal and C-terminal portions of the PB2 cold-adapted equine influenza gene. The clones for the N-terminal sequences are denoted $nei_{cal}$PB2-$N_{1241}$ and $nei_{ca2}$PB2-$N_{1241}$ which are identical and are represented by SEQ ID NO:8. The clones for the C-terminal sequences are denoted $nei_{cal}$PB2-$C_{1231}$ and $nei_{ca}$2PB2-$C_{1231}$, represented by SEQ ID NO:21.

Translation of SEQ ID NO:27 indicates that nucleic acid molecule $nei_{cal}PB2_{2341}$ encodes a full-length equine influenza PB2 protein of about 759 amino acids, referred to herein as $Pei_{cal}PB2_{759}$, having amino acid sequence SEQ ID NO:28 assuming an open reading frame in which the initiation codon spans from nucleotide 28 through nucleotide 30 of SEQ ID NO:27 and the termination codon spans from nucleotide 2305 through nucleotide 2307 of SEQ ID NO:27. The region encoding $Pei_{cal}PB2_{759}$ designated $nei_{cal}PB2_{2277}$ and having a coding strand comprising nucleotides 28 to 2304 of SEQ ID NO:29.

C. Comparison of the nucleic acid sequences of the coding strands of $nei_{wt}$ (SEQ ID NO:24) and $nei_{cal}PB2_{2341}$(SEQ ID NO:25) by DNA alignment reveals the following differences: a T to C base shift at base 370, a A to C base shift at base 1261. and a C to A base shift at base 2037. Comparison of the amino acid sequences of proteins $Pei_{wt}PB2_{759}$ (SEQ ID NO:25) and $Pei_{cal}PB2_{759}$ (SEQ ID NO:28) reveals the following differences: a Y to H shift at amino acid 124 relating to the a T to C shift at base 370 in the DNA sequence, a K to Q shift at amino acid 421 relating to the A to C shift at base 1261 in the DNA sequence. The third nucleotide shift at base 2037 does not result in an amino acid shift.

EXAMPLE 4

This example describes the cloning and sequencing of equine influenza NS (nonstructural) protein nucleic acid molecules for wild type or cold-adapted equine influenza viruses.

A. Nucleic acid molecules encoding wild type or cold-adapted equine influenza virus NS proteins were produced as follows. A PCR product containing an equine NS gene was produced by PCR amplification from equine influenza virus DNA and primers w586 and w587, designated SEQ ID NO:30 and SEQ ID NO:31 respectively. A nucleic acid molecule of 891 nucleotides encoding a wild-type NS protein, denoted $nei_{wt}NS_{891}$, with a coding strand having a nucleic acid sequence designated SEQ ID NO:32 was produced by further PCR amplification using the above-described PCR product as a template and cloned into pCR 2.1 ®TA cloning vector as described in Example 1A. Plasmid DNA was purified and sequenced as in Example 1A, except that primers used in the sequencing kits were only T7 and REV.

Translation of SEQ ID NO:32 indicates that nucleic acid molecule $nei_{wt1}$NS891 encodes a full-length equine influenza NS protein of about 230 amino acids, referred to herein as $Pei_{wt1}NS_{230}$, having amino acid sequence SEQ ID NO:33, assuming an open reading frame in which the initiation codon spans from nucleotide 27 through nucleotide 29 of SEQ ID NO:32 and the termination codon spans from nueleotide 717 through nucleotide 719 of SEQ ID NO:32. The region encoding $Pei_{wt1}NS_{230}$, designated $nei_{wt1}NS_{690}$, and having a coding strand comprising nucleotides 27 to 716 of SEQ ID NO:32 is represented by SEQ ID NO:34.

PCR amplification of a second nucleic acid molecule encoding a wild type equine influenza NS protein in the same manner resulted in molecules $nei_{wt2}NS_{891}$, identical to $nei_{wt1}NS_{891}$ in the coding region; i.e. $nei_{wt2}NS_{690}$, is identical to $nei_{wt1}NS_{690}$. $nei_{wt2}NS_{891}$ differs from $nei_{wt1}NS_{891}$in one nucleotide at base 827 (G to A) which is 111 bases downstream from the stop codon. PCR amplification of a third nucleic acid encoding a wild type equine influenza NS protein in the same manner resulted in a nuckic acid molecule of 888 nucleotides denoted $nei_{wt3}NS_{888}$, with a coding strand with a nucleic acid sequence designated SEQ ID NO:35. $nei_{wt3}NS_{888}$ is identical to $nei_{wt1}NS_{891}$, except that $nei_{wt3}NS_{888}$, lacks two nucleotides on the 5' end and one nucleotide on the 3' end. Translation of SEQ ID NO:35 indicates that nuckic acid molecule $nei_{wt3}NS_{888}$ also encodes $Pei_{wt1}NS_{230}$(SEQ ID NO:33), assuming an open reading frame having an initiation codon which spans from nucleotide 25 through nucleotide 27 of SEQ ID NO:35 and a termination codon which spans from nucleotide 715 through nucleotide 717 of SEQ ID NO:35. The nucleic acid molecule having a coding strand comprising nucleotides 25 to 714 of SEQ ID 35, denoted $nei_{wt3}NS_{690}$, is identical to SEQ ID NO:34.

PCR amplification of a fourth nucleic acid of 468 nucleotides encoding a C-terminal portion of the wild type equine influenza NS protein, denoted $nei_{wt4}NS_{468}$ and having a coding sequence designated SEQ ID NO:36 was produced. Translation of SEQ ID NO:36 indicates that nucleic acid molecule $nei_{wt4}NS_{468}$ encodes a C-terminal portion of equine influenza NS protein of about 97 amino acids, referred to herein as $Pei_{wt4}NS_{97}$, having amino acid sequence SEQ ID NO:37, assuming an open reading frame having a first codon which spans from nucleotide 3 to 5 of SEQ ID NO:36 and a termination codon spans from nucleotide 294 through 296 of SEQ ID NO:36. Because SEQ ID NO:36 is only a partial gene sequence, it does not contain an initiation codon. The region encoding $Pei_{wt4}NS_{97}$, designated $nei_{wt4}NS_{293}$, and having a coding strand comprising nucleotides 1 to 293 of SEQ ID NO:36 is represented by SEQ ID NO:38.

B. A nucleic acid molecule of 888 nucleotides encoding a cold-adapted equine influenza vims NS protein, denoted $nei_{cal} NS_{888}$ with a coding strand having a sequence designated SEQ ID NO:39 was produced and sequenced as described in part A.

Translation of SEQ ID NO:39 indicates that nucleic acid molecule $nei_{cal}NS_{888}$ encodes a full-length equine influenza NS protein of about 230 amino acids, referred to herein as $Pei_{cal}NS_{230}$, having amino acid sequence SEQ ID NO:40, assuming an open reading frame in which the initiation codon spans from nucleotide 27 through nucleotide 29 of SEQ ID NO:39 and the termination codon spans from nucleotide 717 through nucleotide 719 of SEQ ID NO:39. The region encoding $Pei_{cal}NS_{230}$, designated $nei_{cal}NS_{690}$, and having a coding strand comprising nucleotides 27 to 716 of SEQ ID NO:39, is represented by SEQ ID NO:41.

PCR amplification of a second nucleic acid molecule encoding a cold-adapted equine influenza NS protein in the same manner resulted in molecules $nei_{ca2}NS_{887}$, containing one less nucleotide at the 3' end than $nei_{ca1}NS_{888}$, the coding region $nei_{ca2}NS_{690}$ is identical to $nei_{ca1}NS_{690}$.

C. Comparison of the nucleic acid sequences of the coding strands of $nei_{wt}NS_{891}$ (SEQ ID NO:32) and $nei_{cal}NS_{888}$ (SEQ ID NO:39) by DNA alignment reveals the following difference: a A to G shift at base 827 which is 111 bases downstream from the stop codon. The 3' fragment encoding $nei_{wt4}NS_{468}$ (SEQ ID NO:36) has one shift T to C found at base 633 relative to the full-length consensus sequence. Comparison of the amino acid sequences of proteins $Pei_{wt}NS_{230}$ (SEQ ID NO:33) and $Pei_{cal}NS_{230}$(SEQ ID NO:40) reveals that there are no differences between amino acid sequences of the wild type and cold-adapted proteins.

EXAMPLE 5

This example describes the cloning and sequencing of equine influenza PB1 protein (RNA-directed RNA polymerase 1) nucleic acid molecules corresponding to the N-terminal portion of the protein, for wild type or cold-adapted equine influenza viruses.

A. Nucleic acid molecules encoding wild type or cold-adapted equine influenza virus PB1-N proteins were produced as follows. A PCR product containing a N-terminal portion of the equine PB1 gene was produced by PCR amplification from equine influenza virus DNA, and primers T7 and REV. A nuckic acid molecule of 1229 nucleotides encoding a wild type PB1-N protein, denoted $nei_{wt1}PB1-N_{1229}$, with a coding strand having a nucleic acid sequence designated SEQ ID NO:24 was produced by further PCR amplification using the above described PCR product as a template and cloned as described in Example 1B. Plasmid DNA was purified and sequenced as in Example 1B, except that only T7 and REV primers were used in the sequencing kits. Translation of SEQ ID NO:42 indicates that nucleic acid molecule $nei_{wt1}PB1-N_{1229}$ encodes a N-terminal portion of influenza PB1 protein of about 398 amino acids, referred to herein as $Pei_{wt1}PB1-N_{398}$, having amino acid sequence SEQ ID NO:43, assuming an open reading frame in which the initiation codon spans from nucleotide 36 through nucleotide 38 of SEQ ID NO: 42, and the last codon spans from nucleotide 1227 though nucleotide 1229 of SEQ ID NO:42. The region encoding $Pei_{wt1}PB1-N_{398}$, designated $nei_{wt1}PB1-N1194$, and having a coding strand comprising nucleotides 36 to 1229 of SEQ ID NO:42is represented by SEQ ID NO:44.

PCR amplification of a second nucleic acid molecule encoding a wild type equine influenza PB1-N protein in the same manner resulted in a nucleic acid molecule of 673 nucleotides denoted $nei_{wt2}PB1-N_{673}$, with a coding strand with a sequence designated SEQ ID NO:45. Translation of SEQ ID NO:45 indicates that nucleic acid molecule $nei_{wt2}PB1-N_{673}$ encodes $Pei_{wt2}PB1-N_{212}$ (SEQ ID NO:46), assuming an open reading frame having an initiation codon which spans from nucleotide 36 through nucleotide 38 of SEQ ID NO:45 and a last codon which spans from nucleotide 671 through nucleotide 673 of SEQ ID NO: 45. Because SEQ ID NO:45 is only a partial gene sequence, it does not contain a stop codon. The nucleic acid molecule having a coding strand comprising nucleotides 36 to 671 of SEQ ID NO:45, denoted $nei_{wt2}PB1-N_{636}$, is designated SEQ ID NO:47.

B. A nucleic acid molecule of 1225 nucleotides encoding a N-terminal portion of influenza PB1 cold-adapted equine influenza virus PB1-N protein, denoted $nei_{cal}PB1-N_{1225}$, with a coding strand having a sequence designated SEQ ID NO:48 was produced, and sequenced as described in part A.

Translation of SEQ ID NO:48 indicates that nucleic acid molecule $nei_{cal}PB1-N_{1225}$ encodes a N-terminal portion of equine influenza PB-1 protein of about 395 amino acids, referred to herein as $Pei_{cal}PB1-N_{395}$, having amino acid sequence SEQ ID NO:49, assuming an open reading frame in which the initiation codon spans from nucleotide 34 through nucleotide 36 of SEQ ID NO:48, and a last codon which spans from nucleotide 1216 though nucleotide 1218 of SEQ ID NO:48. The region encoding $Pei_{cal}PB1-N_{395}$, designated $nei_{cal} PB1-N_{1185}$, and having a coding strand comprising nucleotides 34 to 1218 of SEQ ID NO:41, is represented by SEQ ID NO:50.

PCR amplification of a second nucleic acid molecule encoding a cold-adapted equine influenza PB1-N protein in the same manner resulted in molecules $nei_{ca2}PB1-N_{1221}$, designated SEQ ID NO:51, containing four less nucleotides at the 5' end than $nei_{cal}PB1-N_{1225}$; the coding region $nei_{ca2}PB1-N1185$, is identical to $nei_{cal}PB1-N_{1185}$.

C. Comparison of the nucleic acid sequences of the coding strands of $nei_{wt}PB1-N_{1229}$ (SEQ ID NO:42) and $nei_{cal}PB1-N_{1225}$ (SEQ ID NO:48) by DNA alignment reveals no differences in the coding regions. Comparison of the amino acid sequences of proteins $Pei_{wt}PB1-N_{395}$ (SEQ ID NO:43) and $Pei_{cal}PB1-N_{395}$ (SEQ ID NO:49) also reveals no differences.

EXAMPLE 6

This example describes the cloning and sequencing of equine influenza PB1 protein (RNA-directed RNA polymerase1) nucleic acid molecules corresponding to the C-terminal portion of the protein, for wild type or cold-adapted equine influenza viruses.

A. Nucleic acid molecules encoding wild type or cold-adapted equine influenza virus PB1-C proteins were produced as follows. A PCR product containing an C-terminal portion of the equine PB1 gene was produced by PCR amplification from equine influenza virus DNA, and primer w569 designated SEQ ID NO:52. A nucleic acid molecule of 1234 nucleotides encoding a wild type PB1-C protein, denoted $nei_{wt1}PB1-C_{1234}$, with a coding strand having a nucleic acid sequence designated SEQ ID NO:53 was produced by further PCR amplification using the above described PCR product as a template and cloned as described in Example 1B. Plasmid DNA was purified and sequenced as in Example 1A, except that different primers were used in the sequencing kits. T7, REV, w569, efPB1-a1, designated SEQ ID NO:55 efPB1-a2, designated SEQ ID NO:56, efPB1-s1, designated SEQ ID NO: 57, efPB1-s2, designated SEQ ID NO:58, and efPB1-s3, designated SEQ ID NO:59 were used in one instance, T7, REV, efPB1-a1, efPB1-a2, efPB1-s1, efPB1-s2, and efPB1-s3 were used in another instance and T7 and REV were used in another instance. Translation of SEQ ID NO:53 indicates that nucleic acid molecule $nei_{wt1}PB1234$ encodes an C-terminal portion of influenza PB1 protein of about 396 amino acids, referred to herein as $Pei_{wt1}PB1\text{-}C_{396}$, having amino acid sequence SEQ ID NO:54, assuming an open reading frame in which the first codon spans from nucleotide 1 through nucleotide 3 of SEQ ID NO:53 and a termination codon which spans from nucleotide 1189 through nucleotide 1191 of SEQ ID NO:53. Because SEQ ID NO:53 is only a partial gene sequence, it does not contain an initiation codon. The region encoding $Pei_{wt1}PB1\text{-}C_{396}$, designated $nei_{wt1}PB1\text{-}C_{1188}$, and having a coding strand comprising nucleotides 1 to 1188 of SEQ ID NO:53 is represented by SEQ ID NO:60.

PCR amplification of a second nucleic acid molecule encoding a wild type equine influenza PB1-C protein in the same manner resulted in a nucleic acid molecule of 1240 nueleotides denoted $nei_{wt2}PB1\text{-}C_{1240}$, with a coding strand with a sequence designated SEQ ID NO:61. Translation of SEQ ID NO:61 indicates that nucleic acid molecule $nei_{wt2}PB1\text{-}N_{1240}$ encodes a molecule designated $Pei_{wt2}PB1\text{-}C_{396}$ (SEQ ID NO: 62) which differs from $Pei_{wt1}PB1\text{-}C_{396}$ (SEQ ID NO:54) in one nucleotide. Nueleotide 382 of $nei_{wt1}PB1\text{-}C_{1234}$, i.e. nucleotide 382 of $nei_{wt1}PB1\text{-}C_{1188}$ was A, while nucleotide 389 of $nei_{wt2}$PB1-C1240, i.e. nucleotide 382 of $nei_{wt2}PB1\text{-}C_{1188}$ was T. Translation of $nei_{wt2}$PB1-C1240 results in an amino acid change of T to S.

B. A nucleic acid molecule of 1241 nucleotides encoding an C-terminal portion of influenza PB1 cold-adapted equine influenza virus PB1-C protein, denoted $nei_{ca1}PB1\text{-}C_{1241}$, with a coding strand having a sequence designated SEQ ID NO:63 was produced, and sequenced as described in part A.

Translation of SEQ ID NO:63 indicates that nucleic acid molecule $nei_{ca1}PB1\text{-}C_{1241}$ encodes an C-terminal portion of equine influenza PB-1 protein of about 396 amino acids, referred to herein as $Pei_{ca1}PB1\text{-}C_{396}$, having amino acid sequence SEQ ID NO:64, assuming an open reading frame in which the first codon spans from nucleotide 8 through nucleotide 10 of SEQ ID NO:63 and a termination codon that spans from nucleotide 1196 through nueleotide 1198 of SEQ ID NO:63. Because SEQ ID NO:63 is only a partial gene sequence, it does not contain an initiation codon. The region encoding $Pei_{ca1}PB1\text{-}C_{396}$, designated $nei_{ca1}PB1\text{-}C_{1188}$, and having a coding strand comprising nucleotides 8 to 1195 of SEQ ID NO:63, is represented by SEQ ID NO:65.

PCR amplification of a second nucleic acid molecule encoding a cold-adapted equine influenza PB1-C protein in the same manner resulted in a nucleic acid molecule of 1241 nucleotides denoted $nei_{ca2}PB1\text{-}C_{1241}$, with a coding strand with a sequence designated SEQ ID NO:66. Translation of SEQ ID NO:66 indicates that nucleic acid molecule $nei_{ca2}PB$ $1\text{-}C_{1241}$ encodes a molecule designated $Pei_{ca2}PB1\text{-}C_{396}$ (SEQ ID NO:67) which differs from $Pei_{ca1}PB1\text{-}C_{396}$ (SEQ ID NO:64) in one nucleotide. Nucleotide 1044 of $nei_{ca1}PB1\text{-}C_{1241}$, i.e. nucleotide 1037 of $nei_{ca1}PB1N_{1188}$ was A, while nucleotide 1044 of $nei_{ca2}PB1\text{-}C_{1241}$, i.e. nueleotide 1037 of $nei_{ca1}PB1\text{-}C_{1188}$ was G. Translation of $nei_{ca2}PB1\text{-}C_{1241}$ results in an amino acid change of R to K.

C. Comparison of the nucleic acid sequences of the coding strands of $nei_{wt1}PB1\text{-}C_{1234}$ (SEQ ID NO:53) and $nei_{ca1}PB1\text{-}C_{1241}$ (SEQ ID NO:63) by DNA alignment reveals the following differences: a C to T shift at base 600 of SEQ ID NO:53, and a T to A shift at base 603 of SEQ ID NO:53. Comparison of the amino acid sequences of proteins $Pei_{wt1}PB1\text{-}C_{396}$ (SEQ ID NO:54) and $Pei_{ca1}PB1\text{-}N_{396}$ (SEQ ID NO :64) reveals the following difference: a H to Q amino acid shift 203 when relating to the T to A base shift at base 603 in the DNA sequences. There is no amino acid shift resulting from the C to T base shift at base 600.

EXAMPLE 7

This example describes the cloning and sequencing of equine influenza PB1 protein (RNA-directed RNA polymerase) nucleic acid molecules for wild type or cold-adapted equine influenza viruses.

A. Nucleic acid molecules encoding wild type or cold-adapted equine influenza virus PB1 proteins were produced as follows. The wild type or cold-adapted equine influenza genes were cloned in two fragments, the N-terminal portion was produced as in Example 5 and the C-terminal portion of the gene was produced as in Example 6.

The DNA sequence for the wild type equine influenza PB1 gene was generated by combining the sequences for the wild type PB1-N protein, $nei_{wt1}PB1\text{-}N_{1229}$ (SEQ ID NO:42) and $nei_{wt2}PB1\text{-}N_{673}$ (SEQ ID NO: 45) with the gene fragments for the wild type PB1-C protein, denoted $nei_{wt1}PB1\text{-}C_{1234}$ (SEQ ID NO:53) and $nei_{wt2}PB1\text{-}C_{1240}$ (SEQ ID NO:-61). The result of combining the N-terminal and C-terminal portions of the PB1 wild type influenza virus yielded a complete DNA sequence of 2341 nucleotides denoted $nei_{wt1}PB1_{2341}$(SEQ ID NO:68). Translation of SEQ ID NO:68 indicates that the nucleic acid molecule $nei_{wt}PB2_{2341}$ encodes a full length equine influenza PB1 protein of about 757 amino acids referred to herein as $Pei_{wt1}PB1_{757}$, having amino acid sequence SEQ ID NO:69, assuming an open reading frame in which the initiation codon spans from nucleotide 25 though nueleotide 27of SEQ ID NO:68 and the termination codon spans from nucleotide 2293 through nucleotide 2295 of SEQ ID NO:68. The region encoding $Pei_{wt}PB1_{757}$ designated $nei_{wt}PB1_{2271}$, and having a coding strand comprising nucleotides 25 to 2292 of SEQ ID NO:68, is SEQ ID NO:70.

B. A DNA sequence of 2341 nucleotides encoding a cold-adapted equine influenza virus PB1, denoted $nei_{ca1}PB1_{2341}$, with a sequence denoted SEQ ID NO:71 was produced by combining the sequences for the N-terminal and C-terminal portions of the PB1 cold-adapted equine influenza gene. The clones for the N-terminal sequences are denoted $nei_{ca1}PB1\text{-}N_{1225}$ (SEQ ID NO:48) and $nei_{ca2}PB1_{1241}$ (SEQ ID NO:63). The clones for the C-tenninal sequences are denoted $nei_{ca1}PB1\text{-}C_{1241}$ (SEQ ID NO:63) and $nei_{ca2}$PB1-C1241, (SEQ ID NO:66).

Translation of SEQ ID NO:71 indicates that nucleic acid molecule $nei_{ca1}PB1_{2341}$ encodes a full-length equine influenza PB1 protein of about 757 amino acids, referred to herein as $Pei_{ca1}PB1_{757}$, having amino acid sequence SEQ ID NO:72, assuming an open reading frame in which the initiation codon spans from nucleotide 25 through nucleotide 27 SEQ ID NO:71 and the termination codon spans from nucleotide 2296 though nucleotide 2298 of SEQ ID NO:71. The region encoding $Pei_{ca1}PB1_{757}$ designated $nei_{ca1}PB_{2271}$ and having a coding strand comprising nucleotides 25 to 2295 of SEQ ID NO:73.

C. Comparison of the nucleic acid sequences of the coding strands of $nei_{wt}PB1_{2341}$ (SEQ ID NO:68) and $nei_{ca1}PB1_{2341}$ (SEQ ID NO:71) by DNA alignment reveals the following differences: a C to T base shift at base 1683, and a T to A base shift at base 1686. Comparison of the amino acid sequences of proteins $Pei_{wt}PB1_{757}$ (SEQ ID NO:69) and $Pei_{cal}PB1_{757}$ (SEQ ID NO:72) reveals the following differences: no shift in base C at amino acid 561 relating to the C to T shift at base 1683 , and a H to Q shift at amino acid 562 relating to the a T to A shift at base 1683 in the DNA sequence.

EXAMPLE 8

This example describes the cloning and sequencing of equine influenza PA protein (RNA polymerase A) nucleic acid molecules corresponding to the C-terminal portion of the protein, for wild type or cold-adapted equine influenza viruses.

A. Nucleic acid molecules encoding wild type or cold-adapted equine influenza virus PA-C proteins were produced as follows. A PCR product containing the C-terminal portion of the equine PA gene was produced by PCR amplification using equine influenza virus DNA and primers C+PA and C-PA, designated SEQ ID NO:74 and SEQ ID NO:75 respectively. A nucleic acid molecule of 1228 nucleotides encoding a wild type PA-C protein, denoted $nei_{wt1}PA\text{-}C_{1228}$, with a coding strand having a nucleic acid sequence designated SEQ ID NO:76 was produced by further PCR amplification using the above-described PCR product as a template and cloned as described in Example 1B. Plasmid DNA was purified and sequenced as in Example 1A, except that different primers were used in the sequencing kits. T7 and REV were used in one instance; PAC-1, designated SEQ ID NO:78, PAC-2, designated SEQ ID NO:79, PAC-3, designated SEQ ID NO:80, PAC-4, designated SEQ ID NO:81, T7 and REV were used in another instance; and PAC-1, PAC-2, T7 and REV were used in another instance.

Translation of SEQ ID NO:76 indicates that nucleic acid molecule $nei_{wt1}PA\text{-}C_{1228}$ encodes a C-terminal portion of influenza PA protein of about 388 amino acids, referred to herein as $Pei_{wt1}PA\text{-}C_{388}$, having amino acid sequence SEQ ID NO:77, assuming an open reading frame having a first codon spans from nucleotide 3 through nucleotide 5 of SEQ ID NO:76 and a termination codon which spans from nucleotide 1167 through nucleotide 1169 of SEQ ID NO:76. Because SEQ ID NO:76 is only a partial gene sequence, it does not contain an initiation codon. The region encoding $Pei_{wt1}PA\text{-}C_{388}$, designated $nei_{wt1}PA\text{-}C_{1164}$, and having a coding strand comprising nucleotides 3 to 1166 of SEQ ID NO:76 is represented by SEQ ID NO:82.

PCR amplification of a second nucleic acid molecule encoding a wild type equine influenza PA-C protein in the same manner resulted in a nucleic acid molecule of 1223 nucleotides denoted $nei_{wt2}PA\text{-}C_{1223}$, with a coding strand with a sequence designated SEQ ID NO:83. $nei_{wt2}PA\text{-}C_{1223}$ is identical to $nei_{wt2}PA\text{-}C_{1228}$, with the exception of a T to C base shift at base 753 and that $nei_{wt2}PA\text{-}C_{1223}$ lacks five nucleotides on the 3' end. Translation of SEQ ID NO:83 indicates that nucleic acid molecule $nei_{wt2}PA\text{-}C_{1223}$ also encodes $Pei_{wt1}PA\text{-}C_{388}$(SEQ ID NO:77), assuming an open reading frame having a first codon which spans from nucleotide 3 through nucleotide 5 of SEQ ID NO:83 and a termination codon which spans from nucleotide 1167 through nucleotide 1169 of SEQ ID NO:83. Because SEQ ID NO:83 is only a partial gene sequence, it does not contain an initiation codon. The nucleic acid molecule having a coding strand comprising nucleotides 3 to 1166 of SEQ ID NO:83, denoted $nei_{wt2}PA\text{-}C_{1223}$, is identical to SEQ ID NO:82.

B. A nucleic acid molecule of 1233 nucleotides encoding a C-terminal portion of influenza PA-C cold-adapted equine influenza virus protein, denoted $nei_{cal}PA\text{-}C_{1233}$, and having a coding strand having a sequence designated SEQ ID NO:84 was produced as described in part A, except that the pCR®-Blunt cloning vector was used.

Translation of SEQ ID NO:84 indicates that nucleic acid molecule $nei_{cal}PA\text{-}C_{1233}$ encodes a C-terminal portion of equine influenza PA protein of about 390 amino acids, referred to herein as $Pei_{cal}PA\text{-}C_{390}$, having amino acid sequence SEQ ID NO:85, assuming an open reading frame having a first codon which spans from nucleotide 3 through nucleotide 5 of SEQ ID NO:84 and a termination codon which spans from nucleotide 1173 through nucleotide 1175 of SEQ ID NO:84. Because SEQ ID NO:84 is only a partial gene sequence, it does not contain an initiation codon. The region encoding $Pei_{cal}PA\text{-}C_{390}$, designated $nei_{cal}PA\text{-}C_{1170}$, and having a coding strand comprising nueleotides 3 to 1172 of SEQ ID NO:84, is represented by SEQ ID NO:86.

PCR amplification of a second nucleic acid molecule encoding a cold-adapted equine influenza PA-C protein in the same manner resulted in molecule $nei_{ca2}PA\text{-}C_{1233}$, containing one A to G base shift at base 953 as compared to $nei_{cal}PA\text{-}C_{1233}$; this base shift does not result in an amino acid change so $Pei_{ca2}PA\text{-}C_{390}$, is identical to $Pei_{cal}PA\text{-}C_{390}$ (SEQ ID NO:85.)

C. Comparison of the nucleic acid sequences of the coding strands of $nei_{wt1}PA\text{-}C_{1228}$ (SEQ ID NO:76) and $nei_{cal}PA\text{-}C_{1233}$ (SEQ ID NO:84) by DNA alignment reveals the following difference: an C to T base shift at base 753 of SEQ ID NO:84. Comparison of the amino acid sequences of proteins $Pei_{wt1}PA\text{-}C_{388}$ (SEQ ID NO:77) and $Pei_{cal}PA\text{-}390$ (SEQ ID NO:85) reveals the following difference: a W to R shift at amino acid 251 when relating to the C to T base shift at base 753 in the DNA sequences.

EXAMPLE 9

This example describes the cloning and sequencing of equine influenza PA protein nucleic acid molecules corresponding to the N-terminal portion of the protein, for wild type or cold-adapted equine influenza viruses.

A nucleic acid molecule of 1216 nucleotides encoding a wild type PA-N protein, denoted $nei_{wt}PA\text{-}N_{1216}$, with a coding strand having a nucleic acid sequence designated SEQ ID NO:94.

Translation of SEQ ID NO:94 indicates that nucleic acid molecule $nei_{wt}PA\text{-}N_{1216}$ encodes a N-terminal portion of influenza PA protein of about 397 amino acids, referred to herein as $Pei_{wt}PA\text{-}N_{397}$, having amino acid sequence SEQ ID NO:96, assuming an open reading frame from the starting methionine (M) through glutamic acid (E) at amino acid 397. The region encoding $Pei_{wt}PA\text{-}N_{397}$ designated $nei_{wt}PA\text{-}N_{1193}$ and having a coding strand comprising nucleotides 24 to 1214 of SEQ ID NO:94, is herein designated SEQ ID NO:95.

B. A nucleic acid molecule of 1217 nucleotides encoding an N-terminal portion of influenza PA-N cold-adapted equine influenza virus protein, denoted $nei_{ca}PA\text{-}N_{1217}$, with a coding strand having a nucleic acid sequence designated SEQ ID NO:97.

Translation of SEQ ID NO:97 indicates that nucleic acid molecule $nei_{ca}PA\text{-}N_{1217}$ encodes a N-terminal portion of influenza PA protein of about 397 amino acids, referred to herein as $Pei_{ca}PA\text{-}N_{397}$, having amino acid sequence SEQ ID NO:99, assuming an open reading frame from the starting methionine (M) through glutamic acid (E) at amino acid 397. The region encoding $Pei_{ca}PA\text{-}N_{397}$, designated $nei_{ca}PA\text{-}N_{1193}$ and having a coding strand comprising nucleotides 25 to 1215 of SEQ ID NO:97, is designated herein as SEQ ID NO:98.

C. Comparison of the amino acid sequences of proteins $Pei_{wt}PA-N_{397}$ (SEQ ID NO:96) and $Pei_{ca}PA-N_{397}$ (SEQ ID NO:99) reveals the following differences: a glutamic acid (E) to lysine (K) at amino acid 59 and an alanine (A) to threonine (T) at amino acid 156.

EXAMPLE 10

This example describes the cloning and sequencing of equine influenza PA protein nucleic acid molecules, for wild type or cold-adapted equine influenza viruses.

A nucleic acid molecule of2148 nucleotides encoding the wild type protein is designed $nei_{wt}PA_{2148}$, and has the coding strand of nucleic acid sequence SEQ ID NO:100.

Translation of SEQ ID NO:100 indicates that nucleic acid molecule $nei_{wt}PA_{2148}$ encodes the equine influenza virus PA protein of about 716 amino acids, referred to herein as $Pei_{wt}$ $PA_{716}$, having amino acid sequence SEQ ID NO:101.

B. A nucleic acid molecule of2148 nucleotides encoding the cold-adapted protein is designated $nei_{ca}PA_{2148}$, and has the coding strand of nucleic acid sequence SEQ ID NO:102.

Translation of SEQ ID NO:102 indicates that nucleic acid molecule $nei_{ca}PA_{2148}$ encodes a protein of about 716 amino acids, referred to herein as $PEI_{ca}PA_{716}$, having amino acid sequence SEQ ID NO:103.

C. Comparison of the wild type and cold-adapted virus sequences reveals three discrepancies: a G to A base shift at base 175, base 466, and base 870. The base change at base 175 results in a glutamic acid (E) to lysine (K) change at amino acid 59. The base change at 466 results in an alanine (A) to threonine (T) change at amino acid 156. The base change at 870 does not result in an amino acid change at amino acid 290.

EXAMPLE 11

This example describes the cloning and sequencing of equine influenza Neuraminidase (NA) protein nucleic acid molecules for cold-adapted equine influenza viruses.

A. Nucleic acid molecules encoding cold-adapted equine influenza virus NA proteins were produced as follows. A PCR product was produced by PCR amplification using equine influenza virus DNA and primers M13 reverse primer (REV) and T7 primer (T7), designated SEQ ID NO:1 and SEQ ID NO:2, respectively. A nucleic acid molecule of 1478 molecules encoding the cold-adapted NA protein, denoted $nei_{ca}$ $NA_{1478}$ with a coding strand having a nucleic acid sequence designated SEQ ID NO:87 was produced.

Translation of SEQ ID NO:87 indicates that nucleic acid molecule $nei_{ca}NA_{1478}$ encodes a full-length protein of 470 amino acids, referred to herein as $Pei_{ca}NA_{470}$, having amino acid sequence SEQ ID NO:88, assuming an open reading frame in which the initiation codons spans from nucleotide 29 through 31 of SEQ ID NO:87 and the termination codon spans from nucleotide 1439 through 1441 of SEQ ID NO:87. The region encoding $Pei_{ca}NA_{470}$, designated $nei_{ca}NA_{1412}$, and having a coding strand comprising nucleotide 29 to 1441 of SEQ ID NO:87, is represented by SEQ ID NO:89.

EXAMPLE 12

This example describes the cloning and sequencing of the N-terminal and C-terminal regions of the equine influenza nucleoprotein (NP) nucleic acid molecules for wild type and cold adapted equine influenza virus.

A. Nucleic acid molecules encoding wild type and cold adapted equine influenza virus NP proteins were produced as follows. Wild-type strains 1 and 2 were cloned into pCR2.1 (Invitrogen), and cold-adapted strains 1 and 2 were cloned into pCR-Blunt cloning vector (Invitrogen). All strains were sequenced using M13 REV and T7 primers, SEQ ID NO: 1 and SEQ ID NO: 2, respectively.

B. N-terminal regions

A nucleic acid molecule of 738 nucleotides encoding the N-terminus of the wild-type strain 1 NP protein, denoted $nei_{wt1}$ $NP-N_{738}$, with a coding strand having a nucleic acid sequence designated SEQ ID NO:104, was produced. Translation of SEQ ID NO:104 indicates that nucleic acid molecule $nei_{wt1}$ $NP-N_{738}$ encodes the N-terminal 246 amino acids of NP protein, designated $Pei_{wt1}$ $NP-N_{246}$, having amino acid sequence SEQ ID NO:105.

A nucleic acid molecule of 693 nucleotides encoding the N-terminus of the wild-type strain 1 NP protein, denoted $nei_{wt1}$ $NP-N_{693}$, with a coding strand having a nucleic acid sequence designated SEQ ID NO:106 was produced. Translation of SEQ ID NO:106 indicates that nucleic acid molecule $nei_{wt1}$ $NP-N_{693}$ encodes the N-terminal 231 amino acids of NP protein, designated $Pei_{wt1}$ $NP-N_{231}$, having amino acid sequence SEQ ID NO:107.

A nucleic acid molecule of 738 nucleotides encoding the N-terminus of the wild-type strain 2 NP protein, denoted $nei_{wt1}$ $NP-N_{738}$, with a coding strand having a nucleic acid sequence designated SEQ ID NO:108, was produced. Translation of SEQ ID NO:108 indicates that nucleic acid molecule $nei_{wt1}NP-N_{738}$ encodes the N-terminal 246 amino acids of NP protein, designated $Pei_{wt2}$ $NP-N_{246}$, having amino acid sequence SEQ ID NO:109.

A nucleic acid molecule of 693 nucleotides encoding the N-terminus of the wild-type strain 2 NP protein, denoted $nei_{wt2}$ $NP-N_{693}$, with a coding strand having a nucleic acid sequence designated SEQ ID NO:110, was produced. Translation of SEQ ID NO:110 indicates that nucleic acid molecule $nei_{wt2}$ $NP-N_{693}$ encodes the N-terminal 231 amino acids of NP protein, designated $Pei_{wt2}$ $NP-N_{231}$, having amino acid sequence SEQ ID NO:111.

An N-terminal protein fragment of 245 amino acids of NP protein, designated $Pei_{ca1}$ $NP-N_{245}$, having amino acid sequence SEQ ID NO:112, was generated.

A nucleic acid molecule of 690 nucleotides encoding the N-terminus of the cold-adapted strain 1 NP protein, denoted $nei_{ca1}NP-N_{690}$, with a coding strand having a nucleic acid sequence designated SEQ ID NO:113, was produced. Translation of SEQ ID NO:113 indicates that nucleic acid molecule $nei_{ca1}$ $NP-N_{690}$ encodes the N-terminal 230 amino acids of NP protein, designated $Pei_{ca1}$ $NP-N_{230}$, having amino acid sequence SEQ ID NO:114.

A nucleic acid molecule of 735 nucleotides encoding the N-terminus of the cold-adapted strain 2 NP protein, denoted $nei_{ca2}$ $NP-N_{735}$, with a coding strand having a nucleic acid sequence designated SEQ ID NO:115 was produced. Translation of SEQ ID NO:115 indicates that nucleic acid molecule $nei_{ca2}$ $NP-N_{735}$ encodes the N-terminal 245 amino acids of NP protein, designated $Pei_{ca2}$ $NP-N_{245}$, having amino acid sequence SEQ ID NO:116.

A nucleic acid molecule of 690 nucleotides encoding the N-terminus of the cold-adapted strain 2, denoted $nei_{ca2}$ $NP-N_{690}$, with a coding strand having a nucleic acid sequence designated SEQ ID NO:117, was produced. Translation of SEQ ID NO:117 indicates that nucleic acid molecule $nei_{ca2}$ $NP-N_{690}$ encodes the N-terminal 230 amino acids of NP protein, designated $Pei_{ca2}$ $NP-N_{230}$, having amino acid sequence SEQ ID NO:118.

C. C-terminal regions

A nucleic acid molecule of 679 nucleotides encoding the C-terminal of the wild type strain 1, denoted $nei_{wt1}$ $NP-C_{679}$, with a coding strand having a nucleic acid sequence designated SEQ ID NO:119, was produced. Translation of SEQ ID NO:119 indicates that nucleic acid molecule $nei_{wt1}$ NP-$C_{679}$ encodes the C-terminal 226 amino acids of NP protein, designated $Pei_{wt1}$ NP-$C_{679}$, having amino acid sequence SEQ ID NO:120.

A nucleic acid molecule of 656 nucleotides encoding the C-terminal of the wild type strain 1, denoted $nei_{wt1}$ NP-$C_{656}$, with a coding strand having a nucleic acid sequence designated SEQ ID NO:121, was produced. Translation of SEQ ID NO:121 indicates that nucleic acid molecule $nei_{wt1}$ NP-$C_{656}$ encodes the C-terminal 218 amino acids of NP protein, designated $Pei_{wt1}$ NP-$C_{218}$, having amino acid sequence SEQ ID NO:122.

A nucleic acid molecule of 679 nucleotides encoding the C-terminal of the wild type strain 1, denoted $nei_{wt2}$ NP-$C_{679}$, with a coding strand having a nucleic acid sequence designated SEQ ID NO:123, was produced. Translation of SEQ ID NO:123 indicates that nucleic acid molecule $nei_{wt1}$ NP-$C_{679}$ encodes the C-terminal 226 amino acids of NP protein, designated $Pei_{wt2}$ NP-$C_{226}$, having amino acid sequence SEQ ID NO:124.

A nucleic acid molecule of 656 nucleotides encoding the C-terminal of the wild type strain 2, denoted $nei_{wt2}$ NP-$C_{656}$, with a coding strand having a nucleic acid sequence designated SEQ ID NO:125, was produced. Translation of SEQ ID NO:125 indicates that nucleic acid molecule $nei_{wt2}$ NP-$C_{656}$ encodes the C-terminal 218 amino acids of NP protein, designated $Pei_{wt2}$ NP-$C_{218}$ having amino acid sequence SEQ ID NO:126.

A nucleic acid molecule of 656 nucleotides encoding the C-terminal of the cold-adapted strain 1, denoted $nei_{ca1}$ NP-$C_{665}$, with a coding strand having a nucleic acid sequence designated SEQ ID NO:127, was produced. Translation of SEQ ID NO:127 indicates that nucleic acid molecule $nei_{ca1}$ NP-$C_{665}$ encodes the C-terminal 222 amino acids of NP protein, designated $Pei_{ca1}$ NP-$C_{222}$, having amino acid sequence SEQ ID NO:128.

A nucleic acid molecule of 642 nucleotides encoding the C-terminal of the cold-adapted strain 1, denoted $nei_{ca1}$ NP-$C_{642}$, with a coding strand having a nucleic acid sequence designated SEQ ID NO:129 was produced. Translation of SEQ ID NO:129 indicates that nucleic acid molecule $nei_{ca1}$NP-$C_{642}$ encodes the C-terminal 214 amino acids of NP protein, designated $Pei_{ca1}$NP-$C_{214}$, having amino acid sequence SEQ ID NO:130.

D. Comparisons

Consensus sequences for the 5' and 3' ends of the NP gene were generated, but there is an approximately 148 base pair gap in the data that prevents the formation of a contiguous sequence when compared to protein and DNA data currently in the GenBank databases (a nucleoprotein from GenBank named flanpg; Gorman et al, J. Virol. 64, 1487 (1990)). The flanpg sequences were used to compare the 5' and 3' fragments of the present NP genes to get relative positions that are used to designate position for the various differences in the bases between the Wild Type and the ca strains. The flanpg sequence allows for the approximately 148 base pairs that are missing between the 5' and 3' fragments needed to construct the entire gene.

The DNA codes for the N-terminal 735-738 bases and the C-terminal 665-679 bases with a gap of approximately 149-166 bases between the two fragments of the Wild Type and cold-adapted (ca) strains, respectively. There are seven discrepancies between the wild type and ca strains. The ca strains have discrepancies at base 146 (G to T) and at base 228 (A to G). At base 492, the wt1 only has a discrepancy versus the other strains of (A to C). At base 541, the ca1 only has a discrepancy versus the other strains of (C to A). There is a base discrepancy at position 645 in the DNA (G to A). At base 670, the ca strains have a discrepancy (G to A). At base 1019, the wt1 only has a discrepancy. versus the other strains of (G to A). There are no other points of discrepancy between the fill-length Wild Type and ca strains.

The full-length sequence is proposed to consist of 1497 bases, however there is no overlap between the 5' and 3' ends of the DNA sequences generated. The sequences listed are for the 5' end and the 3' end of the open reading frame of the gene. The gene is missing approximately 148 base pairs between these two fragment sequences that would generate the complete gene sequence.

A comparison of all the Wild Type and ca strain clones (wt1, wt2, ca1, and ca2) by amino acid translation for the protein sequence coding only for the open reading frame (ORF) from the 5' and 3' DNA fragments was compared to the GenBank nucleoprotein noted above. The DNA codes for the N-terminal 230 amino acids and the C-terminal 214 amino acids with a gap of approximately 55 amino acids between the two fragments. There are seven discrepancies between the ca and Wild Type strains. The ca strains have a discrepancy (G to V) at amino acid 34, and at amino acid 61 (I to M). At amino acid 149, the wt1 only has a discrepancy versus the other strains of (Q to H). At amino acid 166, ca1 only has a discrepancy versus the other strains of (L to M). Although there is a base discrepancy at position 600 in the DNA sequence, there is no change in the corresponding amino acid sequence. At amino acid 209, the ca strains have a discrepancy (G to S). At amino acid 325, the wt1 only has a discrepancy versus the other strains of R to K). There are no other points of discrepancy between the full-length Wild Type and ca stains.

While various embodiments of the present invention have been described in detail it is apparent that modifications and adaptations of those embodiments will occur to those skilled in the art. It is to be expressly understood, however, that such modifications and adaptations are within the scope of the present invention, as set forth in the following claims.

The invention claimed is:

1. An isolated nucleic acid molecule selected from the group consisting of:

a. an isolated nucleic acid molecule that encodes a protein comprising the amino acid sequence of SEQ ID NO: 103; and b. an isolated nucleic acid molecule fully complementary to the nucleic acid molecule of (a).

2. The nucleic acid molecule of claim 1, wherein said nucleic acid molecule comprises SEQ ID NO:102, or a nucleic acid sequence which is fully complementary to SEQ ID NO:102.

3. An isolated virus comprising a nucleic acid molecule that encodes the protein of SEQ ID NO:103.

4. The virus of claim 3, wherein said virus comprises SEQ ID NO: 102.

5. The virus of claim 3, wherein said virus is selected from the group consisting of equine influenza virus and a reassortant influenza virus.

* * * * *